(12) United States Patent
Tilly et al.

(10) Patent No.: US 9,845,482 B2
(45) Date of Patent: Dec. 19, 2017

(54) COMPOSITIONS AND METHODS FOR ENHANCING BIOENERGETIC STATUS IN FEMALE GERM CELLS

(75) Inventors: Jonathan L. Tilly, Windham, NH (US); David A. Sinclair, Chestnut Hill, MA (US)

(73) Assignees: The General Hospital Corporation, Boston, MA (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/447,083

(22) Filed: Apr. 13, 2012

(65) Prior Publication Data

US 2013/0059384 A1 Mar. 7, 2013

Related U.S. Application Data

(60) Provisional application No. 61/502,840, filed on Jun. 29, 2011, provisional application No. 61/600,529, filed on Feb. 17, 2012.

(51) Int. Cl.

| | | |
|---|---|---|
| *C12N 5/075* | (2010.01) |
| *C07C 255/36* | (2006.01) |
| *C07D 213/80* | (2006.01) |
| *C07D 311/30* | (2006.01) |
| *C07H 19/04* | (2006.01) |
| *C07H 19/048* | (2006.01) |
| *C12N 15/873* | (2010.01) |
| *C12N 5/071* | (2010.01) |
| *A61K 35/14* | (2015.01) |
| *A61K 35/28* | (2015.01) |
| *A61K 35/51* | (2015.01) |
| *A61K 35/54* | (2015.01) |
| *A61K 31/05* | (2006.01) |
| *A61K 31/137* | (2006.01) |
| *A61K 31/277* | (2006.01) |
| *A61K 31/352* | (2006.01) |
| *A61K 31/4745* | (2006.01) |
| *A61K 31/498* | (2006.01) |
| *C07D 213/50* | (2006.01) |
| *C07D 233/60* | (2006.01) |
| *C07D 233/88* | (2006.01) |
| *C07D 277/36* | (2006.01) |
| *C07D 277/587* | (2006.01) |
| *C07D 277/64* | (2006.01) |
| *C07D 495/04* | (2006.01) |

(52) U.S. Cl.
CPC ........... *C12N 15/873* (2013.01); *A61K 31/05* (2013.01); *A61K 31/137* (2013.01); *A61K 31/277* (2013.01); *A61K 31/352* (2013.01); *A61K 31/4745* (2013.01); *A61K 31/498* (2013.01); *A61K 35/14* (2013.01); *A61K 35/28* (2013.01); *A61K 35/51* (2013.01); *A61K 35/54* (2013.01); *C07D 213/50* (2013.01); *C07D 233/60* (2013.01); *C07D 233/88* (2013.01); *C07D 277/36* (2013.01); *C07D 277/587* (2013.01); *C07D 277/64* (2013.01); *C07D 495/04* (2013.01); *C12N 5/0609* (2013.01); *C12N 5/0682* (2013.01); *C12N 2501/40* (2013.01); *C12N 2517/10* (2013.01)

(58) Field of Classification Search
None
See application file for complete search history.

(56) References Cited

U.S. PATENT DOCUMENTS

| | | | |
|---|---|---|---|
| 6,762,053 B2 * | 7/2004 | Gardner et al. | ............... 435/407 |
| 6,875,854 B1 | 4/2005 | Castrillon | |
| 7,776,326 B2 * | 8/2010 | Milbrandt | .......... A61K 31/7084 424/94.5 |
| 7,955,846 B2 | 6/2011 | Tilly et al. | |
| 8,062,222 B2 | 11/2011 | Dertinger et al. | |
| 8,338,178 B2 | 12/2012 | Hyde et al. | |
| 8,445,277 B2 | 5/2013 | Hyde et al. | |
| 8,489,337 B2 | 7/2013 | Hyde et al. | |
| 8,527,209 B2 | 9/2013 | Hyde et al. | |
| 8,846,028 B2 | 9/2014 | Hyde et al. | |
| 8,903,660 B2 | 12/2014 | Hyde et al. | |
| 8,999,714 B2 | 4/2015 | Hyde et al. | |
| 2005/0008624 A1 * | 1/2005 | Peled et al. | ................. 424/93.21 |
| 2005/0130302 A1 | 6/2005 | Nakauchi et al. | |
| 2006/0010508 A1 | 1/2006 | Tilly et al. | |

(Continued)

FOREIGN PATENT DOCUMENTS

| | | |
|---|---|---|
| EP | 1233978 A1 | 8/2002 |
| EP | 2 213 288 A1 | 8/2010 |

(Continued)

OTHER PUBLICATIONS

Campbell et al. "The dietary flavonoids apigenin and (−)-epigallocatechin gallate enhance the positive modulation by diazepam of the activation by GABA of recombinant GABAA receptors." Biochemical Pharmacology 68: 1631-1638, 2004.*

Takami et al. "Flavonoids inhibit spontaneous and gonadotropin-induced resumption of meiosis", Biology of Reproduction 62: Abstract 171, 2000.*

Kang et al. "Nicotinamide extends replicative lifespan of human cells", Aging Cell 5: 423-36, 2006.*

Bogan et al. "nicotinic acid, nicotinamide and nicotinamide riboside: a molecular evaluation of NAD+ precursor vitamins in human nutrient", Annual Review of Nutrition 28: 115-30, 2008.*

Von Stetina et al. "Developmental control of oocyte maturation and egg activation in metazoan models," Cold Spring Harbor, Perspectives in Biology 3:a005553, 2011.*

Takeo et al. "Age-associated deterioration in follicular fluid induces a decline in bovine oocyte quality", Reproduction, Fertility and Development, 2016.*

(Continued)

*Primary Examiner* — Emily Cordas
(74) *Attorney, Agent, or Firm* — Saul Ewing Arnstein & Lehr LLP; Peter C. Lauro, Esq.

(57) ABSTRACT

Compositions and methods comprising bioenergetic agents for restoring the quality of aged oocytes, enhancing oogonial stem cells or improving derivatives thereof (e.g., cytoplasm or isolated mitochondria) for use in fertility-enhancing procedures, are described.

14 Claims, 56 Drawing Sheets
(43 of 56 Drawing Sheet(s) Filed in Color)

(56) References Cited

U.S. PATENT DOCUMENTS

| | | | |
|---|---|---|---|
| 2006/0010509 A1 | 1/2006 | Johnson et al. | |
| 2006/0015961 A1 | 1/2006 | Tilly et al. | |
| 2009/0111764 A1 | 4/2009 | Hillis et al. | |
| 2012/0135091 A1* | 5/2012 | Roth et al. | 424/696 |

FOREIGN PATENT DOCUMENTS

| | | |
|---|---|---|
| WO | WO01/30980 | 5/2001 |
| WO | WO-0136445 A1 | 5/2001 |
| WO | 0130980 A3 | 11/2001 |
| WO | WO-2005007687 A1 | 1/2005 |
| WO | WO2005/113752 | 12/2005 |
| WO | WO2005/121321 | 12/2005 |
| WO | WO2006/001938 | 1/2006 |
| WO | 2006105440 A2 | 10/2006 |
| WO | 2009/087568 A2 | 7/2009 |
| WO | 2012142500 A2 | 10/2012 |
| WO | 2013/002879 A1 | 1/2013 |

OTHER PUBLICATIONS

Paramio et al. "Recent advances in in vitro embryo production in small ruminants", Theriogenology 86(1): 152-159, 2016.*
ISR/Written Opinion issued in PCT/US2005/017233, dated Feb. 26, 2007, The General Hospital Corp.
ISR/Written Opinion/IPRP issue in PCT/US2005/017221, dated Jul. 27, 2006, The General Hospital Corp.
ISR/Written Opinion/IPRP issued in PCT/US2005/017234, dated Aug. 10, 2006, The General Hospital Corp.
Supplementary Search Report issued in EP-05669982.7, dated Sep. 17, 2008, The General Hospital Corp.
Supplementary Search Report issued in EP-05783644.7, dated Sep. 23, 2008, The General Hospital Corp.
Supplementary Search Report issued in EP-05782697.6, dated Oct. 15, 2008, The General Hospital Corp.
International Preliminary Report on Patentability issued for PCT/US05/17233, dated Jul. 25, 2008, The General Hospital Corp.
International Preliminart Report on Patentability issued for PCT/US05/17234, dated Jul. 25, 2008, The General Hospital Corp.
Powell, K., Going Against the Grain, PloS Biol 2007; 5:e338 (doi:10.1371/journal.pbio.0050338).
Bazer FW., Strong science challenges conventional wisdom: new perspectives on ovarian biology. Reprod Biol Endocrinol 2004; 2:28.
Gougeon A., Neo-oogenesis in the postnatal ovary: fantasy or reality? Gynecol Obstet Fertil 2005; 33:819-823.
Kayisli UA et al., Stem cells and fertility: what does the future hold? Curr Opin Obstet Gynecol 2006; 18:338-343.
Faddy M. et al., Numbers of ovarian follicles and testing germ line renewal in the postnatal ovary. Facts and fallacies. Cell Cycle 2007; 6:1951-1952.
Oktem O. et al., Stem cells: a perspective on oocytes. Ann NY Acad Sci USA 2008; 1127:20-26.
Zuckerman S., Beyond the Ivory Tower. The Frontiers of Public and Private Science. New York: Taplinger; 1971:22-34.
Zhang D et al., Expression of stem and germ cell markers within nonfollicle structures in adult mouse ovary. Reprod Sci 2008; 15:139-146.
Vermande-Van Eck G., Neo-ovogenesis in the adult monkey. Anat Rec 1956; 125:207-224.
Flaws JA, et al., Chronically elevated luteinizing hormone depletes primordial follicles in the mouse ovary. Biol Reprod 1997; 57:1233-1237.
Dissen GA, et al., Romero C., Hirshfield AN, Ojeda Sr. Nerve growth factor is required for early follicular development in the mammalian ovary. Endocrinology 2001; 142:2078-2086.
Nilsson EE, et al., Bone morphogenetic protein-4 acts as an ovarian follicle survival factor and promotes primordial follicle development. Biol Reprod 2003; 69:1265-1272.

Tomic D et al., Ovarian follicle development requires Smad3, Mol Endocrinol 2004; 18:2224-2240.
Rajkovia A et al., NOBOX deficiency disrupts early folliculogenesis and oocyte-specific gene expression. Science 2004; 305:1157-1159.
Castrillon DH et al., Suppression of ovarian follicle activation in mice by the transcription factor Foxo3a. Science 2004; 301:215-218.
Lohff JC et al., Effect of duration of dosing on onset of ovarian failure in a chemical-induced mouse model of perimenopause. Menopause 2006; 13:482-488.
Reddy P. et al., Oocyte-specific defection of Pten causes premature activation of the primordial follicle pool. Science 2008; 319:611-613.
Gosden RG. Ovarian support of pregnancy in ageing inbred mice. J Reprod Fertil 1975; 42:423-430.
Gosden RG. Effects of age and parity on the breeding potential of mice with one or two ovaries. J. Reprod Fertil 1979; 57:477-487.
Nelson JF et al., Effects of dietary restriction on estrous cyclicity and follicular reserves in aging C57BL/6Jmice. Biol Reprod 1985; 32:515-522.
Eichenlaub-Ritter U et al., the CBA mouse as a model for age-related aneuploidy in man: studies of oocyte maturation, spindle formation and chromosome alignment during meiosis. Chromosoma (Berl) 1988; 96:220-226.
Allen E. Ovogenesis during sexual maturity. Am J Anat 1923; 31:439-482.
Bucci LR et al., Effects of busulfan on murine spermatogenesis: cytotoxicity, sterility, sperm abnormalities and dominant lethal mutations. Mutat Res 1987; 176:259-268.
Brinster RL et al., Germline transmission of donor haplotype following spermatogonial transplantation. Proc Natl Acad Sci USA 1994; 91:11303-11307.
Ogawa T et al., Transplantation of testis germinal cells into mouse seminiferous tubules. Int J. Dev Biol 1997; 41:111-122.
Pelloux MC et al., Effects of busulphan on ovarian folliculogenesis, steroidogenesis and anti-Mullerian activity of rat neonates. Acta Endocrinol 1988; 118:218-226.
Perez GI et al., Apoptosis-associated signaling pathways are required for chemotherapy-mediated female germ cell destruction. Nat Med 1997; 3:1228-1232.
Perez GI et al., Fragmentation and death (a.k.a. apoptosis) of ovulated oocytes. Mol Hum Reprod 1999; 5:414-420.
Morita Y et al., Oocyte apoptosis is suppressed by disruption of the acid sphingomyelinase gene or by sphingosine-1-phosphate therapy. Nat Med 2000; 6:1109-1114.
Baltus AE et al., In germ cells of mouse embryonic ovaries, the decision to enter meiosis precedes premeiotic DNA replication. Nat Genet 2006; 38:1430-1434.
Zhou Q et al., Expression of stimulated by retinoic acid gene 8 (Stra8) and maturation of murine gonocytes and spermatogonia induced by retinoic acid in vitro. Biol Reprod 2008; 78:537-545.
Wang N. et al., Inhibition of histone deacetylase activity amplifies retinoic acid-mediated induction of Stra8 expression and oogenesis in ovaries of adult female mice. Proceedings of the 41st Annual Meeting of the Society for the Study of Reproduction, Kailua-Kona, Big Island, HI; p. 132 (Abstract 291), 2008.
Bowles J et al., Retinoic acid signaling determines germ cell fate in mice. Science 2006; 312:596-600.
Koubova J et al., Retinoic acid regulates sex-specific tijming of meiotic initiation in mice. Proc Natl Acad Sci USA 2006; 103:2474-2479.
Lee H-J et al., Loss of CABLES1, a cyclin-dependent kinase-interacting protein that inhibits cell cycle progression, results in germline expansion at the expense of oocyte quality in adult female mice. Cell Cycle 2007; 6:2678-2684.
Bristol-Gould SK et al., Postnatal regulation of germ cells by activin: the establishment of the initial follicle pool. Dev Biol 2006; 298:132-148.
Lin H. The stem-cell niche theory: lessons from flies. Nat Rev Genet 2002; 3:931-940.
Ogawa T et al., The niche for spermatogonial stem cells in the mammalian testis. Int. J. Hematol 2005; 82: 381-388.

(56) References Cited

OTHER PUBLICATIONS

Bukovsky A et al., Origin of germ cells and formation of new primary follicles in adult human ovaries. Reprod Biol Endocrinol 2004; 2:28.
Bukovsky A et al., Oogenesis in cultures derived from adult human ovaries. Reprod Biol Endocrinol 2005; 3:17.
Bukovsky A et al., Mammalian neo-oogenesis and expression of meiosis-specific protein SCP3 in adult human and monkey ovaries. Cell Cycle 2008; 7:683-686.
Bristol-Gould SK et al., Fate of the initial follicle pool: empirical and mathematical evidence supporting its sufficiency for adult fertility. Dev Biol 2006; 298:149-154.
Peters H. The development of the mouse ovary from birth to maturity. Acta Endocrinol 1969; 62:98-116.
Elvin JA et al., Molecular characterization of the follicle defects in the growth differentiation factor 9-deficient ovary. Mol Endocrinol 1999; 13: 1018-1034.
Myers M et al., Methods for quantifyying follicular numbers within the mouse ovary. Reproduction 2004; 127:569-580.
Huntriss J et al., cDNA cloning and expression of the human NOBOX gene in oocytes and ovarian follicles. Mol Hum Reprod 2006; 12:283-289.
John GN et al., Specificity of the requirement for Foxo3 in primordial follicle activation. Reproduction 2007; 133:855-863.
Ohta H et al., Commitment of fetal male germ cells to spermatogonial stem cells during mouse embryonic development. Biol Reprod 2004; 70:1286-1291.
Hubner K et al., Derivation of oocytes from mouse embryonic stem cells. Science 2003; 300:1251-1256.
Novak I et al., Mouse embryonic stem cells form follicle-like ovarian structures but do not progress through meiosis. Stem Cells 2006; 8:1931-1936.
Kerkis A et al., In vitro differentiation of male mouse embryonic stem cells into both presumptive sperm cells and oocytes. Cloning Stem Cells 2007; 9:535-548.
Nagano MC. In vitro gamete derivation from pluripotent stem cells: progress and perspective. Biol Reprod 2007; 76:546-551.
Dyce PW et al., In vitro germline potential of stem cells derived from fetal porcine skin. Nat Cell Biol 2006; 8:384-390.
Dyce PW et al., From skin cells to ovarian follicles? Cell Cycle 2006; 5:1371-1375.
Danner S et al., Derivation of oocyte-like cells from a clonal pancreatic stem cell line. Mol Hum Reprod 2007; 13:11-20.
Toyooka Y et al., Embryonic stem cells can form germ cells in vitro. Proc Natl Acad Sci USA 2003; 100:11457-11462.
Geijsen N et al., Derivation of embryonic germ cells and male gametes from embryonic stem cells. Nature 2004; 427:148-154.
Lue Y et al., Fate of bone marrow stem cells transplanted into the the testis: implications for men with testicular failure. Am J Pathol 2007; 170;899-908.
Drusenheimer N et al., Putative human male germ cells from bone marrow stem cells. Soc Reprod Fertil Suppl 2007; 63:69-76.
Yeom YI et al., Germline regulatory element of Oct-4 specific for the totipotent cycle of embryonal cells. Development 122:881-894, 1996.
Yoshimizu T et al., Germline-specific expression of the Oct-4/green fluorescent protein (GFP) transgene in mice. Dev Growth Differ 1999; 41:675-684.
Szabo PE et al., Allele-specific expression of imprinted genes in mouse migratory primordial germ cells. Mech Dev 2002; 115:157-160.
Begum S et al., The oocyte population is not renewed in transplanted or irradiated adult ovaries. Hum Reprod 2008; (doi:10.1093/humrep/den249).
Fu X et al., Bone marrow mesenchymal stem cell transplanation improves ovarian function and structure in rats with chemotherapy-induced damage. Cytotherapy 2008; 10:353-363.
Tilly JL et al., Stem cell contribution to ovarian development, function and disease. Endocrinology 2008; (doi:10.1210/en.2008-0458).

Shankle WR et al., Evidence for a postnatal doubling of neuron number in the developing human cerebral cortex between 15 months and 6 years. J Theor Biol 1998; 191:115-140.
Shankle WR et al., Approximate doubling of numbers of neurons in postnatal human cerebral cortex and in 35 specific cytoarchitectural areas from birth to 72 months. Pediatr Dev Pathol 1999; 2:244-259.
Gould E et al., Neurogenesis in the neocortex of adult primates. Science 1999; 286:548-552.
Korr H et al., Facts and fictions regarding post-natal neurogenesis in the developing human cerebral cortex. J Theor Biol 1999; 200:291-297.
Nowakowski RS et al., New Neurons: extraordinary evidence or extraordinary conclusion? Science 2000; 288:771a.
Rakic P. Neurogenesis in the adult primate neocortex: an evaluation of the evidence. Nat Rev Neurosci 2002; 3:65-71.
Blakeslee S. A decade of discovery yields a shock about the brain. New York Times 2000 (Jan.); F1, F4.
Gross CG. Neurogenesis in the adult brain: death of a dogma. Nat Rev Neurosci 2000; 1:67-73.
Gould E et al., Adult-generated hippocampal and neocortical neurons in macaques have a transient existence. Proc Natl Acad Sci USA 2001; 98: 10910-10917.
Gould E et al., Neurogenesis in adult mammals: some progress and problems. J Neurosci 2002; 22:619-623.
Leuner B et al., Diminished neurogenesis in the marmoset brain precedes old age. Proc Natl Acad Sci USA 2007; 104:17169-17173.
Revishchin AV et al., Neural stem cells in the mammalian brain. Int Rev Cytol 2008;265-55-109.
Maurer MH et al., Screening the brain: molecular fingerprints of neural stem cells. Curr Stem Cell Res Ther 2006; 1:65-77.
Taupin P. Therapeutic potential of adult neural stem cells. Rec Patents CNS Drug Discov 2006; 1:299-303.
Beaumont HM et al., A quantitative and cytological study of oogonia and oocytes in the fetal and neonatal rat. Proc R Soc Lond B 1961; 155:557-579.
Baker TG et al., The fine structure of oogonia and oocytes in human ovaries. J Cell Sci 1967; 2:213-224.
Gosden RG. Follicular status at menopause. Hum Reprod 1987; 2:617-621.
Selesniemi K et al., Moderate caloric restriction initiated in rodents during adulthood sustains function of the female reproductive axis into advanced chronological age. Aging Cell 2008; (doi:10.1111/j.1474-9726.2008.00409.x).
Perez GI et al., Absence of the pro-apoptotic Bax protein extends fertility and alleviates age-related health complications in female mice. Proc Natl Acad Sci USE 2007; 104: 5229-5234.
Kirilly D et al., The *Drosophila* ovary: an active stem cell community. Cell Res 2007; 17:15-25.
Pearl R et al., Studies on the physiology of reproduction in the domestic fowl. J Exp Zool 1921; 34:101-118.
Underwood JL et al., Gonad regeneration in grass carp following bilateral gonadectomy. Progressive Fish-Culturist 1986; 48:54-56.
Draper BW et al., nanos1 is required to maintain oocyte production in adult zebrafish. Dev Biol 2007; 305:589-598.
Salooja N et al., Successful pregnancies in women following single autotransplant for acute myeloid leukemia with a chemotherapy ablation protocol. Bone Marrow Transplant 1994; 13:431-435.
Socie G et al., Late Effects Working Party of the European Study Group for Blood and Marrow Transplantation. Nonmalignant late effects after allogeneic stem cell transplantation. Blood 2003; 101:3373-3385.
Oktay K et al., Regeneration of oocytes after chemotherapy: connecting the evidence from mouse to human. J. Clin Oncol 2007; 25:3185-3187.
Tropel P et al., Isolation and Characterization of Mesenchymal Stem Cells from Adult Mouse Bone Marow. Experimental Cell Research, May 1, 2004. 295(2); 395-406.
Logothetou-Rella "Description of primordial germ cells, oogonia, oocytes and embryo-like growth in squash preparations of tissues from hematological malignancies" Histol Histopathol. 11(4): 965-984 (1996).
Nayernia et al. "Derivation of male germ cells from bone marrow stem cells" Lab Invest. 86(7): 654-663 (2006).

(56) References Cited

OTHER PUBLICATIONS

Johnson et al. "Oocyte Generation in Adult Mammalian Ovaries by Putative Germ Cells in Bone Marrow and Peripheral Blood" Cell 122: 303-315 (2005).
Kucia et al. "A population of very small embryonic-like (VSEL) CZCR4+SSEA-1+ Oct-4+ Stem cells identified in adult bone marrow" Luekemia 20: 857-869 (2006).
Pochampally et al. "Serum deprivation of human marrow stromal cells (hMSCs) selects for a subpopulation of early progenitor cells with enhanced expression of OCT-4 and other embryonic genes" Blood 103(5): 1647-1652 (2004).
Hayashi et al. "Mouse preimplantation Embryos Developed from Oocytes Injected with Round Spermatids or Spermatozoa Have Similar but Distinct Patterns of Early Messenger RNA Expression" Biology of Reproduction 69: 1170-1176 (2003).
Hovatta et al. "A culture system using human foreskin fibroblasts as feeder cells allows production of human embryonic stem cells" Human Reproduction 18(7): 1404-1409 (2003).
Bukovsky et al. "Potential new strategies for the treatment of ovarian infertility and degenerative diseases with autologous ovarian stem cells" Expert Opin. Biol. Ther. 6(4): 341-365 (2006).
Eggan et al. "Ovulated oocytes in adult mice derive from non-circulating germ cells." Nature 441; 1109-1114 (2006).
Anderson, Biol Reprod. 1988; 38(1) 1-15.
Decotto et al., Dev cell. 2005; 9(4): 501-10.
Gage, F., Nature 392: 18-24, 1998.
Goswami et al., 2005. Premature Ovarian Failure. Hum Reprod Update 11: 391-410.
Hildebrandt et al., 2000. Detection of Germ-cell Tumor Cells in Peripheral Blood Progenitor Cell Harvests: Impact on Clinical Outcome. Clin Cancer Res 6: 4641-4646.
Samstein et al., Journal of American Society of Nephrology 12: 182-193, 2001.
Virant-Klun et al., Stem Cells and Development, Jul. 2008 pp. 1-43.
Yamashita et al., Journal of Cell Science 118, 665-672, 2005.
Powell "Skeptics demand duplication of controversial fertility claim" Nat Med 11:911 (2005).
Powell "Born or made? Debate on mouse eggs reignites" Nature 441: 795 (2006).
Ainsworth "Bone cells linked to creation of fresh eggs in mammals" Nature 436: 609 (2005).
Greenfeld et al. "Renewed debate over postnatal oogenesis in the mammalian ovary" Bioessays 26:829-32 (2004).
Gosden "Germline stem cells in the postnatal ovary: is the ovary more like a testis?" Hum Reprod Update 10(3) 193-195 (2004).
Albertini "Micromanagement of the ovarian follicle reserve—do stem cells play into the ledger?" Reproduction 127: 513-514 (2004).
Vogel "Controversial study finds unexpected source of oocytes" Science 309: 678-679 (2005).
Hoyer Can the clock be turned back on ovarian aging? Sci Aging Knowledge Environ 10:pe11 (2004).
Telfer "Germline stem cells in the postnatal mammalian ovary: a phenomenon of prosimian primates and mice?" Reprod Biol Endocrinol 2:24 (2004).
Telfer et al. "On regenerating the ovary and generating controversy" Cell 122: 821-22 (2005).
Kerr et al. "Quantification of healthy follicles in the noenatal and adult mouse ovary: evidence for maintenance of primordial follicle supply" Reproduction 132: 95-109 (2006).
Skaznik et al. "Serious doubts over Eggs forever?" Differentiation 74: 1-7 (2006).
Salooja et al. "Late Effects of working party of the European Group for blood and marrow transplantataion. Pregnancy outcomes after peripheral blood or bone marrow transplantation: a retrospective study." Lancet 358: 271-276 (2001).
Samuelsson et al. "Successful pregnancy in a 28 year old patient autographed for acute lymphoblastic leukemia following myeloablative treatment including total body irradiation." Bone Marrow Transplant 12: 659-660 (1993).
Sanders et al. "Pregnancies following high-dose cyclophosphamide with or without high-dose busulfan or total-body irradiation and bone marrow transplantation." Blood 87: 3045-3052 (1996).
Johnson et al. "Germline stem cells and follicular renewal in the postnatal mammalian ovary." Nature 48(11):145-150 (2004).
Hershlag et al. "Return of fertility after autologous stem cell transplantation." Fertility and Sterility 77(2) 419-421 (2002).
Zhou, K, et al. "Production of Offspring from a Germline Stem Cell Line Derived from Neonatal Ovaries" Nature Cell Biology Online Publication, published online Apr. 12, 2009; DOI 10.1038/ncb1869, pp. 1-20.
Tropel et al., Isolation and Characterization of Mesenchymal Stem Cells from Adult Mouse Bone Marrow. Experimental Cell Research, May 1, 2004. 295(2); 395-406.
Wittstock et al., Analytical Biochemistry, 292, 166-169, 2001.
Castrillon et al., (PNAS, 97-17: 9585-9590, 2000).
Clark, et al., (Stem Cells, 22: 169-179, 2004).
Johnson et al. "Germline stem cells and follicular renewal in the postnatal mammalian ovary" Nature 428: 145-150 (2004).
Byskov et al. "Eggs forever?" Differentiation 73: 438-446 (2005).
Johnson et al. "Setting the Record Straight on Data Supporting Postnatal Oogenesis in Female Mammals" Cell Cycle 4:11, 14771-1477 (2005).
Logothetou-Rella Description of primordial germ cells, oogonia, oocytes and embryo-like growth in squash preparations of issues from hematological malignancies: Histology and Histopathology 11: 965-984(1996).
Logothetou-Rella "Meiosis in hematological malignancies. In situ cytogenetic morphology" Histology and Histopathology 11: 943-963 (1996).
Thomson et al., Science, 282: 1145-1147, 1998.
Clark et al., Human Molecular Genetics, 13(7): 727-739, 2004.
Reubinoff et al., Nature Biotechnology, 18: 399-404, 2000.
Lin et al., Stem Cells, 21: 152-161, 2003.
Gosden, Human Reproduction Update, 10(3): 193-195, 2004.
Bukovsky, et al., Reproductive Biology and Endocrinology, 2:20, 2004.
Spradling, Nature, 428: 133-134, 2004.
Balakier et al., "Morphological and Cytogenetic Analysis of Human Giant Oocytes and Giant Embryos" Human Reproduction 17(8): 2394-2401 (2002).
Sotile "Bone Marrow as a Source of Stem Cells and Germ Cells? Perspectives for Transplantation" Cell Tissue Res. 328:1-5 (2007).
Hua, Jinlian et al., Derivation of male germ cell-like lineage from human fetal bone marrow stem cells, Reproductive BioMedicine Online; www.rbmonline.com/Article/3742 on web May 8, 2009, vol. 19, No. 1. 2009-99-105.
Lovell-Badge, Robin, Banking on spermatogonial stem cells: Frozen assets and foreign investments, Nature Medicine, vol. 2, No. 6, Jun. 1996.
Meachem et al., Spermatogonia: stem cells with a great perspective, Reproduction (2001), 121,825-834.
Nistal et al., Decrease in the Number of Human Ap and Ad Spermatogonia and in the Ap/Ad Ratio with Advancing Age, J Androl 1987; 8:64-68.
Paniagua et al., Quantification of cell types throughout the cycle of the human seminiferous epithelium and their DNA content, Anatomy and Embryology (1987) 176: 225-230.
Schulze, Cornelia, Response of the human testis to long-term estrogen treatment: Morphology of Sertoli cells, Leydig cells and spermatogonial stem cells, Cell and Tissue Research (1998) 251: 31-43.
Anderson "An overview of follicular development in the ovary: From embryo to the fertilized ovum in vitro." Md. Med. J. 41: 614-620 (1992).
Johnson et al., "Germline stem cells and follicular renewal in the postnatal mammalian ovary." Nature 428: 145-150 (2004).
Korbling et al. "Peripheral blood stem cell versus bone barrow allotransplantation: does the source of hematopoietic stemm cells matter?" *Blood* 98: 2900-2908 (2001).
Ho et al., "Hematopoietic stem cells: can old cells learn new tricks?" *J Leukoc Biol* 73: 547-555 (2003).

(56) References Cited

OTHER PUBLICATIONS

Sanchez-Ramos "Neural Cells Derived From Adult Bone Marrow and Umbilical Cord Blood." *J Neurosci Res* 69: 880-893 (2002).
Lee "Isolation of multipotent mesenchymal stem cells from umbilical cord blood." *Blood* 103:1669-75 (2004).
Rogers et al. "Lifeline in an Ethical Quagmire: Umbilical Cord Blood as an Alternative to Embryonic Stem Cells." *Sexuality, Reproduction & Menopause* 2: 64-70 (2004).
Green et al. "Do cells outside the testes participate in repopulating the germinal epithelium after irradiation?" *Int. J. Radiat. Biol.* vol. 17 (1): 87-92 (1970).
Morita et al. "Oocyte Apoptosis: Like Sand through an Hourglass" *Dev. Biol.* 213: 1-17 (1999).
Tilly, J.L., "Commuting the Death Sentence: How Oocytes Strive to Survive." *Nat. Rev. Mol. Cell Biol.* 2: 838-848 (2001).
Faddy et al., "The kinetics of pre-antral follicle development in ovaries of CBA/Ca mice during the first 14 weeks of life." *Cell Tissue Kinet.* 20: 551-560 (1987).
Faddy, M.J., "Follicle dynamics during ovarian ageing." *Mol. Cell. Endocrinol.* 163: 43-48 (2000).
Faddy et al., "An Analytical Model for Ovarian Follicle Dynamics." *J. Exp. Zool.* 197: 173-186 (1976).
Richardson et al. "Follicular Depletion During the Menopausal Transition: Evidence for Accelerated Loss and Ultimate Exhaustion." *J. Clin. Endocrinol. Metab.* 65: 1231-1237 (1987).
Borum "Oogenesis in the Mouse, A Study of the Meiotic Prophase." *Exp. Cell Res.* 24: 495-507 (1961).
McLaren, "Meiosis and Differentiation of Mouse Germ Cells." *Symp. Soc. Exp. Biol.* 38: 7-23 (1984).
Peters "Migration of gonocytes into the mammalian gonad and their differentiation." *Phil. Trans. R. Soc. Lond.* B, 259: 91-101 (1970).
Waxman "Chemotherapy and the adult gonad: a review." *J. R. Soc. Med.* 76: 144-8 (1983).
Familiari et al., "Ultrastructure of human ovarian primordial follicles after combination chemotherapy for Hodgkin's disease." *Hum. Reprod.* 8: 2080-7 (1993).
Ried et al. " Radiation-Induced Changes in Long-Term Survivors of Childhood Cancer After Treatment with Radiation Therapy." *Semin. Roentgenol.* 29: 6-14 (1994).
Reichman et al. "Breast Cancer in Young Women: Effect of Chemotherapy on Ovarian Function, Fertility, and Birth Defects." *J. Natl. Cancer Inst. Monogr.* 16: 125-9 (1994).
Tilly "Recent Arguments Against Germ Cell Renewal in the Adult Human Ovary." *Cell Cycle*, 6:8, 879-883, (2007).
Veitia et al, "Recovery of Female Fertility After Chemotherapy, Irradiation, and Bone Marrow Allograft: Further Evidence Against Massive Oocyte Regeneration by Bone Marrow-Derived Germline Stem Cells." *Stem Cells*, DOI: 10.1634/stemcells.2006-0770 (2007).
Lee et al. "Bone Marrow Transplantation Generates Immature Oocytes and Rescues Long-Term Fertility in a Preclinical Mouse Model of Chemotherapy-Induced Premature Ovarian Failure." *J Clin Oncol.*; 25: 3198-3204 (2007).
Liu et al., "Germline stem cells and neo-oogenesis in the adult human ovary." *Dev. Biol.* (DOI: 10.1016/j.ydbio.2007.03.006 (2007).
Gougeon et al. "Regulation of Ovarian Follicular Development in Primates: Facts and Hypotheses." *Endocr Rev.* 17: 121-55 (1996).
Zuckerman "The Number of Oocytes in the mature Ovary." *Recent Prog. Horm. Res.* 6: 63-108 (1951).
Perez et al. *Nature Genetics* 21:200-203 (1999).
Fujiwara, et al., Isolation of a DEAD-family protein gene that encodes a murine homolog of *Drosophila vasa* and its specific expression in germ cell lineage, Proc. Natl. Acad. Sci. USA, vol. 91, pp. 12258-12262, Dec. 1994.
Pacchiarotti, et al., Differentiation Potential of Germ Line Stem Cells Derived from the Postnatal Mouse Ovary, International Society of Differentiation (2010), doi: 10.1016/j.diff.2010.01.001.
Ghadami et al., Intravenously Injected Bone Marrow Cells Restore Ovarian Folliculogenesis and Steroid Hormones Production in Female FSHE (-1-) Mice. Reproductive Sciences, 15(1) (Supplement)—Abstract No. 597, Jan. 2008.
Virant-Klun, et al., Putative Stem Cells with an Embryonic Character Isolated from the Ovarian Surface Epithelium of Women with no Naturally Present Follicles and Oocytes. Differentiation, pp. 1-14, DOI: 10.111/j. 1432-0436.2008.00268.x Feb. 2008.
Webster's Ninth New Collegiate Dictionary, Merriam-Webster Inc., 2000, Springfield, MA (web excerpt—definition of "correspond").
Noce et al., Vasa homolog genes in mammalian germ cell development. Cell Struct Funct 26:131-136, 2001.
K. Zou, et al., "Production of Offspring from a Germline Stem Cell Line Derived from Neonatal Ovaries" Nature Cell Biology Advance Online Publication DOI:1038/ncb 1869: 1-20 (Apr. 12, 2009).
Zuckerman, Recent Prog Horm Res 1951; 6:63-108.
Johnson et al., Nature 2004; 428:145-150.
Spradling, Nature 2004 428:133-134.
Zou et al., Nat Cell Biol 2009: 11:631-636.
Johnson et al., Cell 2005; 122:303-315.
Wang et al., Cell Cycle 2010; 9:339-349.
Niikura et al., Aging 2010; 2:999-1003.
Tilly et al., Biol Reprod 2009; 80:2-12.
Tilly et al., Mol Hum Reprod 2009; 15:393-398.
Niikura et al., Aging 2009; 1:971-978.
Massasa et al., Aging 2010; 2:1-2.
Ventura *Vital Health Stat* 47:1-27, 1989.
Matthews NCHS Data Brief 21:1-8, 2009.
Henderson et al., Nature 218:22-28, 1968.
Hassold et al., Hum Genet 70:11-17, 1985.
Battaglia et al., Hum Reprod 11:2217-2222, 1996.
Hunt et al., Trends Genet 24:86-93, 2008.
Tarin et al., Mol Reprod Dev 61:385-397, 2002.
Tarin et al., Theriogenology 57:1539-1550, 2002.
Bentov et al., Fertil Steril 2010; 93(1):272-5. Epub Sep. 2009.
Bartmann et al., J Assist Reprod Genet 2004; 21:79-83.
Wilding et al., Zygote 2005; 13:317-23.
Zhang et al., Cell Res 16:841-850, 2006.
Van Blerkom et al., Hum Reprod 10:415-424, 1995.
Folstad et al., Biotechnol. Prog. 2002 18(1):1-5.
Cohen et al., Mol Hum Reprod 1998; 4:269-80.
Barritt et al., Hum Reprod 2001; 16:513-6.
Muggleton-Harris et al., Nature 1982; 299:460-2.
Harvey et al., Curr Top Dev Biol 2007; 77:229-49.
Sutovsky et al., Biol Reprod 63:5820590, 2000.
Acton et al., Biol Reprod 2007; 77: 569-76.
CBER 2002 Meeting Documents, Biological Response Modifiers Advisory Committee minutes from May 9, 2002 (publically available from the FDA at http://www.fda.gov/BiologicsBloodVaccines/SafetyAvailability/ucm105852.htm) Letter to.
Sponsors / Researchers—Human Cells Used in Therapy Involving the Transfer of Genetic Material by Means Other Than the Union of Gamete Nuclei (publically available from the FDA at http://www.fda.gov/BiologicsBloodVaccines/SafetyAvailability/ucm105852. htm), Jul. 6, 2001.
Ramalho-Santos et al., Hum Reprod Update. 2009 (5):55 3-72.
Pacchiarotti et al., Differentiation 2010 79:159-170.
Tarín et al., Biol Reprod 2001 65:141-150.
Pan et al., Dev Biol 2008 316:397-407.
Duncan et al., Biol Reprod 2009 81:768-776.
Sinclair Mech Ageing Dev 2005 126(9):987-1002.
Selesniemi et al. Aging Cell 7:622-629, 2008.
Yang et al., Cell 2008.
Hafner et al. Aging 2010, vol. 2, No. 12, pp. 914-923.
Tarín et al., Hum Reprod 1995 10:1563-1565.
Yang et al., Exp Gerontol 2006 41: 718-726.
ISR issued in PCT/US2012/033643 (WO-2012/142500), dated Oct. 10, 2012.
Written Opinion issued in PCT/US2012/033643 (WO-2012/142500), dated Oct. 10, 2012.
ISR issued in PCT/US2012/033672, dated Oct. 16, 2012.
Written Opinion issued in PCT/US2012/033672, dated Oct. 16, 2012.
Short et al., PNAS USA, Apr. 12, 2005 102(15): 5618-5623.
Lu et al., Anal. Chem., Oct. 1, 2004 76(19): 5705-5712.

(56) References Cited

OTHER PUBLICATIONS

Barbosa et al.—"The enzyme CD38 (a NAD glycohydrolase, EC 3.2.2.2) is necessary for the development fo diet-induced obesity", The FASEB Journal (2007), vol. 21, pp. 3629-3639.

Verschooten et al.—"The Flavonoid Luteolin Increases the Resistance of Normal, but not Malignant Keratinocytes, Againt UVBV-Induced Apoptosis", Journal of Investigative Dermatology (2010), vol. 130, pp. 2277-2285.

Psotova et al.—"Chemoprotective Effect of Plant Phenolics Against Anthracycline-induced Toxicity on Rate Cardiomyocytes. Part III. Apigenin, Baicalelin, Kaempherol, Luteolin and Quercetin", Phytotherapy Research (2004), vol. 18, pp. 516-521.

Liu et al.—"Luteolin Isolated from the Medicinal Plant *Elsholtzia rugulosa* (Labiatae) Prevents Copper-Mediated Toxicity in β-Amyloid Precursor Protein Swedish Mutation Overexpressing SH-SY5Y Cells", Molecules (2011), vol. 16, pp. 2084-2096.

Dragicevig et al.—"Green Tea Epigallocatechin-3-Gallate (EGCG) and Other Flavonoids Reduce Alzheimer's Amyloid-Induced Mitochondrial Dysfunction", Journal of Alzheimer's Disease 26, (2011), pp. 507-521.

Sasaki et al.—"Stimulation of Nicotinamide Adenine Diucleotide Biosynthetic Pathways Delays Axonal Degeneration after Axotomy", The Journal of Neuroscience, Aug. 16, 2006, 26(33), pp. 8484-8491.

Revollo et al.—"Nampt/PBEF/Visfatin Regulates Insulin Secretion in β Cells as a Systemic NAD Biosynthetic Enzyme", Cell Metabolism 6, Nov. 2007, pp. 363-375.

Nikiforov et al.—"Metabolism: Pathways and Subcellular Compartmentation of NAD Biosynthesis in Human Cells: From Entry of Extracellular Precursors to Mitochondrial NAD Generation", J. Biol. Chem., (2011), vol. 286, pp. 21767-21778.

Kawamura et al.—"Sirt3 protects in vitro-fertilized mouse preimplantation embryos against oxidative stress-induced p53-mediated developmental arrest", The Journal of Clinical Investigation, vol. 120, No. 8, Aug. 2010, pp. 2817-2828.

Kang et al.—"Nicotinamide extends replicative lifespan of human cells", Aging Cell, (2006), vol. 5, pp. 423-426.

Hara et al.—"Metabolism and Bioenergetics: Elevation of Cellular NAD Levels by Nicotinic Acid and Involvement of Nicotinic Acid Phosphoribosyltransferase in Human Cells", The Journal of Biological Chemistry, (2007), vol. 282, pp. 24574-24582.

Formentini et al.—"Detection and pharmacological modulation of nicotinamide mononucleotide (NMN) in vitro and in vivo", Biochemical Pharmacology, (2009), vol. 77, pp. 1612-1620.

Coussens et al.-"Sirt1 Deficiency Attenuates Spermatogenesis and Germ Cell Function", PLoS ONE, Feb. 2008, vol. 3, Issue 2, pp. 1-8.

Belenky et al.—"Nicotinamide Riboside Promotes Sir2 Silencing and Extends Lifespan via Nrk and URh1/Pnp1/Meu1 Pathways to NAD+", Cell 129, May 4, 2007, pp. 473-484.

Yang et al.—"Synthesis of Nicotinamide Riboside and Derivatives: Effective Agents for Increasing Nicotinamide Adenine Dinucleotide Concentrations in Mammalian Cells", J. Med. Chem., (2007), vol. 50, pp. 6458-6461.

Tracey Baas et al., "Repowering the Ovary" Science Business Exchange, vol. 5, No. 10.

Office Action issued in Chinese application No. 201280018195.1, filed Apr. 13, 2012.

Y.-T Huang et al., "Effects of luteolin and quercetin, inhibitors of tyrosine kinase, on cell growth and metastasis-associated properties in A431 cells overexpressing epidermal growth factor receptor" British Journal of Pharmacology (1999) 128, 999-1010.

E. Kellenberger et al., "Flavonoids as inhibitors of human CD38" Bioorganic & Medicinal Chemistry Letters 21 (2011) 3939-3942.

N. Igosheva et al., "Maternal diet-induced obesity alters mitochondrial activity and redox status in mouse oocytes and zygotes" PLoS ONE www.plosone.org(2010) 5: 4-e10074, 1-8.

Supplemental European Search Report dated Mar. 18, 2015 issued in European Application No. 12804411.2.

Kong Ling-Hong et al., "Mitochondria transfer from self-granular cells to improve embryos' quality", Chin J. Obstet Gynecol, 39(2): 105-107 (2004).

Perez G I et al, "Further Studies on the role of Mitochondria in Controlling Oocyte Apoptosis", Biology of Reproduction, New York, NY [U.A.]: Academ. Press, US. (20000101), vol. 62, Suppl. 01, (2000).

Yi, Y., et al., "Mitochondria transfer can enhance the murine embryo development", Journal of Assisted Reproduction and Genetics, 2007, vol. 24, No. 10: 445-449.

Tachibana, M., et al., "Mitochondrionl Gene Replacement in Primate Offspring and Embryonic Stem Cells", Nature, 2009, vol. 461, No. 7262: 367-372.

Lonergan, T., et al, "Mitochondria in stem cells", Mitochondria, 2007, vol. 7, No. 5: 289-296.

White, Y. A. R., et al., "Oocyte formation by mitotically active germ cells purified from ovaries of reproductive-age women", Nature Medicine, 2012, vol. 18, No. 3: 413-421.

Woods, D. C., et al., "The next (re)generation of ovarian biology and fertility in women: is current science tomorrow's practice?", Fertility and Sterility, 2012, vol. 98, No. 1: 3-10.

Expert Report, Chilean Patent Application No. 2989-2013, Sep. 14, 2016.

Office Action issued for Chinese Patent Application No. 201280040259.8 dated Feb. 24, 2017.

Office Action issued for Chinese Patent Application No. 201280040259.8 dated Feb. 24, 2017, English translation.

M. Daya-Makin et al., "Erbstatin and Tyrphostins Block Protein-Serine Kinase Activation and Meiotic Maturation of Sea Star Oocytes" Biochimica et Biophysica Acta, 1093 87-94, (1991).

* cited by examiner

FIG. 3A
FIG. 3B
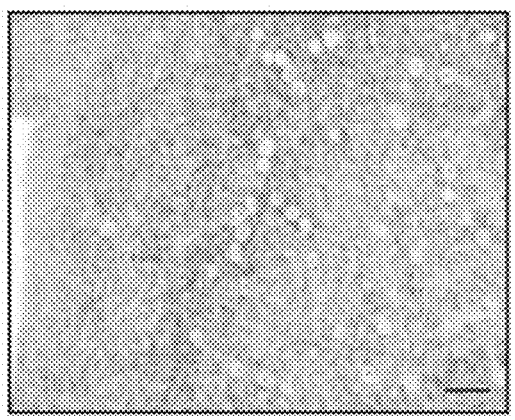
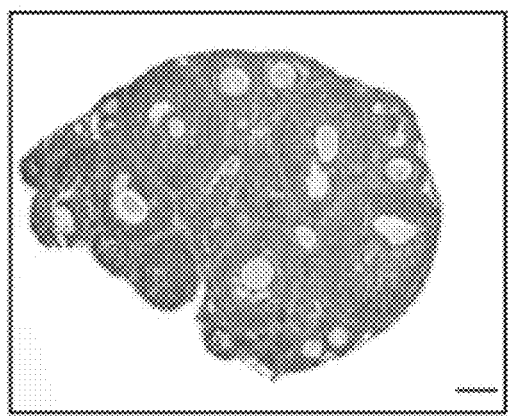
FIG. 3C
FIG. 3D
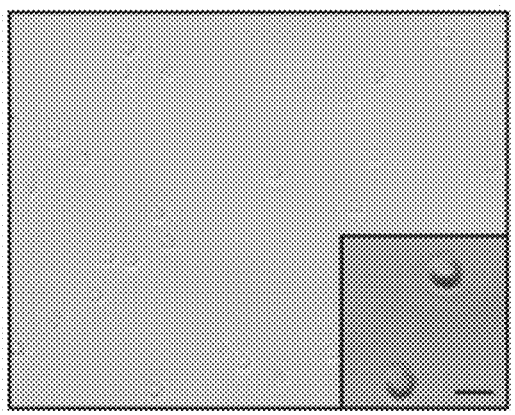
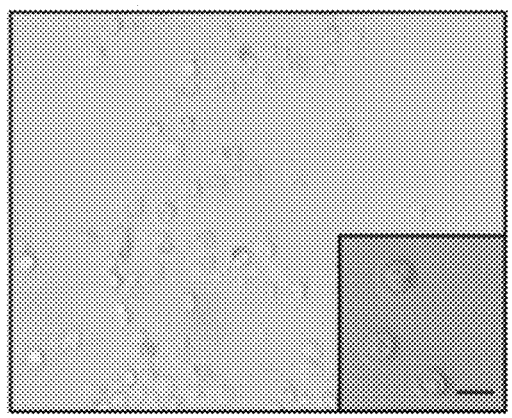
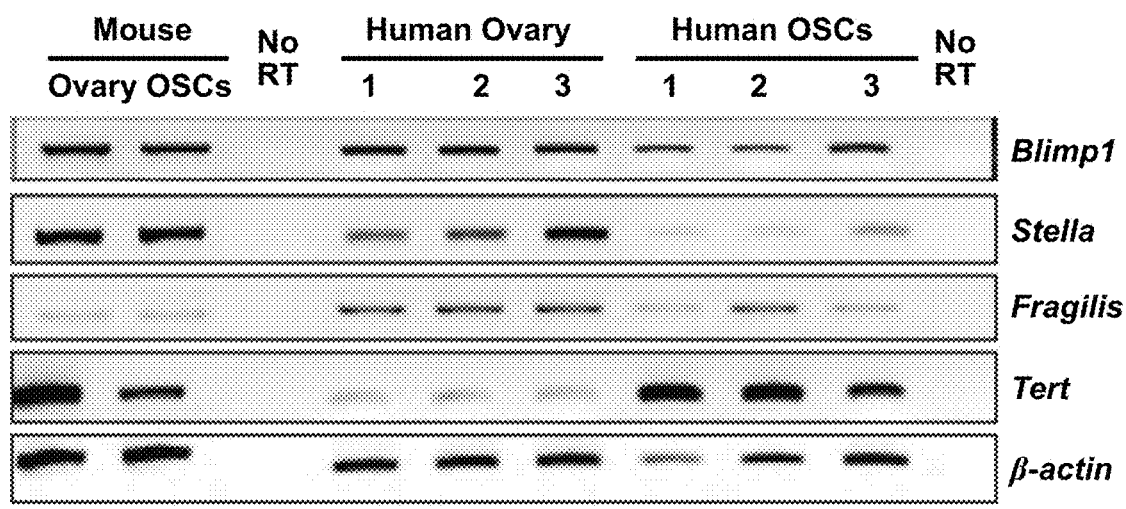
FIG. 3E Ectoderm Endoderm Mesoderm

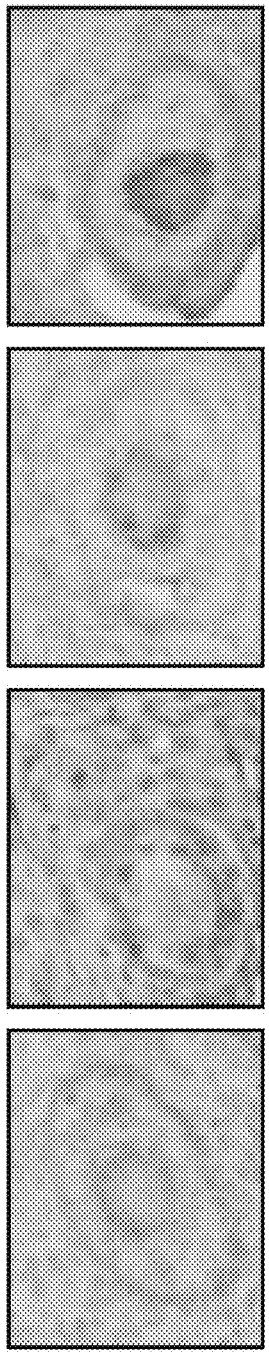
FIG. 4A
FIG. 4B
FIG. 3K

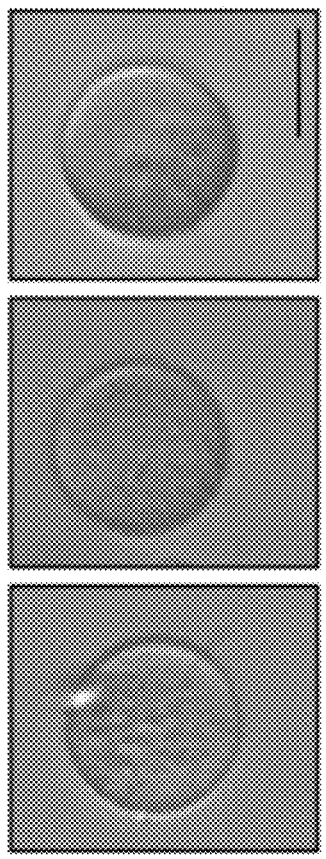
FIG. 7A
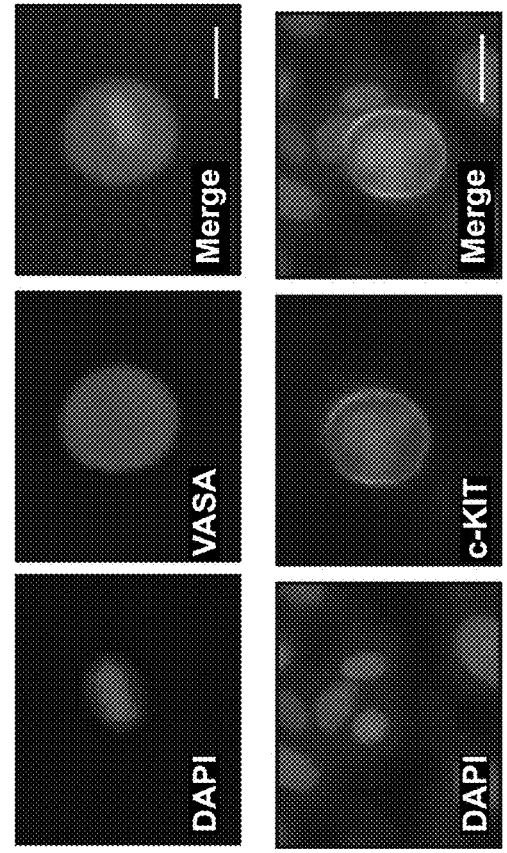
FIG. 7B
FIG. 7C

Example of FACS-based isolation of germ cells from bone marrow mononuclear cell preparations, based on cell-surface expression of VASA Example of FACS-based isolation of germ cells from peripheral blood mononuclear cell preparations, based on cell-surface expression of VASA

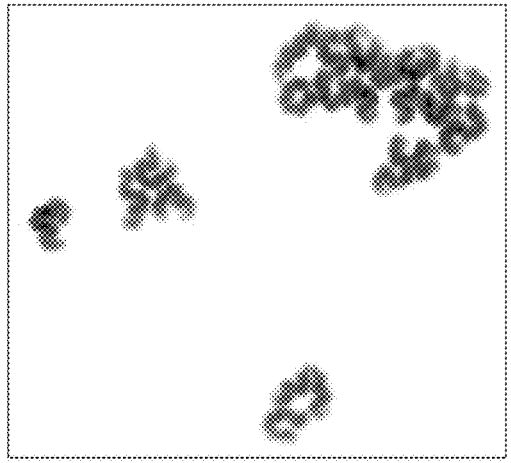
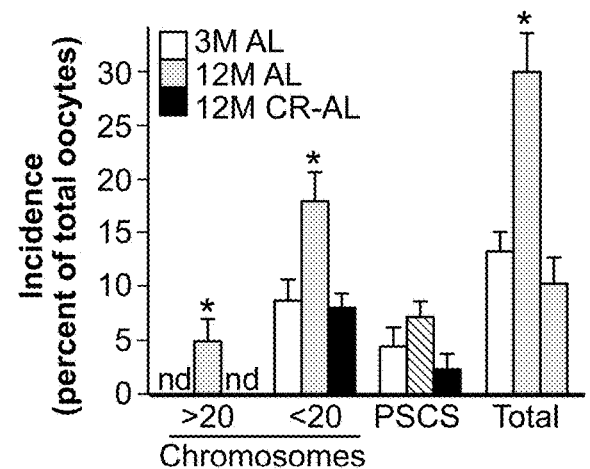
FIG. 19A
FIG. 19B
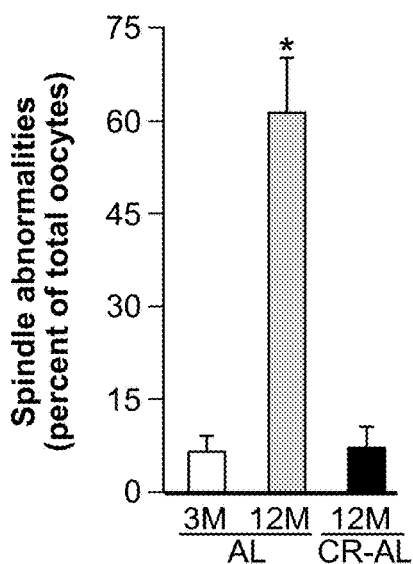
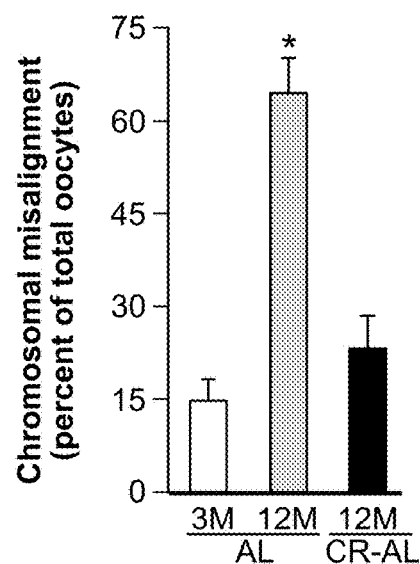
FIG. 20A
FIG. 20B

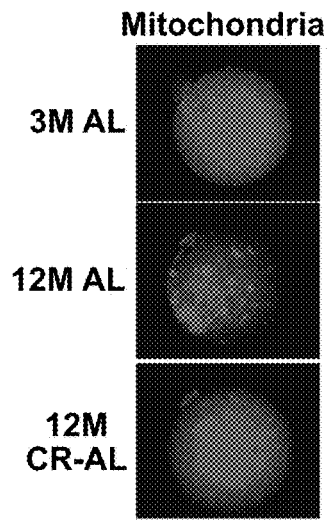 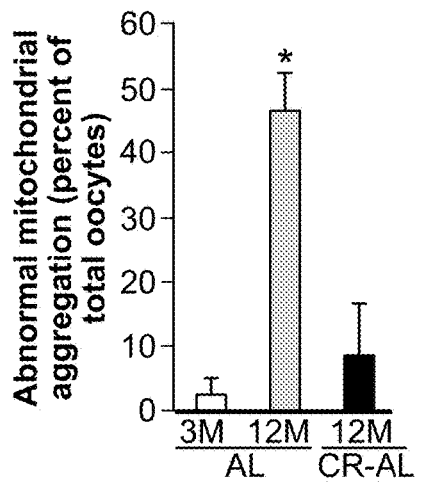 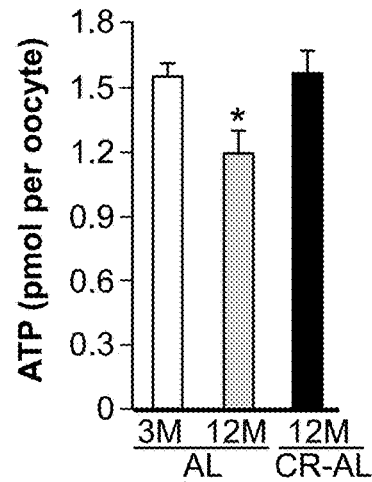
FIG. 21A   FIG. 21B   FIG. 21C
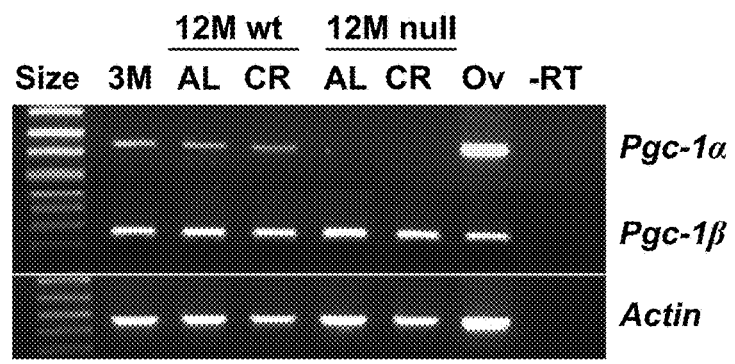
FIG. 22A

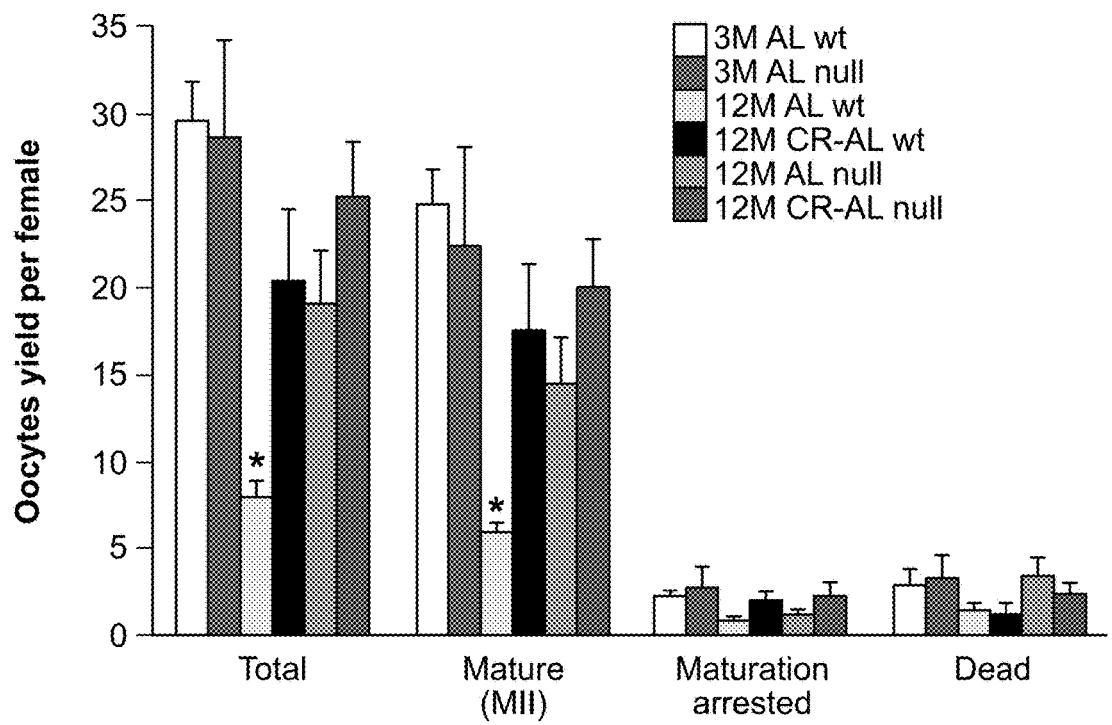
FIG. 22B
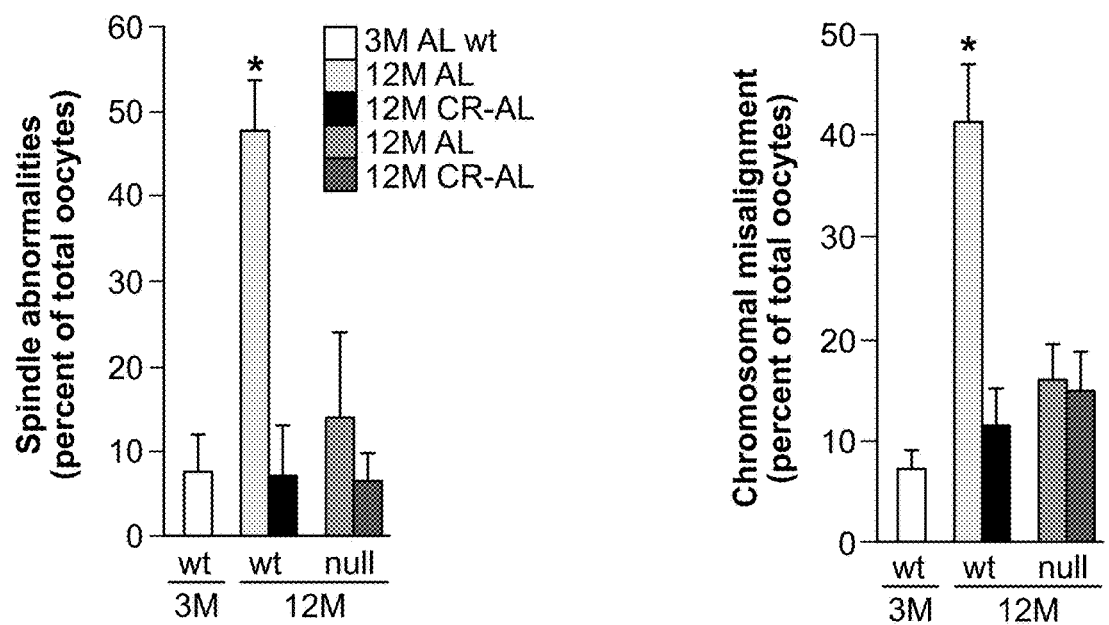
FIG. 22C
FIG. 22D

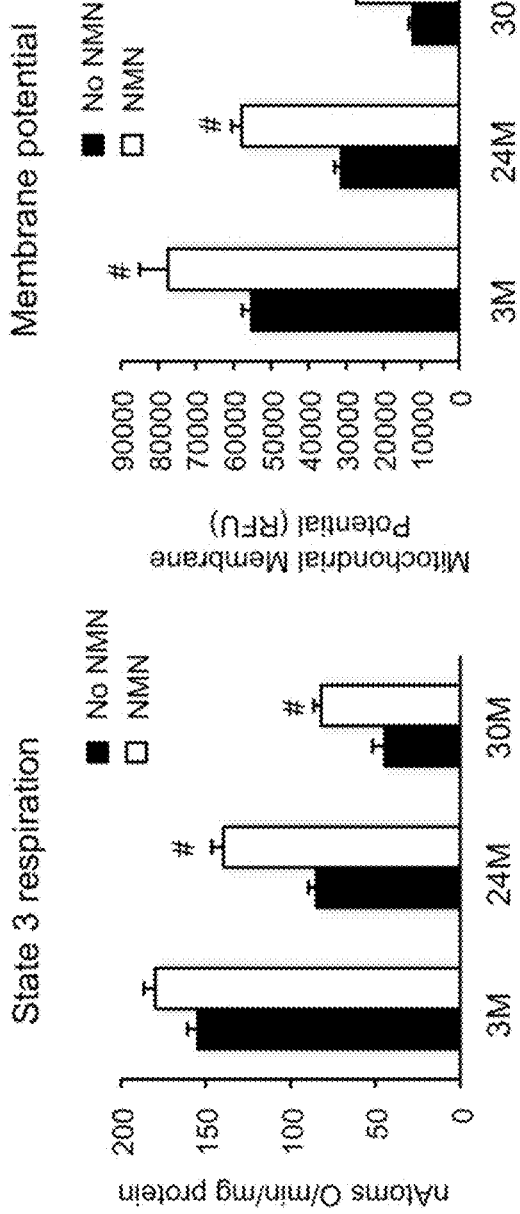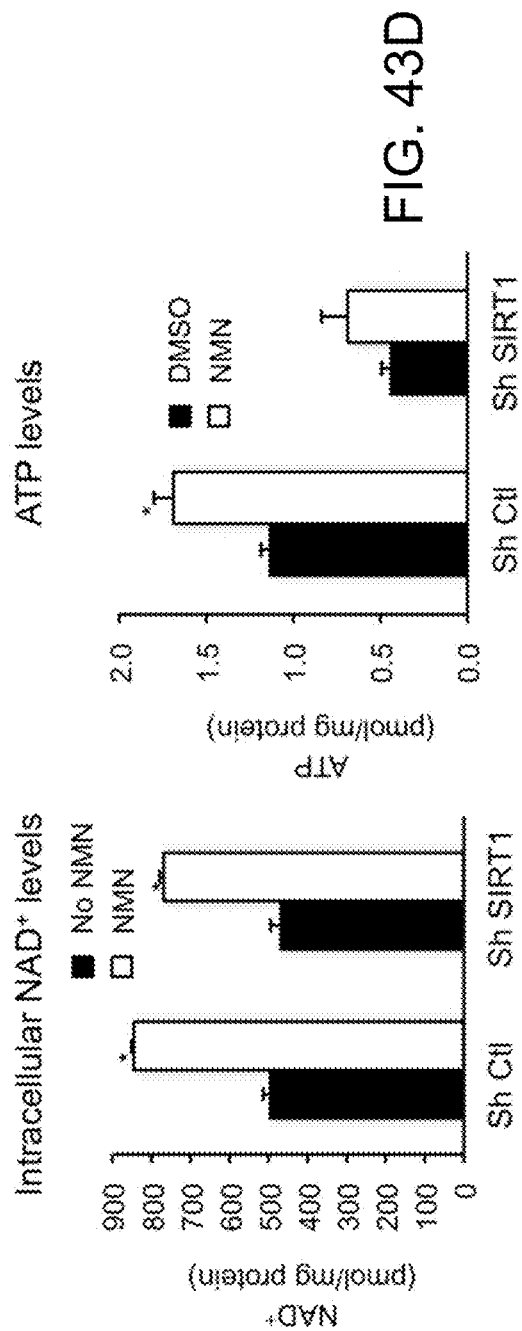
FIG. 43A
FIG. 43B
FIG. 43C
FIG. 43D

COMPOSITIONS AND METHODS FOR ENHANCING BIOENERGETIC STATUS IN FEMALE GERM CELLS

CROSS-REFERENCE TO RELATED SUBJECT MATTER

This application claims benefit under 35 U.S.C. §119(e) of U.S. provisional application Ser. No. 61/502,840, filed Jun. 29, 2011, and U.S. provisional application Ser. No. 61/600,529, filed Feb. 17, 2012, the entire disclosures of which are incorporated herein by reference.

STATEMENT OF RIGHTS TO INVENTIONS MADE UNDER FEDERALLY SPONSORED RESEARCH

This work was supported in part by National Institutes of Health Grant No. NIH R37-AG012279. The government has certain rights to the invention.

BACKGROUND OF THE INVENTION

Since the early 1950s, clinical management of problems associated with ovarian insufficiency and failure, including infertility due to aging or insults, has been restricted by the belief that the pool of oocytes set forth at birth is not amenable to replacement or renewal (Zuckerman, *Recent Prog Horm Res* 1951 6:63-108). In other words, any therapeutic intervention had to conform to manipulation of the existing stockpile of oocyte-containing follicles to produce a desired clinical outcome. In 2004, however, studies with mice challenged the idea of a fixed ovarian reserve of oocytes being endowed at birth (Johnson et al., *Nature* 2004 428:145-150). Based on results from several experimental approaches, it was concluded that ovaries of adult female mammals retain rare germline or oogonial stem cells (OSCs) that routinely produce new oocytes in a manner analogous to germline stem cell support of sperm production in the adult testis (Spradling, *Nature* 2004 428:133-134). Several years later, OSCs were successfully isolated from neonatal and adult mouse ovaries (Zou et al., *Nat Cell Biol* 2009 11:631-636; Pachiarotti et al., *Differentiation* 2010 79:159-170). Collectively, these investigations, along with several other reports from studies of mice (Johnson et al., *Cell* 2005 122:303-315; Wang et al., *Cell Cycle* 2010 9:339-349; Niikura et al., *Aging* 2010 2:999-1003) have conceptually validated the use of OSCs as agents for transplantation and as targets for new therapies to modulate ovarian function and female fertility (Tilly et al., *Biol Reprod* 2009 80:2-12; Tilly et al., *Mod Hum Reprod* 2009; 15:393-398). In addition, the identification of dormant OSCs in atrophic ovaries of aged mice, which spontaneously resume oocyte formation when exposed to a young adult ovarian environment, indicates that ovarian aging may be reversible (Niikura et al., *Aging* 2009 1:971-978; Massasa et al., *Aging* 2010; 2:1-2). The clinical utility of OSCs is now further confirmed by evidence shown herein that a comparable population of oocyte-producing stem cells exists in, and can be purified from, ovaries of healthy reproductive-age women.

Although these new studies indicate that oocyte numbers in adult ovaries are amenable to therapeutic expansion through OSC-based technology, ovarian aging and failure is determined by both a decline in oocyte number as well as a decline in the quality of the oocytes present in the ovaries. Hence, it is imperative to identify methods for improving oocyte quality, especially in women of advancing maternal age. During the past few decades, because of cultural and social changes, women in the developed world have significantly delayed childbirth. For example, first birth rates for women 35-44 years of age in the United States have increased by more than 8-fold over the past 40 years (Ventura *Vital Health Stat* 2009 47:1-27; Matthews, *NCHS Data Brief* 2009 21:1-8). It is well known that pregnancy rates in women at 35 or more years of age are significantly lower, both naturally and with assisted reproduction. The decline in live birth rate reflects a decline in response to ovarian stimulation by gonadotropin hormones (follicle-stimulating hormone or FSH, and luteinising hormone or LH), reduced oocyte and embryo quality and pregnancy rates, and an increased incidence of miscarriages and fetal aneuploidy. In fact, aging-associated chromosomal and meiotic spindle abnormalities in eggs are considered the major factors responsible for the increased incidence of infertility, fetal loss (miscarriage) and conceptions resulting in birth defects—most notably trisomy 21 or Down syndrome—in women at advanced reproductive ages (Henderson et al., *Nature* 1968 218:22-28; Hassold et al., *Hum Genet* 1985 70:11-17; Battaglia et al., *Hum Reprod* 1996 11:2217-2222; Hunt et al., *Trends Genet* 2008 24:86-93). Although the occurrence and consequences of aging-related aneuploidy in oocytes of humans and animal models have been extensively studied (Tarín et al., *Biol Reprod* 2001 65:141-150; Pan et al., *Dev Biol* 2008 316:397-407; Duncan et al., *Biol Reprod* 2009 81:768-776), approaches to maintain fidelity of chromosome segregation during meiotic cell division with age have remained elusive. At present there is no known intervention to improve the pregnancy outcome of older female patients. In animal studies, chronic administration of pharmacologic doses of anti-oxidants during the juvenile period and throughout adult reproductive life has been reported to improve oocyte quality in aging female mice (Tarín et al., *Mol Reprod Dev* 2002 61:385-397). However, this approach has significant long-term negative effects on ovarian and uterine function, leading to higher fetal death and resorptions as well as decreased litter frequency and size in treated animals (Tarín et al., *Theriogenology* 2002 57:1539-1550). Thus, clinical translation of chronic anti-oxidant therapy throughout reproductive life for maintaining or improving oocyte quality in aging females is impractical.

Mitochondrial dysfunction has a major role in reproductive senescence and, therefore, reproductive function in older women might be improved by the use of mitochondrial nutrients (Bentov et al., *Fertil Steril* 2010 93:272-275). Aging and age-related pathologies are frequently associated with loss of mitochondrial function, due to decreased mitochondrial numbers (biogenesis and mitophagy), increased aggregation of mitochondria, diminished mitochondrial activity (production of ATP, which is the main source of energy for cells) and mitochondrial membrane potential and/or accumulation of mitochondrial DNA (mtDNA) mutations and deletions. As oocytes age and oocyte mitochondrial energy production decreases, many of the critical processes of oocyte maturation required to produce a competent egg, especially nuclear spindle activity and chromosomal segregation, become impaired (Bartmann et al., *J. Assist Reprod Genet* 2004 21:79-83; Wilding et al., *Zygote* 2005 13:317-23). Nicotinamide adenine dinucleotide ($NAD^+$) is a small molecule regulator of many other processes including signaling pathways, cell-cell communication, and epigenetic changes. Once thought to be very stable, levels of $NAD^+$ rise in response to dieting and exercise. Increased NAD+ levels are also associated with the diet known as caloric restriction (CR), which is known to delay numerous aspects of aging and diseases, including infertility (Sinclair *Mech Ageing Dev* 2005 26:987; Selesniemi et al. *Aging Cell* 7:622-629, 2008).

NAD$^+$ levels are important for the proper function of mitochondria and the cells that contain them. Cells with low mitochondrial NAD$^+$ are prone to cell dysfunction and death (Yang et al., *Cell* 2008). Obesity and aging both reduce mitochondrial NAD$^+$ levels, resulting in decreased mitochondrial function, increased cell death, and an acceleration of age-related diseases (Hafner et al. *Aging* 2010 2:1-10). As oocytes age and oocyte mitochondrial energy production decreases, many of the processes of oocyte maturation, especially meiotic spindle activity and chromosomal segregation, become impaired (Bartmann et al., *J Assist Reprod Genet* 2004 21:79-83; Wilding et al., *Zygote* 2005 13:317-23). Raising NAD$^+$ levels is a viable option for increasing the bioenergetics and viability of cells, organs, tissues, and embryonic development. Downstream mediators include the sirtuin deacylases (SIRT1-7) and the poly-ADP ribose polymerases (PARPs). It is known to those skilled in the art that increasing NAD$^+$ levels and boosting mitochondrial function can mimic the health benefits of caloric restriction (Yang et al., *Exp Gerontol* 2006 41: 718-726).

The link between chronic anti-oxidant therapy for maintaining oocyte quality in females of advanced reproductive age is established (Tarín et al., *Hum Reprod* 1995 10:1563-1565) and data supporting a key role for mitochondrial dysfunction in eggs as a driving force behind age-related fertility problems are available. For example, experimentally-induced oxidative stress in isolated mouse oocytes reduces ATP levels, which increases meiotic spindle abnormalities leading to chromosomal misalignment (Zhang et al., *Cell Res* 2006 16:841-850). Additionally, while meiotic maturation of human oocytes can proceed over a range of ATP concentrations, oocytes with a higher ATP content show a much greater potential for successful embryogenesis, implantation and development (Van Blerkom et al., *Hum Reprod* 1995 10:415-424).

Along these same lines, heterologous transfer of cytoplasmic extracts from young donor oocytes (viz. obtained from different women) into the oocytes of older women with a history of reproductive failure, a procedure known as ooplasmic transplantation or ooplasmic transfer, demonstrated improved embryo development and delivery of live offspring. Unfortunately, however, the children born following this procedure exhibit mitochondrial heteroplasmy or the presence of mitochondria from two different sources (Cohen et al., *Mod Hum Reprod* 1998 4:269-280; Barritt et al., *Hum Reprod* 2001 16:513-516; Muggleton-Harris et al., *Nature* 1982 299:460-462; Harvey et al., *Curr Top Dev Biol* 2007 77:229-249). This is consistent with the fact that maternally-derived mitochondria present in the egg are used to "seed" the embryo with mitochondria, as paternally-derived mitochondria from the sperm are destroyed shortly after fertilization (Sutovsky et al., *Biol Reprod* 2000 63:582-590). Although the procedure involves transfer of cytoplasm and not purified mitochondria from the donor eggs, the presence of donor mitochondria in the transferred cytoplasm, confirmed by the passage of "foreign" mitochondria into the offspring, is widely believed to be the reason why heterologous ooplasmic transfer provides a fertility benefit (Harvey et al. *Curr Top Dev Biol* 2007 77:229-249). Irrespective, the health impact of induced mitochondrial heteroplasmy in these children is as yet unknown; however, it has been demonstrated that a mouse model of mitochondrial heteroplasmy produces a phenotype consistent with metabolic syndrome (Acton et al., *Biol Reprod* 2007 77: 569-576).

Arguably, the most significant issue with heterologous ooplasmic transfer is tied to the fact that mitochondria also contain genetic material that is distinct from nuclear genes contributed by the biological mother and biological father. Accordingly, the children conceived following this procedure have three genetic parents (biological mother, biological father, egg donor), and thus represent an example of genetic manipulation of the human germline for the generation of embryos. Ooplasmic transplantation procedures that result in mitochondrial heteroplasmy are therefore now regulated and largely prohibited by the FDA. For details, see CBER 2002 Meeting Documents, Biological Response Modifiers Advisory Committee minutes from May 9, 2002, which are publically available from the FDA and "Letter to Sponsors/Researchers—Human Cells Used in Therapy Involving the Transfer of Genetic Material By Means Other Than the Union of Gamete Nuclei", which is also publically available from the FDA on the worldwide web. While use of autologous mitochondria from somatic cells would avoid mitochondrial heteroplasmy, the somatic mitochondria are nonetheless inadequate, as they are prone to mitochondrial DNA damage and deletions resulting in heritable mutations. Autologous sources of female germ cells, namely OSCs and compositions obtained thereof (e.g., OSC cytoplasm or isolated mitochondria), in ooplasmic transplantation procedures would prevent mitochondrial heteroplasmy, and alleviate ethical and safety concerns currently associated with the procedure. Importantly, oocytes, which are prone to aging-associated defects, are not of high enough quantity or quality to be reliably used in such procedures.

Accordingly, it is desirable to restore the quality of aged oocytes, as well as to further enhance OSCs or improve derivatives thereof (e.g., cytoplasm or isolated mitochondria) for use in conducting a range of assisted reproductive technologies.

SUMMARY OF THE INVENTION

The present invention provides for the use of agents to enhance mitochondrial numbers, mitochondrial activity, cellular energy levels or cellular energy-producing potential (collectively referred to as "bioenergetic status") in oocytes, postnatal female germline stem cells (also referred to herein as OSCs) and/or preimplantation embryos prior to conducting and/or following methods of in vitro fertilization, or following exposure of ovaries, oocytes, OSCs and/or preimplantation embryos in vivo. In certain embodiments, agents for such uses include soluble precursors to NAD$^+$ (e.g., tryptophan, quinolinic acid, nicotinamide mononucleotide, nicotinamide riboside, and nicotinic acid), fisetin, quercetin, resveratrol, DOI, hydroxytyrosol, pyrroloquinoline quinone, metformin, apigenin, luteolin, tryphostin 8, berberine, a CD38 inhibitor, SRT-1720, a Sirt1 activator, a compound of any one of formulas I-XV, or functional derivatives thereof. These agents will be collectively referred to herein as "bioenergetic agents."

In one aspect, the invention provides a composition containing one or more of an oocyte, an oogonial stem cell (OSC) or the progeny of an OSC, and a bioenergetic agent (e.g., one or more of soluble precursors to NAD$^+$ (e.g., tryptophan, quinolinic acid, nicotinamide mononucleotide, nicotinamide riboside, and nicotinic acid), fisetin, quercetin, resveratrol, DOI, hydroxytyrosol, pyrroloquinoline quinone, metformin, apigenin, luteolin, tryphostin 8, berberine, a CD38 inhibitor, SRT-1720, STRT1 activator, a compound of any one of formulas I-XV, or functional derivatives thereof).

In another aspect, the invention provides an isolated cell having enhanced mitochondrial function, where the cell is one or more of an oocyte, an oogonial stem cell (OSC) or the progeny of an OSC, where the cell has been contacted with a bioenergetic agent (one or more of soluble precursors to $NAD^+$ (e.g., tryptophan, quinolinic acid, nicotinamide mononucleotide, nicotinamide riboside, and nicotinic acid), fisetin, quercetin, resveratrol, DOI, hydroxytyrosol, pyrroloquinoline quinone, metformin, apigenin, luteolin, tryphostin 8, berberine, a CD38 inhibitor, SRT-1720, STRT1 activator, a compound of any one of formulas I-XV, or functional derivatives thereof).

In yet another aspect, the invention provides a composition containing OSC mitochondria or oocyte mitochondria and a bioenergetic agent that is one or more of soluble precursors to $NAD^+$ (e.g., tryptophan, quinolinic acid, nicotinamide mononucleotide, nicotinamide riboside, and nicotinic acid), fisetin, quercetin, resveratrol, DOI, hydroxytyrosol, pyrroloquinoline quinone, metformin, apigenin, luteolin, tryphostin 8, berberine, a CD38 inhibitor, SRT-1720, a SIRT1 activator, a compound of any one of formulas I-XV, or functional derivatives thereof.

In still another aspect, the invention provides an isolated mitochondria, where the mitochondria has been contacted with a bioenergetic agent that is any one or more of one or more of soluble precursors to $NAD^+$ (e.g., tryptophan, quinolinic acid, nicotinamide mononucleotide, nicotinamide riboside, and nicotinic acid), fisetin, quercetin, resveratrol, DOI, hydroxytyrosol, pyrroloquinoline quinone, metformin, apigenin, luteolin, tryphostin 8, berberine, a CD38 inhibitor, SRT-1720, a SIRT1 activator, a compound of any one of formulas I-XV, or functional derivatives thereof.

In another aspect, the invention provides an isolated cell-free composition containing OSC mitochondria or oocyte mitochondria and a bioenergetic agent that any one or more of one or more of soluble precursors to $NAD^+$ (e.g., tryptophan, quinolinic acid, nicotinamide mononucleotide, nicotinamide riboside, and nicotinic acid), fisetin, quercetin, resveratrol, DOI, hydroxytyrosol, pyrroloquinoline quinone, metformin, apigenin, luteolin, tryphostin 8, berberine, a CD38 inhibitor, SRT-1720, a SIRT1 activator, a compound of any one of formulas I-XV, or functional derivatives thereof.

In another aspect, the invention provides a method of preparing an oocyte for in vitro fertilization (IVF), the method involving transferring a composition containing OSC mitochondria and a bioenergetic agent that is one or more of any one or more of one or more of soluble precursors to $NAD^+$ (e.g., tryptophan, quinolinic acid, nicotinamide mononucleotide, nicotinamide riboside, and nicotinic acid), fisetin, quercetin, resveratrol, DOI, hydroxytyrosol, pyrroloquinoline quinone, metformin, apigenin, luteolin, tryphostin 8, berberine, a CD38 inhibitor, SRT-1720, a SIRT1 activator, a compound of any one of formulas I-XV, or functional derivatives thereof, into an autologous oocyte, thereby preparing the oocyte for in vitro fertilization. In one embodiment, the composition containing OSC mitochondria is a purified preparation of mitochondria obtained from the OSC.

In yet another aspect, the invention provides an oocyte prepared according to the method of the previous aspect or any other aspect of the invention delineated herein.

In yet another aspect, the invention provides a method of in vitro fertilization, the method involving the steps of (a) incubating an OSC from a female subject with a bioenergetic agent that is any one or more of one or more of soluble precursors to $NAD^+$ (e.g., tryptophan, quinolinic acid, nicotinamide mononucleotide, nicotinamide riboside, and nicotinic acid), fisetin, quercetin, resveratrol, DOI, hydroxytyrosol, pyrroloquinoline quinone, metformin, apigenin, luteolin, tryphostin 8, berberine, a CD38 inhibitor, SRT-1720, SIRT1 activator, a compound of any one of formulas I-XV, or functional derivatives thereof; (b) obtaining a composition containing OSC mitochondria from the OSC; (c) transferring the composition into an isolated, autologous oocyte; and (d) fertilizing the autologous oocyte in vitro to form a zygote. In one embodiment, the method further involves transferring a preimplantation stage embryo derived from the zygote, into the uterus of a female subject. In one embodiment, step a) is optional and step b) further involves incubating the composition containing OSC mitochondria with a bioenergetic agent that is any one or more of one or more of soluble precursors to $NAD^+$ (e.g., tryptophan, quinolinic acid, nicotinamide mononucleotide, nicotinamide riboside, and nicotinic acid), fisetin, quercetin, resveratrol, DOI, hydroxytyrosol, pyrroloquinoline quinone, metformin, apigenin, luteolin, tryphostin 8, berberine, a CD38 inhibitor, SRT-1720, a SIRT1 activator, a compound of any one of formulas I-XV, or functional derivatives thereof.

In still another aspect, the invention provides a method of preparing an oocyte for in vitro fertilization, the method involving transferring a composition containing oocyte mitochondria and a bioenergetic agent that is any one or more of one or more of soluble precursors to $NAD^+$ (e.g., tryptophan, quinolinic acid, nicotinamide mononucleotide, nicotinamide riboside, and nicotinic acid), fisetin, quercetin, resveratrol, DOI, hydroxytyrosol, pyrroloquinoline quinone, metformin, apigenin, luteolin, tryphostin 8, berberine, a CD38 inhibitor, SRT-1720, a SIRT1 activator, a compound of any one of formulas I-XV, or functional derivatives thereof, into an autologous oocyte, thereby preparing the oocyte for in vitro fertilization. In one embodiment, the composition containing oocyte mitochondria is oocyte cytoplasm without a nucleus. In another embodiment, the composition containing oocyte mitochondria is a purified preparation of mitochondria obtained from the oocyte. In oen embodiment, the method further involves fertilizing the oocyte in vitro to form a zygote and transferring a preimplantation stage embryo derived from said zygote, into the uterus of the female subject. In another embodiment, the zygote and pre-implantation stage embryo is incubated with a bioenergetic agent selected from the group consisting of tryptophan, quinolinic acid, nicotinamide mononucleotide, nicotinamide riboside, nicotinic acid, fisetin, quercetin, resveratrol, DOI, hydroxytyrosol, pyrroloquinoline quinone, metformin, apigenin, luteolin, tryphostin 8, berberine, a SIRT1 activator, a CD38 inhibitor, a compound of any one of formulas I-XV, and functional derivatives thereof.

In still another aspect, the invention provides an oocyte prepared according to the method of the previous aspect or any other aspect of the invention delineated herein.

In yet another aspect, the invention provides a method of in vitro fertilization, the method involving the steps of (a) incubating an oocyte from a female subject with a bioenergetic agent that is any one or more of one or more of soluble precursors to $NAD^+$ (e.g., tryptophan, quinolinic acid, nicotinamide mononucleotide, nicotinamide riboside, and nicotinic acid), fisetin, quercetin, resveratrol, DOI, hydroxytyrosol, pyrroloquinoline quinone, metformin, apigenin, luteolin, tryphostin 8, berberine, a CD38 inhibitor, SRT-1720, a SIRT1 activator, a compound of any one of formulas I-XV, or functional derivatives thereof; (b) obtaining a composition containing oocyte mitochondria from the oocyte; (c) transferring the composition into an isolated, autologous oocyte; and (d) fertilizing the autologous oocyte in vitro to form a zygote. In one embodiment, the method further involves transferring a preimplantation stage embryo derived from the zygote, into the uterus of a female subject. In another embodiment, step a) is optional and step b) further involves incubating the composition containing oocyte mitochondria with a bioenergetic agent that is any one or more of one or more of soluble precursors to $NAD^+$ (e.g., tryptophan, quinolinic acid, nicotinamide mononucleotide, nicotinamide riboside, and nicotinic acid), fisetin, quercetin, resveratrol, DOI, hydroxytyrosol, pyrroloquinoline quinone, metformin, apigenin, luteolin, tryphostin 8, berberine, a CD38 inhibitor, SRT-1720, a SIRT1 activator, a compound of any one of formulas I-XV, or functional derivatives thereof.

In still another aspect, the invention provides a method of in vitro fertilization, the method involving the steps of: incubating an oocyte from a female subject with a bioenergetic agent that is any one or more of one or more of soluble precursors to $NAD^+$ (e.g., tryptophan, quinolinic acid, nicotinamide mononucleotide, nicotinamide riboside, and nicotinic acid), fisetin, quercetin, resveratrol, DOI, hydroxytyrosol, pyrroloquinoline quinone, metformin, apigenin, luteolin, tryphostin 8, berberine, a CD38 inhibitor, SRT-1720, a SIRT1 activator, a compound of any one of formulas I-XV, or functional derivatives thereof; and fertilizing the oocyte in vitro to form a zygote.

In still another aspect, the invention provides a composition containing a solution selected from the group consisting of cell culture medium, oocyte retrieval solution, oocyte washing solution, oocyte in vitro maturation medium, ovarian follicle in vitro maturation medium, oocyte in vitro fertilization medium, embryo culture medium, cleavage medium, vitrification solution, cryopreservation solution and embryo thawing medium and a bioenergetic agent that is any one or more of one or more of soluble precursors to $NAD^+$ (e.g., tryptophan, quinolinic acid, nicotinamide mononucleotide, nicotinamide riboside, and nicotinic acid), fisetin, quercetin, resveratrol, DOI, hydroxytyrosol, pyrroloquinoline quinone, metformin, apigenin, luteolin, tryphostin 8, berberine, a CD38 inhibitor, SRT-1720, a SIRT1 activator, a compound of any one of formulas I-XV, or functional derivatives thereof.

In still another aspect, the invention provides a method of improving fertility in a female subject, the method containing administering to the subject a bioenergetic agent that is any one or more of one or more of soluble precursors to $NAD^+$ (e.g., tryptophan, quinolinic acid, nicotinamide mononucleotide, nicotinamide riboside, and nicotinic acid), fisetin, quercetin, resveratrol, DOI, hydroxytyrosol, pyrroloquinoline quinone, metformin, apigenin, luteolin, tryphostin 8, berberine, a CD38 inhibitor, SRT-1720, a SIRT1 activator, a compound of any one of formulas I-XV, or functional derivatives thereof, in an amount effective to improve oocyte and/or OSC quality, de novo production and/or ovulated oocyte yield, thereby improving fertility in the female subject. In one embodiment, the bioenergetic agent is systemically administered to the female subject. In another embodiment, the bioenergetic agent is locally administered to an ovary of the female subject. In yet another embodiment, the pregnancy outcomes of the female subject are improved compared to a reference standard.

In still another aspect, the invention provides a method of in vitro fertilization, the method containing the steps of:
(a) administering to a female subject a bioenergetic agent that is any one or more of one or more of soluble precursors to $NAD^+$ (e.g., tryptophan, quinolinic acid, nicotinamide mononucleotide, nicotinamide riboside, and nicotinic acid), fisetin, quercetin, resveratrol, DOI, hydroxytyrosol, pyrroloquinoline quinone, metformin, apigenin, luteolin, tryphostin 8, berberine, a CD38 inhibitor, SRT-1720, a SIRT1 activator, a compound of any one of formulas I-XV, or functional derivatives thereof in an amount effective to improve oocyte and/or OSC de novo production, quality and/or ovulated oocyte yield;
(b) obtaining an oocyte from the female subject; and
(c) fertilizing the oocyte in vitro to form a zygote. In one embodiment, the bioenergetic agent is systemically administered to the female subject. In another embodiment, the bioenergetic agent is locally administered to an ovary of the female subject. In another embodiment, step a) is conducted prior to steps b) and c) and/or after steps b) and c). In another embodiment, the method further involving step d) transferring a preimplantation stage embryo derived from the zygote, into the uterus of the female subject and continuing to administer to the female subject the bioenergetic agent. In another embodiment, step b) and/or step c) further contains incubating the oocyte with a bioenergetic agent that is any one or more of one or more of soluble precursors to $NAD^+$ (e.g., tryptophan, quinolinic acid, nicotinamide mononucleotide, nicotinamide riboside, and nicotinic acid), fisetin, quercetin, resveratrol, DOI, hydroxytyrosol, pyrroloquinoline quinone, metformin, apigenin, luteolin, tryphostin 8, berberine, a CD38 inhibitor, SRT-1720, a SIRT1 activator, a compound of any one of formulas I-XV, or functional derivatives thereof.

In another embodiment, the pregnancy outcomes of the female subject are improved compared to a reference standard.

In still another aspect, the invention provides a method of sustaining embryonic development in a pregnant female subject in need thereof, the method containing administering to the subject a therapeutically effective amount of a bioenergetic agent that is any one or more of one or more of soluble precursors to $NAD^+$ (e.g., tryptophan, quinolinic acid, nicotinamide mononucleotide, nicotinamide riboside, and nicotinic acid), fisetin, quercetin, resveratrol, DOI, hydroxytyrosol, pyrroloquinoline quinone, metformin, apigenin, luteolin, tryphostin 8, berberine, a CD38 inhibitor, SRT-1720, a SIRT1 activator, a compound of any one of formulas I-XV, or functional derivatives thereof, thereby sustaining embryonic development in the pregnant female subject. In one embodiment, the bioenergetic agent is systemically administered to the female subject. In another embodiment, the bioenergetic agent is locally administered to an ovary of the female subject.

In still another aspect, the invention provides a method of restoring ovarian function in a female subject in need thereof, containing administering a therapeutically effective amount of a bioenergetic agent that is any one or more of one or more of soluble precursors to $NAD^+$ (e.g., tryptophan, quinolinic acid, nicotinamide mononucleotide, nicotinamide riboside, and nicotinic acid), fisetin, quercetin, resveratrol, DOI, hydroxytyrosol, pyrroloquinoline quinone, metformin, apigenin, luteolin, tryphostin 8, berberine, a CD38 inhibitor, SRT-1720, a SIRT1 activator, a compound of any one of formulas I-XV, or functional derivatives thereof, thereby restoring ovarian function in the female subject.

In one embodiment, the bioenergetic agent is systemically administered to the female subject. In another embodiment, the bioenergetic agent is locally administered to an ovary of the female subject. In another embodiment, where the female subject has premature ovarian failure.

In still another aspect, the invention provides a method of preparing a tissue or cell thereof from a female subject for harvest, the method containing administering an effective amount of a bioenergetic agent that is any one or more of one or more of soluble precursors to $NAD^+$ (e.g., tryptophan, quinolinic acid, nicotinamide mononucleotide, nicotinamide riboside, and nicotinic acid), fisetin, quercetin, resveratrol, DOI, hydroxytyrosol, pyrroloquinoline quinone, metformin, apigenin, luteolin, tryphostin 8, berberine, a CD38 inhibitor, SRT-1720, a SIRT1 activator, a compound of any one of formulas I-XV, or functional derivatives thereof to the female subject, thereby preparing the tissue or cell thereof from the female subject for harvest. In one embodiment, the tissue is ovary, ovarian follicle, bone marrow or peripheral blood.

In still another aspect, the invention provides a method of producing an oocyte, containing culturing a stem cell that is an OSC, embryonic stem cell, pancreatic stem cell, skin stem cell or induced pluripotent stem cell (iPS cell) in the presence of a bioenergetic agent that is any one or more of one or more of soluble precursors to $NAD^+$ (e.g., tryptophan, quinolinic acid, nicotinamide mononucleotide, nicotinamide riboside, and nicotinic acid), fisetin, quercetin, resveratrol, DOI, hydroxytyrosol, pyrroloquinoline quinone, metformin, apigenin, luteolin, tryphostin 8, berberine, a CD38 inhibitor, SRT-1720, a SIRT1 activator, a compound of any one of formulas I-XV, or functional derivatives thereof, under conditions sufficient to differentiate the stem cell into an oocyte.

In another aspect, the invention features a composition containing an isolated cell that is an oocyte, an oogonial stem cell (OSC) or the progeny of an OSC and a bioenergetic agent for use in in vitro fertilization.

In another aspect, the invention features an isolated cell having enhanced mitochondrial function relative to a reference, where the cell is an oocyte, an oogonial stem cell (OSC) or the progeny of an OSC, and where the cell has been contacted with a bioenergetic agent for use in in vitro fertilization.

In another aspect, the invention features a bioenergetic agent that is tryptophan, quinolinic acid, nicotinamide mononucleotide, nicotinamide riboside, nicotinic acid, fisetin, quercetin, resveratrol, DOI, hydroxytyrosol, pyrroloquinoline quinone, metformin, apigenin, luteolin, tryphostin 8, berberine, CD38 inhibitor, a compound of any one of formulas I-XV, or functional derivatives thereof for use in one or more of improving the fertility of a female, sustaining embryonic development in a pregnant female, restoring or increasing ovarian function in a female, preparing a tissue or cell thereof from a female for harvest or preparing an oocyte.

In various embodiments of any of the above aspects or any aspect of the invention delineated herein, the bioenergetic agent is one or more of soluble precursors to $NAD^+$ (e.g., tryptophan, quinolinic acid, nicotinamide mononucleotide, nicotinamide riboside, and nicotinic acid), fisetin, quercetin, resveratrol, DOI, hydroxytyrosol, pyrroloquinoline quinone, metformin, apigenin, luteolin, tryphostin 8, berberine, a CD38 inhibitor, SRT-1720, a SIRT1 activator, a compound of any one of formulas I-XV, or functional derivatives thereof. In various embodiments of any of the above aspects or any aspect delineated herein, the bioenergetic agent is a compound shown in FIG. 29.

In various embodiments of any of the above aspects or any aspect delineated herein, a composition of the invention further contains a solution selected from one or more of cell culture medium, oocyte retrieval solution, oocyte washing solution, oocyte in vitro maturation medium, ovarian follicle in vitro maturation medium, oocyte in vitro fertilization medium, vitrification solution and cryopreservation solution. In various embodiments, the composition contains ovarian tissue, ovarian follicles, bone marrow, umbilical cord blood or peripheral blood. In other embodiments, the OSC is an isolated non-embryonic stem cell that is mitotically competent and expresses one or more of Vasa, Oct-4, Dazl, Stella and optionally a stage-specific embryonic antigen. In other embodiments, the OSC is obtained from ovarian tissue. In various embodiments, the OSC is obtained from a non-ovarian tissue. In particular embodiments, the non-ovarian tissue is blood or bone marrow. In various embodiments, the cell is an ovarian stem cell, where the cell has been contacted with a bioenergetic agent. In other embodiments, the contacted cell has increased mitochondrial DNA copy number and/or increased ATP-generating capacity. In still other embodiments, the number of mitochondria is increased by about 10%, 20%, 30%, 40%, 50% or 60%. In various embodiments of any of the above aspects or any aspect delineated herein, increased mitochondrial function is detected by assaying mtDNA content, ATP, NAD+/NADH, mitochondrial mass, membrane potential, and gene expression of known mitochondrial mass regulators and electron transport chain components.

In various embodiments of any of the above aspects or any aspect delineated herein, the cell is in a solution that is any one or more of cell culture medium, oocyte retrieval solution, oocyte washing solution, oocyte in vitro maturation medium, ovarian follicle in vitro maturation medium, oocyte in vitro fertilization medium, vitrification solution and cryopreservation solution. In other embodiments, the mitochondria is in a cell that is one or more of an oocyte, an oogonial stem cell (OSC) or the progeny of an OSC. In particular embodiments, cell is in a mixture with ovarian tissue, ovarian follicles, bone marrow, umbilical cord blood or peripheral blood.

In various embodiments of any of the above aspects or any aspect delineated herein, the composition containing OSC mitochondria is OSC cytoplasm without a nucleus. In various embodiments, the composition containing oocyte mitochondria is oocyte cytoplasm without a nucleus. In various embodiments, the composition containing OSC mitochondria is a purified preparation of mitochondria obtained from the OSC. In other embodiments, the composition containing an oocyte mitochondria is a purified preparation of mitochondria obtained from the oocyte.

In other embodiments of any of the above aspects or any aspect delineated herein, the mitochondria is in a cell that is one or more of an oocyte, an oogonial stem cell (OSC) or the progeny of an OSC, and a bioenergetic agent. In various embodiments of any of the above aspects or any aspect delineated herein, the cell is in a mixture with ovarian tissue, ovarian follicles, bone marrow, umbilical cord blood or peripheral blood. In still other embodiments, the pregnancy outcomes of the female subject are improved compared to a reference standard. In still other embodiments, the bioenergetic agent is systemically administered to the female subject or is locally administered to an ovary of the female subject.

Other features and advantages of the invention will be apparent from the detailed description, and from the claims. Thus, other aspects of the invention are described in the following disclosure and are within the ambit of the invention.

BRIEF DESCRIPTION OF THE DRAWINGS

The following Detailed Description, given by way of example, but not intended to limit the invention to specific embodiments described, may be understood in conjunction with the accompanying figures, incorporated herein by reference.

The patent or application file contains at least one drawing executed in color. Copies of this patent or patent application publication with color drawing(s) will be provided by the U.S. Patent and Trademark Office upon request and payment of necessary fees.

FIG. 1 depicts validation of a fluorescence activated cell sorting (FACS)-based protocol for OSC isolation.

FIG. 3 depicts isolation of VASA-positive cells from adult mouse and human ovaries using FACS. In FIGS. 3a and b, the representative histological appearance of adult ovarian tissue used for human (a) and mouse (b) OSC isolation is shown. Scale bars, 100 µm. In FIGS. 3c and d, the morphology of viable cells isolated by FACS based on cell-surface expression of VASA is shown. Scale bars, 10 µm. FIG. 3e provides the gene expression profile of starting ovarian material and freshly-isolated OSCs, showing assessment of 3 different patients as examples for human tissue analysis (No RT: PCR of RNA sample without reverse transcription; β-actin, sample loading control). In FIG. 3f through FIG. 3k, a teratoma formation assay showing an absence of tumors in mice 24 weeks after receiving injections of mouse OSCs (3f) compared with development of tumors in mice 3 weeks after injection of mouse embryonic stem cells (ESCs)_is shown (FIG. 3g through FIG. 3j; panels 3h through 3j show examples of cells from all three germ layers, with neural rosette highlighted in panel 3h, inset), along with a summary of the experimental outcomes (3k).

FIG. 4 depicts functional eggs obtained from mouse OSCs after intraovarian transplantation. In FIGS. 4a and 4b, examples of growing follicles containing GFP-negative and GFP-positive (brown against a blue hematoxylin counterstain) oocytes are shown in ovaries of wild-type mice injected with GFP-expressing OSCs 5-6 months earlier. In FIGS. 4d and 4; examples of GFP-positive eggs (in cumulus-oocyte complexes) obtained from the oviducts are shown following induced ovulation of wild-type female mice that received intraovarian transplantation of GFP-expressing OSCs 5-6 months earlier. These eggs were in-vitro fertilized using wild-type sperm, resulting in 2-cell embryos that progressed through preimplantation development (examples of GFP-positive embryos at the 2-cell, 4-cell, 8-cell, compacted morula (CM), expanded morula (EM), blastocyst (B) and hatching blastocyst (FIB) stage are shown) to form hatching blastocysts 5-6 days after fertilization.

FIG. 6 depicts evaluation of mouse and human ovary-derived VASA-positive cells in defined cultures.

FIG. 7 depicts spontaneous oogenesis from cultured mouse and human OSCs. FIGS. 7a through 7c provide examples of immature oocytes formed by mouse OSCs in culture, as assessed by morphology (7a), expression of oocyte marker proteins VASA and KIT (7b; note cytoplasmic localization of VASA), and the presence of mRNAs encoding the oocyte marker genes Vasa, Kit, Msy2 (also referred to as Y box protein 2 or Ybx2), Nobox, Lhx8, Gdf9, Zp1, Zp2 and Zp3 (7c; No RT: PCR of RNA sample without reverse transcription; β-actin, sample loading control). Scale bars, 25 µm.

FIG. 9 depicts ploidy analysis of human fibroblasts and mouse OSCs in culture.

FIG. 10 depicts generation of oocytes from human OSCs in human ovary tissue. Direct (live-cell) GFP fluorescence analysis of human ovarian cortical tissue following dispersion, re-aggregation with GFP-hOSCs (10a) and in-vitro culture for 24-72 hours (10b, 10c) is shown. Note the formation of large single GFP-positive cells surrounded by smaller GFP-negative cells in compact structures resembling follicles (FIGS. 10b and 10c; scale bars, 50 µm). Examples of immature follicles containing GFP-positive oocytes (brown, highlighted by black arrowheads, against a blue hematoxylin counterstain) in adult human ovarian cortical tissue injected with GFP-hOSCs and xenografted into NOD/SCID female mice are shown (FIG. 10d, 1 week post-transplant; FIG. 10f, 2 weeks post-transplant). Note comparable follicles with GFP-negative oocytes in the same grafts. As negative controls, all immature follicles in human ovarian cortical tissue prior to GFP-hOSC injection and xenografting (10e) or that received vehicle injection (no GFP-hOSCs) prior to xenografting (10g) contained GFP-negative oocytes after processing for GFP detection in parallel with the samples shown above.

FIG. 12 depicts cryopreservation and thawing of human ovarian cortical tissue and freshly-isolated human OSCs.

FIG. 19 depicts prevention of aging-associated aneuploidy in MII oocytes by CR. (A) Example of a hyperploid MII oocyte containing 21 chromosomes (DAPI staining of DNA shown in blue). (B) Incidence of hyperploidy, hypoploidy and premature sister chromatid separation (and total chromosomal defects from all 3 endpoints combined) in MII oocytes of 3 M AL-fed, 12 M AL-fed and 12 M CR-AL-fed females (mean±SEM, n=18-23 mature oocytes analyzed per group in each experiment replicated 4 times using a total of 20-34 mice per group; *, P<0.05 vs. 3 M AL-fed females; nd, none detected).

FIG. 21 depicts maintenance of normal mitochondrial dynamics in oocytes of aged females by CR. (A) Representative mitochondrial distribution in MII oocytes from 3 M AL-fed, 12 M AL-fed and 12 M CR-AL-fed mice (staining shown in red). (B) Incidence of abnormal mitochondrial aggregation in MIT oocytes from 3 M AL-fed, 12 M AL-fed and 12 M CR-AL-fed mice (mean±SEM, n=23-46 oocytes analyzed per group from 3 independent experiments using 4-11 mice per group; *, P<0.05 vs. 3 M AL-fed females). (C) Cytoplasmic ATP levels in individual MII oocytes from 3 M AL-fed, 12 M AL-fed and 12 M CR-AL-fed mice (mean±SEM, n=38-145 total oocytes analyzed per group from 5-7 independent experiments using a total of 5-21 mice per group; *, P<0.05 vs. 3 M AL-fed females).

were exposed to the indicated test compounds for 24 hours and then assessed for mitochondrial density.

Figure 33:
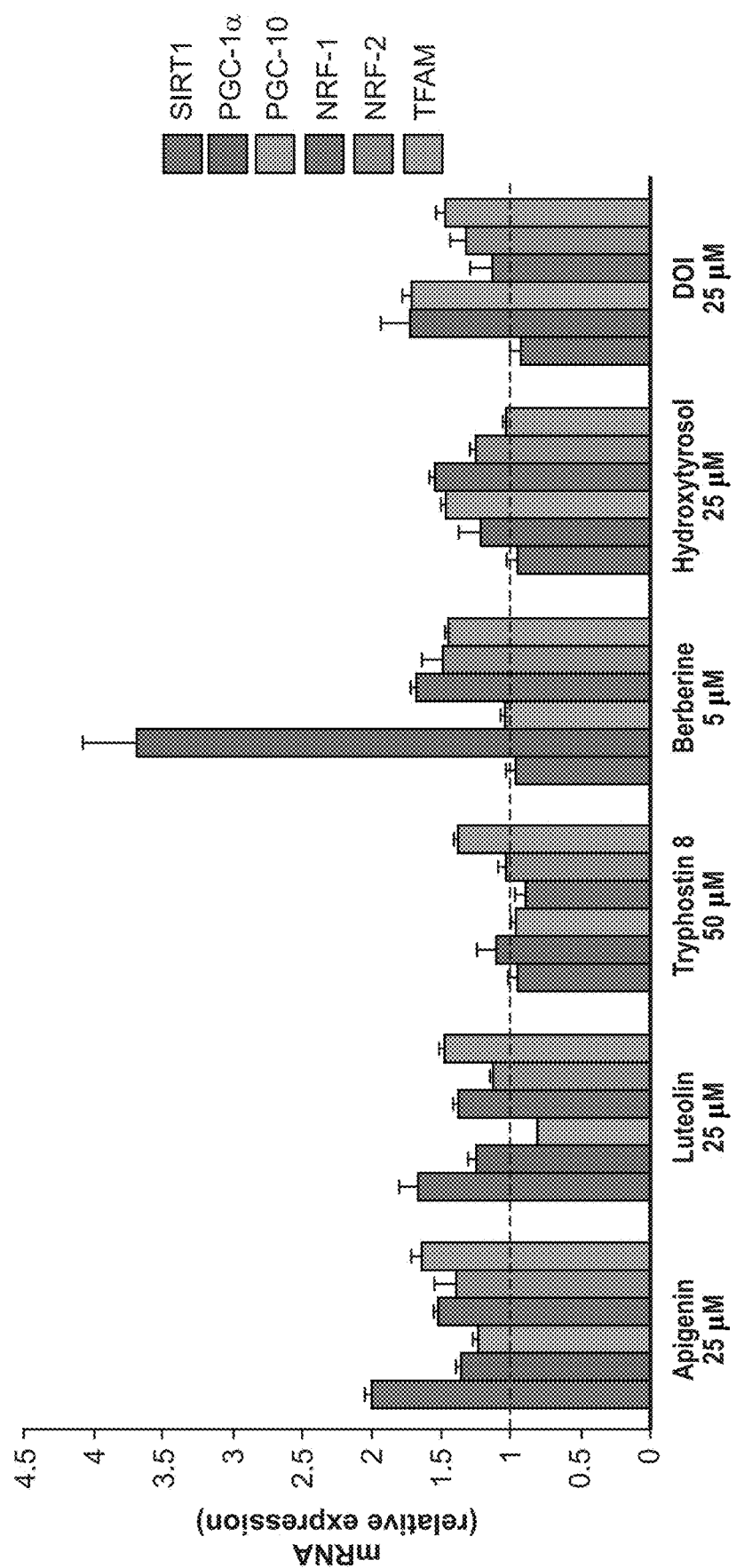

FIG. 33 depicts mRNA levels of genes known to drive mitochondrial biogenesis and energetics. Mouse OSCs maintained in culture (Zou et al., *Nat Cell Biol* 2009 11:631-636) were exposed to the indicated test compounds for 24 hours and then assessed for expression levels of genes known to drive mitochondrial biogenesis.

Figure 34:
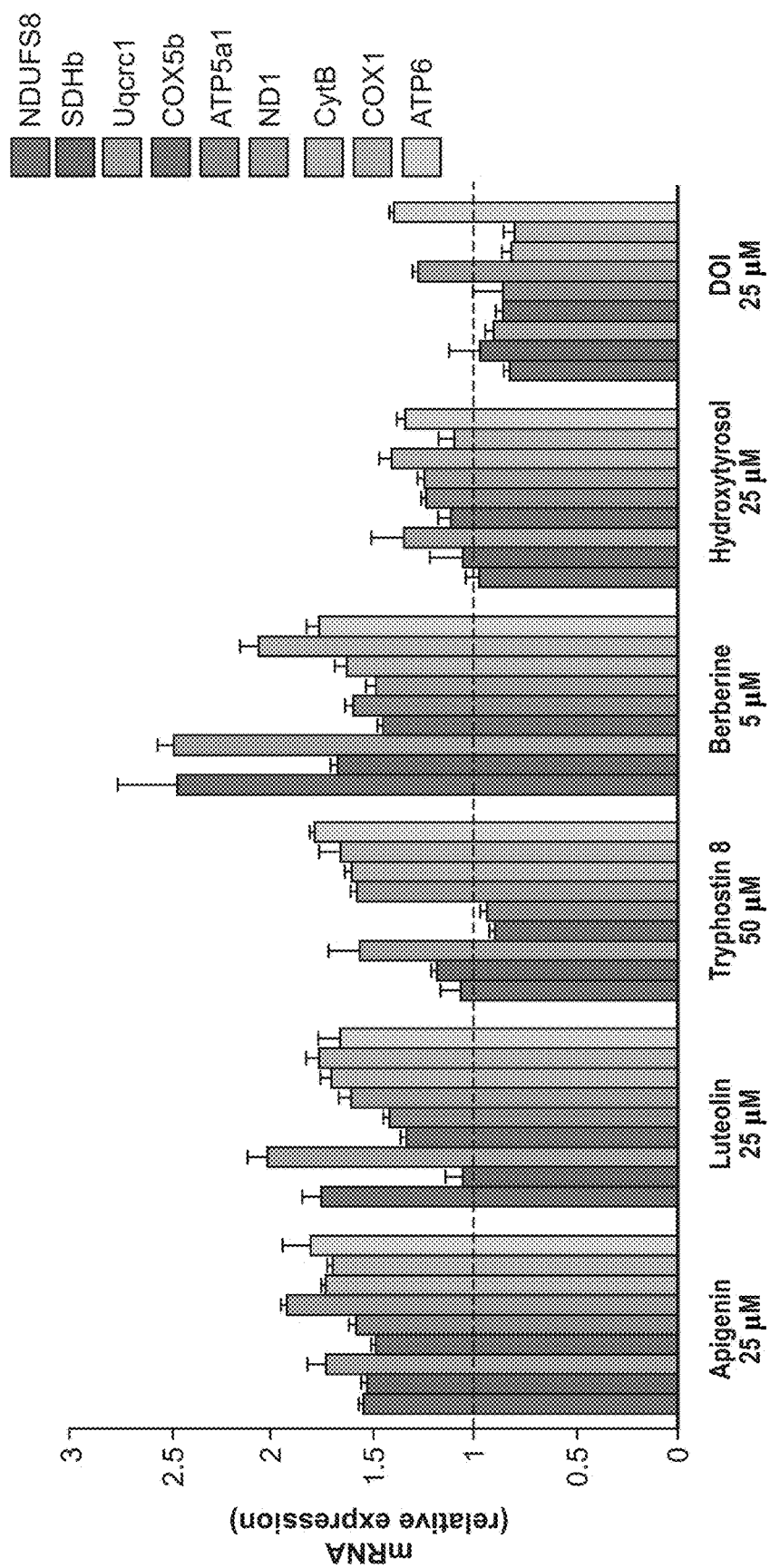

FIG. 34 depicts mRNA levels of genes encoding mitochondrial electron transport chain components. Mouse OSCs maintained in culture (Zou et al., *Nat Cell Biol* 2009 11:631-636) were exposed to the indicated test compounds for 24 hours and then assessed for expression levels of genes encoding mitochondrial electron transport chain components.

Figure 35A:
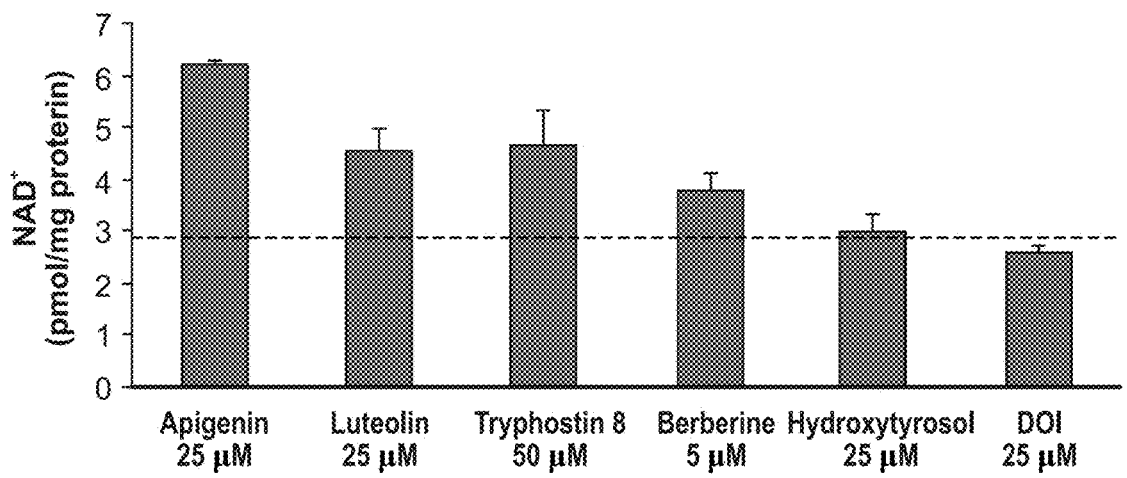
Figure 35B:
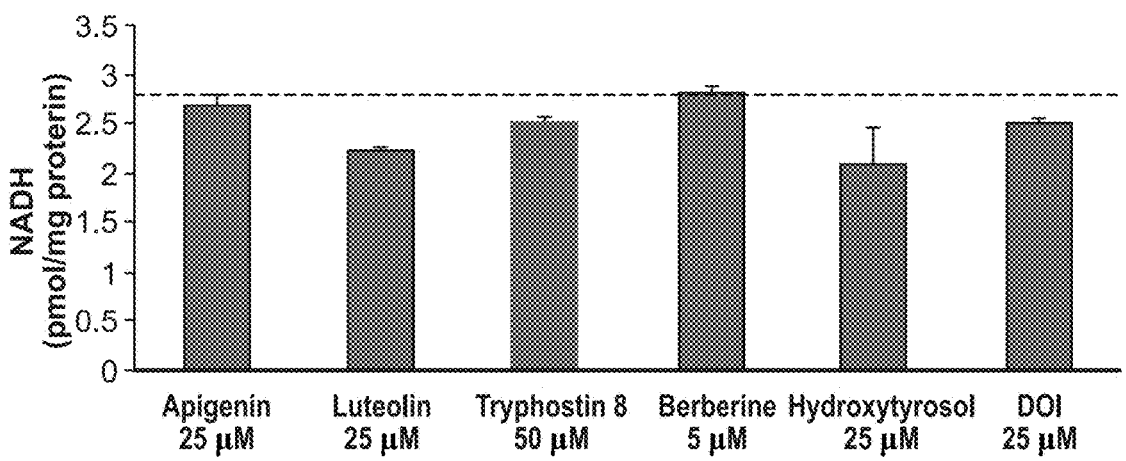

FIG. 35 depicts levels of NAD+ (A) and NADH (B) in OSCs treated with mitochondrial enhancers. Mouse OSCs maintained in culture (Zou et al., *Nat Cell Biol* 2009 11:631-636) were exposed to the indicated test compounds for 24 hours and then assessed for levels of NAD+ and NADH.

Figure 36:
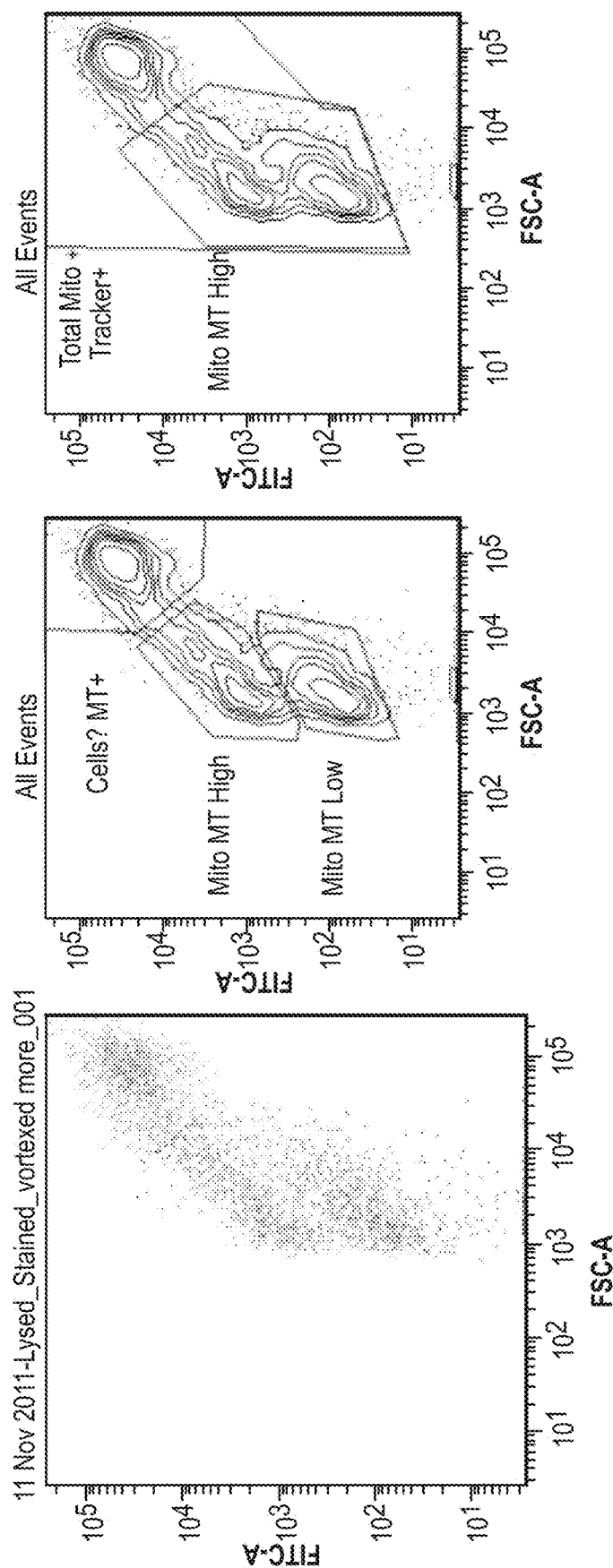

FIG. 36 depicts mitochondria following staining with mitotracker M7514 and cell lysis. Human OSCs were incubated with M7514, and then lysed to release the stained mitochondria using osmotic shock. The entire population (mitochondria from lysed cells and residual unlysed stained cells) was analyzed by FACS. The left panel shows mitochondria from lysed cells, which are easily distinguishable from mitochondria contained in residual unlysed cells based on size (forward scatter; FSC-A). Fluorescence intensity (FITC-A) revealed two distinct populations of mitochondria from lysed cells, one having high intensity (Mito MT high), and one having low intensity (Mito MT Low). Functional mitochondria are known to have a greater uptake and retention of the stain, and thus fluoresce at a higher intensity.

Figure 37A:
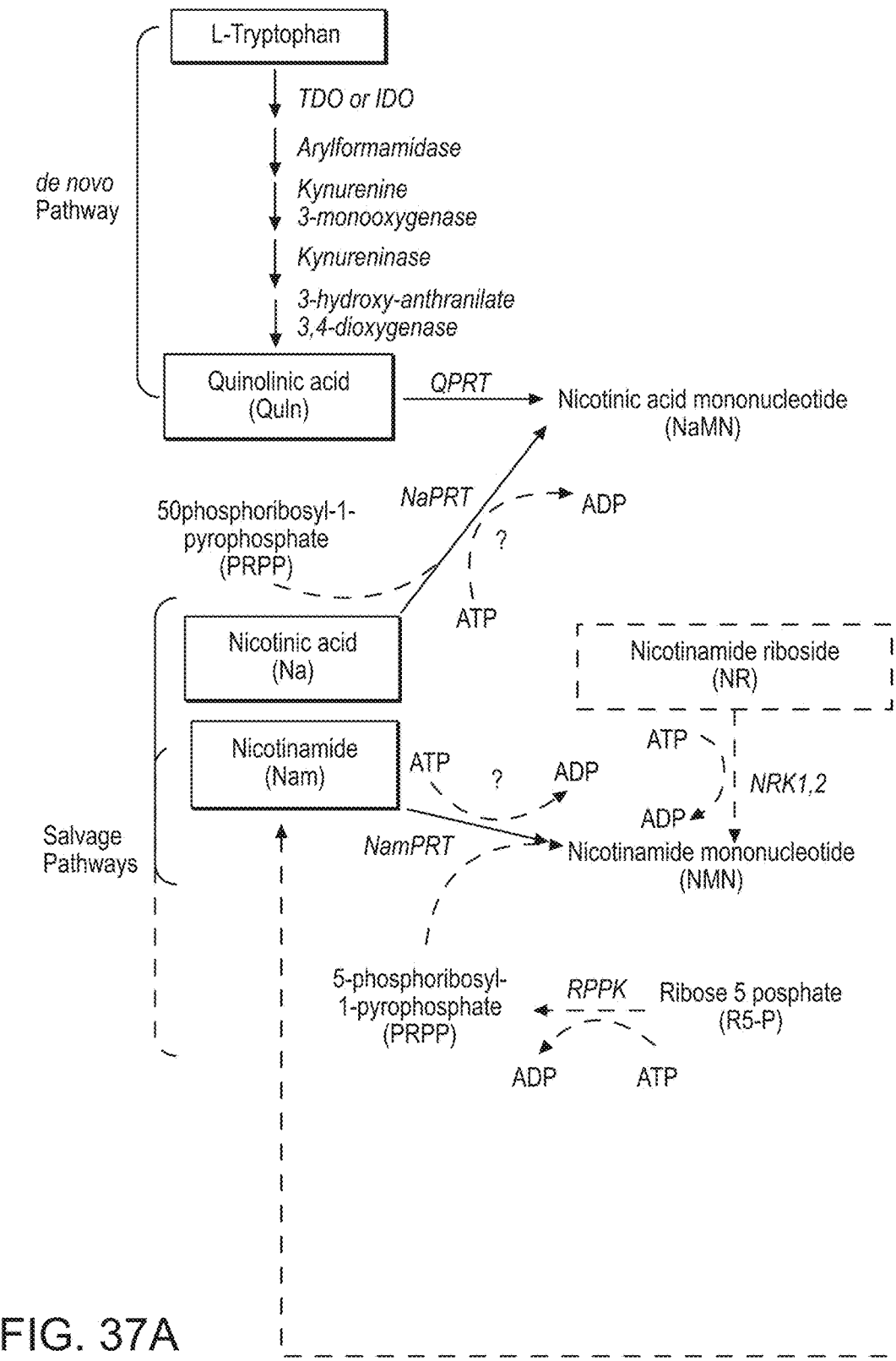
Figure 37B:
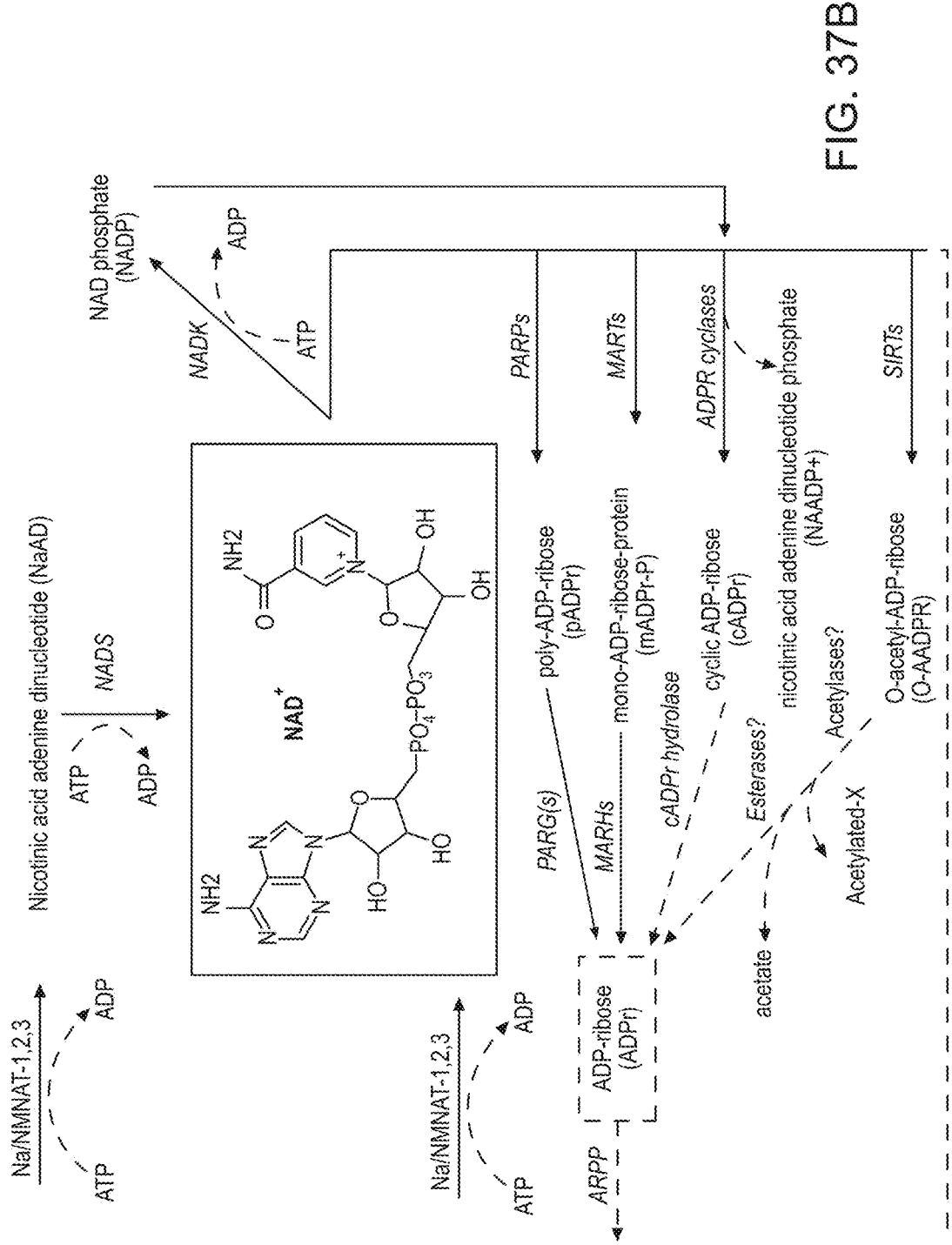

FIG. 37 is a schematic diagram depicting pathways for the synthesis and degradation of $NAD^+$ in mammalian cells (Hassa, P. et al., Microbiol. Mol. Biol. Rev. September 2006 vol. 70 no. 3 789-829).

Figure 38:
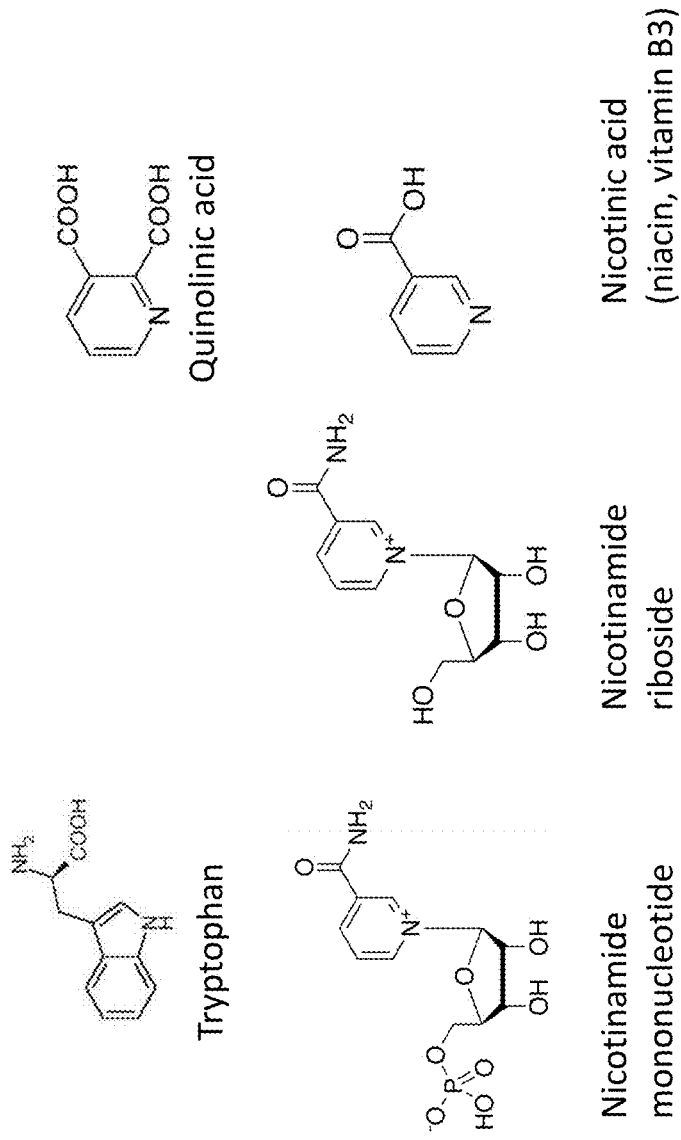

FIG. 38 shows the structures of exemplary soluble precursors to $NAD^+$. These agents can be used to raise cellular $NAD^+$ levels and boost cellular energetics in damaged and/or aged cells.

Figure 39:
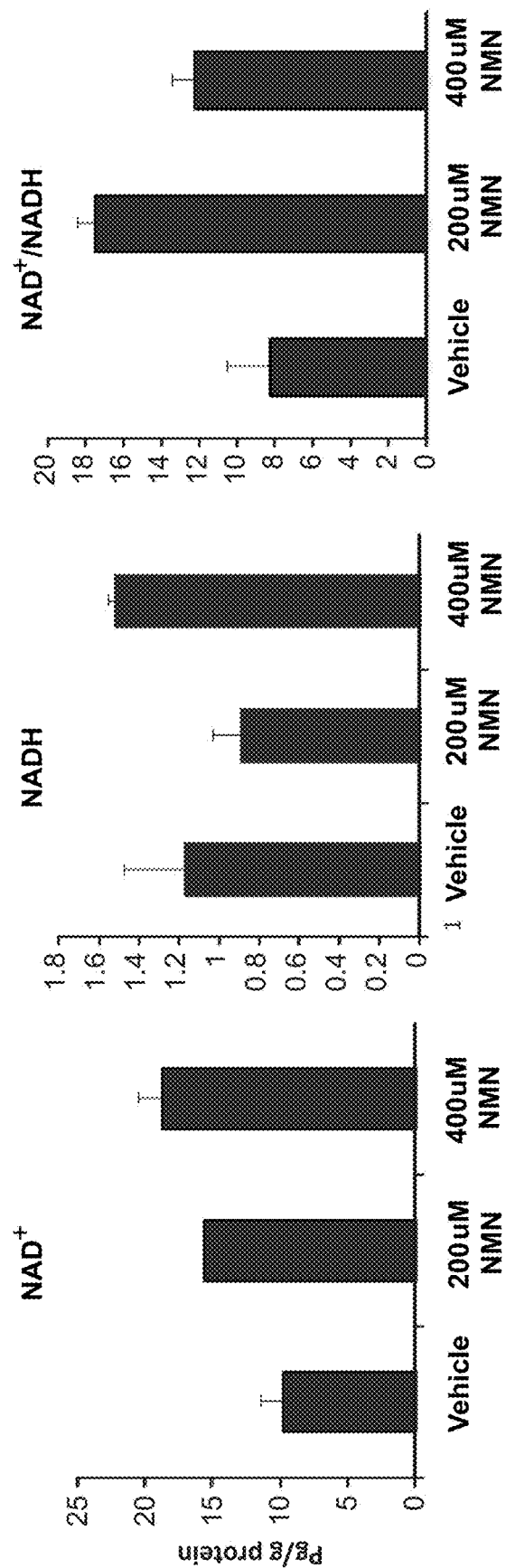

FIGS. 39A-39C are graphs showing that nicotinamide mononucleotides raise cellular $NAD^+$ and NAD+/NADH in murine oogonial stem cells (OSCs). Oogonial stem cells were isolated from dissociated ovaries using a FACS based sorting protocol to purify OSCs free of contaminating oocytes (see Example 1). Cells were maintained in culture medium consisted of minimum essential medium α (MEMα), 10% FBS, 1 mM sodium pyruvate, 1 mM nonessential amino acids, 2 mM L-glutamine, 0.1 mM β-mercaptoethanol (Sigma Aldrich Corporation, St. Louis, Mo., USA), 10 ng/ml-1 LIF (Millipore), 1× N-2 MAX Media Supplement (R&D) 10 ng/ml EGF (Epidermal growth factor, Recombinant human; Gibco Division of ThermoFisher Scientific, Waltham, Mass., USA), 40 ng/ml human GDNF (glial cell line-derived neurotrophic factor; R&D systems), 1 ng/ml human bFGF (basic fibroblast growth factor; Gibco Division of ThermoFisher Scientific, Waltham, Mass., USA).

Figure 40:
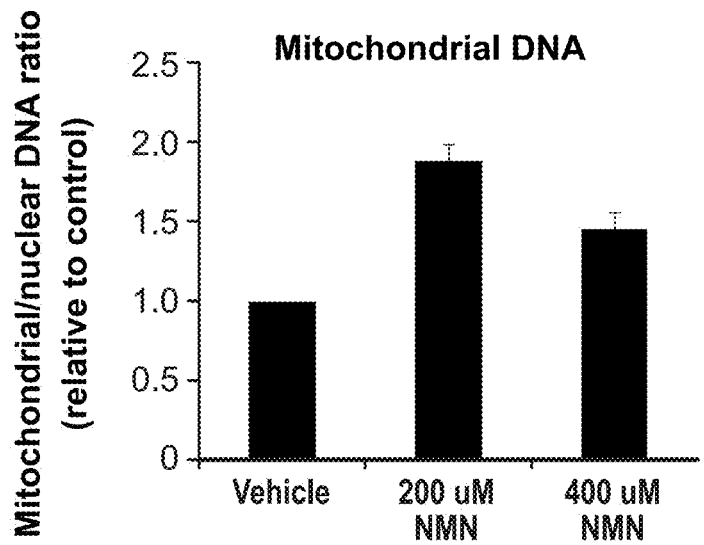

FIG. 40 is a graph showing that nicotinamide mononucleotide increases mitochondrial DNA content in murine OSCs. Total cellular DNA was isolated from cells at the indicated time points using DNEASY® Blood & Tissue Kit (Qiagen, Venlo, The Netherlands) according to the manufacturer's instructions. Mt DNA copy number was quantified using LIGHTCYCLER®480 SYBR® Green I Master (Roche Applied Science, Penzberg, Germany) using a LIGHTCYCLER®480 PCR machine (Roche Applied Science, Penzberg, Germany).

Figure 41:
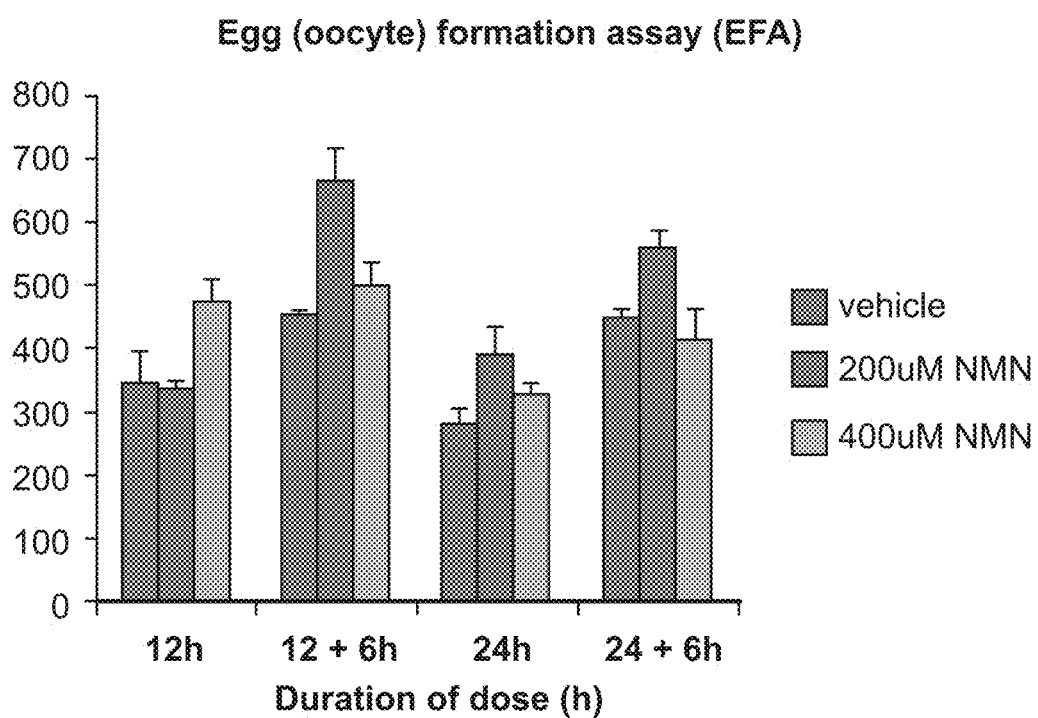

FIG. 41 is a graph showing that nicotinamide mononucleotide increases spontaneous oocyte formation in cultured murine oogonial stem cells. For assessment of spontaneous oocyte formation, each well of a 24-well plate was seeded with 25,000 OSCs, and the number of oocytes formed and released into the medium per well was assessed the second day after seeding as well as the designated time points after NMN treatment.

Figure 42:
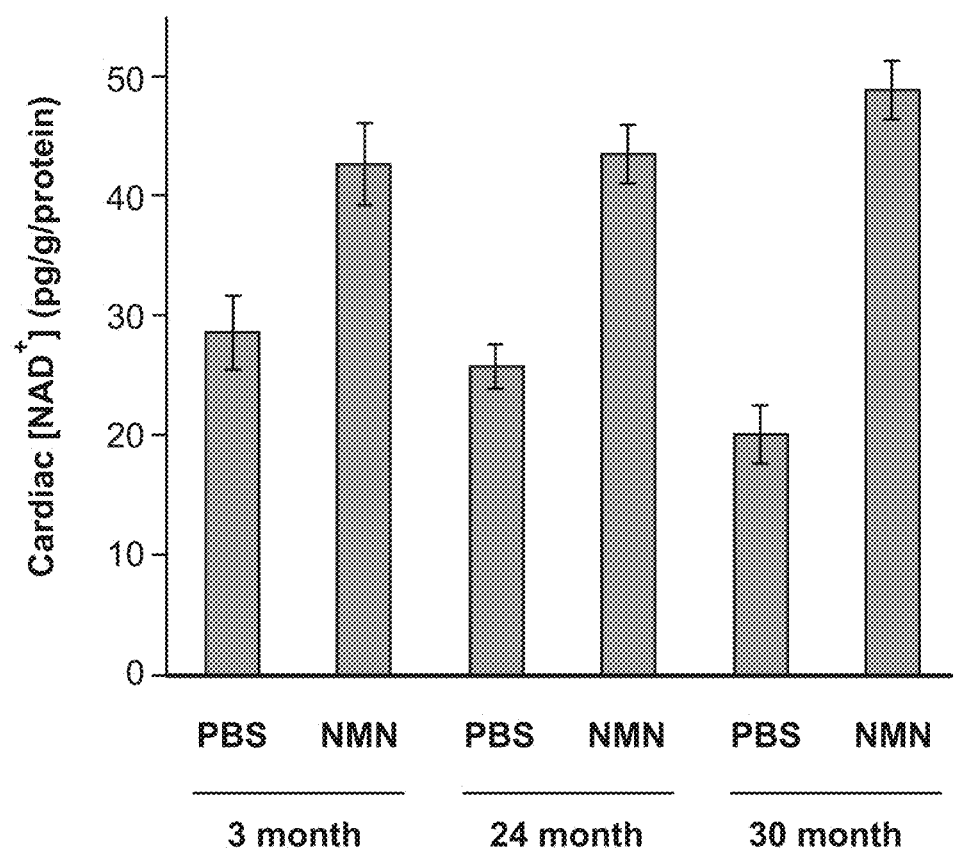

FIG. 42 is a graph showing that the $NAD^+$ precursor NMN raises $NAD^+$ levels in vivo in young and old mice. Cardiac $[NAD^+]$ declines with age and is reversed by NMN treatment (n=3; 200 mg·kg·d. I.P. for 1 week).

FIGS. 43A-D are graphs showing the restorative effects of an $NAD^+$ precursor (NMN) on mitochondrial function in vivo. The decline in mitochondrial function in skeletal muscle of 24-month old mice is completely reversed by NMN (nicotinamide mononucleotide) after only 1 week of treatment (FIGS. 43A, B). NMN is delivered by intraperitoneal (I.P.) injection and raises NAD levels in brain, heart and skeletal muscle ~30-100%. NMN increases mitochondrial function in C2C12 cells in a SIRT1-dependent manner (FIGS. 43C, D). sh Ctl=scrambled shRNA, Sh SIRT1=shRNA against SIRT1.

Figure 44:
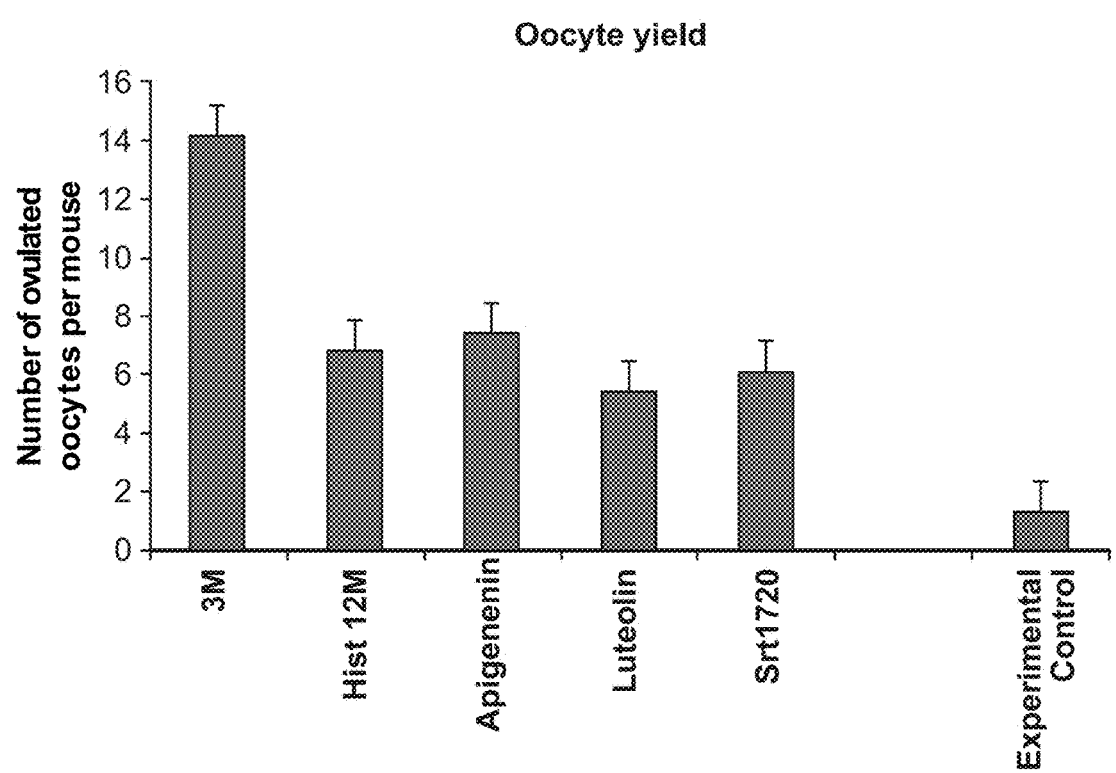

FIG. 44 is a bar graph showing the effects of apigenenin, luteolin and SRT-1720 on oocyte yield from aged female mice.

FIG. 45 is a bar graph showing the effects of apigenenin, luteolin and SRT-1720 on the percentage of mature, metaphase II oocytes retrieved following superovulation as compared to aged female mice.

FIG. 46 is a bar graph showing that apigenenin, luteolin and SRT-1720 improve the quality of oocytes in aged mice as compared to aged female mice.

DETAILED DESCRIPTION OF THE INVENTION

Definitions

Unless otherwise defined, all technical and scientific terms used herein have the same meaning as commonly understood by one of ordinary skill in the art to which this invention belongs. In case of conflict, the present application, including definitions will control.

The term "administration" or "administering" includes routes of introducing a compound(s) to a subject to perform their intended function. Examples of routes of administration that can be used include injection (subcutaneous, intravenous, parenterally, intraperitoneally, intrathecal), oral, and transdermal. The pharmaceutical preparations are, of course, given by forms suitable for each administration route. For example, these preparations are administered in tablets or capsule form, by injection, or inhalation. Oral administration is preferred. The injection can be bolus or can be continuous infusion. Depending on the route of administration, the compound can be coated with or disposed in a selected material to protect it from natural conditions which may detrimentally effect its ability to perform its intended function.

The agent can be administered alone, or in conjunction with either another agent as described above (e.g. another bioenergetic agent) or with a pharmaceutically-acceptable carrier, or both. The compound can be administered prior to the administration of the other agent, simultaneously with the agent, or after the administration of the agent. Furthermore, the compound can also be administered in a proform which is converted into its active metabolite, or more active metabolite in vivo.

As used herein, the term "advanced maternal age" as it relates to humans refers to a woman who is 34 years of age or older. As used herein, the term "oocyte-related infertility" as it relates to humans refers to an inability to conceive after one year of unprotected intercourse which is not caused by an anatomical abnormality (e.g., blocked oviduct) or pathological condition (e.g., uterine fibroids, severe endometriosis, Type II diabetes, polycystic ovarian disease)

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkyl has 30 or fewer carbon atoms in its backbone (e.g., $C_1$-$C_{30}$ for straight chain, $C_3$-$C_{30}$ for branched chain), preferably 26 or fewer, and more preferably 20 or fewer. Likewise, preferred cycloalkyls have from 3-10 carbon atoms in their ring structure, and more preferably have 3, 4, 5, 6 or 7 carbons in the ring structure.

Moreover, the term alkyl as used throughout the specification and claims is intended to include both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)). The term "alkyl" also includes unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six, and most preferably from one to four carbon atoms in its backbone structure, which may be straight or branched-chain. Examples of lower alkyl groups include methyl, ethyl, n-propyl, i-propyl, tert-butyl, hexyl, heptyl, octyl and so forth. In preferred embodiment, the term "lower alkyl" includes a straight chain alkyl having 4 or fewer carbon atoms in its backbone, e.g., $C_1$-$C_4$ alkyl.

The term "alkoxy," as used herein, refers to an alkyl or a cycloalkyl group which is linked to another moiety though an oxygen atom. Alkoxy groups can be optionally substituted with one or more substituents.

The terms "alkoxyalkyl," "polyaminoalkyl" and "thioalkoxyalkyl" refer to alkyl groups, as described above, which further include oxygen, nitrogen or sulfur atoms replacing one or more carbons of the hydrocarbon backbone, e.g., oxygen, nitrogen or sulfur atoms.

The terms "alkenyl" and "alkynyl" refer to unsaturated aliphatic groups analogous in length and possible substitution to the alkyls described above, but that contain at least one double or triple bond, respectively. For example, the invention contemplates cyano and propargyl groups.

The term "aryl" refers to the radical of aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles," "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "halogen" or "halo" designates —F, —Cl, —Br or —I.

The term "haloalkyl" is intended to include alkyl groups as defined above that are mono-, di- or polysubstituted by halogen, e.g., fluoromethyl and trifluoromethyl.

The term "hydroxyl" means —OH.

The term "heteroatom" as used herein means an atom of any element other than carbon or hydrogen. Preferred heteroatoms are nitrogen, oxygen, sulfur and phosphorus.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon. Heteroaryl groups may be optionally substituted with one or more substituents. Examples of heteroaryl groups include, but are not limited to, pyridyl, furanyl, benzodioxolyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, and indolyl.

The term "heterocyclic" as used herein, refers to organic compounds that contain at least one atom other than carbon (e.g., S, O, N) within a ring structure. The ring structure in these organic compounds can be either aromatic or non-aromatic. Some examples of heterocyclic moeities include, are not limited to, pyridine, pyrimidine, pyrrolidine, furan, tetrahydrofuran, tetrahydrothiophene, and dioxane. "Bioenergetic agents," as used herein, refer to agents that enhance mitochondrial numbers, mitochondrial activity, cellular energy levels or cellular energy-producing potential (bioenergetic status) in oocytes, OSCs and/or preimplantation embryos prior to conducting and/or following methods of in vitro fertilization, or following exposure of ovaries, oocytes, OSCs and/or preimplantation embryos in vivo. In particular, by enhancing mitochondrial numbers or activity, bioenergetic agents of the invention improve oocyte or OSC production and quality, for example, by preventing or decreasing aging-related increases in oocyte aneuploidy, chromosomal misalignment on the metaphase plate, meiotic spindle abnormalities, and/or mitochondrial dysfunction (aggregation, impaired ATP production). Bioenergetic agents include Sirt1 activators. Exemplary Sirt1 activators are listed in Table 1 (below).

TABLE 1

Sirt1 Activators
Compound:

Resveratrol (3,5,4'-Trihydroxy-trans-stilbene)
Butein (3,4,2',4'-Tetrahydroxychalcone)
Piceatannol (3,5,3',4'-Tetrahydroxy-transstilbene)
Isoliquiritigen (4,2',4'-Trihydroxychalcone)
Fisetin (3,7,3',4'-Tetrahydroxyflavone)
5,7,3',4',5'-Pentahydroxyflavone
Luteolin (5,7,3',4'-Tetrahydroxyflavone)
3,6,3',4'-Tetrahydroxyflavone
Quercetin (3,5,7,3',4'-Pentahydroxyflavone)
7,3',4',5'-Tetrahydroxyflavone
Kaempferol (3,5,7,4'-Tetrahydroxyflavone)
6-Hydroxyapigenin (5,6,7,4'-Tetrahydroxyflavone; Scutellarein)
3,4,2',4',6'-Pentahydroxychalcone
Apigenin (5,7,4'-Trihydroxyflavone)
Hinokitiol (b-Thujaplicin; 2-hydroxy-4-isopropyl-2,4,6-cycloheptatrien-1-one)
Daidzein (7,4'-Dihydroxyisoflavone)
Naringenin (5,7,4'-Trihydroxyflavanone)
3,6,2',4'-Tetrahydroxyflavone
L-(+)-Ergothioneine ((S)-a-Carboxy-2,3-dihydro-N,N,N-trimethyl-2-thioxo-1Himidazole-4-ethanaminium inner salt)
3,5,7,3',4'-Pentahydroxyflavanone
Deoxyrhapontin (3,5-Dihydroxy-4'-methoxystilbene 3-O-β-D-glucoside)
Flavanone
7,8,3',4'-Tetrahydroxyflavone
7,4'-Dihydroxyflavone
Caffeic Acid Phenyl Ester
3,6,2',3'-Tetrahydroxyflavone
4'-Hydroxyflavone
Pelargonidin chloride (3,5,7.4'-Tetrahydroxyflavylium chloride)
5,4'-Dihydroxyflavone
(−)-Epicatechin (Hydroxy Sites: 3,5,7,3',4')
5,7-Dihydroxyflavone
trans-Stilbene
Morin (3,5,7,2',4'-Pentahydroxyflavone)
Flavone
(−)-Catechin (Hydroxy Sites: 3,5,7,3',4')
Rhapontin (3,3',5-Trihydroxy-4'-methoxystilbene 3-O-B-β-glucoside)
(−)-Gallocatechin (Hydroxy Sites: 3,5,7,3',4',5')
Chalcone
(+)-Catechin (Hydroxy Sites: 3,5,7,3',4')
(+)-Epicatechin (Hydroxy Sites: 3,5,7,3',4')
MCI-186 (3-Methyl-1-phenyl-2-pyrazolin-5-one)
5-Hydroxyflavone
HBED (N,N'-Di-(2-hydroxybenzyl)ethylenediamine-N,N'-diacetic acid•HCl•H2O)
cis-Stilbene
Genistein (5,7,4'-Trihydroxyisoflavone)
Ambroxol (trans-4-(2-Amino-3,5-dibromobenzylamino) cyclohexane•HCl)
U-83836E ((−)-2-((4-(2,6-di-1-Pyrrolidinyl-4-pyrimidinyl)-1-piperazinyl)methyl)-3,4-dihydro-2,5,7,8-tetramethyl-2H-1-benzopyran-6-ol•2HCl)

CD38 inhibitors are also useful as bioenergetic agents. Exemplary CD38 inhibitors are listed in Tables 2A and 2B (below).

TABLE 2A

CD38 Inhibitors

1-[(2-Acetoxyethoxy)methyl]-3-(aminocarbonyl)-pyridinium chloride
1-[(2-Benzyloxyethoxy)methyl]-3-(aminocarbonyl)-pyridinium chloride
1-{[2-(4-Methoxy-phenoxy)ethoxy]methyl}-3-(aminocarbonyl)-pyridinium chloride
1-{[2-(4-Phenoxy-phenoxy)ethoxy]methyl}-3-(aminocarbonyl)-pyridinium chloride
1-{[2-(4-Nitro-phenoxy)ethoxy]methyl}-3-(aminocarbonyl)-pyridinium chloride
1-{[2-(3-Trifluoromethyl-phenoxy)ethoxy]methyl}-3-(aminocarbonyl)-pyridiniumchloride
1-{[2-(8'-Quinolyloxy)ethoxy]methyl}-3-(aminocarbonyl)-pyridinium chloride
1,2-Dimethoxy-ethylene-bis-N,N'-3-(aminocarbonyl)-pyridinium dichloride
1,4-Dimethoxy-butylene-bis-N,N'-3-(aminocarbonyl)-pyridinium dichloride
1,4-Dimethoxy-butyne-bis-N,N'-3-(aminocarbonyl)-pyridinium dichloride
1,4-Dimethoxy-hexamethylene-bis-N,N'-3-(aminocarbonyl)-pyridinium dichloride
(E)-1-{[4-(8'-Quinolyloxy)but-2-enyloxy]methyl}-3-(aminocarbonyl)-pyridinium chloride
1-{[2-(4-Phenoxy-phenoxy)ethoxy]methyl}-6-(aminocarbonyl)-quinolinium chloride
1-{[2-(4-Phenoxy-phenoxy)ethoxy]methyl}-3-(aminocarbonyl)-4-amino-pyridinium chloride Additional CD38 inhibitors are listed Luteolinidin
Kuromanin
Luteolin
Delphinidin
Pelargonidin
Malvidin
Quercetagetinidin
Peonidin
Myricetin
Cyanidin
Diosmetinidin
Quercetin
Robinetin
Petunidin
Fisetinidin
Quercetagetin
rac-Taxifolin
rac-Catechin
Piceatannol
Resveratrol
Apigenin in Table 2B.

Preferred bioenergetic agents for such uses include, but are not limited to, soluble precursors to $NAD^+$ tryptophan, quinolinic acid, nicotinamide mononucleotide, nicotinamide riboside, and nicotinic acid), fisetin, quercetin, hydroxytyrosol (4-(2-Hydroxyethyl)-1,2-benzenediol), pyrroloquinoline quinone (PQQ), metformin, apigenin, luteolin, tryphostin 8, berberine a CD3 inhibitor, and SRT-1720, a compound of any one of formulas I-XV, and functional derivatives thereof.

DOI (2,5-dimethoxy-4-iodo-phenylisopropylamine) is a phenylalkylamine that has been characterized as a 5-HT2-selective agonist.

Fisetin (2-(3,4-dihydroxyphenyl)-3,7-dihydroxychromen-4-one) is described, for example, by Herzig, *Monatshefte für Chemie* 1891 12: 177-90; Gábor et al.,

*Nature* 1966 212 (5067): 1273; and Maher et al, *PLoS ONE* 2011 6 (6): e21226, each of which is incorporated by reference. Quercetin is described, for example, by Bentz, *The Journal of Young Investigators: Appalachian State University*. [Online] Apr. 1, 2009, which is incorporated herein by reference.

Resveratrol (3,5,4'-trihydroxy-trans-stilbene) is described, for example, by Takaoka, *Nippon Kagaku Kaishi* 1939 60: 1090-1100; Hathway et al., *Biochemical Journal* 1959 72: 369-374; and Nonomura et al., *Yakugaku Zasshi* 1963 83: 988-990, each of which is incorporated by reference.

Pyrroloquinoline quinone (4,5-Dihydro-4,5-dioxo-1H-pyrrolo[2,3-f]quinoline-2,7,9-tricarboxylic acid) is described, for example, by Hauge *J Biol Chem* 1964 239: 3630-9; Anthony et al, *Biochem J* 1967 104: 960-9; Salisbury et al., *Nature* 1979 280: 843-4; Westerling et al., *Biochem Biophys Res Commun* 1979 87: 719-24; Ameyama *FEBS Lett* 1981 130: 179-83, each of which is incorporated by reference.

Metformin (N,N-dimethylimidodicarbonimidic diamide) is described, for example, by Werner. *J Chem Soc, Transactions* 1921 121:1790-5; Shapiro et al., *J Am. Chem Soc.* 1959 81:2220-5; Patent FR 2322860 1975 French; and *Pharmaceutical Manufacturing Encyclopedia (Sittig's Pharmaceutical Manufacturing Enyclopedia)*. 3rd ed. Vol. 3. Norwich, N.Y.: William Andrew; 2007, each of which is incorporated by reference.

Apigenin (5,7-Dihydroxy-2-(4-hydroxyphenyl)-4H-1-benzopyran-4-one) is described, for example, by *Merck Index*, 11th Edition, 763, which is incorporated herein by reference.

Luteolin (2-(3,4-Dihydroxyphenyl)-5,7-dihydroxy-4-chromenone) is described, for example, by Mann *Secondary Metabolism* 1992 (2nd ed.). Oxford, UK: Oxford University Press. pp. 279-280; and López-Lázaro *Mini Rev Med Chem* 2009 9: 31-59.

Tryphostin 8 (2[(4-hydroxyphenyl)methylidene]propanedinitrile) is described, for example, by Martin; *Biochem. Pharmacol,* 1998 56: 483; Wolbring, et al.; *J. Biol. Chem,* 1994 269: 22470; Stanley, et al., *J. Immunol.* 1990 145: 2189, and Gazit, et al., *J. Med. Chem,* 1989 32: 2344.

Berberine (9,10-dimethoxy-5,6-dihydro[1,3]dioxolo[4,5-g]isoquino[3,2-a]isoquinolin-7-ium) is described, for example, by Dewick *Medicinal Natural Products: A Biosynthetic Approach* (3rd ed.). West Sussex, England: Wiley. 2009 p. 357-358.

SRT-1720 (N-[2[3-(piperazin-1-ylmethyl)imidazo[2,1-b][1,3]thiazol-6-yl]phenyl]quinoxaline-2-carboxamide) is described, for example, by Milne et al., *Nature* 2007 450: 712-6.

"Oogonial stem cells" (OSCs), also known as female germline stem cells, are derived from postnatal sources and express markers including Vasa, Oct-4, Dazl, Stella and optionally an SSEA. OSCs are mitotically competent (i.e., capable of mitosis) and do not express oocyte markers including growth/differentiation factor-9 ("GDF-9") and zona pellucida glycoproteins (e.g., zona pellucida glycoprotein-3, "ZP3"), or markers of meiotic recombination such as synaptonemal complex protein-3 ("SYCP3" or "SCP3"). OSCs can be obtained from the postnatal ovary. OSCs are known in the art and are described in U.S. application Ser. No. 11/131,114, filed on May 17, 2005 and published as U.S. Patent Pub. No. 20060010508, the contents of which are incorporated herein by reference. OSCs are additionally described by Zou et al., *Nat Cell Biol* 2009 11:631-636 and Pacchiarotti et al. *Differentiation* 2010 79:159-170, the contents of which are incorporated herein by reference. Preferably, the OSC of the invention is a human OSC.

As used herein, the "progeny of an OSC" refers to all daughter cells derived from OSCs of the invention, including progenitor cells and differentiated cells, which maintain oogenic potential (i.e., the ability to form an oocyte). Preferably, the OSC progeny of the invention is a human OSC progeny.

OSCs may additionally be obtained from the bone marrow, peripheral blood or umbilical cord blood. Bone marrow derived OSCs of the invention can also circulate throughout the body and most preferably can be localized in bone marrow, peripheral blood and ovary. Bone marrow derived OSCs express markers including Oct 4, Vasa, Dazl, Stella, Fragilis, and optionally Nobox, Kit and Sca-1. Bone marrow derived OSCs are mitotically competent (i.e., capable of mitosis) and do not express GDF-9, zona pellucida proteins (e.g., ZP3) or SCP3. For additional details on bone marrow-derived OSCs, see, U.S. application Ser. No. 11/131,153, filed on May 17, 2005 and published as U.S. Patent Pub. No. 20060010509, the contents of which are incorporated herein by reference for their description of OSCs in the bone marrow. For additional details on peripheral blood and umbilical cord blood derived OSCs, see U.S. application Ser. No. 11/131,152, filed on May 17, 2005 and published as U.S. Patent Pub. No. 20060015961, the contents of which are incorporated herein by reference for their description of OSCs in the peripheral blood.

Oct-4, also referred to as POU domain class 5 transcription factor 1 or Pou5f1, is a gene expressed in female germline stem cells and their progenitor cells. The Oct-4 gene encodes a transcription factor that is involved in the establishment of the mammalian germline and plays a significant role in early germ cell specification (reviewed in Scholer, *Trends Genet.* 1991 7(10):323-329). In the developing mammalian embryo, Oct-4 is down-regulated during the differentiation of the epiblast, eventually becoming confined to the germ cell lineage. In the germline, Oct-4 expression is regulated separately from epiblast expression. Expression of Oct-4 is a phenotypic marker of totipotency (Yeom et al., *Development* 1996 122:881-888).

Stella, also commonly referred to as developmental pluripotency associated 3 or Dppa3, is a gene expressed in female germline stem cells and their progenitor cells. Stella is a novel gene specifically expressed in primordial germ cells and their descendants, including oocytes (Bortvin et al., *BMC Developmental Biology* 2004 4(2):1-5). Stella encodes a protein with a SAP-like domain and a splicing factor motif-like structure. Embryos deficient in Stella expression are compromised in preimplantation development and rarely reach the blastocyst stage. Thus, Stella is a maternal factor implicated in early embryogenesis.

Dazl is a gene expressed in female germline stem cells and their progenitor cells. The autosomal gene Dazl is a member of a family of genes that contain a consensus RNA binding domain and are expressed in germ cells. Loss of expression of an intact Dazl protein in mice is associated with failure of germ cells to complete meiotic prophase. Specifically, in female mice null for Dazl, loss of germ cells occurs during fetal life at a time coincident with progression of germ cells through meiotic prophase. In male mice null for Dazl, germ cells were unable to progress beyond the leptotene stage of meiotic prophase I. Thus, in the absence of Dazl, progression through meiotic prophase is interrupted (Saunders et al., *Reproduction* 2003 126:589-597).

Vasa, also referred to as DEAD box polypeptide 4 or Ddx4, is a gene expressed in female germline stem cells and their progenitor cells. Vasa is a component of the germplasm that encodes a DEAD-family ATP-dependent RNA helicase (Liang et al., *Development* 1994 120:1201-1211; Lasko et al., *Nature* 1988 335:611-167). The molecular function of Vasa is directed to binding target mRNAs involved in germ cell establishment (e.g., Oskar and Nanos), oogenesis, (e.g., Gruken), and translation onset (Davis et al., *Development* 1996 110:521-528). Vasa is required for pole cell formation and is exclusively restricted to the germ cell lineage throughout the development. Thus, Vasa is a molecular marker for the germ cell lineage in most animal species (Toshiaki et al., *Cell Structure and Function* 2001 26:131-136).

Stage-Specific Embryonic Antigens are optionally expressed in female germline stem cells and expressed in female germline stem cell progenitors of the invention. Stage-Specific Embryonic Antigen-1 (SSEA-1) is a cell surface embryonic antigen whose functions are associated with cell adhesion, migration and differentiation. During hypoblast formation, SSEA-1 positive cells can be identified in the blastocoel and hypoblast and later in the germinal crescent. SSEA-1 functions in the early germ cell and neural cell development. (D'Costa et al., *Int J. Dev. Biol.* 1999 43(4):349-356; Henderson et al., *Stem Cells* 2002 20:329-337). In specific embodiments, expression of SSEAs in female germline stem cells may arise as the cells differentiate. SSEAs useful in the invention include SSEA-1, -2, -3, and -4.

The term "autologous" as used herein refers to biological compositions obtained from the same subject. In one embodiment, the biological composition includes OSCs, OSC-derived compositions and oocytes. Accordingly, in conducting methods of the invention, the female germ cell cytoplasm or mitochondria used for transfer and the recipient oocyte into which the aforementioned compositions are transferred are obtained from the same subject.

The term "increase" as used herein generally means an increase of at least 5%, for example an increase by at least about 10%, or at least about 20%, or at least about 30%, or at least about 40%, or at least about 50%, or at least about 60%, or at least about 70%, or at least about 80%, or at least about 90% or up to and including a 100% increase (i.e. substantially above levels of detection), or any increase between 5-100% as compared to a reference level, as that term is defined herein, and as determined by a method that achieves statistical significance ($p<0.05$).

The term "isolated" as used herein refers to an OSC, mitochondrion or composition derived from an OSC (e.g., cytoplasm, mitochondrial preparation), which has been physically separated or removed from its natural biological environment. An isolated OSC, mitochondrion or composition need not be purified. The biological sample can include, for example, bone marrow, peripheral blood, umbilical cord blood, ovary or spleen or cells obtained from bone marrow, peripheral blood, ovary or spleen. Preferably, the composition comprises at least 50%, 75%, 85%, 90%, 95% or 100% of the cell type or organelle of interest relative to other cell types or organelles.

As used herein, the term "low ovarian reserve" as it relates to humans refers to a woman who exhibits a circulating Follicle Stimulating Hormone (FSH) level greater than 15 miu/ml in a "day 3 FSH test," as described in Scott et al., *Fertility and Sterility*, 1989 51:651-4, or a circulating Anti-Mullerian Hormone (AMH) level less than 0.6 ng/ml, or an antral follicle count less than 7 as measured by ultrasound.

The term "exogenous" as used herein refers to transferred cellular material (e.g., mitochondria) that is removed from one cell and transferred into another cell. Preferably, the cells and transferred materials are autologous. For example, OSC derived mitochondria that have been transferred into an oocyte, even if both are derived from the same subject, would be exogenous.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

Compounds that increase the activity of sirtuins, e.g., SIRT1, are referred to as "SIRT1 activators." Exemplary compounds are listed in Tables 1, 2A, and 2B, and are described, e.g., in WO 05/002672, WO 05/002555, US 20050136537, US 20060025337, WO 2005/065667 and WO 2007/084162, and include polyphenols, e.g. plant polyphenols.

The term "reduced" or "reduce" or "decrease" as used herein generally means a decrease of at least 5%, for example a decrease by at least about 10%, or at least about 20%, or at least about 30%, or at least about 40%, or at least about 50%, or at least about 60%, or at least about 70%, or at least about 80%, or at least about 90% or up to and including a 100% decrease (i.e. substantially absent or below levels of detection), or any decrease between 5-100% as compared to a reference level, as that term is defined herein, and as determined by a method that achieves statistical significance ($p<0.05$).

A "subject" is a vertebrate, including any member of the class mammalia, including humans, domestic and farm animals, and zoo, sports or pet animals, such as mouse, rabbit, pig, sheep, goat, cattle and higher primates.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The term "reduced" or "reduce" or "decrease" as used herein generally means a decrease by a statistically significant amount. However, for avoidance of doubt, "reduced"

means a decrease by at least 5% as compared to a reference level, for example a decrease by at least about 10%, or at least about 20%, or at least about 30%, or at least about 40%, or at least about 50%, or at least about 60%, or at least about 70%, or at least about 80%, or at least about 90% or up to and including a 100% decrease (i.e. substantially absent or below levels of detection), or any decrease between 5-100% as compared to a reference level, as that term is defined herein.

The term "increase" as used herein generally means an increase by a statistically significant amount. However, for avoidance of doubt, "increase" means an increase by at least 5% as compared to a reference level, for example an increase by at least about 10%, or at least about 20%, or at least about 30%, or at least about 40%, or at least about 50%, or at least about 60%, or at least about 70%, or at least about 80%, or at least about 90% or up to and including a 100% increase (i.e. significantly above levels of detection), or any increase between 10-100% as compared to a reference level, as that term is defined herein.

As used herein, the term "standard" or "reference" refers to a measured biological parameter including but not limited to defects such as aneuploidy, mutation, chromosomal misalignment, meiotic spindle abnormalities, and/or mitochondrial dysfunction (aggregation, impaired ATP production), or the reduction or elimination of such defects, in a known sample against which another sample is compared; alternatively, a standard can simply be a reference number that represents an amount of the measured biological parameter that defines a baseline for comparison. The reference number can be derived from either a sample taken from an individual, or a plurality of individuals or cells obtained therefrom (e.g., oocytes, OSCs). That is, the "standard" does not need to be a sample that is tested, but can be an accepted reference number or value. A series of standards can be developed that take into account an individual's status, e.g., with respect to age, gender, weight, height, ethnic background etc. A standard level can be obtained for example from a known sample from a different individual (e.g., not the individual being tested). A known sample can also be obtained by pooling samples from a plurality of individuals (or cells obtained therefrom) to produce a standard over an averaged population. Additionally, a standard can be synthesized such that a series of standards are used to quantify the biological parameter in an individual's sample. A sample from the individual to be tested can be obtained at an earlier time point (presumably prior to the onset of treatment) and serve as a standard or reference compared to a sample taken from the same individual after the onset of treatment. In such instances, the standard can provide a measure of the efficacy of treatment.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Other definitions appear in context throughout this disclosure.

Compositions and Methods of the Invention
Bioenergetic Agents for Use in the Invention In certain embodiments, the invention relates to any one of the compositions, tissues, cells (e.g., OSCs, oocytes), or methods described herein, wherein the bioenergetic agent is a compound of formula I or a compound of formula II:

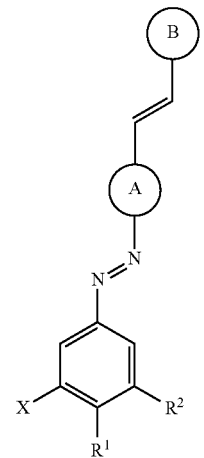

I

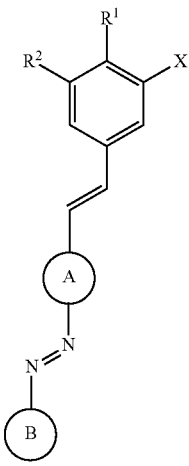

II wherein

is an aryl heterocycle diradical;

is heteroaryl;
  X is halo;
  $R^1$ is hydroxy, alkoxy, or amino; and
  $R^2$ is hydroxy, alkoxy, or amino.

In certain embodiments, the invention relates to any one of the aforementioned compositions, tissues, cells (e.g., OSCs, oocytes), or methods, wherein

is a diradical of azaindole, benzo(b)thiene, benzimidazole, benzofuran, benzoxazole, benzothiazole, benzothiadiazole, benzotriazole, benzoxadiazole, furan, imidazole, imidazopyridine, indole, indoline, indazole, isoindoline, ioxazole, isothiazole, isoquinoline, oxadiazole, oxazole, purine, pyran, pyrazine, pyrazole, pyridine, pyrimidine, pyrrole, pyrrolo[2,3-d]pyrimidine, pyrazolo[3,4-d]pyrimidine, quinoline, quinazoline, triazole, thiazole, thiobenzene, tetrahydroindole, tetrazole, thiadiazole, thiophene, thiomorpholine, or triazole.

In certain embodiments, the invention relates to any one of the aforementioned compositions, tissues, cells (e.g., OSCs, oocytes), or methods, wherein

is a diradical of furan, imidazole, isoxazole, isothiazole, oxadiazole, oxazole, pyrrole, triazole, thiazole, tetrazole, thiadiazole, thiophene, or triazole.

In certain embodiments, the invention relates to any one of the aforementioned compositions, tissues, cells (e.g., OSCs, oocytes), or methods, wherein

is a diradical of imidazole.

In certain embodiments, the invention relates to any one of the aforementioned compositions, tissues, cells (e.g., OSCs, oocytes), or methods, wherein

is azainadolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl imidazopyridinyl, indolyl, indolinyl, indazolyl, isoindolinyl, isoxazolyl isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, or triazolyl.

In certain embodiments, the invention relates to any one of the aforementioned compositions, tissues, cells (e.g., OSCs, oocytes), or methods, wherein

is furanyl, imidazolyl, isoxazolyl, isothiazolyl, oxadiazolyl, oxazolyl, pyrrolyl, thiazolyl, tetrazolyl, thiadiazolyl, thienyl, or triazolyl.

In certain embodiments, the invention relates to any one of the aforementioned compositions, tissues, cells (e.g. OSCs, oocytes), or methods, wherein

is imidazolyl.

In certain embodiments, the invention relates to any one of the aforementioned compositions, tissues, cells (e.g., OSCs, oocytes), or methods, wherein X is bromo.

In certain embodiments, the invention relates to any one of the aforementioned compositions, tissues, cells (e.g., OSCs, oocytes), or methods, wherein $R^1$ is hydroxy.

In certain embodiments, the invention relates to any one of the aforementioned compositions tissues, cells (e.g., OSCs, oocytes), or methods, wherein $R^2$ is alkoxy.

In certain embodiments, the invention relates to any one of the aforementioned compositions, tissues, cells e.g., OSCs, oocytes), or methods, wherein $R^2$ is methoxy.

In certain embodiments, the invention relates to any one of the compositions, tissues, cells (e.g., OSCs, oocytes), or methods described herein, wherein the bioenergetic agent is a compound of formula III:

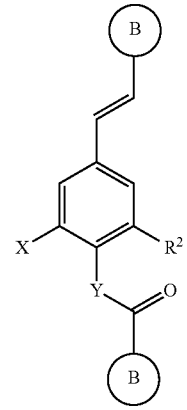

III wherein, independently for each occurrence,

is heteroaryl:
X is halo;
$R^2$ is hydroxy, alkoxy, or amino; and
Y is —O— or —NH—.

In certain embodiments, the invention relates to any one of the aforementioned compositions, tissues, cells (e.g. OSCs, oocytes), or methods, wherein

is azainadolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, or triazolyl.

In certain embodiments, the invention relates to any one of the aforementioned compositions, tissues, cells (e.g., OSCs, oocytes), or methods, wherein

is furanyl, imidazolyl, isoxazolyl, isothiazolyl, oxadiazolyl, oxazolyl, pyrrolyl, thiazolyl, tetrazolyl, thiadiazolyl, thienyl, or triazolyl.

In certain embodiments, the invention relates to any one of the aforementioned compositions, tissues, cells (e.g., OSCs, oocytes), or methods, wherein

is imidazolyl.

In certain embodiments, the invention relates to any one of the aforementioned compositions, tissues, cells (e.g., OSCs, oocytes), or methods, wherein X is bromo.

In certain embodiments, the invention relates to any one of the aforementioned compositions, tissues, cells (e.g., OSCs, oocytes), or methods, wherein $R^2$ is alkoxy.

In certain embodiments, the invention relates to any one of the aforementioned compositions, tissues, cells (e.g., OSCs, oocytes), or methods, wherein $R^2$ is methoxy.

In certain embodiments, the invention relates to any one of the aforementioned compositions, tissues, cells (e.g., OSCs, oocytes), or methods, wherein Y is —O—.

In certain embodiments, the invention relates to any one of the compositions, tissues, cells (e.g., OSCs, oocytes), or methods described herein, wherein the bioenergetic, agent is a compound of formula IV:

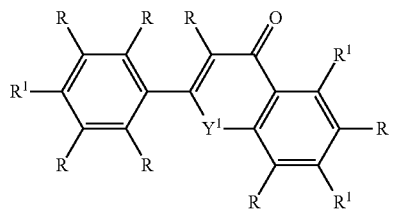

wherein, independently for each occurrence,
R is —H, halo, aryl, nitro, alkyl, hydroxy, alkoxy, or amino;
$R^1$ is hydroxy, alkoxy, or amino; and
$Y^1$ is —S—, —O—, or —NH—.

In certain embodiments, the invention relates to any one of the aforementioned compositions, tissues, cells (e.g., OSCs, oocytes), or methods, wherein one instance of R is hydroxy. In certain embodiments, the invention relates to any one of the aforementioned compositions, oocytes, or methods, wherein one instance of R is hydroxy; and the remaining instances of R are —H.

In certain embodiments, the invention relates to any one of the aforementioned compositions, tissues, cells (e.g., OSCs, oocytes), or methods, wherein $R^1$ is hydroxy.

In certain embodiments, the invention relates to any one of the aforementioned compositions, tissues, cells (e.g., OSCs, oocytes), or methods, wherein $Y^1$ is —O—.

In certain embodiments, the invention relates to any one of the compositions, tissues, cells (e.g., OSCs, oocytes), or methods described herein, wherein the bioenergetic agent is a compound of formula V:

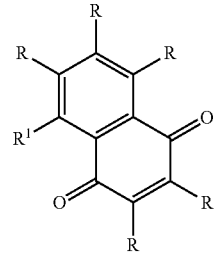

wherein, independently for each occurrence,
R is —H, halo, aryl, nitro, alkyl, hydroxy, alkoxy, or amino; and
$R^1$ is hydroxy, alkoxy, or amino.

In certain embodiments, the invention relates to any one of the aforementioned compositions, tissues, cells (e.g., OSCs, oocytes), or methods, wherein R is —H.

In certain embodiments, the invention relates to any one of the aforementioned compositions, cells (e.g., OSCs, oocytes), or methods, wherein $R^1$ is hydroxy.

In certain embodiments, the invention relates to any one of the compositions, tissues, cells (e.g., OSCs, oocytes), or methods described herein, wherein the bioenergetic agent is a compound of formula VI:

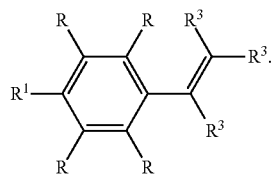

wherein, independently for each occurrence,
R is —H, halo, aryl, nitro, alkyl, hydroxy, alkoxy, or amino;
R1 is hydroxy, alkoxy, or amino;
$R^3$ is —H, cyano, —$CO_2R^4$, or —C(O)N($R^4$)$_2$; and
$R^4$ is —H or alkyl.

In certain embodiments, the invention relates to any one of the aforementioned compositions, tissues, cells (e.g., OSCs, oocytes), or methods, wherein R is —H.

In certain embodiments, the invention relates to any one of the aforementioned compositions, tissues, cells (e.g., OSCs, oocytes), or methods, wherein at least one instance of $R^3$ is cyano. In certain embodiments, the invention relates to any one of the aforementioned compositions, tissues, cells (e.g., OSCs, oocytes), or methods, wherein at least two instances of $R^3$ are cyano.

In certain embodiments, the invention relates to any one of the compositions, tissues, cells (e.g., OSCs, oocytes), or methods described herein, wherein the bioenergetic agent is a compound of formula VII:

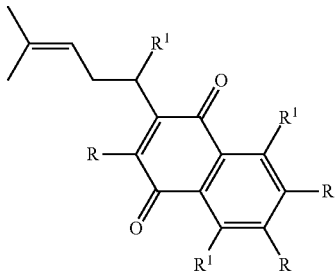

VII wherein, independently for each occurrence,
R is —H, halo, aryl, nitro, alkyl, hydroxy, alkoxy, or amino; and
$R^1$ is hydroxy, alkoxy, or amino.

In certain embodiments, the invention relates to any one of the aforementioned compositions, tissues, cells e.g., OSCs, oocytes), or methods, wherein R is —H.

In certain embodiments, the invention relates to any one of the aforementioned compositions, tissues, cells (e.g. OSCs, oocytes), or methods, wherein $R^1$ is hydroxy.

In certain embodiments, the invention relates to any one of the compositions, tissues, cells (e.g., OSCs, oocytes), or methods described herein, wherein the bioenergetic agent is compound of formula VIII:

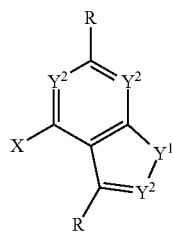

VIII wherein, independently for each occurrence,
R is —H, halo, aryl, nitro, alkyl, hydroxy, alkoxy, or amino;
X is halo;
$Y^1$ is —O—, —S—, or —NH—; and
$Y^2$ is |N— or =CR—.

In certain embodiments, the invention relates to any one of the aforementioned compositions, tissues, cells (e.g., OSCs, oocytes), or methods, wherein R is —H.

In certain embodiments, the invention relates to any one of the aforementioned compositions, tissues, cells (e.g., OSCs, oocytes), or methods, wherein X is chloro.

In certain embodiments, the invention relates to any one of the aforementioned compositions, tissues, cells (e.g., OSCs, oocytes), or methods, wherein $Y^1$ is —NH—.

In certain embodiments, the invention relates to any one of the aforementioned compositions, tissues, cells (e.g., OSCs, oocytes), or methods, wherein $Y^2$ is =N—.

In certain embodiments, the invention relates to any one of the compositions, tissues, cells (e.g., OSCs, oocytes), or methods described herein, wherein the bioenergetic agent is a compound of formula IX:

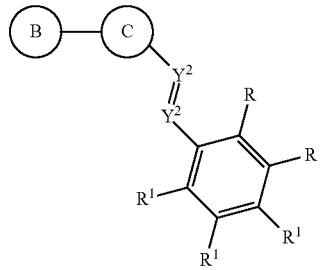

IX wherein, independently for each occurrence,

is a five-membered, unsaturated heterocycle diradical;

is heteroaryl;
R is —H, halo, aryl, nitro, alkyl, hydroxy, alkoxy, or amino;
$R^1$ is hydroxy, alkoxy, or amino; and
$Y^2$ is =N— or =CR—.

In certain embodiments, the invention relates to any one of the aforementioned compositions, tissues, cells (e.g., OSCs, oocytes), or methods, wherein

is azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, iothiazolyl, isoquinolinyl, oxadiazolyl, oxazolyl, purinyl, pyranyl, pyrazinyl, pyrazolyl, pyrdinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, or triazolyl.

In certain embodiments, the invention relates to any one of the aforementioned compositions, tissues, cells (e.g., OSCs, oocytes), or methods, wherein R is —H.

In certain embodiments, the invention relates to any one of the aforementioned compositions, tissues, cells (e.g., OSCs, oocytes), or methods, wherein $R^1$ is hydroxy.

In certain embodiments, the invention relates to any one of the aforementioned compositions, tissues, cells (e.g., OSCs, oocytes), or methods, wherein one instance of $Y^2$ is =N—.

In certain embodiments, the invention relates to any one of the compositions, tissues, cells (e.g., OSCs, oocytes), or methods described herein, wherein the bioenergetic agent is a compound of formula X:

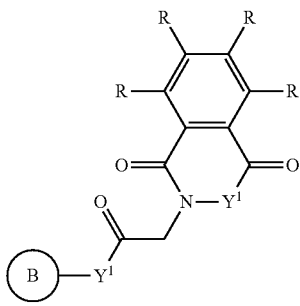

X wherein, independently for each occurrence,

is heteroaryl;

R is —H, halo, aryl, nitro, alkyl, hydroxy, alkoxy, or amino;

$Y^1$ is —S—, —O—, or —NH—.

In certain embodiments, the invention relates to any one of the aforementioned compositions, tissues, cells (e.g., OSCs, oocytes), or methods, wherein

is azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, or triazolyl.

In certain embodiments, the invention relates to any one of the aforementioned compositions, tissues, cells (e.g., OSCs, oocytes), or methods, wherein R is —H.

In certain embodiments, the invention relates to any one of the aforementioned compositions, tissues, cells (e.g., OSCs, oocytes), or methods, wherein $Y^1$ is —NH—.

In certain embodiments, the invention relates to any one of the compositions, tissues, cells (e.g., OSCs, oocytes), or methods described herein, wherein the bioenergetic agent is a compound of formula XI:

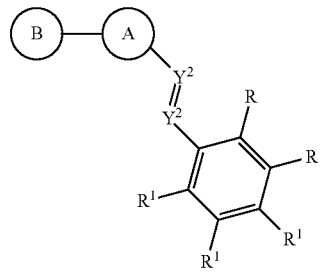

XI wherein, independently for each occurrence.

is an aryl heterocycle diradical;

is heteroaryl;

R is —H, halo, aryl, nitro, alkyl, hydroxy, alkoxy, or amino;

$R^1$ is hydroxy, alkoxy, or amino; and $Y^2$ is =N— or =CR—.

In certain embodiments, the invention relates to any one of the aforementioned compositions, tissues, cells (e.g., OSCs, oocytes), or methods, wherein

is azaindolyl, benzo(b)thienyl, benzimidazolyl, benzofuranyl, benzoxazolyl, benzothiazolyl, benzothiadiazolyl, benzotriazolyl, benzoxadiazolyl, uranyl, imidazolyl, imidazopyridinyl, indolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, or triazolyl.

In certain embodiments, the invention relates to any one of the aforementioned compositions, tissues, cells (e.g., OSCs, oocytes), or methods, wherein R is —H.

In certain embodiments, the invention relates to any one of the aforementioned compositions, tissues, cells (e.g., OSCs, oocytes), or methods, wherein $R^1$ is hydroxy.

In certain embodiments, the invention relates to any one of the aforementioned compositions, tissues, cells (e.g., OSCs, oocytes), or methods, wherein one instance of $Y^2$ is =N—.

In certain embodiments, the invention relates to any one of the compositions, tissues, cells (e.g., OSCs, oocytes), or methods described herein, wherein the bioenergetic agent is, a compound of formula XII:

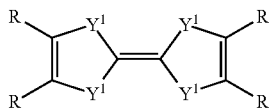 XII wherein, independently for each occurrence,

R is —H, halo, aryl, nitro, alkyl, hydroxy, alkoxy, or amino; and $Y^1$ is —S—, —O—, or —NH—.

In certain embodiments, the invention relates to any one of the aforementioned compositions, tissues, cells (e.g., OSCs, oocytes), or methods, wherein at least one instance of R is —H.

In certain embodiments, the invention relates to any one of the aforementioned compositions, tissues, cells (e.g., OSCs, oocytes), or methods, wherein at least one instance of $Y^1$ is —S—.

In certain embodiments, the invention relates to any one of the compositions, tissues, cells (e.g., OSCs, oocytes), or methods described herein, wherein the bioenergetic agent is a compound of formula XIII:

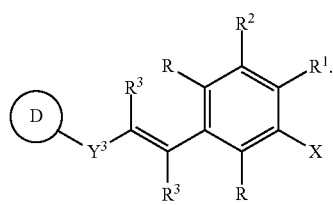 XIII wherein, independently for each occurrence,

is aryl or heteroaryl;

R is —H, halo, aryl, nitro, alkyl, hydroxy, alkoxy, or, amino;

$R^1$ is hydroxy, alkoxy, or amino;

$R^2$ is hydroxy, alkoxy, or amino;

$R^3$ is —H, cyano, —$CO_2R^4$, or —$C(O)N(R^4)_2$;

X is halo;

$Y^3$ is a bond, —C(O)-d, —C(O)NH-d, —NH—C(O)-d, or —C(O)NH—$CH_2$-d; and d is a bond to

.

In certain embodiments, the invention relates to any one of the aforementioned compositions, tissues, cells (e.g., OSCs, oocytes), or methods, wherein R is —H In certain embodiments, the invention relates to any one of the aforementioned compositions, tissues, cells (e.g., OSCs, oocytes), or methods, wherein $R^1$ is hydroxy.

In certain embodiments, the invention relates to any one of the aforementioned compositions, tissues, cells (e.g., OSCs, oocytes), or methods, wherein $R^2$ is alkoxy. In certain embodiments, the invention relates to any one of the aforementioned compositions, oocytes, or methods, wherein $R^2$ is methoxy.

In certain embodiments, the invention relates to any one of the aforementioned compositions, tissues, cells (e.g., OSCs, oocytes), or methods, wherein one instance of $R^3$ is cyano.

In certain embodiments, the invention relates to any one of the aforementioned compositions, tissues, cells (e.g., OSCs, oocytes), or methods, wherein R is —H.

In certain embodiments, the invention relates to any one of the aforementioned compositions, tissues, cells (e.g., OSCs, oocytes), or methods, wherein X is bromo.

In certain embodiments, the invention relates to any one of the aforementioned compositions, tissues, cells (e.g., OSCs, oocytes), or methods, wherein $Y^3$ is a bond. In certain embodiments, the invention relates to, any one, of the aforementioned compositions (e.g., OSCs, oocytes), or methods, wherein $Y^3$ is —C(O)-d. In certain embodiments, the invention relates to any one of the aforementioned compositions, tissues, cells (e.g., OSCs, oocytes), or methods, wherein $Y^3$ is —C(O)N-d. In certain embodiments, the invention relates to any one of the aforementioned compositions, tissues, cells (e.g., OSCs, oocytes), or methods, wherein $Y^3$ is —NH—C(O)-d. In certain embodiments, the invention relates to any one of the aforementioned compositions, tissues, cells (e.g., OSCs, oocytes), or methods, wherein $Y^3$ is —C(O)NH—$CH_2$-d.

In certain embodiments, the invention relates to any one of the compositions, tissues, cells (e.g., OSCs, oocytes), or methods described herein, wherein the bioenergetic agent is a compound of formula XIV:

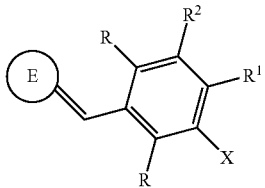 XIV wherein, independently for each occurrence,

is a five-membered heterocycle radical;

R is —H, halo, aryl, nitro, alkyl, hydroxy, alkoxy, or amino;

$R^1$ is hydroxy, alkoxy, or amino;

$R^2$ is hydroxy, alkoxy, or amino; and

X is halo.

In certain embodiments, the invention relates to any one of the aforementioned compositions, tissues, cells (e.g., OSCs, oocytes), or methods, wherein R is —H In certain embodiments, the invention relates to any one of the aforementioned compositions, tissues, cells (e.g., OSCs, oocytes), or methods, wherein $R^1$ is hydroxy.

In certain embodiments, the invention relates to any one of the aforementioned compositions, tissues, cells (e.g., OSCs, oocytes), or methods, wherein R² is alkoxy. In certain embodiments, the invention relates to any one of the aforementioned compositions, oocytes, or methods, wherein R² is methoxy.

In certain embodiments, the invention relates to any one of the aforementioned compositions, tissues, cells (e.g., OSCs, oocytes), or methods, wherein X is bromo.

In certain embodiments, the invention relates to any one of the compositions, tissues, cells (e.g., OSCs, oocytes), or methods described herein, wherein the bioenergetic agent is a compound of formula XV:

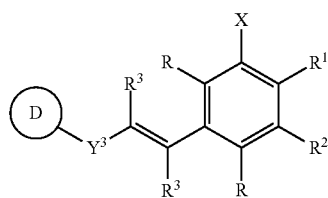

wherein, independently for each occurrence,

is aryl or heteroaryl;
R is —H, halo, aryl, nitro, alkyl, hydroxy, alkoxy, or amino.
R¹ is hydroxy, alkoxy, or amino;
R² is hydroxy, alkoxy, or amino;
R³ is —H, cyano, —CO₃R⁴, or —C(O)N(R⁴)₂;
X is halo;
Y³ is a bond, —C(O)-d, —C(O)N-d, —NH—C(O)-d, or —C(O)NH—CH₂-d; and
d is a bond to

In certain embodiments, the invention relates to any one of the aforementioned compositions, tissues, cells (e.g., OSCs, oocytes), or methods, wherein R is —H In certain embodiments, the invention relates to any one of the aforementioned compositions, tissues, cells (e.g., OSCs, oocytes), or methods, wherein R¹ is hydroxy.

In certain embodiments, the invention relates to any one of the aforementioned compositions, tissues, cells (e.g., OSCs, oocytes), or methods, wherein R² is alkoxy. In certain embodiments, the invention relates to any one of the aforementioned compositions, oocytes, or methods, wherein R² is methoxy.

In certain embodiments, the invention relates to any one of the aforementioned compositions, tissues, cells (e.g., OSCs, oocytes), or methods, wherein one instance of R³ is cyano.

In certain embodiments, the invention relates to any one of the aforementioned compositions, tissues, cells (e.g., OSCs, oocytes), or methods, wherein R³ is —H.

In certain embodiments, the invention relates to any one of the aforementioned compositions, tissues, cells (e.g., OSCs, oocytes), or methods, wherein X is bromo.

In certain embodiments, the invention relates to any one of the aforementioned compositions, tissues, cells (e.g., OSCs, oocytes), or methods, wherein Y³ is a bond. In certain embodiments, the invention relates to any one of the aforementioned compositions, oocytes, or methods, wherein Y³ is —C(O)-d. In certain embodiments, the invention relates to any one of the aforementioned compositions, tissues, cells (e.g., OSCs, oocytes), or methods, wherein Y³ is —C(O)NH-d. In certain embodiments, the invention relates to any one of the aforementioned compositions, tissues, cells OSCs, oocytes), or methods, wherein Y³ is —NH—C(O)-d. In certain embodiments, the invention relates to any one of the aforementioned compositions, tissues, cells (e.g., OSCs, oocytes), or methods, wherein Y³ is —C(O)NH—CH₂-d.

In certain embodiments, the invention relates to any one of the compositions, tissues, cells (e.g., OSCs, oocytes), or methods described herein, wherein the bioenergetic agent is

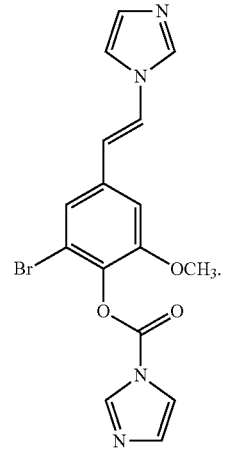 [SMILES: COc1cc(/C=C/n2ccnc2)cc(Br)c1OC(=O)n1ccnc1]

In certain embodiments, the invention relates to any one of the compositions, tissues, cells (e.g., OSCs, oocytes), or methods described herein, wherein the bioenergetic agent is selected from the group consisting of

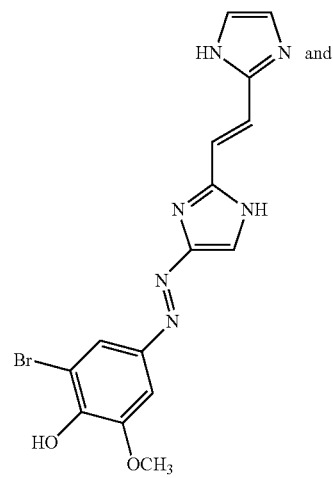

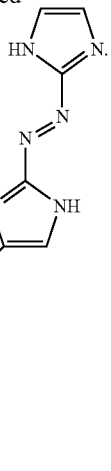

In certain embodiments, the invention relates to any one of the compositions, tissues, cells (e.g., OSCs, oocytes), or methods described herein, wherein the bioenergetic agent is selected from the group consisting of

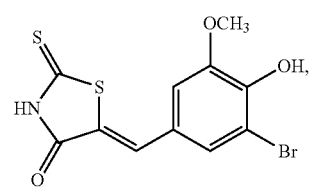

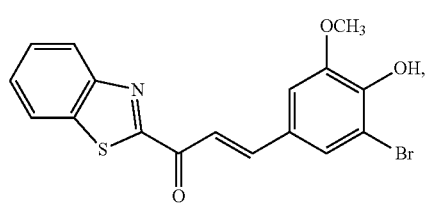

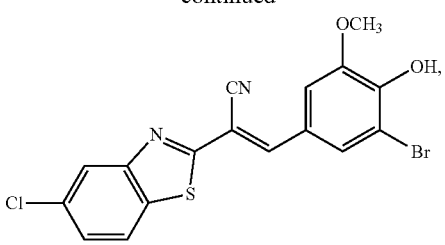

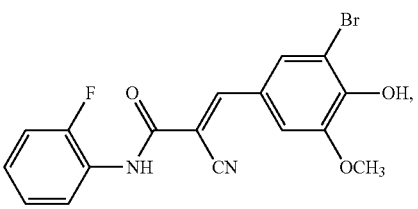

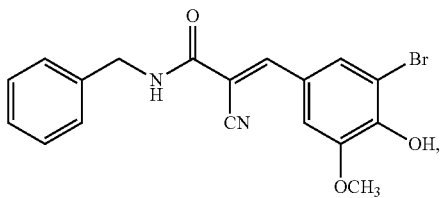

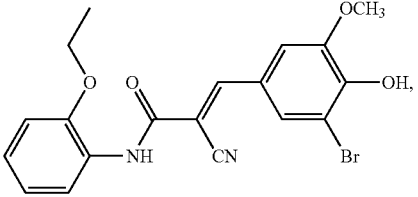

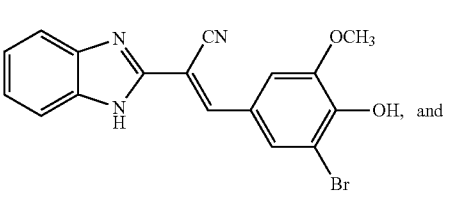

, and

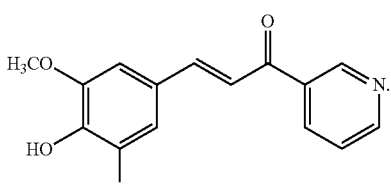

In certain embodiments, the invention relates to any one of the compositions, tissues, cells (e.g., OSCs, oocytes), or methods described herein, wherein the bioenergetic agent is selected from the group consisting of

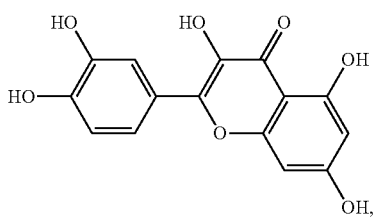

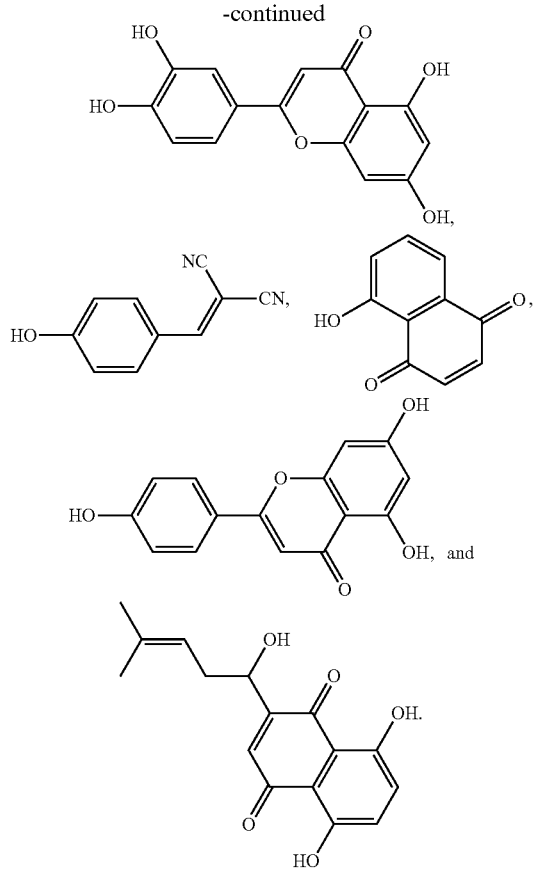

In certain embodiments, the invention relates to any one of the compositions, tissues, cells (e.g., OSCs, oocytes), or methods described herein, wherein the bioenergetic agent is selected from the group consisting of

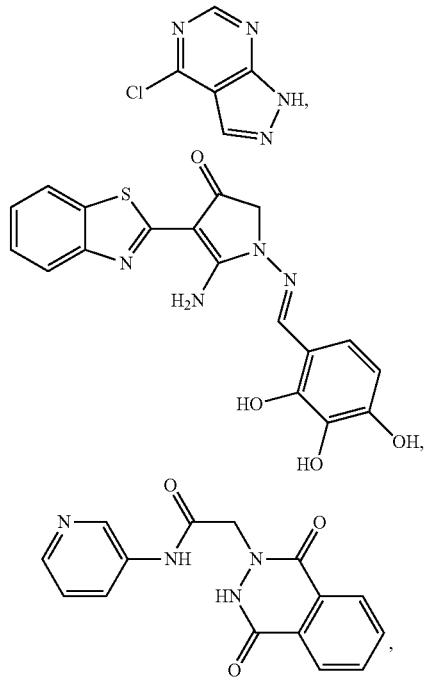

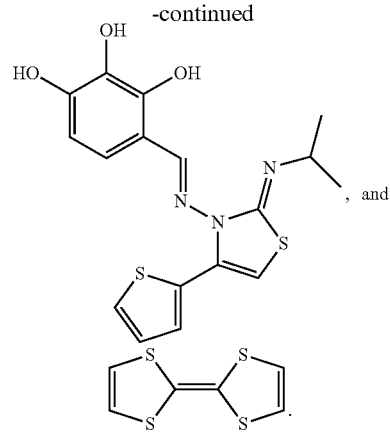

in certain embodiments, the invention relates to any one of the compositions, tissues, cells (e.g., OSCs, oocytes), or methods, described herein, wherein the bioenergetic agent is selected from the group consisting of α-lineolic acid, lineolic acid, stearic acid, elaidic acid, arachidonic acid, oleic acid, and palmitoleic acid.

In alternate embodiments, one or more of the following bioenergetic agents is specifically excluded from the methods of the invention: tryptophan, quinolinic acid, nicotinamide mononucleotide, nicotinamide riboside, nicotinic acid, fisetin, quercetin, hydroxytyrosol, pyrroloquinoline quinone (PQQ), metformin, apigenin, luteolin, tryphostin 8, berberine, SRT-1720, and

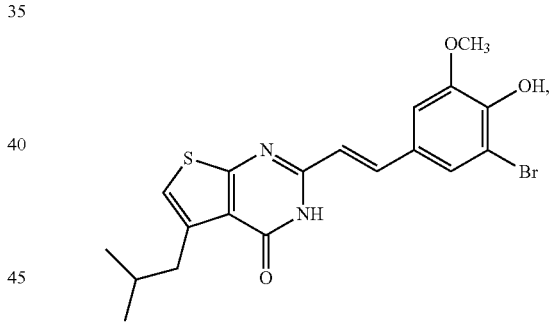

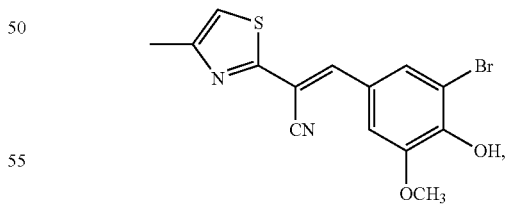

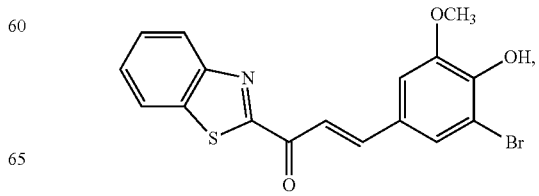

-continued

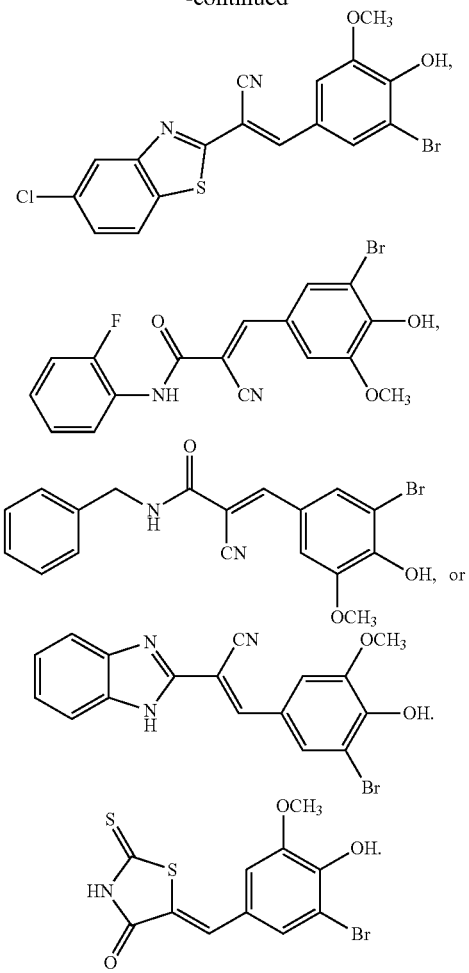

Pharmaceutically acceptable salts and prodrugs of the bioenergetic agents described herein may also be used.

Isolation of Oocytes and OSCs

Standard methods for the isolation of oocytes from human subjects using procedures such as transvaginal ultrasound guided oocyte retrieval are well known in the art. See Fabbri et al., *Hum Reprod* 2001 16:411-416.

Figure 14:
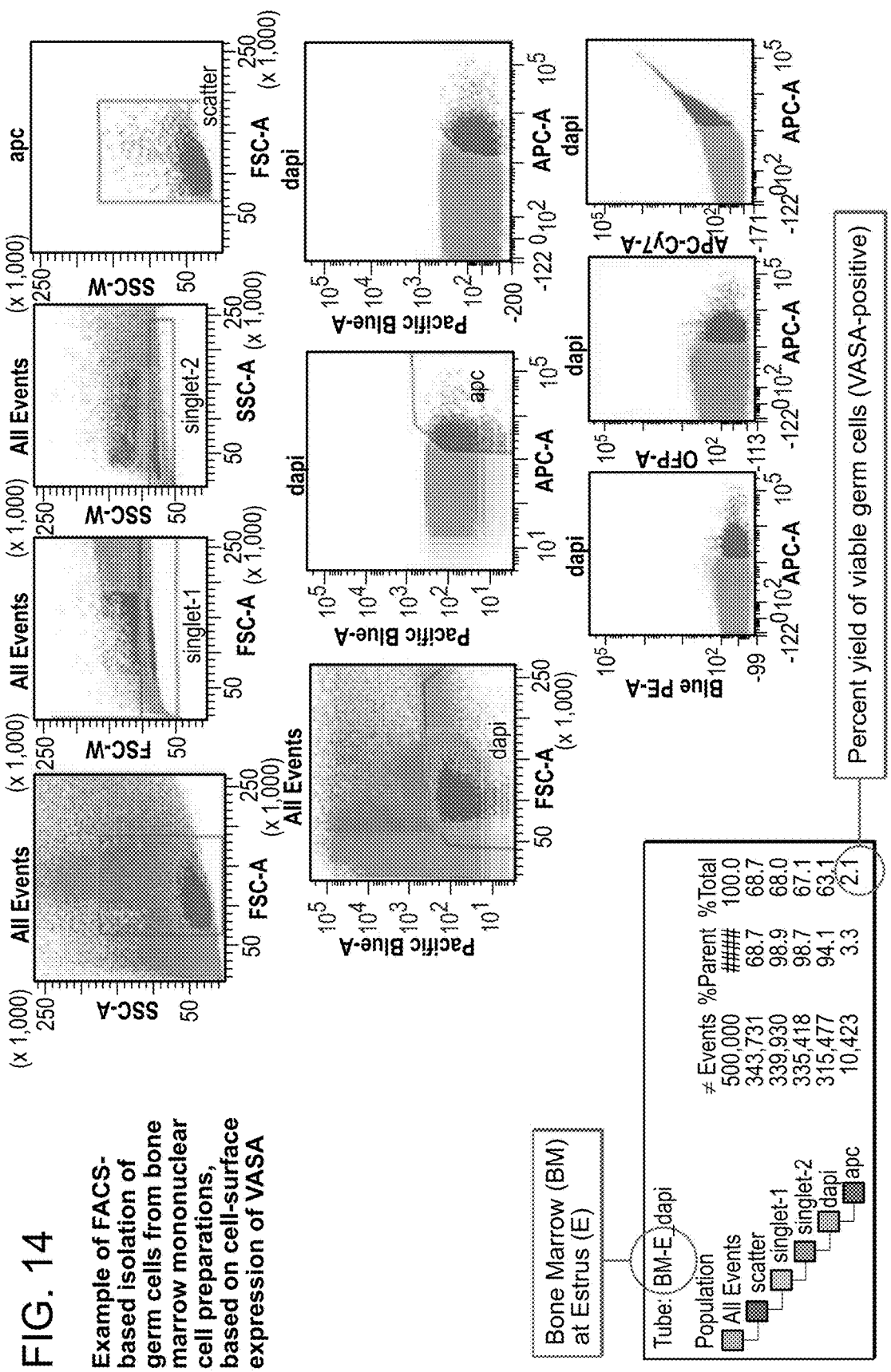
FIG. 14 depicts fluorescence activated cell sorting (FACS)-based germ cell purification from bone marrow preparations of adult female mice during estrus of the female reproductive cycle using cell surface expression of Vasa to isolate the cells.
Figure 15:
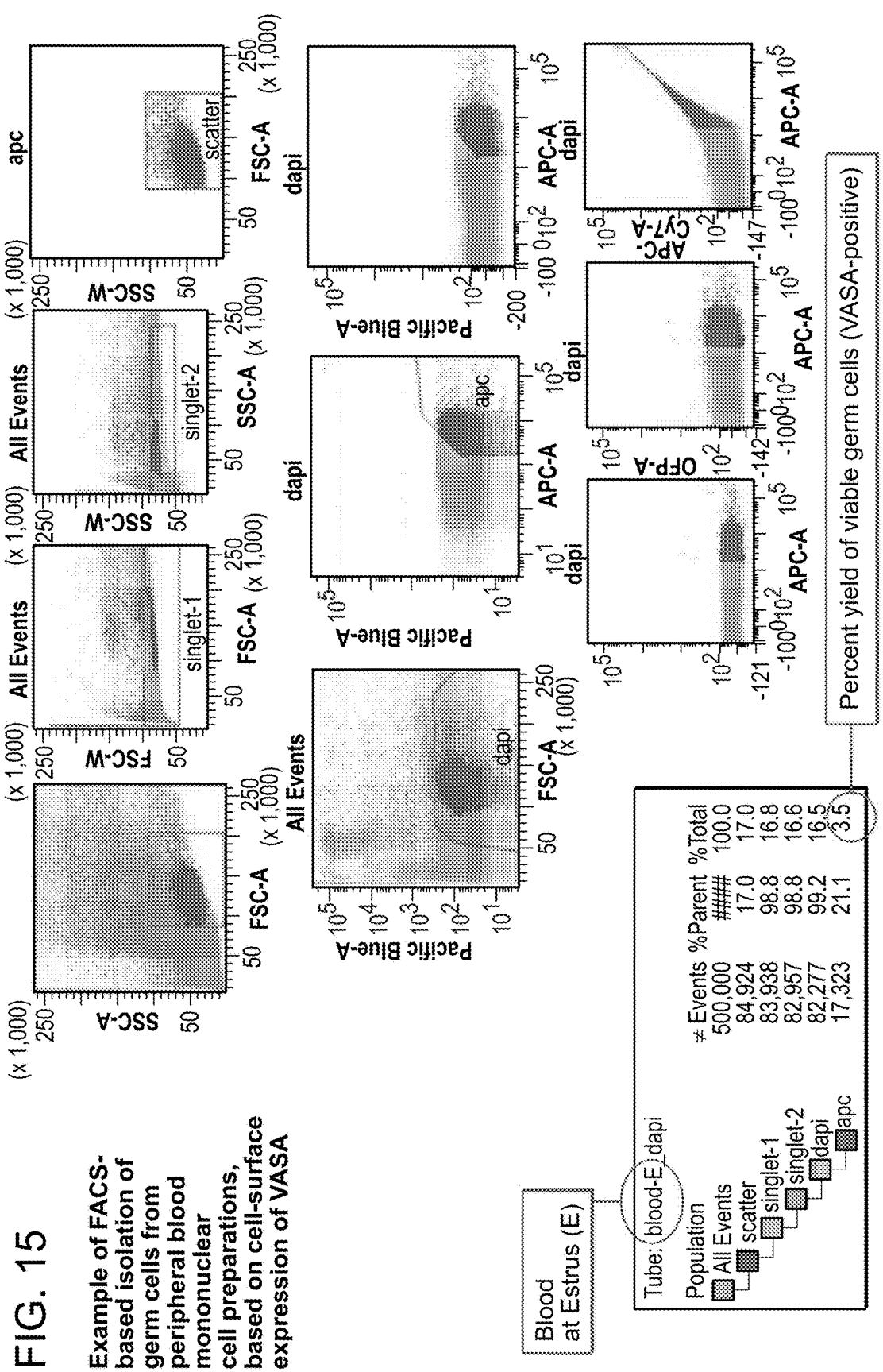
FIG. 15 depicts fluorescence activated cell sorting (FACS)-based germ cell purification from peripheral blood preparations of adult female mice during estrus of the female reproductive cycle using cell surface expression of Vasa to isolate the cells.

Prior to isolation of OSCs, adult ovarian cortical tissue can be obtained using a minor laparoscopic procedure known in the art to collect a small (e.g., 3×3×1 mm) ovarian biopsy, which is then processed for OSC isolation. See Gook et al., *Hum Reprod* 2004 20:72-78. Isolation of human OSCs from adult ovarian cortical tissue can be performed as described in Example 1, FIG. 1 or as previously described. See, for example, paragraph 0116 of U.S. Patent Pub. No. 20060010508, filed as U.S. application Ser. No. 11/131,114 on May 17, 2005 and Zou et al., *Nat Cell Biol* 2009 11:631-636. OSCs can also be obtained from non-ovarian sources, such as bone marrow or peripheral blood. Bone marrow and peripheral blood derived OSCs can be isolated by standard means known in the art for the separation of stem cells from, for example, the marrow or blood (e.g., cell sorting). Optionally, the isolation protocol includes generation of a kit+/lin− fraction that is depleted of hematopoietic cells. Additional selection means based on the unique profile of gene expression (e.g., Vasa, Oct-4, Dazl, Stella, Fragilis) can be employed to further purify populations of cells to an extent where they become substantially free of the biological sample from which they were obtained (e.g. bone marrow, peripheral blood, umbilical cord blood). For example, the methods described in Example 1, FIG. 1 have been applied to a mononuclear fraction of blood cells and bone marrow cells to obtain the purified OSCs from non-ovarian sources. Briefly, cells were incubated with a rabbit anti-VASA antibody (COOH-Antibody 577-716) for 20 minutes (ab13840; Abcam, Cambridge, Mass., USA), washed, and incubated with goat anti-rabbit IgG conjugated to allophcocyanin (APC) for 20 minutes, and washed again. Labeled cells in the eluate were isolated by fluorescence-activated cell sorting (FACS) using a FACSARIA II® cytometer (BD Biosciences, San Jose, Calif., Jose; provided by Harvard Stem Cell Institute, Boston, Mass.), gated against negative (unstained and no primary antibody) controls. Propidium iodide was added to the cell suspension just prior to sorting for dead cell exclusion. Results obtained using cell surface expression of Vasa to isolate OSCs from non-ovarian sources are provided in FIGS. 14 and 15, where the FACS based germ cell purification of bone marrow and peripheral blood preparations from adult female mice during estrus of the female reproductive cycle is shown. Other antibodies for use in isolation methods include those described in U.S. Pat. Nos. 7,884,193, 7,226,994 and 6,875,854, the contents of which are incorporated herein by reference.

Preparation of Ooctye and OSC Derived Compositions and Methods of Transfer

Methods for the preparation and transfer of purified mitochondria are known in the art and can be carried out as previously described. See, for example, Perez et al., *Cell Death Differ* 2007 14:524-533 and Perez et al., *Nature* 2000, 403:500-1, the contents of which are expressly incorporated herein by reference. Briefly, OSCs and/or oocytes can be isolated and cultured as described above. Optionally, OSCs and/or oocytes can be isolated and cultured in the presence of one or more bioenergetic agents prior to mitochondrial extraction or preparation. To obtain mitochondria from OSCs, OSC progeny and/or oocytes, 2 ml of mitochondrial lysis buffer (0.3 M sucrose, 1 mM EDTA, 5 mM MOPS, 5 mM $KH_2PO_4$, 0.1% BSA) is added to each plate, and the cells are removed using a cell scraper if necessary. The cell suspension is transferred into a small glass tissue bouncer and homogenized until smooth (approximately 10 up-and-down strokes), and the lysate is centrifuged at 600×g for 30 minutes at 4° C. The supernatant is removed and spun at 10,000×g for 12 minutes at 4° C., and the resulting crude mitochondrial pellet is resuspended in 0.2 ml of 0.25 M sucrose. This sample is then layered over a 25-60% Percoll density gradient diluted with 0.25 M sucrose and centrifuged at 40,000×g for 20 minutes at 17° C. The interface band is extracted from the gradient and washed in 2 volumes of 0.25 M sucrose before a final centrifugation at 14,000×g for 10 min at 4° C. to yield a mitochondrial pellet.

The mitochondrial pellet can also be prepared as described Frezza et al. *Nature Protocols* 2007 2:287-295, the contents of which are incorporated herein by reference. In specific embodiments of the invention, the total OSC-derived mitochondrial population in a tissue, cell, lysed cell, or fraction thereof can be isolated, characterized and/or enumerated using a FACS-based method with a fluorescent probe that specifically binds to mitochondria in a mitochondrial membrane potential (MMP)-independent manner. Fluorescent probes that specifically bind to mitochondria in a MMP-independent manner include, but are not limited to, accumulation dependent probes (e.g., JC-1 (red spectrum; INVITROGEN® T3168), MitoTracker Deep Red FM (IN-VITROGEN® M22426) and JC-1 (green spectrum; INVIT- ROGEN® T3168)). Functional (e.g., respiring) mitochondria can be sorted and collected, preferably with exclusion of residual unlysed cells and non-functional mitochondria, based on size and fluorescence intensity using mitochondrial tracking probes that indicate mitochondrial mass including, but not limited to, non-oxidation dependent probes (e.g., MitoTracker Green FM (INVITROGEN® M7514)). Details of an exemplary protocol for conducting FACS with a non-oxidation dependent probe are provided below in Example 10. Optionally, the FACS-based method can also be employed to selectively yield a pure population of functional (e.g., respiring) mitochondria using a mitochondrial membrane fluorescent probe that specifically binds to mitochondria in a MMP-dependent manner. Fluorescent probes that specifically bind to mitochondria in a MMP-dependent manner include, but are not limited to, reduced oxidative state mitotracker probes (e.g., MitoTracker Red CM-H2XRos (Invitrogen M7513) and MitoTracker Orange CM-H2TMRos (INVITROGEN® M7511). Furthermore, dual-labeling using MMP-dependent and MMP-independent probes can be conducted to quantitate the ratio of functional to total mitochondria in a tissue, cell, lysed cell or fraction derived thereof. When using probes for differential screening based on MMP, spectral color is the major determining factor to designate functional mitochondria, and forward scatter can be used to distinguish the fluorescent mitochondria released from lysed cells from those still contained in residual unlysed cells.

Mitochondrial pellets can also be prepared as described by Taylor et al., Nat Biotechnol. 2003 March; 21(3): 239-40; Hanson et al., Electrophoresis. 2001 March; 22(5): 950-9; and Hanson et al., J Biol Chem. 2001 May 11; 276(19): 16296-301. In specific embodiments of the invention, the total OSC-derived mitochondrial population in a tissue, cell, lysed cell, or fraction thereof can be isolated, characterized and/or enumerated using a differential centrifugation method as described herein at Example 11 or using a sucrose gradient separation procedure as described herein at Example 12.

Following isolation, assessment of mitochondrial DNA (mtDNA) integrity (e.g., mutations and deletions) can be conducted according to methods known in the art (Duran et al., *Fertility and Sterility* 2011 96(2):384-388; Aral et al., *Genetics and Molecular Biology* 2010 33:1-4; Chan et al., *Molecular Human Reproduction* 2005 11(12):843-846; Chen et al., *BMC Medical Genetics* 2011 12:8). Populations of mitochondria sorted according to functional parameters (e.g., MMP dependent/active or MMP-independent/active plus inactive) or mitochondria from less preferred OSC sources, including samples of limited size, can be now be obtained according to the methods of the invention.

Optionally, one or more bioenergetic agents can be added to the mitochondrial preparation prior to mitochondrial extraction from cells, mitochondrial isolation from cell extracts or mitochondrial injection. Microinjection needles and holding pipettes can be made using a Sutter puller (Sutter Instruments, Novato, Calif., USA) and a De Fonbrune Microforge (EB Sciences, East Granby, Conn., USA). The microinjection needles have inner diameters of 5 µm with blunt tips. The material to be injected is aspirated into the needle by negative suction. Between about $1 \times 10^3$- to about $5 \times 10^4$ mitochondria from OSCs or their progeny can be injected (e.g., about 1, 2, 3, 4, 5, 6, 7, 8 to $9 \times 10^3$; about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 to about $5 \times 10^4$ mitochondria). The material (e.g., mitochondrial suspension) in sucrose (e.g., 5-7 pl containing approximately $1 \times 10^3$-$5 \times 10^4$ mitochondria from OSCs or their progeny) can be injected into oocytes using a Piezo micromanipulator. Oocytes that survive the microinjection procedure are transferred for culture and optionally, assessment or cryopreservation prior to in vitro fertilization or intrauterine insemination. Optionally, mitochondrial suspensions can be co-injected with a single sperm during in vitro fertilization, in a process referred to as intracytoplasmic sperm injection (ICSI). Optionally, oocytes can be cultured in the presence of one or more bioenergetic agents prior to cryopreservation, in vitro fertilization or intrauterine insemination. Methods of oocyte cryopreservation are well known in the art. For details, see Porcu et al., *Mol Cell Endocrinol* 2000 169:33-37; Mandelbaum, *Hum Reprod* 2000 15:43-47; Fabbri et al., *Mod Cell Endocrinol* 2000 169:39-42, the contents of which are incorporated herein by reference.

Methods for the preparation and transfer of nuclear-free cytoplasmic fractions are known in the art and can be carried out as previously described. See, for example, Cohen et al., *Mod Hum Reprod* 1998 4:269-280, the contents of which are incorporated herein by reference. Briefly, approximately 4 hours after egg retrieval, recipient eggs are exposed to 0.1% hyaluronidase, and mature eggs are selected for injection. All corona cells are removed with fine bore pipettes. Ooplasmic transfer can be performed by electrofusion of OSC ooplast with intact MII oocytes. After exposure to 0.1% hyaluronidase zonae are opened mechanically using a microspear. OSCs and/or oocytes are exposed to hHTF medium containing cytochalasin B (CCB; Sigma Aldrich Corporation, St Louis, Mo., USA) for 10 min at 37° C. Partitioning of human MII oocytes involves variable cytochalasin B concentration depending on their sensitivity (~2.5 mg/ml). Ooplasts of various sizes are separated from OSCs and/or oocytes by withdrawing a portion of ooplasm enclosed in the plasma membrane. Ooplasts can optionally be combined with bioenergetic agents. Alignment and electrofusion in a mannitol solution is performed after insertion of the ooplast into the perivitelline space of the recipient egg from which the polar body was removed. This can be done with a wide-bored polished microtool ~30-40 µm in diameter. The ooplast is sucked into the microtool and released once the tool is placed deeply into the perivitelline space. Oocytes that survive the electrofusion procedure are transferred for culture and optionally, assessment or cryopreservation prior to in vitro fertilization or intrauterine insemination. Optionally, oocytes can be cultured in the presence of one or more bioenergetic agents prior to cryopreservation in vitro fertilization or intrauterine insemination.

Alternatively, conventional intracytoplasmic sperm injection (ICSI) methods can be employed in connection with the transfer of nuclear-free cytoplasmic fractions or isolated mitochondria, either with or without bioenergetic agents. See, for example, Cohen et al., *Mol Hum Reprod* 1998 4:269-280, the contents of which are incorporated herein by reference. As one example, the zonae of the recipient eggs are opened mechanically over the polar body area using a microspear. The polar body is removed after re-positioning the oocyte on the holding pipette in such a way that the zona can be dissected using the closed microspear. The same position is used to insert the ooplast ~90° left of the area, which had contained the polar body. The zona is closed tight using the same tool. Electrofused cells are washed and incubated in HTF for 40-90 min prior to ICSI. Spermatozoa are immobilized in 10% polyvinylpyrrolidone (PVP) for ICSI. The procedure is performed in HTF while the short side of the aperture is at approximately 3 o'clock. The ICSI tool is moved through the artificial gap in order to avoid extrusion of ooplasm upon indentation of the zona during standard ICSI. Zygotes can be cultured in the presence of one or more bioenergetic agents prior to uterine transfer.

Standard methods of in vitro fertilization are well known in the art. Couples are generally first evaluated to diagnose their particular infertility problem(s). These may range from unexplained infertility of both partners to severe problems of the female (e.g., endometriosis resulting in nonpatent oviducts with irregular menstrual cycles or polycystic ovarian disease) or the male (e.g., low sperm count with morphological abnormalities, or an inability to ejaculate normally as with spinal cord lesions, retrograde ejaculation, or reversed vasectomy). The results of these evaluations also determine the specific procedure to be performed for each couple.

Procedures often begin with the administration of a drug to down-regulate the hypothalamic/pituitary system (gonadotropin-releasing hormone or GnRH agonist). This process decreases serum concentrations of the gonadotropins, and developing ovarian follicles degenerate, thereby providing a set of new follicles at earlier stages of development. This permits more precise control of the maturation of these new follicles by administration of exogenous gonadotropins in the absence of influences by the hypothalamic pituitary axis. The progress of maturation and the number of growing follicles (usually four to ten stimulated per ovary) are monitored by daily observations using ultrasound and serum estradiol determinations. When the follicles attain preovulatory size (18-21 mm) and estradiol concentrations continue to rise linearly, the ovulatory response is initiated by exogenous administration of human chorionic gonadotropin (hCG).

Prior to the transplantation procedure, individual oocytes can be evaluated morphologically and transferred to a petri dish containing culture media and heat-inactivated serum and optionally, oocytes can be cultured in the presence of one or more bioenergetic agents. A semen sample is provided by the male partner and processed using a "swim up" procedure, whereby the most active, motile sperm will be obtained for insemination. If the female's oviducts are present, a procedure called GIFT (gamete intrafallopian transfer) can be performed at this time. By this approach, oocyte-cumulus complexes surrounded by sperm are placed directly into the oviducts by laparoscopy, wither with or without bioenergetic agents. This procedure best simulates the normal sequences of events and permits fertilization to occur within the oviducts. Not surprisingly, GIFT has the highest success rate with 22% of the 3,750 patients undergoing ova retrieval in 1990 having a live delivery. An alternative procedure ZIFT (zygote intrafallopian transfer) permits the selection of preimplantation embryos derived from in vitro fertilized zygotes to be transferred to oviducts the day following ova retrieval, either with or without bioenergetic agents. Extra zygotes and/or preimplantation embryos can be cryopreserved at this time for future transfer or for donation to couples without female gametes. Most patients having more serious infertility problems, however, will require an additional one to two days incubation in culture so that preimplantation embryos in the early cleavage states can be selected for transfer to the uterus. This IVF-UT (in vitro fertilization uterine transfer) procedure entails the transcervical transfer of several 2-6 cell (day 2) or 8-16 (day 3) preimplantation embryos to the fundus of the uterus (4-5 preimplantation embryos provides optimal success).

Procedures for in vitro fertilization are also described in U.S. Pat. Nos. 6,610,543 6,585,982, 6,544,166, 6,352,997, 6,281,013, 6,196,965, 6,130,086, 6,110,741, 6,040,340, 6,011,015, 6,010,448, 5,961,444, 5,882,928, 5,827,174, 5,760,024, 5,744,366, 5,635,366, 5,691,194, 5,627,066, 5,563,059, 5,541,081, 5,538,948, 5,532,155, 5,512,476, 5,360,389, 5,296,375, 5,160,312, 5,147,315, 5,084,004, 4,902,286, 4,865,589, 4,846,785, 4,845,077, 4,832,681, 4,790,814, 4,725,579, 4,701,161, 4,654,025, 4,642,094, 4,589,402, 4,339,434, 4,326,505, 4,193,392, 4,062,942, and 3,854,470, the contents of which are specifically incorporated by reference for their description of these procedures.

Alternatively, patients may elect to have the oocyte, optionally comprising exogenous, autologous OSC mitochondria, reimplanted and fertilized in vivo using Intrauterine Insemination (IUI). IUI is a well known process that involves preparing and delivering a highly concentrated amount of active motile sperm directly through the cervix into the uterus. There are several techniques available for preparing the sperm for IUI. First, sperm is separated from seminal fluid. One method of sperm separation is known as "Density Gradient Separation". In this technique, motile sperm are separated from dead sperm and other cells through the use of viscous solution. After preparation, the sperm concentrate is placed through the cervix into the uterus by using a thin, flexible catheter and fertilization of the reimplanted oocyte follows.

Culture Medium

Physiologically compatible solutions can be formulated or supplemented with effective amounts of bioenergetic agents or functional derivatives thereof for conducting the methods of the invention (e.g., IVF, cryopreservation, gamete preparation, cell and/or embryo washing or culture). *Cell culture medium*, embryo culture medium and cryopreservation solutions, for example, are well known in the art and can be formulated or supplemented as needed using standard methods known in the art for the preparation of physiological solutions. Commercially available medium for the preparation and handling of gametes for in vitro fertilization includes G-IVF™ PLUS, available from Invitrolife, which is a bicarbonate buffered medium containing human serum albumin and gentamicin as an antibacterial agent. SAGE Media™ maturation medium for oocytes contains sodium chloride, potassium chloride, sodium bicarbonate, glucose, sodium pyruvate, phenol red, gentamicin, nonessential and essential amino acids, magnesium sulfate, sodium phosphate, calcium chloride, D-calcium pantothenate, chlorine chloride, folic acid, i-inositol, nicotinamide, pyridoxine, HCL, riboflavin, and thiamine, supplemented with a final concentration of 75 mIU/ml FSH and 75 mIU/ml LH supplemented with a final concentration of 75 mIU/ml FSH and 75 mIU/ml LH. Media products for freezing and containment of human blastocysts include SAGE Media™ equilibration solution and vitrification solution available from SAGE In Vitro Fertilization, Inc. Ovarian follicle maturation medium is also well known in the art and described, for example, by Telfer et al., *Hum Reprod* 2008 23:1151-1158, the contents of which are expressly incorporated herein by reference. The SAGE Media™ equilibration solution is a MOPS buffered solution of modified HTF containing nonessential and essential amino acids, gentamicin sulfate (0.01 g/L), 7.5% (v/v) each of DMSO and ethylene glycol and 12 mg/mL human albumin. The vitrification solution is a MOPS buffered solution of modified human tubal fluid (HTF) containing nonessential and essential amino acids, gentamicin sulfate (0.01 g/L), and 15% (v/v) each of DMSO and ethylene. SAGE blastocyst medium is formulated for use with in vitro fertilization procedures involving the culture of human embryos from the compaction phase on day 3 of development to the blastocyst stage and consists of sodium chloride, potassium chloride, potassium phosphate, magnesium sulfate, calcium lactate, sodium bicarbonate, glucose, sodium pyruvate, taurine, glutathione, alanyl-glutamine, L-asparagine, L-aspartic acid, glycine, L-proline, L-serine, L-arginine, L-cystine, L-histidine, L-isoleucine, L-leucine, L-lysine, L-methionine, L-phenylalanine, L-threonine, L-tryptophan, L-tyrosine, L-valine, D-calcium pantothenate, choline chloride, folic acid, I-inositol, nicotinamide, pyridoxine, riboflavin, thiamine, gentamicin and phenol red. SAGE cleavage medium is formulated for use with in vitro fertilization procedures involving the culture of cleavage stage human embryos and consists of sodium chloride, potassium chloride, magnesium sulfate, calcium lactate, sodium bicarbonate, glucose, sodium pyruvate, alanyl-glutamine, taurine, L-asparagine, L-aspartic acid, glycine, L-proline, L-serine, sodium citrate, EDTA, gentamicin and phenol red. SAGE fertilization medium is formulated for use with in vitro procedures involving the fertilization of human oocytes and consists of sodium chloride, potassium chloride, magnesium sulfate, potassium phosphate, calcium lactate, sodium bicarbonate, glucose, sodium pyruvate, glutamine, taurine, L-Asparagine, L-Aspartic acid, glycine, L-Proline, L-Serine, sodium citrate, EDTA, gentamicin and phenol red. Several products are commercially available from LIFEGLOBAL® Group LLC, USA, including solutions for embryo washing and handling (consisting of sodium chloride, potassium chloride, calcium chloride, potassium phosphate, magnesium sulfate, sodium bicarbonate, glucose, lactate na salt, sodium pyruvate, amino acids, edta, gentamicin phenol red, and HEPES, optionally enriched with selected non-essential amino acids); oocyte retrieval and washing (consisting of sodium chloride, potassium chloride, calcium chloride, potassium phosphate, magnesium sulfate, sodium bicarbonate, glucose, lactate na salt, sodium pyruvate, gentamicin, phenol red, and HEPES); embryo culture from day 1 to the blastocyst stage (consisting of sodium chloride, potassium chloride, calcium chloride, potassium phosphate, magnesium sulfate, sodium bicarbonate, glucose, lactate na salt, sodium pyruvate, amino acids, edta, gentamicin and phenol red); maintenance of embryos during the biopsy procedure (consisting of sodium chloride, potassium chloride, potassium phosphate, sodium bicarbonate, glucose sodium lactate, sodium pyruvate, amino acids, edta, phenol red, gentamicin sulfate, HEPES, sucrose and human serum albumin); embryo freezing (consisting of sodium chloride, calcium chloride, potassium chloride, potassium phosphate, magnesium chloride, sodium phosphate, and human serum albumin) and embryo thawing (consisting of sodium chloride, calcium chloride, potassium chloride, potassium phosphate, magnesium chloride, sodium phosphate, human serum albumin and optionally 1,2-propanediol and sucrose). EARLY CLEAVAGE MEDIA™ (ECM®) is available from Irvine Scientific, Santa Ana, Calif., USA, and is intended for use in culturing human gametes during fertilization (IVF) and growth of embryos through day 3 of development. This solution consists of glucose sodium, pyruvate sodium, lactate (d/l), sodium chloride, potassium chloride, magnesium sulfate, calcium chloride, sodium bicarbonate, alanyl-glutamine, taurine, sodium citrate, edta, disodium, dehydrate, phenol red, gentamicin, and sulfate. A culture medium for human gametes and embryos during fertilization and growth of embryos up to day 5/6 of development is also available from Irvine Scientific, Santa Ana, Calif., USA, and consists of sodium chloride, potassium chloride, potassium phosphate, calcium chloride, magnesium sulfate, sodium bicarbonate, sodium pyruvate, glucose, sodium lactate, EDTA, dipeptide, alanyl-glutamine, phenol red, gentamicin, alanine, asparagines, aspartic acid, glutamic acid, glycine, proline, serine, arginine, cystine, histidine, isoleucine, leucine, lysine, methionine, phenylalanine, threonine, tryptophan, tyrosine and valine.

Accordingly, appropriate selection or formulation of medium for use in conducting assisted reproductive technologies (e.g., IVF) is routinely practiced by physicians and clinical laboratories. An effective amount of any one or more of the bioenergetic agents or functional derivatives thereof can be added to the medium of interest either prior to, during or following protocols conducted in connection with assisted reproductive technologies, which are well known in the art. The concentration, time and other conditions used will be optimized to achieve maximum exposure of the bioenergetic agents or functional derivatives thereof to the desired tissues or cells of interest, including, but not limited to, ovarian tissue, oocytes, OSCs or derivatives thereof (e.g., cytoplasm or isolated mitochondria) or preimplantation embryos. Tissues and/or cells of interest can be treated, ex vivo, using medium comprising bioenergetic agents or functional derivatives thereof prior to or during procedures associated with assisted reproductive technologies known in the art including, but not limited to, oocyte or OSC maturation and collection, ovarian follicle maturation, ovarian tissue or ovarian cell grafting, ovarian tissue or ovarian cell transplantation, cryopreservation, in vitro fertilization, as well as the culture of human oocytes, zygotes and preimplantation embryos.

The present invention also provides methods of producing an oocyte, comprising culturing a stem cell, including but not limited to, an OSC, embryonic stem cell, skin stem cell, pancreatic stem cell, and induced pluripotent stem cell (iPS cell) in the presence of a bioenergetic agent or a functional derivative thereof, under conditions sufficient to differentiate the stem cell into an oocyte.

Stem cells can undergo self-renewing cell division to give rise to phenotypically and genotypically identical daughters for an indefinite time and ultimately can differentiate into at least one final cell type. Stem cells are defined as cells that have extensive, and perhaps indefinite, proliferation potential that differentiate into several cell lineages, and that can repopulate tissues upon transplantation. The quintessential stem cell is the embryonic stem (ES) cell, as it has unlimited self-renewal and multipotent differentiation potential. These cells are derived from the inner cell mass of the blastocyst, or can be derived from the primordial germ cells from a post-implantation embryo (embryonic germ cells or EG cells). ES and EG cells have been derived from mouse, non-human primates and humans. When introduced into mouse blastocysts or blastocysts of other animals, ES cells can contribute to all tissues of the mouse (animal). When transplanted in post-natal animals, ES and EG cells generate teratomas, which again demonstrates their multipotency.

Somatic stem cells have been identified in most organ tissues. Accordingly, in some embodiments, the stem cells useful for the oocyte differentiation and/or maturation culture methods described herein include, but are not limited to OSCs, mesenchymal stem cells, bone-marrow derived stem cells, hematopoietic stem cells, chrondrocyte progenitor cells, skin stem cells (e.g., epidermal stem cells), gastrointestinal stem cells, neural stem cells, hepatic stem cells, adipose-derived mesenchymal stem cells, pancreatic progenitor and/or stem cells, hair follicular stem cells, endothelial progenitor cells and smooth muscle progenitor cells.

An "induced pluripotent stem (iPS) cell" is a cell that exhibits characteristics similar to embryonic stem cells (ESCs) including, for example, unlimited self renewal in vitro, a normal karyotype, a characteristic gene expression pattern including stem cell marker genes like Oct3/4, Sox2, Nanog, alkaline phosphatase (ALP) and stem cell-specific antigen 3 and 4 (SSEA3/4), and the capacity to differentiate into specialized cell types (Hanna et al., *Science* 2007 318: 1920-1923; Meissner A. et al. *Nat Biotechnol* 2007 25(10): 1177-81, Okita K. et al. *Nature* 2007 448(7151): 313-7, Takahashi K. et al. *Cell* 2007 131(5): 861-72, Wernig M. et al. *Nature* 2007 448(7151): 318-24, Yu J. et al. *Science* 2007 318(5858): 1917-20, and Park, I. H. et al. *Nature* 2008 451(7175): 141-6. The state of the art generation of iPS cells from fibroblast cultures has been described in Takahashi, Okita, Nakagawa, Yamanaka Nature Protocols (2007) 2(12).

Conditions for the differentiation and/or maturation of cells, including stem cells, progenitor cells and reprogrammed cells into oocytes are known in the art and are described, for example, by Danner S. et al. *Mod Hum Reprod.* 2007 January; 13(1):11-20, Dyce P. W. et al. *PLoS One.* 2011; 6(5), Dyce P. W. et al. *Stem Cells Dev.* 2011 May; 20(5):809-19, Linher K. et al. *PLoS One.* 2009 Dec. 14; 4(12), Dyce P. W. et al. *Nat Cell Biol.* 2006 April; 8(4):384-90, Panula S. et al. *Hum Mol Genet.* 2011 Feb. 15; 20(4): 752-62, Park T. S. et al., *Stem Cells* 2009 April; 27(4):783-95, Hua J. et al., *Stem Cells Dev.* 2008 June; 17(3):399-411, Aflatoonian B. et al. *Reproduction* 2006 November; 132(5): 699-707, Ko K. et al. *Semin Reprod Med.* 2006 November; 24(5):322-9, Ko K. et al. *Front Biosci.* 2010 Jan. 1; 15:46-56, Psathaki O. E. et al. *Stem Cells Dev.* 2011 Mar. 8. [Epub ahead of print], and Hübner K. et al. *Science* 2003 May 23; 300(5623):1251-6, the contents of which are expressly incorporated herein by reference. In particular, methods described by Telfer E. et al. *Hum Reprod.* 2008; 23(5): 1151-8 describing a two-step serum-free culture system to support development of human oocytes from primordial follicles in the presence of activin can be used together with the bioenergetic agents or functional derivatives thereof. An effective amount of any one or more of the bioenergetic agents or functional derivatives thereof can be added to the culture medium of interest either prior to, during or following oocyte differentiation and/or maturation protocols, which are well known in the art. The concentration, time and other conditions used will be optimized to achieve maximum exposure of the bioenergetic agents or functional derivatives thereof to the stem cells and oocyte derivatives thereof.

Methods of Improving Fertility and/or Restoring Reproductive Function

Bioenergetic agents and functional derivatives thereof can be used in a variety of therapeutic applications for the treatment of infertility, reproductive disorders or symptoms of reproductive aging in female subjects. In some instances, the menopausal female subjects can be in a stage of either peri- or post-menopause, with said menopause caused by either normal (e.g., aging) or pathological (e.g., surgery, disease, ovarian damage) processes. Restoration of reproductive (e.g., ovarian) function can relieve adverse symptoms and complications associated with menopause, including, but not limited to, somatic disorders such as osteoporosis, cardiovascular disease, somatic sexual dysfunction, hot flashes, vaginal drying, sleep disorders, depression, irritability, loss of libido, hormone imbalances, and the like, as well as cognitive disorders, such as loss of memory; emotional disorders, depression, and the like.

Thus, the present invention provides methods for improving fertility in a female subject comprising administering a bioenergetic agent or a functional derivative thereof, in an amount effective to improve oocyte and/or OSC de novo production, quality and/or ovulated oocyte yield.

The present invention also provides methods of in vitro fertilization comprising the steps of:

a) administering to a female subject a bioenergetic agent or a functional derivative thereof, in an amount effective to improve oocyte and/or OSC de novo production, quality and/or ovulated oocyte yield;

b) obtaining an oocyte from the female subject (including obtaining the oocyte from an OSC or tissue of a female subject e.g., an in vitro derived or matured oocyte); and c) fertilizing the oocyte in vitro to form a zygote.

Step b) and/or step c) can further comprise incubating the oocyte or source thereof with a bioenergetic agent or a functional derivative thereof. Administration of the bioenergetic agent can occur before oocyte, OSC or ovarian tissue harvest and continue throughout the procedure, including after transferring the zygote, or a preimplantation stage embryo into the uterus of the female subject (or a surrogate female subject) and continuing, or initiating, administration of the bioenergetic agent to the pregnant female subject.

The present invention also provides methods of restoring ovarian function in a female subject in need thereof comprising administering a therapeutically effective amount of a bioenergetic agent or a functional derivative thereof, thereby restoring ovarian function in the female subject. In general, restoring ovarian function provides restoration of reproductive health benefits, including but not limited to, normal hormone production, menstrual cycling and adequate oocyte and OSC reserves. The female subject in need of restored ovarian function can have, for example, premature ovarian failure.

The present invention also provides methods for sustaining, maintaining and/or prolonging embryonic development in a pregnant female subject in need thereof comprising administering a therapeutically effective amount of a bioenergetic agent or a functional derivative thereof.

In some embodiments, methods of the invention have beneficial effects on pregnancy outcomes, which include but are not limited to, a greater number of viable embryo transfers, increased fertilization and pregnancy rates (e.g., with corresponding decreases in the number of implanted embryos), decreased rates of multiple births, and improved implantation, gestation and embryogenesis, collectively referred to herein as "pregnancy success" when compared to a reference standard. A standard can permit one of skill in the art to determine the amount of pregnancy success by evaluating the relative increase and/or decrease of one or more parameters (e.g., viable embryo transfers, fertilization and pregnancy rates, numbers of implanted embryos, multiple births, implantation, and length of gestation and embryogenesis). A standard serves as a reference level for comparison, such that results can be normalized to an appropriate standard in order to infer the presence, absence or extent of a pregnancy success. In one embodiment, a standard is obtained from the same individual as that being tested, at an earlier time point (i.e., before initiation of treatment with a bioenergetic agent or functional derivative thereof). Thus, one or more parameters contributing to pregnancy success from a patient is compared to previous history associated with the same parameters, which acts as a reference. This type of standard is generally the most accurate for diagnostic, prognostic and efficacy monitoring purposes, since a majority of factors will remain relatively similar in one individual over time. The standard should ideally be obtained prior to the onset of treatment. However, a standard can be obtained from an individual after the treatment as it can still provide information about improvement or regression of the treatment. A standard can also be obtained from another individual or a plurality of individuals, wherein a standard represents an average level pregnancy success among a population of individuals with or without treatment. Thus, the level of pregnancy success in a standard obtained in this manner is representative of an average level in the given population, such as a general population of females of reproductive age.

The present invention also provides methods of preparing a tissue or cell thereof from a female subject for harvest (e.g., removal from the body), comprising administering an effective amount of a bioenergetic agent or a functional derivatives thereof, to the female subject, thereby preparing said tissue or cell thereof from the female subject for harvest. The tissue can be, for example, ovary, ovarian follicle, bone marrow and peripheral blood and the cell can be, for example, an oocyte or an OSC. Harvested tissues and/or cells of interest can optionally be treated, ex vivo, using medium comprising bioenergetic agents or functional derivatives thereof prior to or during procedures associated with assisted reproductive technologies known in the art including, but not limited to, oocyte or OSC maturation and collection, ovarian follicle maturation, grafting, transplantation, cryopreservation, in vitro fertilization, as well as the culture of human embryos and zygotes.

By "an effective amount" or "therapeutically effective amount" is meant the amount of a required a bioenergetic agent or a functional derivative thereof, or composition comprising the agent to ameliorate the symptoms of a disorder (e.g., infertility, age related reproductive decline) relative to an untreated patient. The effective amount of agents used to practice the present invention for therapeutic treatment varies depending upon the manner of administration, the age, body weight, and general health of the subject. Ultimately, the attending physician will decide the appropriate amount and dosage regimen. Such amount is referred to as an "effective" amount" or "therapeutically effective amount."

Generally, doses of the compounds of the present invention would be from about 0.01 mg/kg per day to about 2000 mg/kg per day. In one embodiment, 0.01, 0.05, 0.1, 0.5, 1, 3, 5, 10, 15, 20, 25, 50, 75, 100, 125, 150, 200, 300, 400, 500, 600, 700, 800, 900, 1000, 1200, 1500, 1700, 1800, 1900, 2000 mg of a bioenergetic agent (e.g., Sirt1 activator, CD38 inhibitor) is administered to a subject. Effective doses range from about 0.01 mg/kg per day to about 2000 mg/kg per day, where the bottom of the range is any integer between 0.01 and 1999, and the top of the range is any integer between 0.02 and 1000. It is expected that doses ranging from about 5 to about 2000 mg/kg will be suitable—depending on the specific bioenergetic agent used. Lower doses will result from certain forms of administration, such as intravenous administration and pharmaceutical. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of a composition of the present invention.

The invention provides methods of administering pharmaceutical compositions and formulations comprising bioenergetic agents or functional derivatives thereof. In alternative embodiments, the compositions of the invention are formulated with a pharmaceutically acceptable carrier. In alternative embodiments, the pharmaceutical compositions and formulations of the invention can be administered parenterally, topically, orally or by local administration, such as by aerosol or transdermally. The pharmaceutical compositions can be formulated in any way and can be administered in a variety of unit dosage forms depending upon the condition or disease (e.g., type of reproductive disorder) and the degree of illness, the general medical condition of each patient, the resulting preferred method of administration and the like. Details on techniques for formulation and administration of pharmaceuticals are well described in the scientific and patent literature, see, e.g., the latest edition of Remington's Pharmaceutical Sciences, Maack Publishing Co, Easton Pa. ("Remington's").

Bioenergetic agents or functional derivatives thereof can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., bioenergetic agents, or functional derivatives thereof) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g. improved oocyte or OSC production and quality and/or increased yield of ovulated oocytes.

Pharmaceutical formulations of this invention can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., bioenergetic agents, or functional derivatives thereof) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In one embodiment, oil-based pharmaceuticals are used for administration of nucleic acid sequences of the invention. Oil-based suspensions can be formulated by suspending an active agent in a vegetable oil, such as *arachis* oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto et al., J. Pharmacol. Exp. Ther. 1997 281:93-102.

Pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

In practicing this invention, the pharmaceutical compounds can also be administered by in intranasal, intraocular and intravaginal routes including suppositories, insufflation, powders and aerosol formulations (for examples of steroid inhalants, see e.g., Rohatagi J. Clin. Pharmacol. 1995 35:1187-1193; Tjwa et al., Ann. Allergy Asthma Immunol. 1995 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In practicing this invention, the pharmaceutical compounds can be delivered transdermally, by a topical route, formulated as applicator sticks, solutions, suspensions, emulsions, gels, creams, ointments, pastes, jellies, paints, powders, and aerosols.

In practicing this invention, the pharmaceutical compounds can also be delivered as microspheres for slow release in the body. For example, microspheres can be administered via intradermal injection of drug which slowly release subcutaneously; see Rao J. Biomater Sci. Polym. Ed. 1995 7:623-645; as biodegradable and injectable gel formulations, see, e.g., Gao Pharm. Res. 1995 12:857-863; or, as microspheres for oral administration, see, e.g., Eyles J. Pharm. Pharmacol. 1997 49:669-674.

In practicing this invention, the pharmaceutical compounds can be parenterally administered, such as by intravenous (IV) administration or administration into a body cavity or directly into the ovary. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

The pharmaceutical compounds and formulations of the invention can be lyophilized. The invention provides a stable lyophilized formulation comprising a composition of the invention, which can be made by lyophilizing a solution comprising a pharmaceutical of the invention and a bulking agent, e.g., mannitol, trehalose, raffinose, and sucrose or mixtures thereof.

The compositions and formulations of the invention can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed J. Microencapsul. 1996 13:293-306; Chonn Curr. Opin. Biotechnol. 1995 6:698-708; Ostro Am. J. Hosp. Pharm. 1989 46:1576-1587.

The formulations of the invention can be administered for prophylactic and/or therapeutic treatments. In alternative embodiments, for therapeutic applications, compositions are administered to a subject in need of improved oocyte or OSC production and quality and/or increased yield of ovulated oocytes in an amount sufficient to cure, alleviate or partially arrest the clinical manifestations of the reproductive disorder or its complications, e.g., infertility, menopause, premature ovarian failure; this can be called a therapeutically effective amount.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones J. Steroid Biochem. Mol. Biol. 1996 58:611-617; Groning Pharmazie 199651:337-341; Fotherby Contraception 1996 54:59-69; Johnson J. Pharm. Sci. 1995 84:1144-1146; Rohatagi Pharmazie 1995 50:610-613; Brophy Eur. J. Clin. Pharmacol. 1983 24:103-108; the latest Remington's, supra. The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, the degree and amount of cholesterol homeostasis generated after each administration, and the like. The formulations should provide a sufficient quantity of active agent to effectively treat, prevent or ameliorate conditions, diseases or symptoms, e.g., improve oocyte or OSC production and quality and/or increase yield of ovulated oocytes.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington's, supra.

The present invention is additionally described by way of the following illustrative, non-limiting Examples that provide a better understanding of the present invention and of its many advantages.

EXAMPLES

In Examples 1-6, validated protocols are employed to demonstrate that OSCs can be reliably isolated from tissues of healthy young women and propagated in vitro for use in subsequent clinical procedures. In Example 7, CR during adulthood is shown to improve oocyte quality and yield in female mice on the verge of reproductive failure due to advancing maternal age. In Example 8, similar to CR, bioenergetic factors are shown to increase mitochondrial parameters in OSCs. The following examples are put forth for illustrative purposes only and are not intended to limit the scope of what the inventors regard as their invention.

Example 1: FACS-Based Protocol for OSC Isolation

The VASA antibody used by Zou et al., *Nat Cell Biol* 2009 11:631-636 to isolate mouse OSCs by immunomagnetic sorting is a rabbit polyclonal against the last 25 amino acids of the COOH-terminus of human VASA (DDX4) (ab13840; Abcam, Cambridge, Mass., USA). This region shares 96% overall homology with the corresponding region of mouse VASA (MVH). For comparative studies, a goat polyclonal antibody against the first 145 amino acids of the $NH_2$-terminus of human VASA (AF2030; R&D Systems) was used, which shares 91% overall homology with the corresponding region of mouse VASA.

Figure 1A:
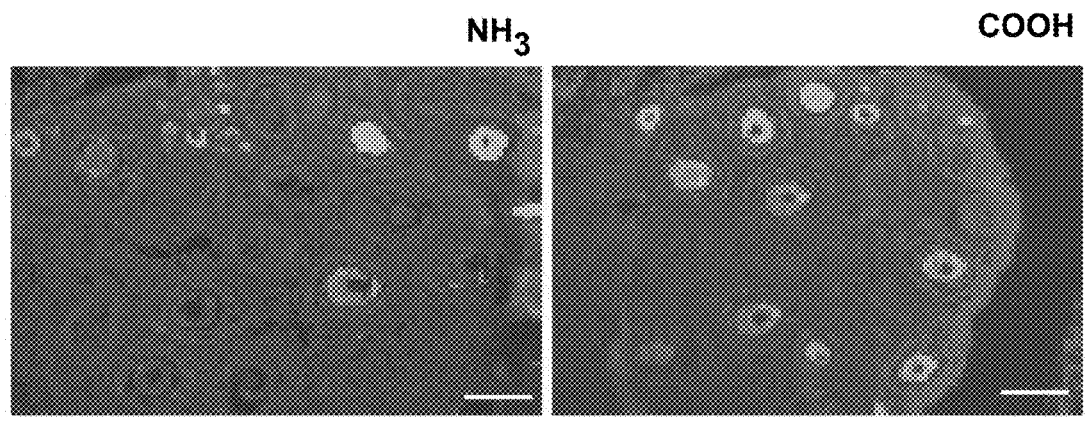
In FIG. 1a, immunofluorescence analysis of VASA expression (green with blue DAPI counterstain) is shown in adult mouse ovaries using antibodies against the $NH_2$ or COOH terminus of VASA (scale bars, 50 µm).

Immunofluorescence analysis of young adult (2-month-old) mouse ovaries using either antibody showed an identical pattern of VASA expression that was restricted, as expected, to oocytes (FIG. 1a). Each antibody was then used for immunomagnetic sorting of dispersed young adult mouse ovary tissue (Zou et al., *Nat Cell Biol* 2009 11:631-636). For each preparation of cells, ovaries from 4 mice were pooled and dissociated by mincing followed by a two-step enzymatic digestion involving a 15-minute incubation with 800 U/ml collagenase [type IV; prepared in Hank's balanced salt solution minus calcium and magnesium (HBSS)] followed by a 10-minute incubation with 0.05% trypsin-EDTA. Digestions were carried out in the presence of 1 μg/ml DNase-I (Sigma Aldrich Corporation, St. Louis, Mo., USA) to minimize stickiness within the cell preparations, and trypsin was neutralized by addition of 10% fetal bovine serum (FBS; HYCLONE®, GE Healthcare Bio-Sciences, Pittsburgh, Pa., USA). Ovarian dispersates were filtered through a 70-μm nylon mesh and blocked in a solution composed of 1% fatty-acid free bovine serum albumin (BSA; Sigma Aldrich Corporation, St. Louis, Mo., USA) with either 1% normal goat serum (Millipore; for subsequent reactions using ab13840 against VASA-COOH) or 1% normal donkey serum (Sigma Aldrich Corporation, St. Louis, Mo., USA; for subsequent reactions using AF2030 against VASA-$NH_2$) in HBSS for 20 minutes on ice. Cells were then reacted for 20 minutes on ice with a 1:10 dilution of VASA antibody that recognizes either the COOH terminus (ab13840) or $NH_2$ terminus (AF2030). Afterwards, cells were washed 2 times in HBSS and incubated for 20 minutes on ice with a 1:10 dilution of either goat anti-rabbit IgG-conjugated microbeads (Miltenyi; ab13840 detection) or biotin-conjugated donkey anti-goat IgG (Santa Cruz Biotechnology; AF2030 detection) followed by incubation with streptavidin-conjugated microbeads (Miltenyi). After one additional wash in HBSS, the cell preparations were loaded onto MACS columns and separated according to manufacturer's specifications (Miltenyi). For experiments to visualize potential antibody-bead interaction with individual oocytes, adult female mice were superovulated by injection of pregnant mare serum gonadotropin (PMSG, 10 IU; Sigma Aldrich Corporation, St. Louis, Mo., USA) followed by human chorionic gonadotropin (hCG, 10 IU; Sigma Aldrich Corporation, St. Louis, Mo., USA) 46-48 hours later. Oocytes were collected from oviducts 15-16 hours after hCG injection, denuded of cumulus cells using hyaluronidase (Irvine Scientific, Santa Ana, Calif., USA) and washed with human tubal fluid (HTF; Irvine Scientific, Santa Ana, Calif., USA) supplemented with BSA. Dispersed ovarian cells or isolated oocytes were blocked and incubated with primary antibodies against VASA as described above. After washing in HBSS, cells were reacted with species-appropriate secondary antibodies conjugated to 2.5-µm Dynabeads (INVITROGEN®). Suspensions were placed into 1.5 ml Eppendorf tubes for separation using a Dynal MPC®-S Magnetic Particle Concentrator.

Figure 1B:
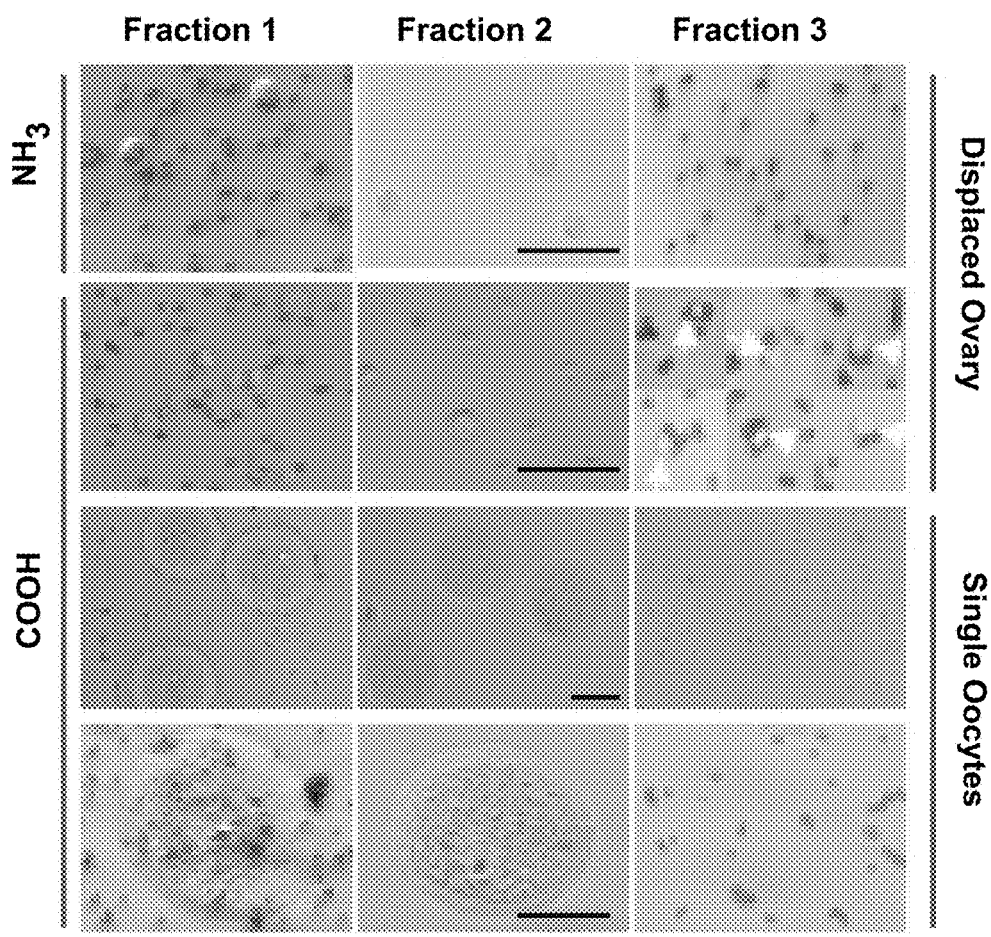
In FIG. 1b, immunomagnetic sorting of dispersed mouse ovaries or isolated oocytes is shown using antibodies against the $NH_2$ or COOH terminus of VASA. Fraction 1 contains cells plus beads prior to separation, Fraction 2 is a wash or flow-through fraction (non-immunoreactive) and Fraction 3 is a bead fraction (VASA-positive cells, highlighted by white arrows).
Figure 2:
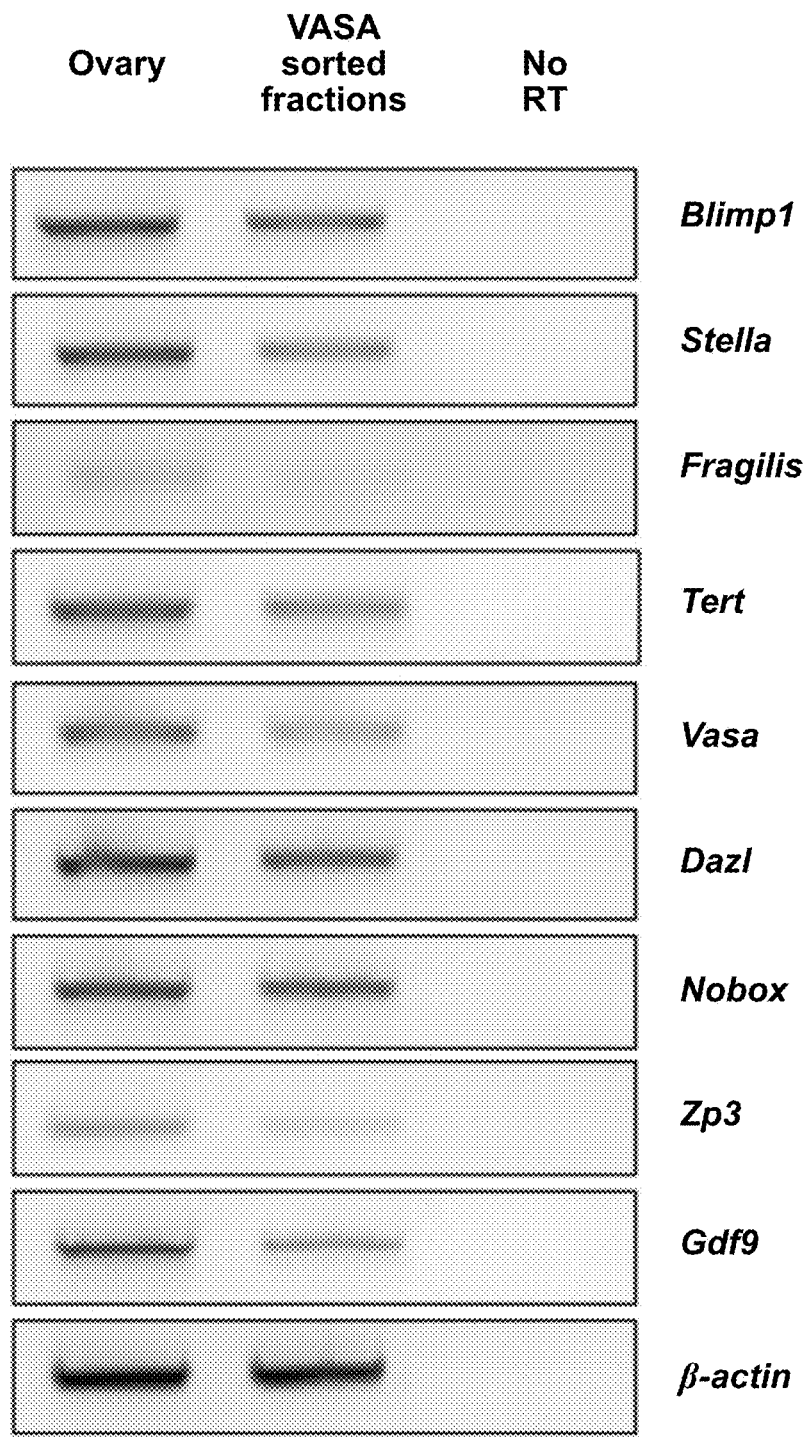
FIG. 2 depicts OSC fractions isolated from adult mouse ovaries by immunomagnetic bead sorting that contain contaminating oocytes. Gene expression analysis of germline markers (Blimp1, Stella, Fragilis, Tert, Vasa, Dazl) and oocyte-specific markers (Nobox, Zp3, Gdf9) is shown in young adult mouse ovaries (positive control) or the final cell fraction obtained following VASA-COOH antibody-based immunomagnetic bead sorting of dispersed young adult mouse ovaries (No RT, PCR of sorted cell RNA sample without reverse transcription; β-actin, sample loading control).

No cells were obtained in the bead fraction when the VASA-$NH_2$ antibody was used; however, 5-8 µm cells bound to the magnetic beads were observed when the VASA-COOH antibody was used (FIG. 1b). Analysis of these cells revealed a germline gene expression pattern consistent with that reported for OSCs isolated previously by Zou et al., *Nat Cell Biol* 2009 11:631-636 using immunomagnetic sorting (FIG. 2). Although isolated oocytes assessed in parallel using the VASA-COOH antibody were always detected in the non-immunoreactive wash fraction (FIG. 1b), additional marker analysis of the VASA-positive cell fraction obtained by immunomagnetic sorting revealed several oocyte-specific mRNAs including Nobox, Zp3 and Gdf9 (FIG. 2). These findings indicate that while oocytes do not exhibit cell surface expression of VASA when analyzed as individual entities (FIG. 1b), oocytes are nonetheless a contaminating cell type following immunomagnetic sorting of OSCs from dispersed ovary tissue. This outcome most likely reflects either a non-specific physical carry-over of oocytes during the bead centrifugation steps or reactivity of cytoplasmic VASA in plasma membrane-compromised (damaged) oocytes with the COOH antibody. Either case would be alleviated by use of FACS.

The reactivity of each antibody with dispersed mouse ovarian cells was next assessed by FACS. For each experiment, ovarian tissue (mouse: 4 ovaries pooled; human: 10×10×1 mm thick, cortex only) was dissociated, blocked and reacted with primary antibody (ab13840 for VASA-COOH or AF2030 for VASA-$NH_2$) as described above. After washing with HBSS, cells were incubated with a 1:500 dilution of goat anti-rabbit IgG conjugated to Alexa Fluor 488 (INVITROGEN®; ab13840 detection) or donkey anti-goat IgG conjugated to Alexa Fluor 488 (INVITROGEN®; AF2030 detection) for 20 minutes on ice, and washed with HBSS. Labeled cells were then filtered again (35-µm pore diameter) and sorted by FACS using a FACSARIA II® cytometer (BD Biosciences, San Jose, Calif., USA), gated against negative (unstained and no primary antibody) controls. Propidium iodide was added to the cell suspension just prior to sorting for dead cell exclusion. Freshly-isolated VASA-positive viable cells were collected for gene expression profiling, assessment of teratoma formation capacity or in-vitro culture. For some experiments, cells were fixed in 2% neutral-buffered paraformaldehyde (PFA) and permeabilized with 0.1% Triton-X100 prior to reaction with primary antibody against the $NH_2$ terminus of VASA (AF2030) and detection by FACS after reaction with donkey anti-goat IgG conjugated to Alexa Fluor 488. For re-sort experiments, viable cells were reacted with VASA-COOH antibody (ab13840) and sorted by FACS after reaction with a goat anti-rabbit IgG conjugated to allophcocyanin (APC) (Jackson Immunoresearch). Resultant APC-positive (VASA-COOH positive) viable cells were then either left intact or fixed and permeabilized prior to incubation with VASA-$NH_2$ antibody (AF2030), followed by incubation with donkey anti-goat IgG conjugated to Alexa Fluor 488 and FACS analysis.

Figure 1C:
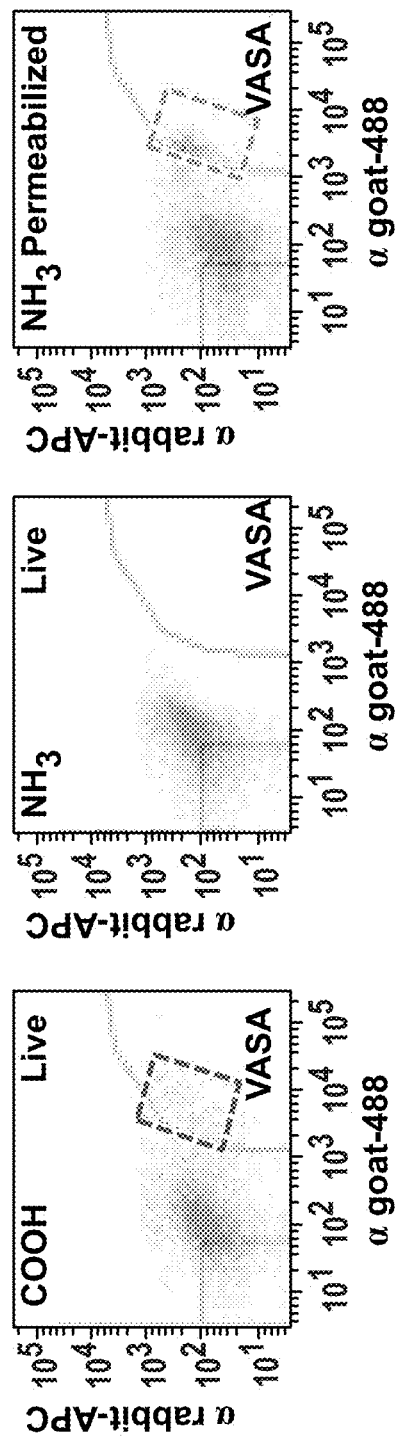
In FIG. 1c, FACS analysis of live or permeabilized cells from dispersed mouse ovaries using antibodies against the $NH_2$ or COOH terminus of VASA is shown. Viable VASA-positive cells are only detected with the COOH antibody (red dashed box) whereas permeabilization enables isolation of VASA-positive cells using the $NH_2$ antibody (blue dashed box).
Figure 1D:
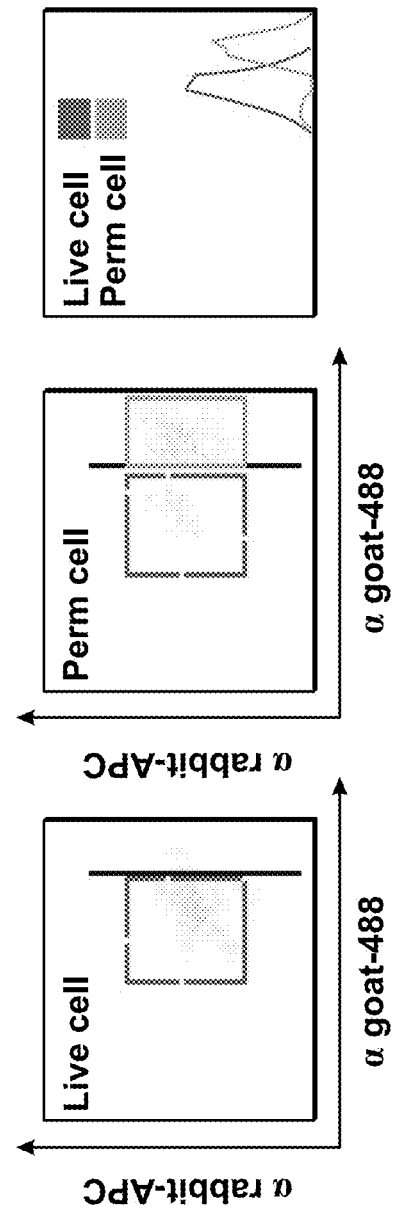
In FIG. 1d, permeabilization of viable VASA-positive cells (red dashed box) obtained with the COOH antibody enables re-isolation of the same cells by FACS using the $NH_2$ antibody (blue dashed box).
Figure 1E:
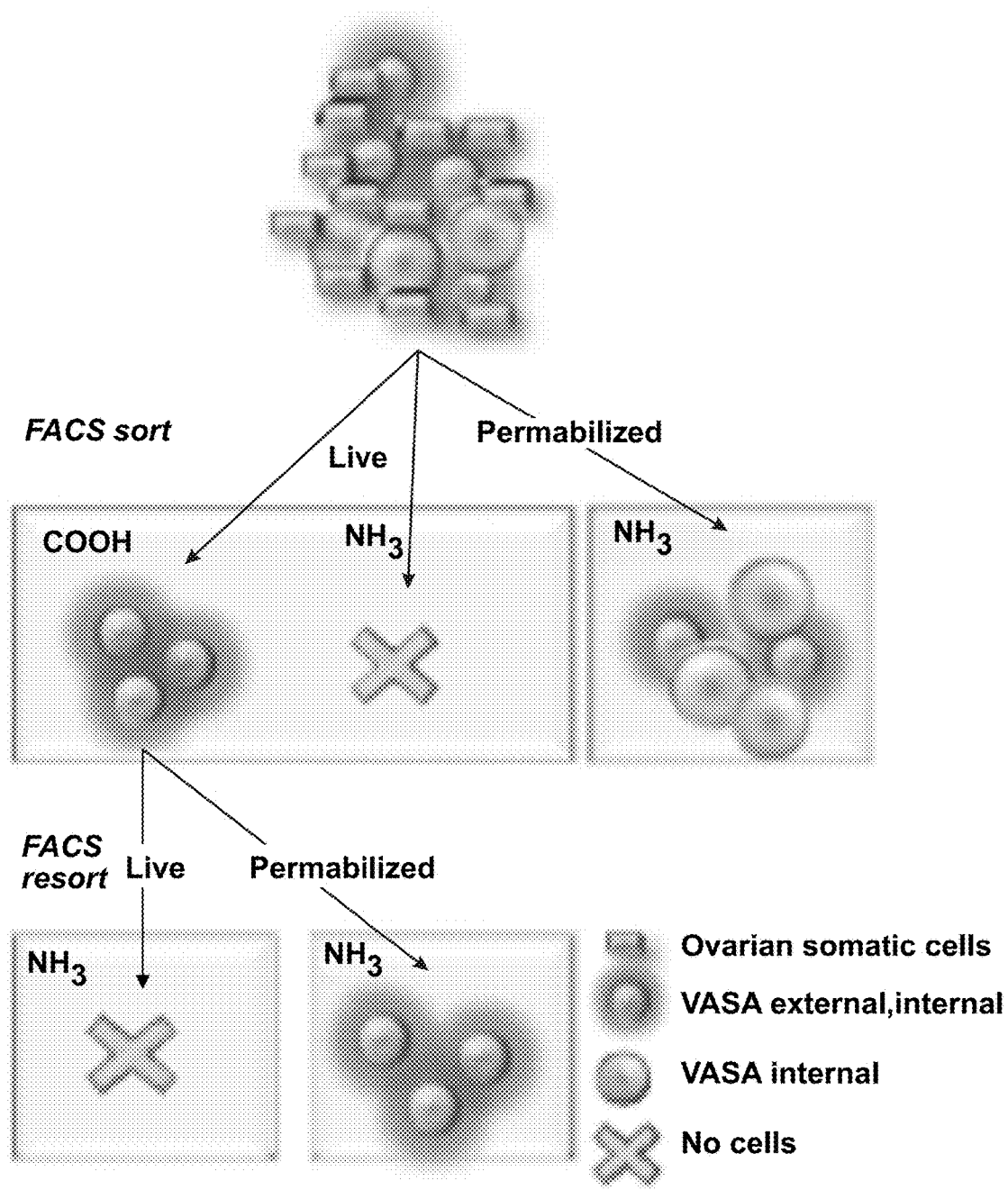
In FIG. 1e, a schematic representation of the FACS protocols employed using the VASA-COOH antibody for isolation of viable OSCs is shown.
Figure 1F:
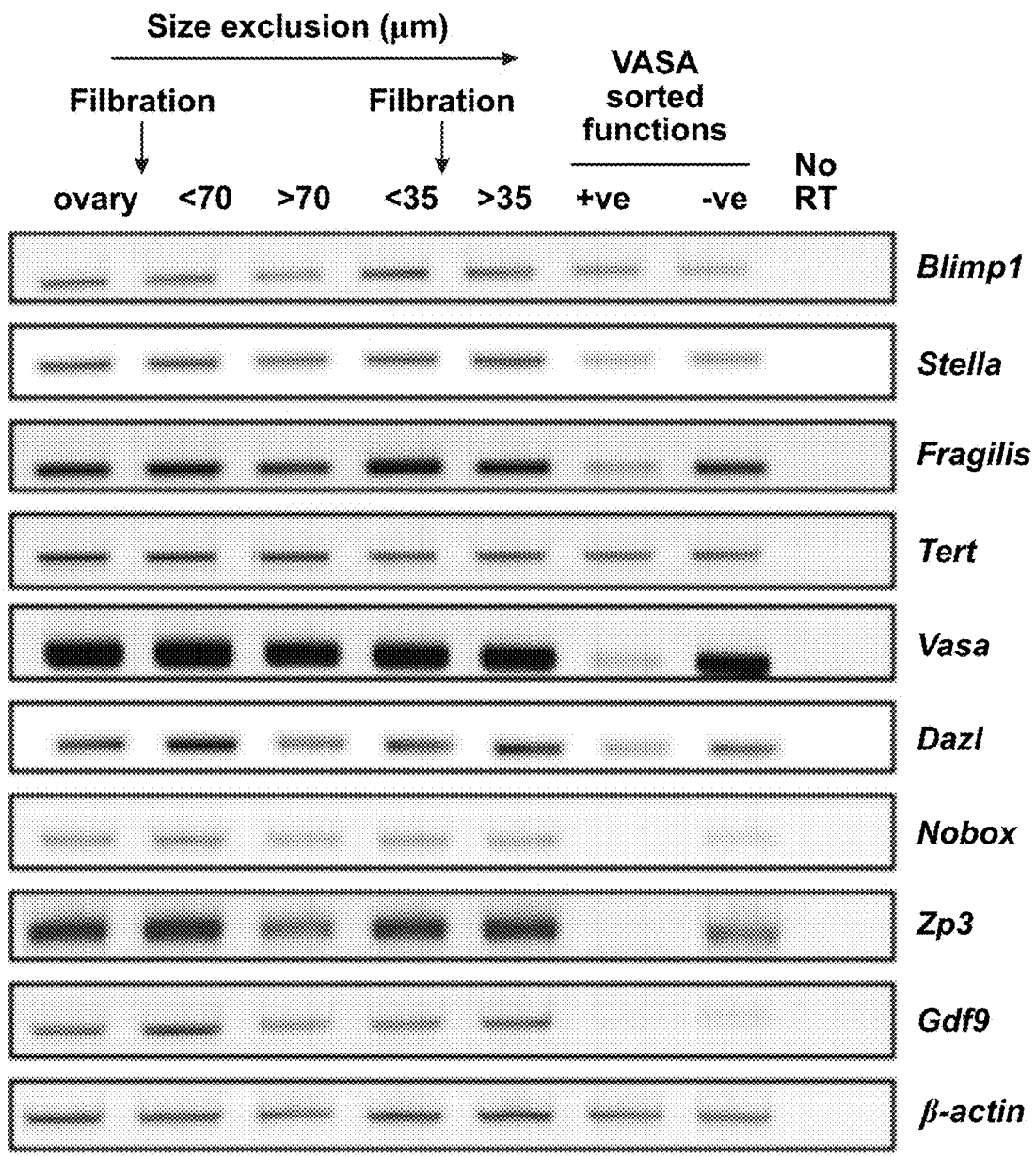
FIG. 1f depicts gene expression analysis of germline markers Blimp1 (also referred to as PR domain containing 1 with ZNF domain or Prdm1), Stella, Fragilis (also referred to as interferon induced transmembrane protein 3 or Ifitm3), Tert (telomerase reverse transcriptase), Vasa, Dazl (deleted in azoospermia like) and oocyte markers Nobox (newborn ovary homeobox), Zp3 (zona pellucida glycoprotein 3), Gdf9 (growth differentiation factor 9) in each cell fraction produced during the ovarian dispersion process to obtain cells for FACS-based isolation of OSCs using the VASA-COOH antibody (+ve, VASA-positive viable cell fraction after FACS; –ve, VASA-negative viable cell fraction after FACS; No RT, PCR of RNA sample without reverse transcription; β-actin, sample loading control).

In agreement with the magnetic bead sorting results, viable VASA-positive cells were obtained only when the COOH antibody was used (FIG. 1c). However, if the ovarian cells were permeabilized prior to FACS, a VASA-positive cell population was obtained using the $NH_2$ antibody (FIG. 1c). Furthermore, if the viable VASA-positive cells isolated by FACS using the COOH antibody were permeabilized and re-sorted, the same cell population was recognized by the VASA-$NH_2$ antibody (FIG. 1d). As a final means to confirm validity of this OSC isolation method, fractions of cells at each step of the protocol were assessed by gene expression analysis using a combination of markers for germ cells (Blimp1/Prdm1, Stella/Dppa3, Fragilis/Ifitm3, Tert, Vasa, Dazl) and oocytes (Nobox, Zp3, Gdf9). To obtain cells for FACS, ovarian tissue was minced and enzymatically digested using collagenase and trypsin, passed through a 70-µm filter to remove large tissue clumps, and then passed through a 35-µm filter to obtain a final fraction of cells. Every fraction of cells through each step of the protocol, with the exception of the VASA-positive viable cell fraction obtained by FACS, expressed all germline and oocyte markers (FIG. 1f). While the FACS-sorted VASA-positive cell fraction expressed all germline markers, no oocyte markers were detected (FIG. 1f). Thus, unlike the oocyte contamination observed when OSCs are isolated by immunomagnetic sorting using the VASA-COOH antibody (see FIG. 2), use of this same antibody with FACS provides a superior strategy to obtain adult ovary-derived OSC fractions free of oocytes.

Example 2: Isolation of OSCs from Human Ovaries

Figures 12A, 12B:
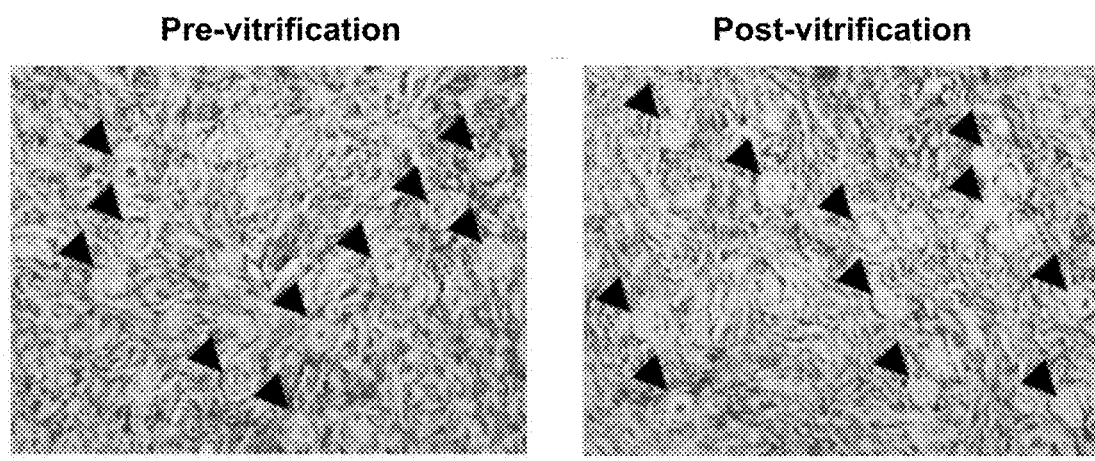
FIGS. 12a and 12b show the histological appearance of adult human ovarian cortical tissue before and after vitrification, highlighting the maintenance of tissue integrity and the large numbers of oocytes (black arrowheads) that survive the freeze-thaw procedure.

With written informed consent, ovaries were surgically removed from 6 female patients between 22-33 (28.5±4.0) years of age with Gender Identity Disorder for sex reassignment at Saitama Medical Center. The outer cortical layer was carefully removed, vitrified and cryopreserved (Kagawa et al., *Reprod. Biomed.* 2009 Online 18:568-577; FIG. 12). Briefly, 1 mm-thick cortical fragments were cut into 100-$mm^2$ (10×10 mm) pieces, incubated in an equilibration solution containing 7.5% ethylene glycol (EG) and 7.5% dimethylsulfoxide (DMSO) at 26 C for 25 minutes, and then incubated in a vitrification solution containing 20% EG, 20% DMSO and 0.5 M sucrose at 26 C for 15 minutes prior to submersion into liquid nitrogen. For experimental analysis, cryopreserved ovarian tissue was thawed using the Cryotissue Thawing Kit (Kitazato Biopharma) and processed immediately for histology, xenografting or OSC isolation. Using the COOH antibody, viable VASA-positive cells between 5-8 µm in diameter were also consistently isolated by FACS from human ovarian cortical tissue biopsies of all patients between 22-33 years of age, with a percent yield (1.7%±0.6% VASA-positive versus total viable cells sorted; mean±SEM, n=6) that was comparable to the yield of OSCs from young adult mouse ovaries processed in parallel (1.5%±0.2% VASA-positive versus total viable cells sorted; mean±SEM, n=15). This percent yield is the incidence of these cells in the final pool of viable single cells sorted by FACS, which represents a fraction of the total number of cells present in ovaries prior to processing. To estimate the incidence of OSCs per ovary, the genomic DNA content per ovary of 1.5-2 month-old mice was determined (1,774.44±426.15 µg; mean±SEM, n=10) and divided into genomic DNA content per fraction of viable cells sorted per ovary (16.41±4.01 µg; mean±SEM, n=10). Assuming genomic DNA content per cell is equivalent, how much of the total ovarian cell pool is represented by the total viable sorted cell fraction obtained after processing was determined. Using this correction factor, the incidence of OSCs per ovary was estimated to be 0.014%±0.002% [0.00926×(1.5%±0.2%)]. With respect to OSC yield, this number varied across replicates but between 250 to slightly over 1,000 viable VASA-positive cells per adult ovary were consistently obtained after FACS of dispersates initially prepared from a pool of 4 ovaries.

Figure 3H:
Figure 3I:
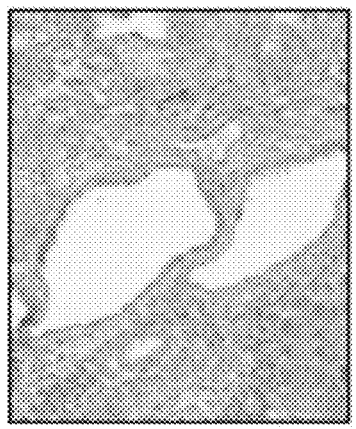
Figure 3J:
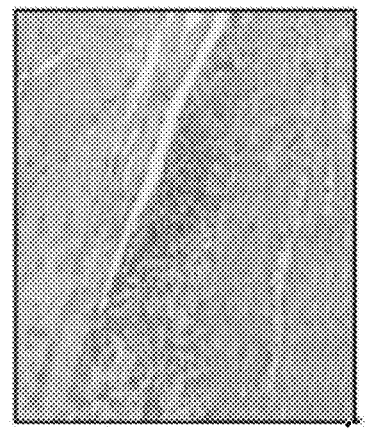
Figure 3G:
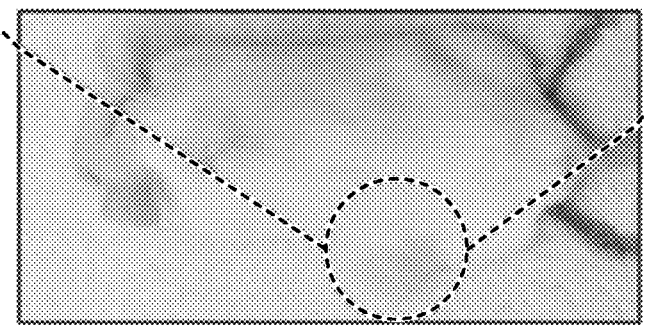
Figure 3F:
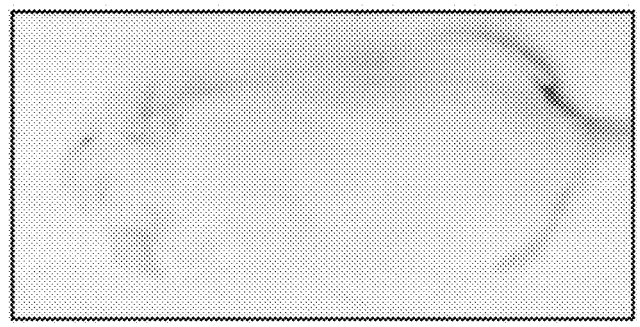

Analysis of freshly-isolated VASA-positive cells from both mouse and human ovaries (FIG. 3a, 3b) revealed a similar size and morphology (FIG. 3c, 3d), and a matched gene expression profile rich in markers for early germ cells (Saitou et al., Nature 2002 418:293-300; Ohinata et al., Nature 2005 436:207-213; Dolci et al., Cell Sci. 2002 115:1643-1649) (Blimp1, Stella, Fragilis and Tert; FIG. 3e), These results agree with the morphology and gene expression profile of mouse OSCs reported in the scientific literature (Zou et al., Nat Cell Biol 2009 11:631-636, Pacchiarotti et al., Differentiation 2010 79:159-170).

To further define characteristic features of VASA-positive cells obtained from adult ovaries, mouse OSCs were tested using an in-vivo teratoma formation assay. This was important, since a recent study has reported the isolation of Oct3/4-positive stem cells from adult mouse ovaries that possess the teratoma-forming capacity of embryonic stem cells (ESCs) and induced pluripotent stem cells (iPSCs) (Gong et al., Fertil. Steril. 2010 93:2594-2601). Ovaries were collected from a total of 100 young adult female mice, dissociated and subject to FACS for isolation of VASA-COOH positive viable cells, as described above. Freshly isolated mouse OSCs were injected subcutaneously near the rear haunch of NOD/SCID female mice ($1×10^5$ cells injected per mouse). As a control, mouse embryonic stem cells (mESC v6.5) were injected into age-matched female mice in parallel ($1×10^5$ cells injected per recipient mouse). Mice were monitored weekly for up to 6 months for tumor formation.

As expected, 100% of the mice transplanted with mouse ESCs used as a positive control developed teratomas within 3 weeks; however, no teratomas were observed in mice transplanted in parallel with VASA-positive cells isolated from adult mouse ovaries, even at 24 weeks post-transplant (FIGS. 3f-k). Thus, while OSCs express numerous stem, cell and primitive germ cell markers (Zou et al., Nat Cell Biol 2009 11:631-636, Pacchiarotti et al., Differentiation 2010 79:159-170; see also FIG. 1f and FIG. 3e), these cells are clearly distinct from other types of pluripotent stem cells described to date.

Example 3: Generation of Oocytes from FACS-Purified Mouse OSCs

The ability of FACS-purified mouse OSCs, engineered to express GFP through retroviral transduction (after their establishment as actively-dividing germ cell-only cultures in vitro) to generate oocytes following transplantation into ovaries of adult female mice was assessed. To ensure the outcomes obtained were reflective of stable integration of the transplanted cells into the ovaries and also were not complicated by pre-transplantation induced damage to the gonads, $1×10^4$ GFP-expressing mouse OSCs were injected into ovaries of non-chemotherapy conditioned wild-type recipients at 2 months of age and animals, were maintained for 5-6 months prior to analysis. Between 7-8 months of age, transplanted animals were induced to ovulate with exogenous gonadotropins (a single intraperitoneal injection of PMSG (10 IU) followed by hCG (10 IU) 46-48 hours later), after which their ovaries and any oocytes released into the oviducts were collected. Ovulated cumulus-oocyte complexes were transferred into HTF supplemented with 0.4% BSA, and assessed by direct fluorescence microscopy for GFP expression. Developing follicles containing GFP-positive oocytes were readily detectable, along with follicles containing GFP-negative oocytes, in ovaries of females that received GFP-expressing mouse OSCs initially purified by FACS (FIG. 4a).

After oviductal flushing, complexes containing expanded cumulus cells surrounding centrally-located oocytes both lacking and expressing GFP were observed. Mixing of these complexes with sperm from wild-type males resulted in fertilization and development of preimplantation embryos. For in-vitro fertilization (IVF), the cauda epididymides and vas deferens were removed from adult wild-type C57BL/6 male mice and placed into HTF medium supplemented with BSA. Sperm were obtained by gently squeezing the tissue with tweezers, capacitated for 1 hour at 37° C., and then mixed with cumulus-oocyte complexes ($1-2×10^6$ sperm/ml in HTF medium supplemented with BSA) for 4-5 hours. Inseminated oocytes were then washed of sperm and transferred to fresh medium. At 4-5 hours post-insemination, oocytes (fertilized and unfertilized) were transferred to 50 µl drops of KSOM-AA medium (Irvine Scientific, Santa, Ana, Calif., USA), and the drops were covered with mineral oil to support further preimplantation embryonic development. Light and fluorescence microscopic examination was performed every 24 hours for a total of 144 hours to monitor embryo development to the hatching blastocyst stage (Selesniemi et al., Proc. Natl. Acad. Sci. USA 2011 108:12319-12324). Ovarian tissue harvested at the time of ovulated oocyte collection from the oviducts was fixed and processed for immunohistochemical detection of GFP expression using a mouse monoclonal antibody against GFP (sc9996; Santa Cruz Biotechnology) along with the MOM™ kit (Vector Laboratories), as detailed previously (Lee et al. J. Clin. Oncol. 2007 25:3198-3204). Ovaries from non-transplanted wild-type female mice and from TgOG2 transgenic female mice served as negative and positive controls, respectively, for GFP detection.

Figure 4C:
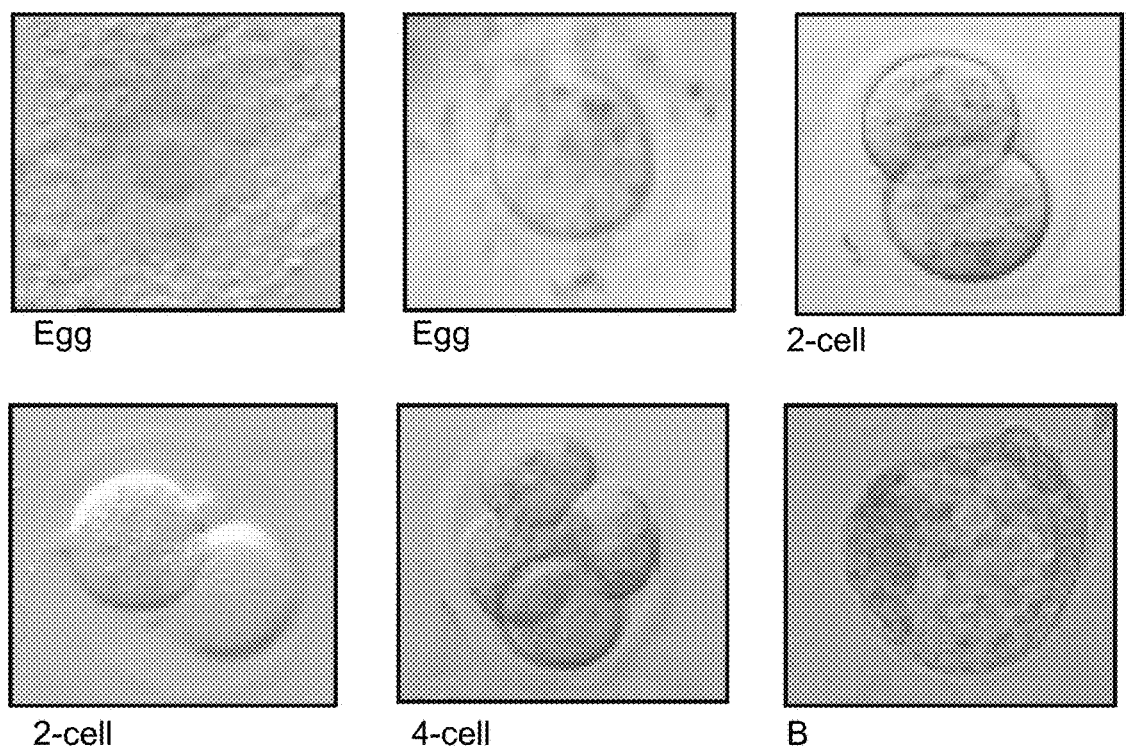
In FIG. 4c, examples of ovulated GFP-negative eggs (in cumulus-oocyte complexes), and resultant embryos (2-cell, 4-cell, compact morula (CM) and early blastocyst (EB) stage embryos are shown as examples) generated by IVF are shown, following induced ovulation of wild-type female mice that received intraovarian transplantation of GFP-expressing OSCs 5-6 months earlier.
Figure 4D:
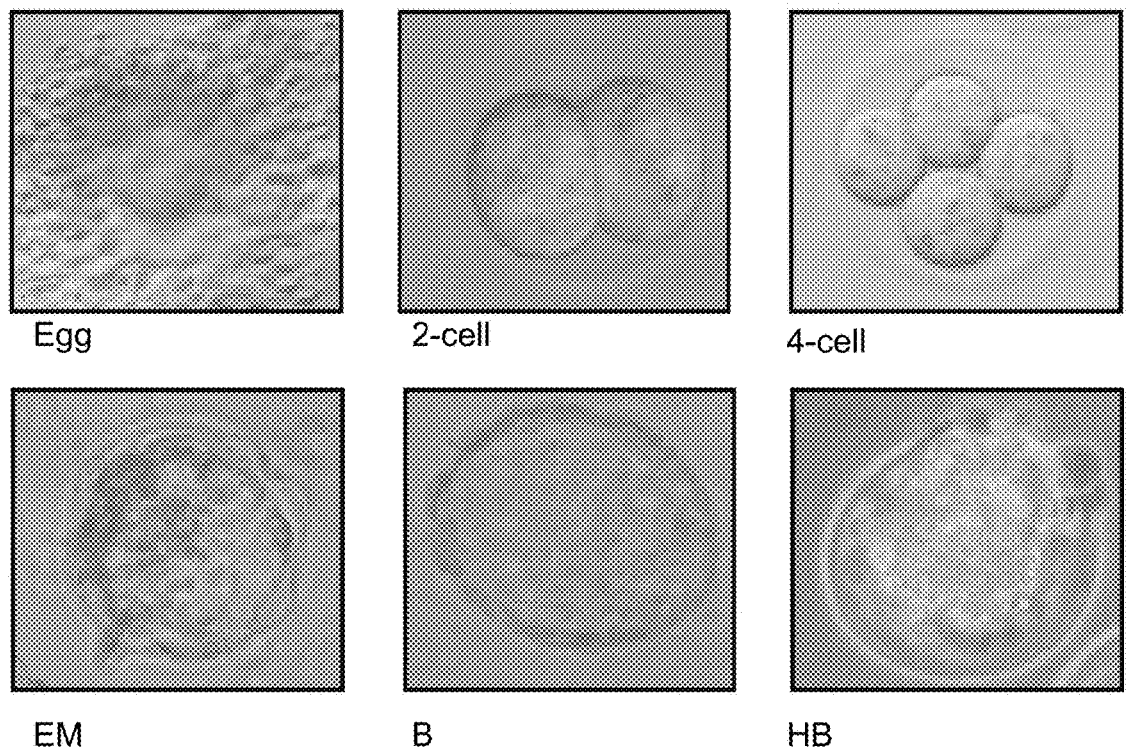
Figure 4E:
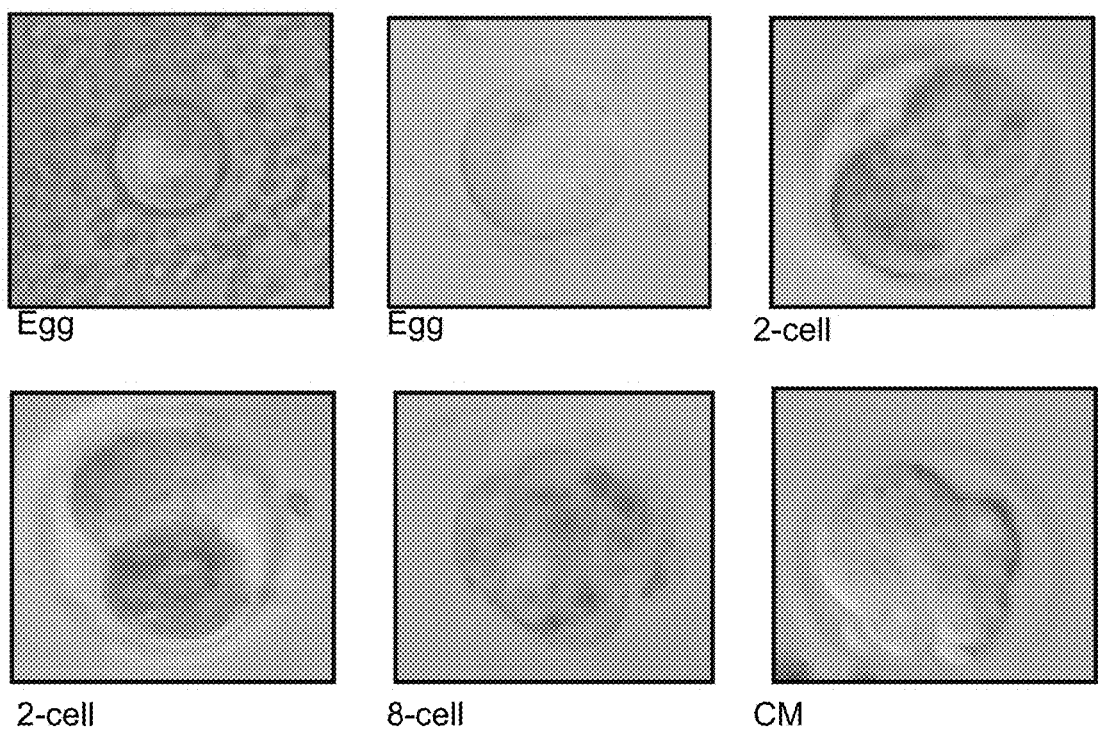
Figure 5B:
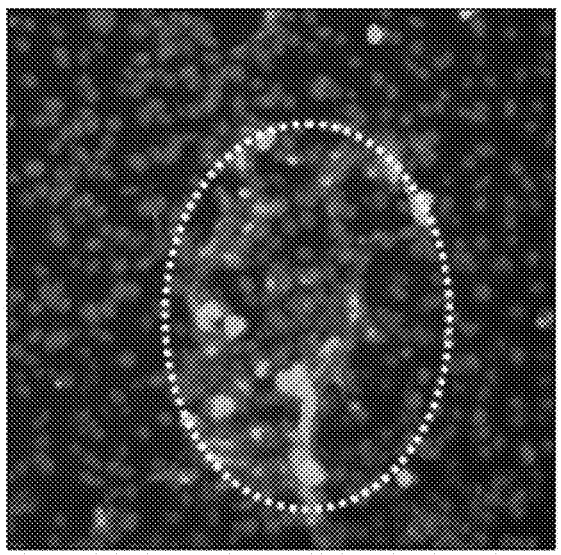
FIG. 5 depicts germ cell colony formation by mouse and human OSCs in vitro. Immunofluorescence-based analysis of VASA expression is shown in FIGS. 5b and 5d; (green with blue DAPI counterstain) in typical germ cell colonies formed by mouse (5a, 5b) and human (5c, 5d) OSCs after establishment on mouse embryonic fibroblasts (MEFs) in vitro (typical colonies are highlighted by white dashed lines).
Figure 5D:
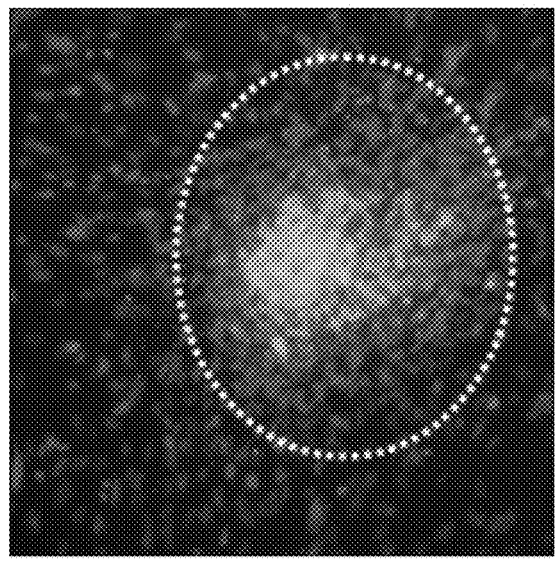
Figure 5A:
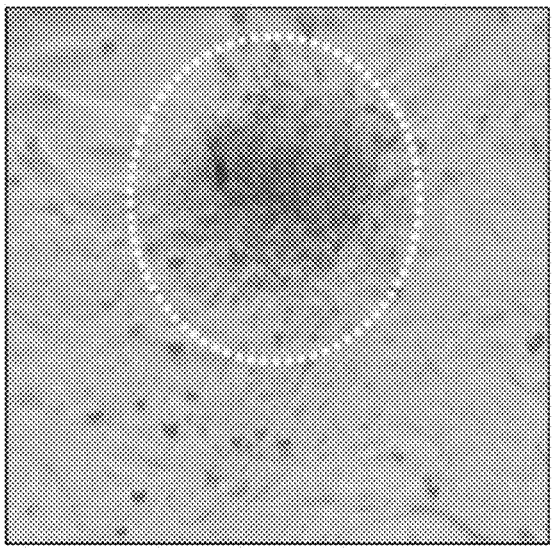
Figure 5C:
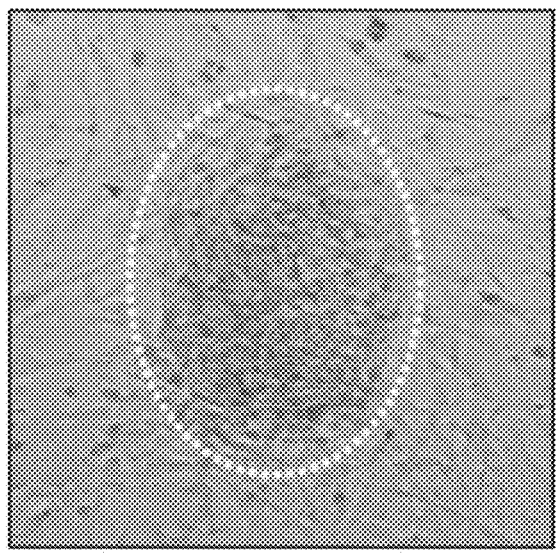

Preimplantation embryos derived from fertilized GFP-positive eggs retained GFP expression through the hatching blastocyst stage (FIG. 4b-d). From the 5 adult wild-type female mice transplanted with GFP-expressing OSCs 5-6 months earlier, a total of 31 cumulus-oocyte complexes were retrieved from the oviducts, 23 of which successfully fertilized to produce embryos. The presence of cumulus cells around each oocyte made it impossible to accurately determine the numbers of GFP-negative versus GFP-positive oocytes ovulated. However, evaluation of the 23 embryos produced following in-vitro fertilization (IVF) revealed that 8 were GFP-positive, with all 5 mice tested releasing at least one egg at ovulation that fertilized to produce a GFP-positive embryo. These findings indicate that OSCs purified by VASA-COOH antibody-based FACS, like their previously reported counterparts isolated by immunomagnetic sorting (Zou et al., *Nat Cell Biol* 2009 11:631-636), generate functional oocytes in vivo. However, our data also show that chemotherapy conditioning prior to transplantation is not, as previously reported (Zou et al., *Nat Cell Biol* 2009 11:631-636), required for OSCs to engraft and generate functional oocytes in adult ovary tissue.

Example 4: In-Vitro Characterization of Candidate Human OSCs

Using parameters described previously for in-vitro propagation of mouse OSCs (Zou et al., *Nat Cell Biol* 2009 11:631-636), adult mouse and human ovary-derived VASA-positive cells were placed into defined cultures with mitotically-inactive mouse embryonic fibroblasts (MEFs) as feeders. Briefly, cells were cultured in MEMα (INVITROGEN®) supplemented with 10% FBS (HYCLONE®, GE Healthcare Bio-Sciences, Pittsburgh, Pa., USA), 1 mM sodium pyruvate, 1 mM non-essential amino acids, 1×-concentrated penicillin-streptomycin-glutamine (INVITROGEN®), 0.1 mM β-mercaptoethanol (Sigma), 1×-concentrated N-2 supplement (R&D Systems), leukemia inhibitory factor (LIF; $10^3$ units/ml; Millipore), 10 ng/ml recombinant human epidermal growth factor (rhEGF; INVITROGEN®), 1 ng/ml basic fibroblast growth factor (bFGF; INVITROGEN®), and 40 ng/ml glial cell-derived neurotropic factor (GDNF; R&D Systems). Cultures were refreshed by the addition of 40-80 µl of new medium every other day, and cells were re-plated on fresh MEFS every two weeks. To assess proliferation, MEF-free OSC cultures were treated with 10 µM BrdU (Sigma Aldrich Corporation, St. Louis, Mo., USA) for 48 hours prior to fixation in 2% PFA for dual immunofluorescence-based detection of BrdU incorporation (mitotically-active cells) and VASA expression (germ cells), as described (Zou et al., *Nat Cell Biol* 2009 11:631-636). No signal was detected if primary antibodies were omitted or replaced with an equivalent dilution of normal rabbit serum (not shown).

Figure 6A:
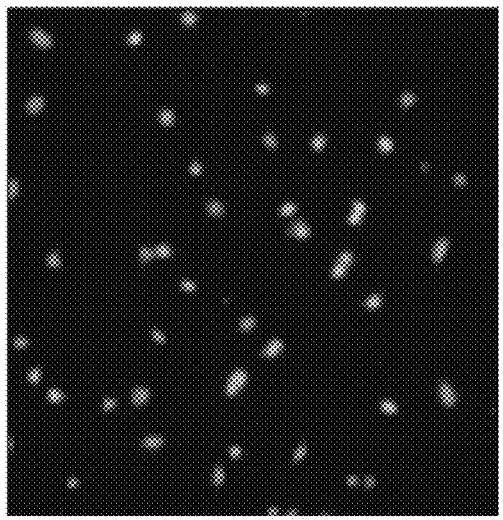
FIGS. 6a through 6d show assessment of OSC proliferation by dual detection of VASA expression (green) and BrdU incorporation (red) in mouse (6a, 6b) and human (6c, 6d) OSCs maintained in MEF-free cultures.
Figure 6B:
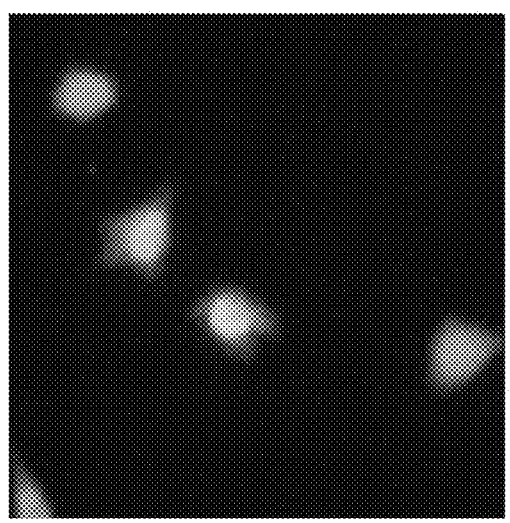
Figure 6C:
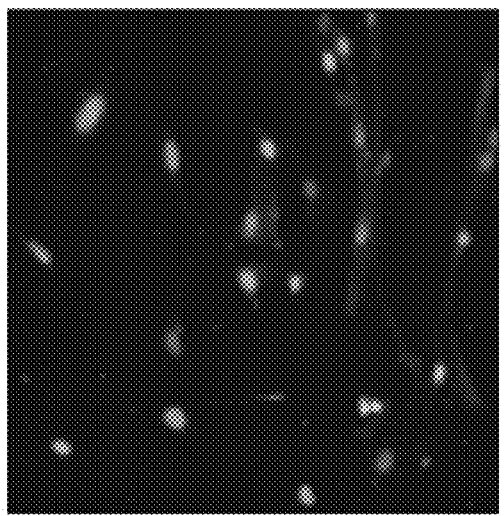
Figure 6D:
Figure 6E:
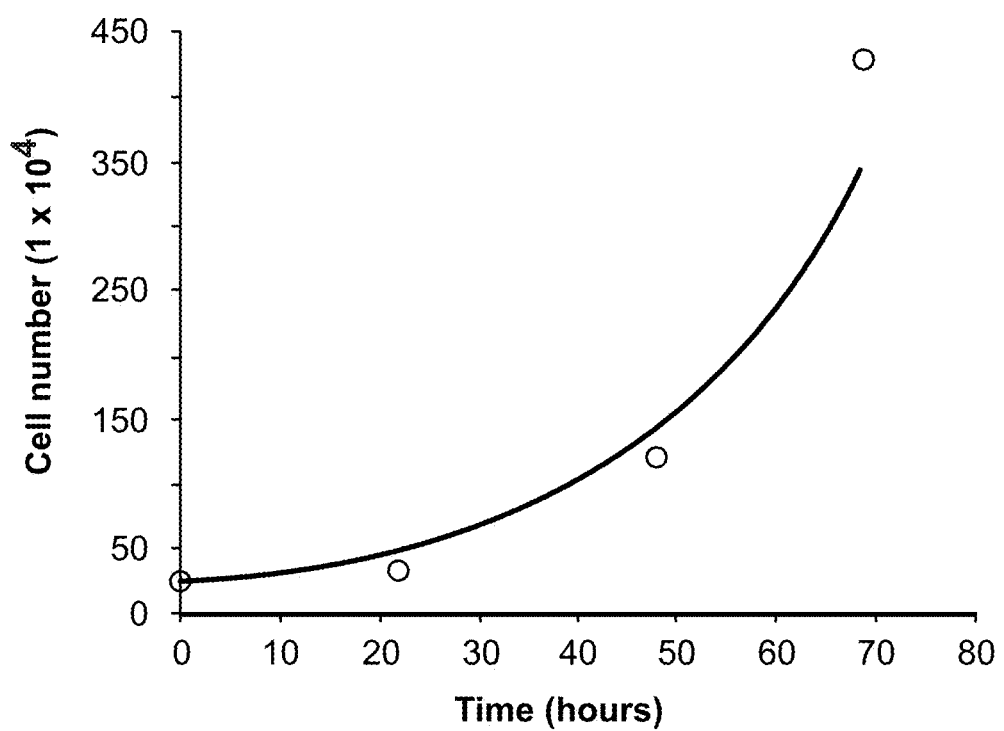
FIG. 6e shows the typical growth curve for MEF-free cultures of mouse OSCs after passage and seeding $2.5 \times 10^4$ cells per well in 24-well culture plates.
Figure 6F:
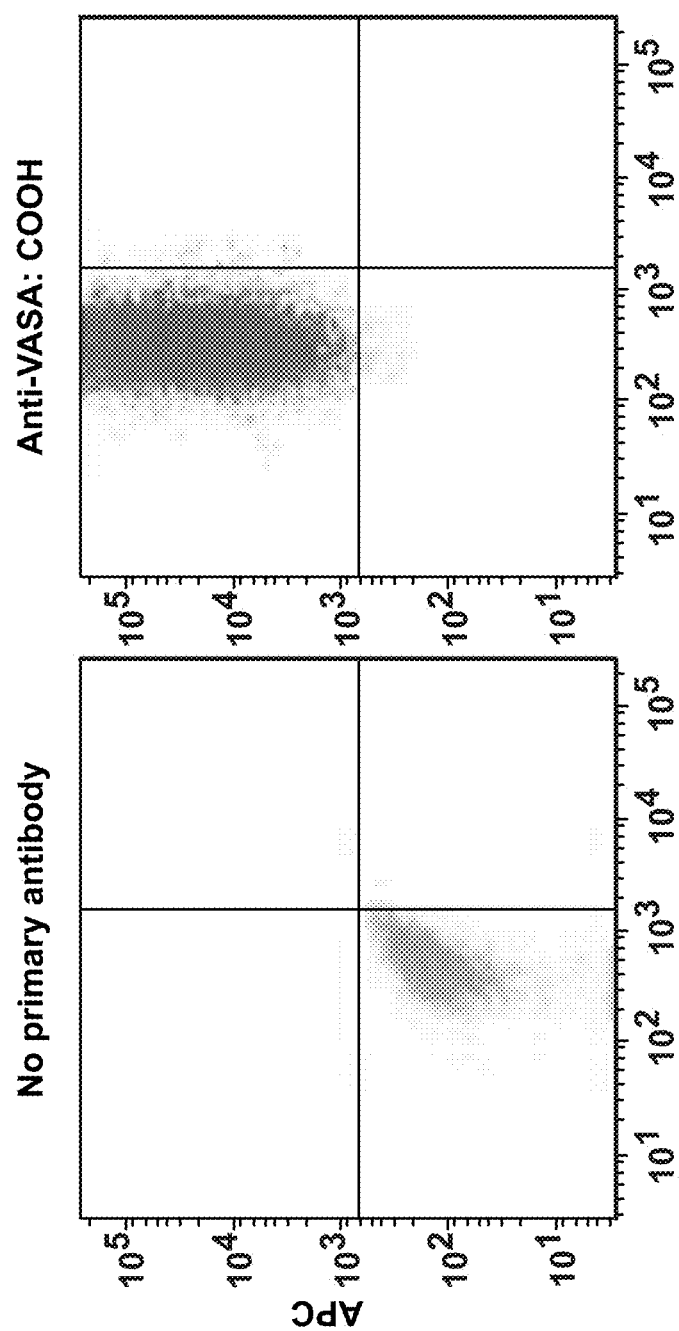
FIG. 6f shows FACS analysis using the COOH antibody to detect cell-surface expression of VASA in mouse OSCs after months of propagation (example shown, passage 45).

Freshly-isolated OSCs could be established as clonal lines, and the colony formation efficiency for human OSCs not seeded onto MEFs ranged from 0.18% to 0.40%. Accurate assessment of colony formation efficiency could not be performed using MEFs as initial feeders, the latter of which greatly facilitates establishment of mouse and human OSCs in vitro. After 10-12 weeks (mouse) or 4-8 weeks (human) in culture, actively-dividing germ cell colonies became readily apparent (FIG. 5). Once established and proliferating, the cells could be re-established as germ cell-only cultures in the absence of MEFs without loss of proliferative potential. Dual analysis of VASA expression and bromodeoxyuridine (BrdU) incorporation in MEF-free cultures revealed large numbers of double-positive cells (FIG. 6a-d), confirming that adult mouse and human ovary-derived VASA-positive cells were actively dividing. At this stage, mouse cells required passage at confluence every 4-5 days with cultures split 1:6-1:8 (estimated doubling time of 14 hours; FIG. 6e) The rate of mouse OSC proliferation was approximately 2-3 fold higher than that of human germ cells maintained in parallel, the latter of which required passage at confluence every 7 days with cultures split 1:3-1:4. Cell surface expression of VASA remained, detectable on the surface of more than 95% of the cells after months of propagation (FIG. 6f). The remaining cells not detected by FACS using the VASA-COOH antibody were large (35-50 µm diameter) spherical cells spontaneously produced by mouse and human OSCs during culture, which exhibited cytoplasmic expression of VASA and are described in detail in Example 5.

Figure 6G:
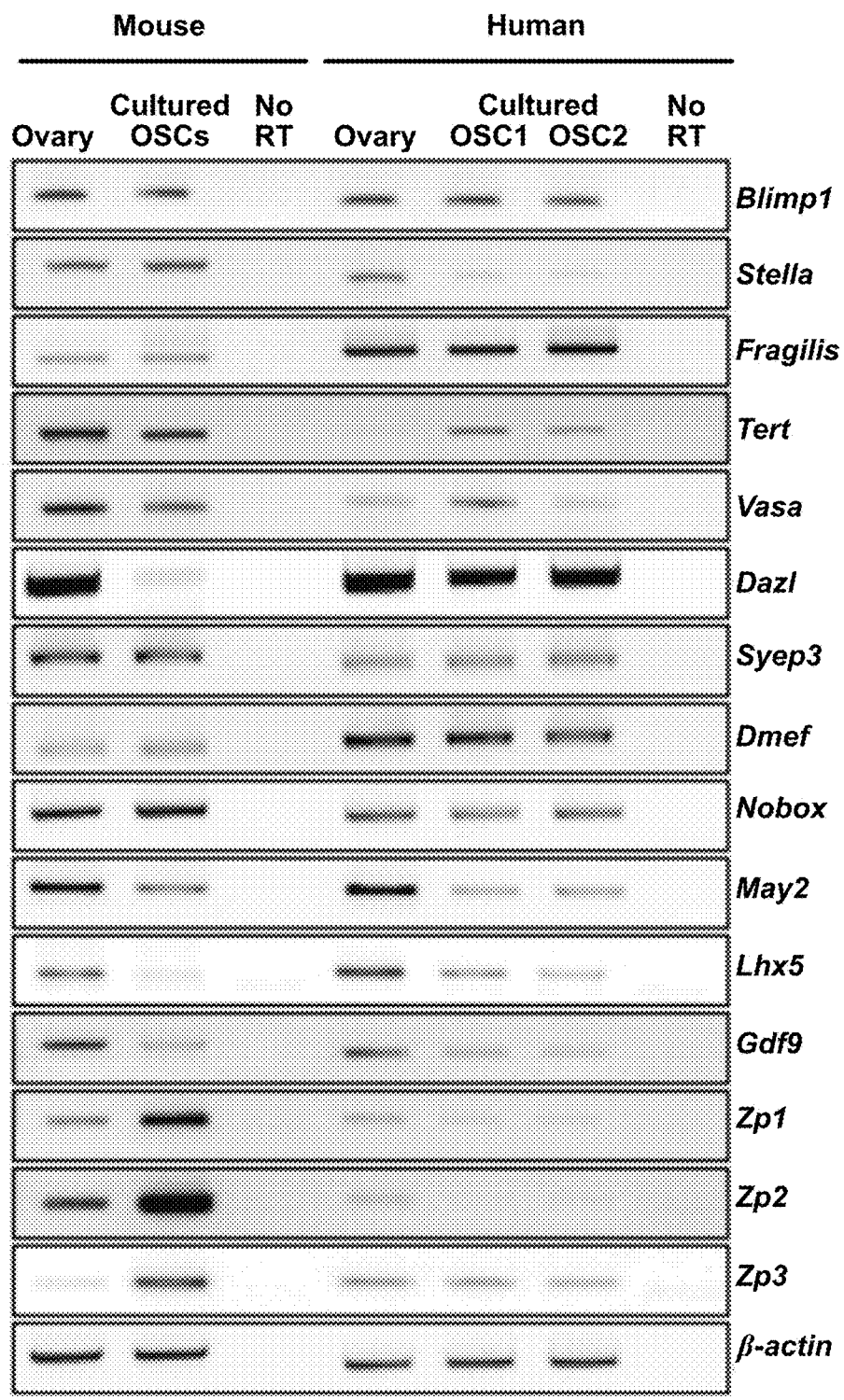
FIG. 6g indicates the gene expression profile of starting ovarian material and cultured mouse and human OSCs after 4 or more months of propagation in vitro (No RT, PCR of RNA sample without reverse transcription; β-actin, sample loading control). Two different human OSC lines (OSC1 and OSC2) established from two different patients are shown as examples.

Gene expression analysis of the cultured cells confirmed maintenance of early germline markers (FIG. 6g), Several oocyte-specific markers were also detected in these cultures. Levels of mRNA were assessed by RT-PCR using a SuperScript®VILO™ cDNA Synthesis Kit (INVITROGEN®) and Platinum Taq polymerase (INVITROGEN®). All products were sequenced to confirm identity. Sequences of forward and reverse primers used, along with GenBank accession numbers of the corresponding genes, are provided in Table 3 (mouse) Table 4 (human).

TABLE 3

PCR primers used to analyze gene expression in mouse cell and tissue samples.

| Gene | Accession number | Primer sequences (5' to 3'; F, forward; R, reverse) | Size (bp) |
| --- | --- | --- | --- |
| Blimp1 | NM_007548 | F: CGGAAAGCAACCCAAAGCAATAC<br>R: CCTCGGAACCATAGGAAACATTC | 483 |
| Stella | NM_139218 | F: CCCAATGAAGGACCCTGAAAC<br>R: AATGGCTCACTGTCCCGTTCA | 354 |
| Fragilis | NM_025378 | F: GTTATCACCATTGTTAGTGTCATC<br>R: AATGAGTGTTACACCTGCGTG | 151 |
| Tert | NM_009354 | F: TGCCAATATGATCAGGCACTCG<br>R: ACTGCGTATAGCACCTGTCACC | 305 |
| Vasa | NM_001145885 | F: GGAAACCAGCAGCAAGTGAT<br>R: TGGAGTCCTCATCCTCTGG | 213 |
| Dazl | NM_010021 | F: GTGTGTCGAAGGGCTATGGAT<br>R: ACAGGCAGCTGATATCCAGTG | 328 |
| Msy2 | NM_016875 | F: CCTCCCCACTTTCCCATAAT<br>R: AATGGGTGGGAAGAAAAAC | 235 |

TABLE 3-continued

PCR primers used to analyze gene expression in mouse cell and tissue samples.

| Gene | Accession number | Primer sequences (5' to 3'; F, forward; R, reverse) | Size (bp) |
|---|---|---|---|
| Sycp3 | NM_011517 | F: AGCAGAGAGCTTGGTCGGG<br>R: TCCGGTGAGCTGTCGCTGTC | 100 |
| Dmc1 | NM_010059.2 | F: CTCACGCTTCCACAACAAGA<br>R: TCTCGGGGCTGTCATAAATC | 81 |
| Nobox | NM_130869 | F: CCCTTCAGTCACAGTTTCCGT<br>R: GTCTCTACTCTAGTGCCTTCG | 379 |
| Lhx8 | NM_010713 | F: CGTCAGTCCCAACCATTCTT<br>R: TTGTTGGTGAGCATCCATGT | 157 |
| Gdf9 | NM_008110 | F: TGCCTCCTTCCCTCATCTTG<br>R: CACTTCCCCCGCTCACACAG | 709 |
| Zp1 | NM_009580 | F: GTCCGACTCCTGCAGAGAAC<br>R: TGATGGTGAAGCGCTGATAG | 208 |
| Zp2 | NM_011775 | F: AAGGTCTTGAGCAGGAACGA<br>R: GGGTGGAAAGTAGTGCGGTA | 152 |
| Zp3 | NM_011776 | F: CCGAGCTGTGCAATTCCCAGA<br>R: AACCCTCTGAGCCAAGGGTGA | 183 |
| β-actin | NM_007393 | F: GATGACGATATCGCTGCGCTG<br>R: GTACGACCAGAGGCATACAGG | 440 |

TABLE 4

PCR primers used to analyze gene expression in human cell and tissue samples.

| Gene | Accession number | Primer sequences (5' to 3'; F, forward; R, reverse) | Size (bp) |
|---|---|---|---|
| Blimp1 | NM_001198 | F: AAACATGACCGGCTACAAGACCCT<br>R: GGCACACCTTGCATTGGTATGGTT | 332 |
| Stella | NM_199286 | F: AGCAGTCCTCAGGGAAATCGAAGA<br>R: TATGGCTGAAGTGGCTTGGTGTCT | 276 |
| Fragilis | NM_021034 | F: ATGTCGTCTGGTCCCTGTTC<br>R: GGGATGACGATGAGCAGAAT | 205 |
| Tert | NM_198253 | F: AGACGGTGTGCACCAACATCTACA<br>R: TGTCGAGTCAGCTTGAGCAGGAAT | 271 |
| Vasa | NM_024415 | F: TTGTTGCTGTTGGACAAGTGGGTG<br>R: GCAACAAGAACTGGGCACTTTCCA | 283 |
| Dazl | NM_001190811 | F: TCGAACTGGTGTGTCCAAAGGCTA<br>R: TAGGATTCATCGTGGTTGTGGGCT | 260 |
| Msy2 | NM_015982 | F: ACCCTACCCAGTACCCTGCT<br>R: GCAAGAAAAGCAACCAGGAG | 248 |
| Sycp3 | NM_001177949 | F: TATGGTGTCCTCCGGAAAAA<br>R: AACTCCAACTCCTTCCAGCA | 238 |
| Nobox | NM_001080413 | F: ATAAACGCCGAGAGATTGCCCAGA<br>R: AAGTCTGGTCAGAAGTCAGCAGCA | 375 |
| Lhx8 | NM_001001933 | F: CAAGCACAATTTGCTCAGGA<br>R: GGCACGTAGGCAGAATAAGC | 230 |
| Gdf9 | NM_005260 | F: TCACCTCTACAACACTGTTCGGCT<br>R: AAGGTTGAAGGAGGCTGGTCACAT | 344 |
| Zp1 | NM_207341 | F: CGCCATGTTCTCTGTCTCAA<br>R: CGTTTGTTCACATCCCAGTG | 219 |

TABLE 4 -continued

PCR primers used to analyze gene expression in human cell and tissue samples.

| Gene | Accession number | Primer sequences (5' to 3'; F, forward; R, reverse) | Size (bp) |
|---|---|---|---|
| Zp2 | NM_003460 | F: TCTTCTTCGCCCTTGTGACT<br>R: CTCAGGGTGAGCTTTTCTGG | 217 |
| Zp3 | NM_001110354 | F: AGCAGGACCCAGATGAACTCAACA<br>R: AAGCCCACTGCTCTACTTCATGGT | 274 |
| β-actin | NM_001101 | F: CATGTACGTTGCTATCCAGGC<br>R: CTCCTTAATGTCACGCACGAT | 250 |

To extend the mRNA analyses of Blimp1, Stella and Fragilis, immunofluorescence analysis of these three classic primitive germline markers was performed (Saitou et al., Nature 2002 418:293-300; Ohinata et al., Nature 2005 436:207-213). For analysis of cultured OSCs, cells were washed with 1x-concentrated phosphate-buffered saline (PBS), fixed in 2% PFA for 45 minutes at 20° C., washed 3 times with PBS-T (PBS containing 0.01% Triton-X100) and incubated for 1 hour at 20° C. in blocking buffer (PBS containing 2% normal goat serum and 2% BSA). The cells were then incubated for 1 hour at 20° C. with a 1:1:00 dilution of one of the following primary antibodies: a biotinylated mouse monoclonal against BLIMP1 (ab81961, Abcam, Cambridge, Mass., USA), a rabbit polyclonal against STELLA (ab19878; Abcam, Cambridge, Mass.) or a rabbit polyclonal against FRAGILIS (mouse: ab15592, human: ab74699; Abcam, Cambridge, Mass., USA). Cells were washed and incubated for 30 minutes at 20 C with a 1:500 dilution of streptavidin-conjugated Alexa Fluor 488 (INVITROGEN®; BLIMP1 detection) or goat anti-rabbit IgG conjugated to Alexa Fluor 488 (STELLA and FRAGILIS detection) in the presence of rhodamine-phalloidin (INVITROGEN®). Cells were washed, incubated with 4',6-diamidino-2-phenylindole dihydrochloride (DAPI; Sigma Aldrich Corporation, St. Louis, Mo., USA) and washed 3 additional times before imaging. No signal was detected if primary antibody was omitted or replaced with normal serum (not shown).

For assessment of oocytes generated in vitro by mouse and human OSCs, individual oocytes were collected from culture supernatants, washed, fixed with 2% PFA containing 0.5% BSA for 45 minutes at 37° C., washed and blocked for 1 hour at 20° C. in PBS containing 0.5% BSA and either 5% normal goat serum (VASA or LHX8 detection) or 1% normal donkey serum (c-KIT detection). After blocking, oocytes were incubated for 2 hours at 20° C. with a 1:100 dilution (in PBS with 0.5% BSA) of one of the following primary antibodies: a goat polyclonal against c-KIT (sc1494, Santa Cruz Biotechnology), a rabbit polyclonal against VASA (ab13840, Abcam, Cambridge, Mass., USA) or a rabbit polyclonal against LHX8 (ab41519, Abcam, Cambridge, Mass., USA). Cells were then washed and incubated with a 1:250 dilution of goat anti-rabbit IgG conjugated to Alexa Fluor 568 (INVITROGEN®; VASA detection) or Alexa Fluor 488 (LHX8 detection), or a 1:250 dilution of donkey anti-goat IgG conjugated to Alexa Fluor 488 (c-KIT detection). Cells were washed, incubated with DAPI and washed 3 additional times before imaging. No signal was detected if primary antibody was omitted or replaced with normal serum.

For these latter experiments, detection of oocyte-specific expression of VASA, c-KIT and, for human ovaries, LHX8 in ovarian tissue sections served as a positive control. Mouse and human ovarian tissue was fixed in 4% PFA, paraffin-embedded and sectioned (6-μm) prior to high temperature antigen retrieval using 0.01 M sodium citrate buffer (pH 6.0). After cooling, sections were washed and blocked for 1 hour at 20° C. using TNK buffer (0.1 M Tris-HCl, 0.55 M NaCl, 0.1 mM KCL, 0.5% BSA, and 0.1% Triton-X100 in phosphate-buffered Wine) containing either 1% normal goat serum (VASA-COOH or LHX8 detection) or 1% normal donkey serum (VASA-NH$_2$ or c-KIT detection). Sections were then incubated with a 1:100 dilution of primary antibody (in TNK buffer with 1% normal serum) overnight at 4 C, washed in PBS, and incubated for 30 minutes at 20° C. with a 1:500 dilution of goat anti-rabbit IgG conjugated to Alexa Fluor 568 (VASA-COOH detection in human ovary), goat anti-rabbit IgG conjugated to Alexa Fluor 488 (detection of VASA-COOH in mouse ovary or LHX8) or donkey anti-goat IgG conjugated to Alexa Fluor 488 (c-KIT or VASA-NH$_2$ detection). After washing with PBS, sections were cover-slipped using Vectashield containing DAPI (Vector Labs). No signal was detected if primary antibody was omitted or replaced with normal serum.

Figure 6H:
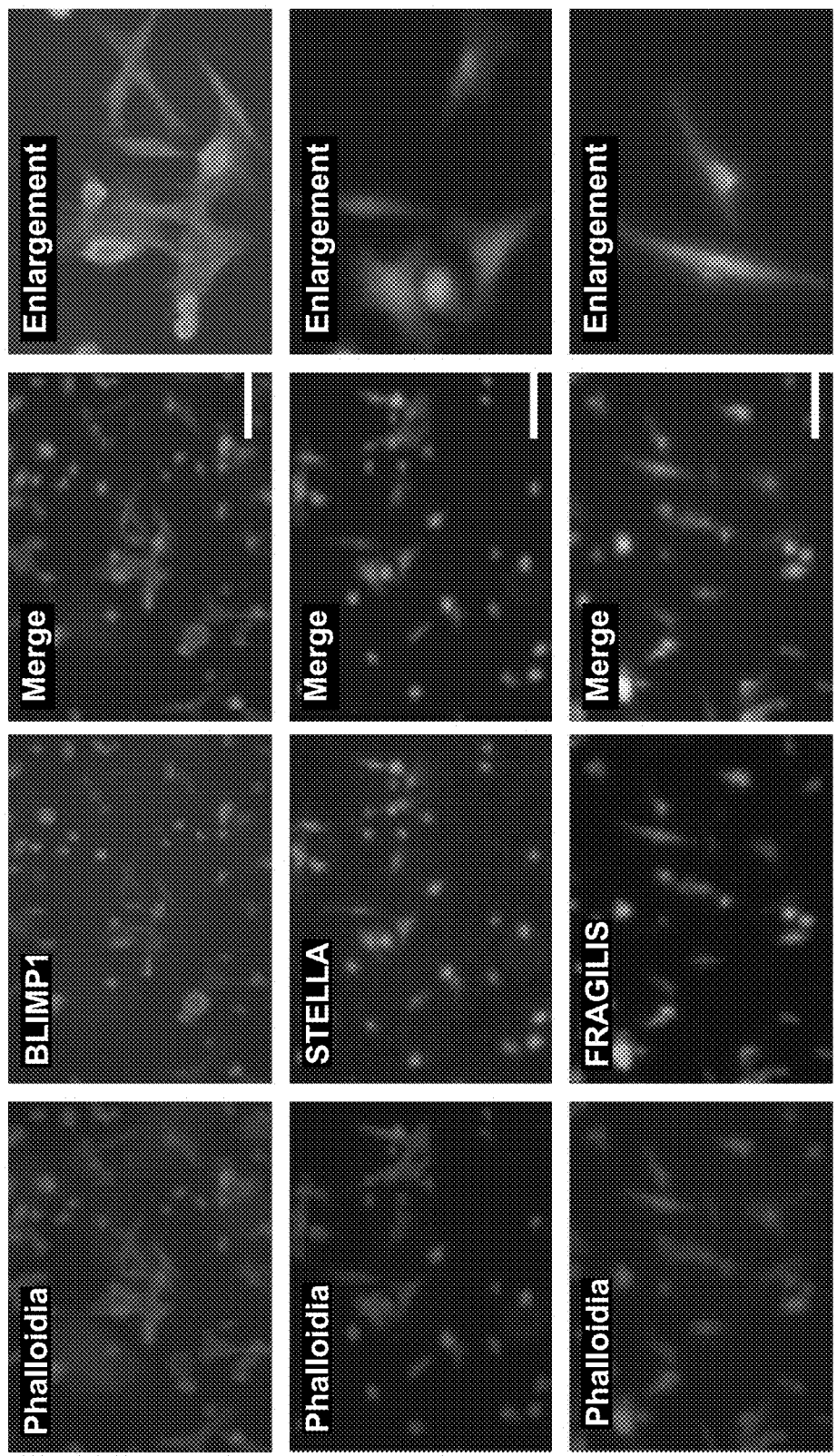
FIGS. 6h and 6i show representative immunofluorescence analysis of BLIMP1, STELLA and FRAGILIS expression (green) in mouse (h) and human (i) OSCs in MEF-free cultures. Cells were counterstained with DAPI (blue) and rhodamine-phalloidin (red) to visualize nuclear DNA and cytoplasmic F-actin, respectively.
Figure 6I:
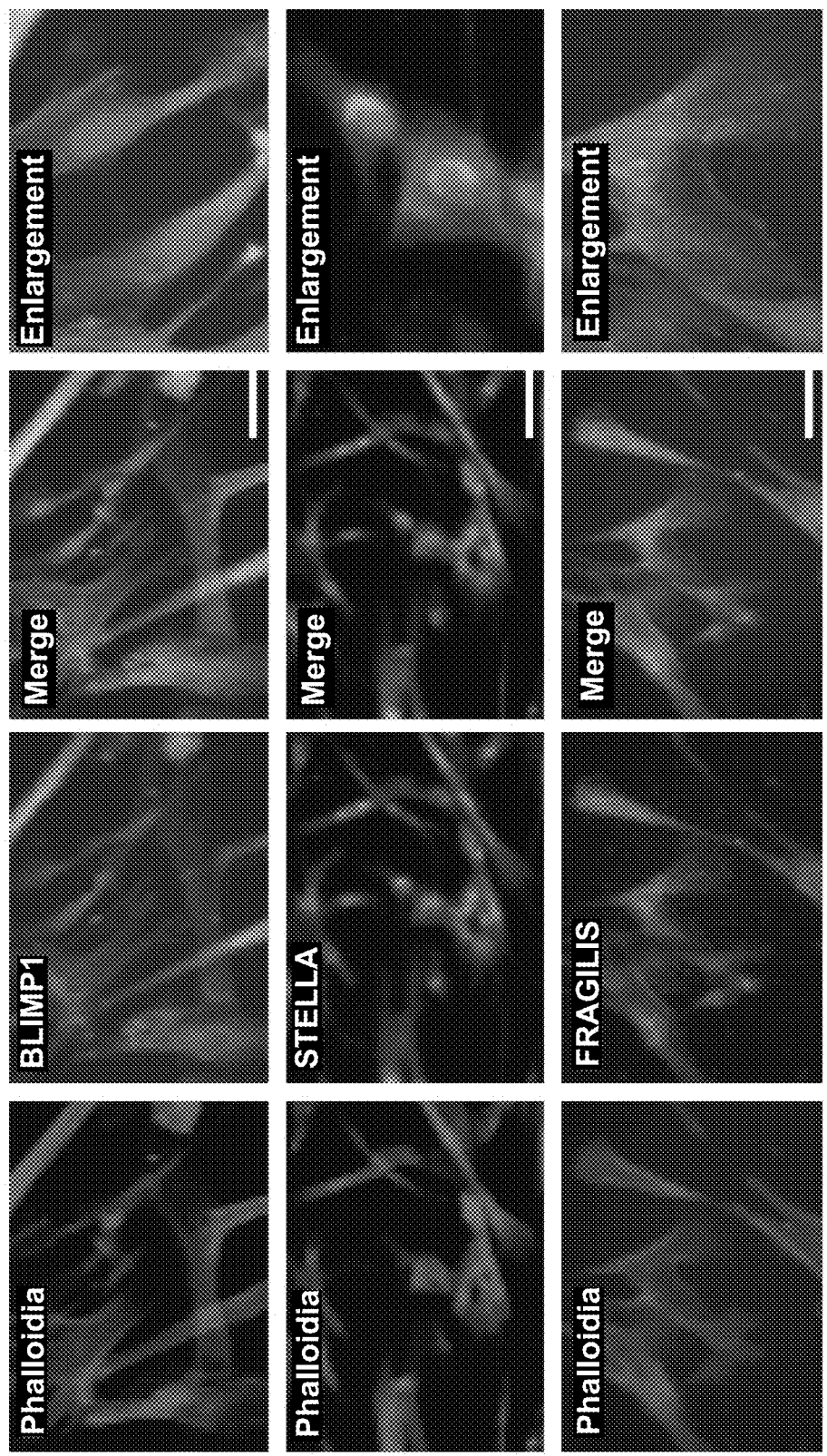

All three proteins were easily and uniformly detected in mouse (FIG. 6h) and human (FIG. 6i) OSCs maintained in vitro. Notably, detection of FRAGILIS in these cells agrees with a recent study reporting that this protein can also be used to isolate OSCs from mouse ovaries by immunomagnetic bead sorting (Zou et al., Stem Cells Dev. 2011 doi: 10.1089/scd.2011.0091).

Example 5: In-Vitro Oogenic Capacity of Candidate Human OSCs

Figure 7D:
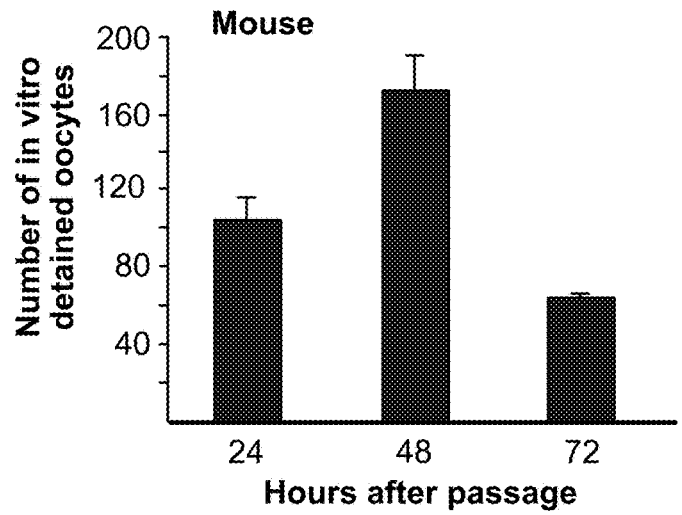
FIG. 7d indicates the number of immature oocytes formed by mouse OSCs 24, 48 and 72 hours after passage and seeding $2.5 \times 10^4$ cells per well in 24-well culture plates (culture supernatants were collected at each time point for determination, and thus the values represent numbers generated over each 24 hour block, not cumulative numbers; mean±SEM, n=3 independent cultures).
Figure 7E:
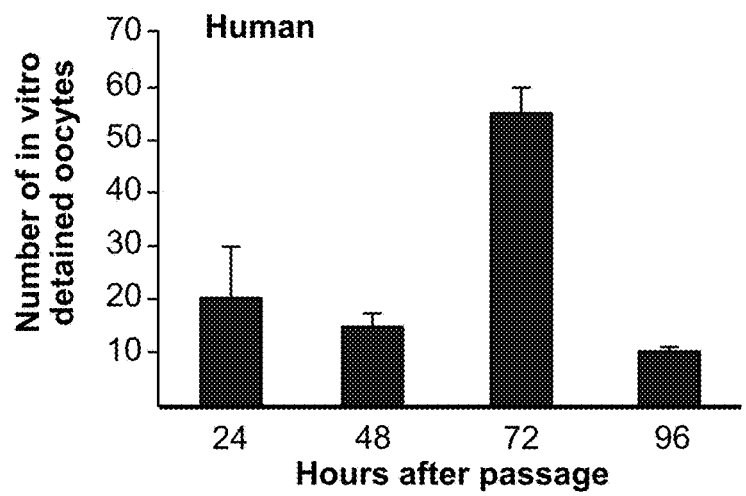
FIGS. 7e through 7g show in-vitro oogenesis from human OSCs, with examples of immature oocytes formed by human OSCs in culture (7f, morphology; 7g, expression of oocyte marker proteins VASA, KIT, MSY2 and LHX8) and numbers formed following passage and seeding of $2.5 \times 10^4$ cells per well in 24-well culture plates (7e; mean±SEM, n=3 independent cultures) shown. The presence of mRNAs encoding oocyte marker genes (Vasa, Kit, Msy2, Nobox, Lhx8, Gdf9, Zp1, Zp2, Zp3) in human OSC-derived oocytes is shown in panel c along with results for mouse OSC-derived oocytes. Scale bars, 25 µm.
Figure 7F:
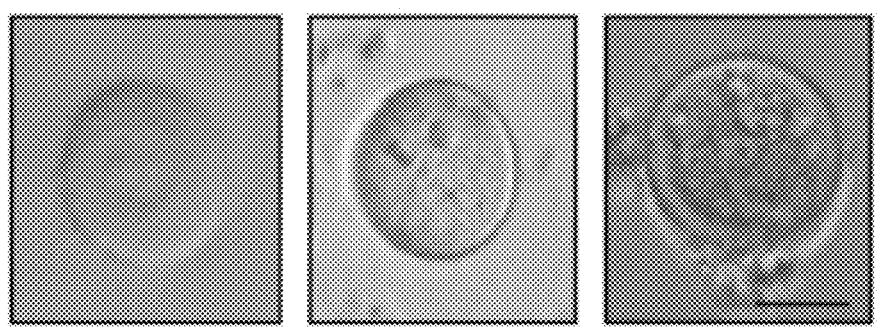
Figure 7G:
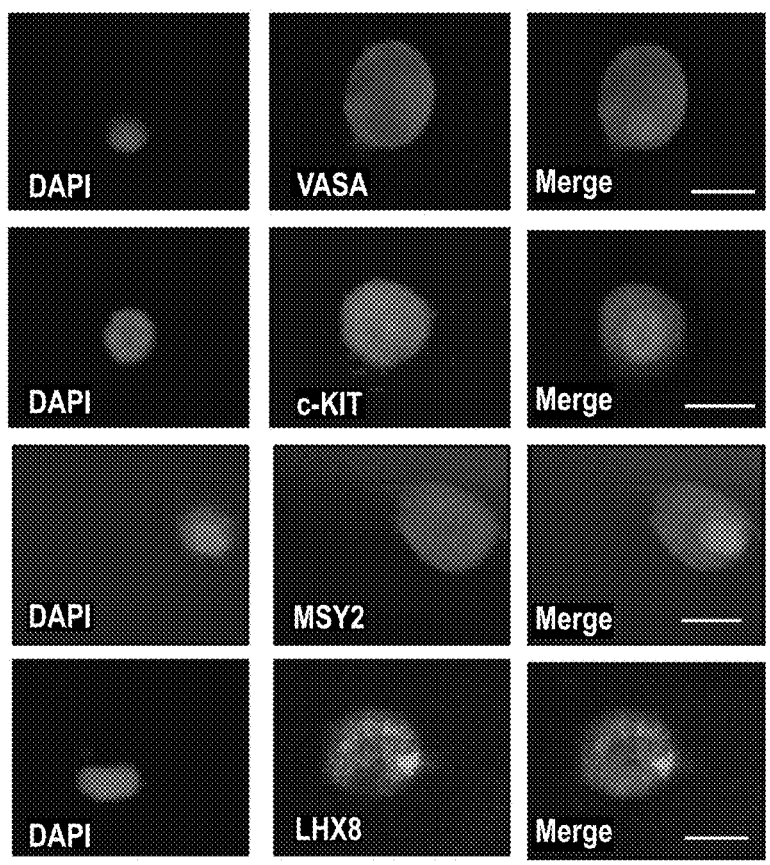

Consistent with results from others (Pacchiarotti et al., Differentiation 2010 79:159-170), mouse OSCs cultured in vitro spontaneously generated large (35-50 μm in diameter) spherical cells that by morphology (FIG. 7a) and gene expression analysis (FIG. 7b, c) resembled oocytes. Peak levels of in-vitro oogenesis from mouse OSCs were observed within 24-48 hours after each passage (FIG. 7d), followed by a progressive decline to nearly non-detectable levels each time OSCs regained confluence. Parallel analysis of VASA-positive cells isolated from adult human ovaries and maintained in vitro revealed that these cells, like mouse OSCs, also spontaneously generated oocytes as deduced from both morphological (FIG. 7f) and gene expression (FIG. 7c, g) analyses. The kinetics of in-vitro oogenesis from human OSCs differed slightly from mouse OSCs in that peak levels of oocyte formation were observed at 72 hours after each passage (FIG. 7e). In addition to detection of many widely accepted oocyte markers (Vasa, c-Kit, Nobox, Lhx8, Gdf9, Zp1, Zp2, Zp3; (Suzumori et al., *Mech. Dev.* 2002 111:137-141; Rajkovic et al., *Science* 2004 305: 1157-1159; Pangas et al., *Proc. Natl. Acad. Sci. USA* 2006 103:8090-8095; Elvin et al., *Mol. Endocrinol.* 1999 13:1035-1048; Zheng et al., *Semin. Reprod. Med.* 2007 25:243-251), mouse and human OSC-derived oocytes also expressed the diplotene oocyte stage-specific marker Msy2 (FIG. 7c). MSY2 is a mammalian homologue of Xenopus FRGY2, a germ cell-specific nucleic acid-binding Y-box protein that is essential for meiotic progression and gametogenesis in both sexes (Gu et al., *Biol. Reprod.* 1998 59:1266-1274; Yang et al., *Proc. Natl. Acad. Sci. USA* 2005 102:5755-5760). Through empirical testing of commercially-available antibodies using adult human ovarian cortical tissue as a positive control, four such antibodies against oocyte markers were identified that specifically reacted with immature oocytes present in adult human ovaries (VASA, c-KIT, MSY2, LHX8; FIG. 8); all four of these proteins were also detected in oocytes generated by human OSCs in vitro (FIG. 7g).

Figure 7H:
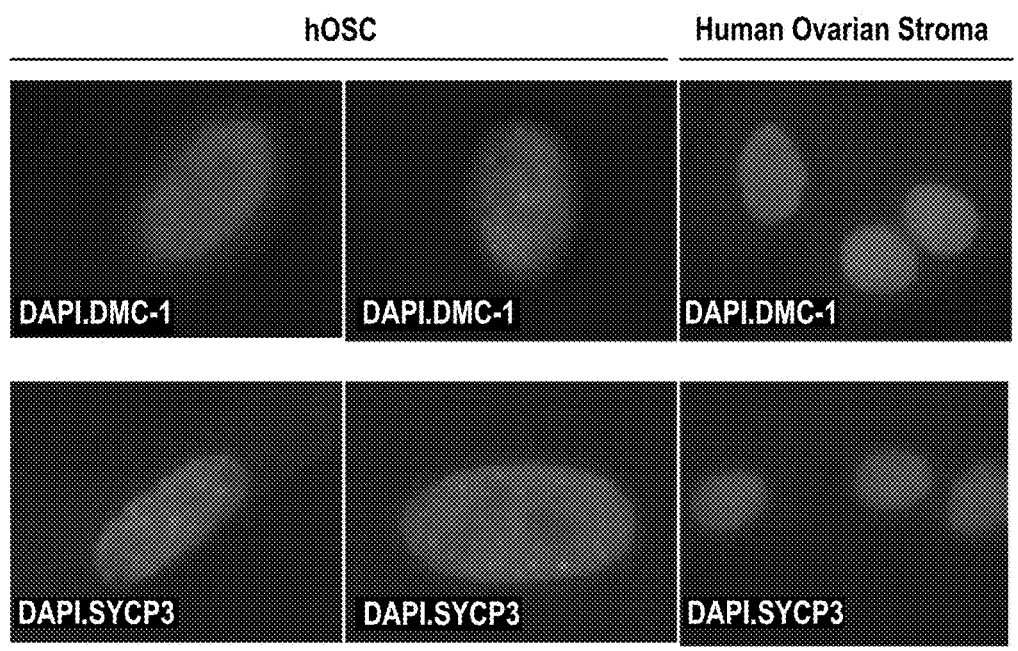
In FIG. 7h, immunofluorescence-based detection of the meiotic recombination markers, DMC1 (dosage suppressor of mck1 homolog) and SYCP3 (synaptonemal complex protein 3) (red against blue DAPI counterstain), is shown in nuclei of cultured human OSCs; human ovarian stromal cells served as a negative control.

The presence of mRNA encoding the meiotic marker MSY2 in oocytes newly formed from human OSCs in vitro prompted us to next explore the prospects of meiotic entry in these cultures. Immunofluorescence analysis of attached (non-oocyte germline) cells 72 hours after passage identified cells with punctate nuclear localization of the meiosis-specific DNA recombinase, DMC1, and the meiotic recombination protein, synaptonemal complex protein 3 (SYCP3) (FIG. 7h). Both proteins are specific to germ cells and are necessary for meiotic recombination (Page et al., *Annu. Rev. Cell Dev. Biol.* 2004 20:525-558; Yuan et al., *Science* 2002 296:1115-1118; Kagawa et al., *FEBS J.* 2010 277:590-598).

Figure 7I:
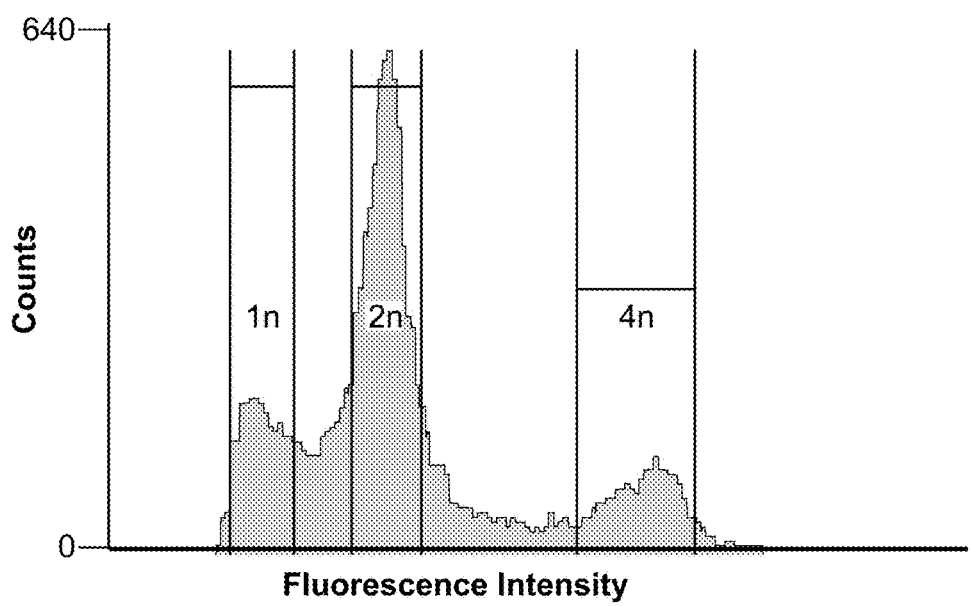
In FIG. 7i, FACS-based ploidy analysis of cultured human OSCs is shown 72 hours after passage. Results from ploidy analysis of cultured human fibroblasts (negative control) and cultured mouse OSCs are presented in FIG. 9.
Figure 8A:
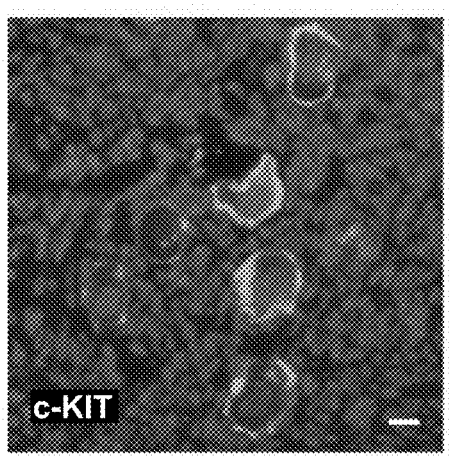
FIG. 8 depicts the detection of oocyte-specific markers in adult human ovaries. Immunofluorescence analysis of VASA (8a, red), KIT (8b, green), MSY2 (8c, red) and LHX8 (8d, green) expression in oocytes in adult human ovarian cortical tissue is shown (see also FIG. 10h). Sections were counterstained with DAPI (blue) for visualization of nuclei. Scale bars, 25 µm.
Figure 8B:
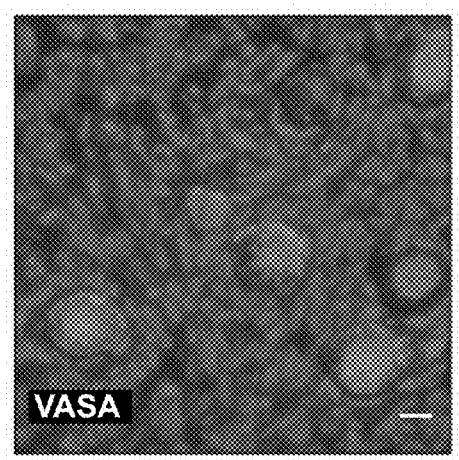
Figure 8C:
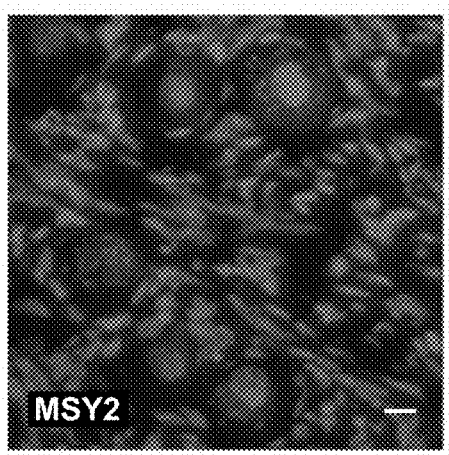
Figure 8D:
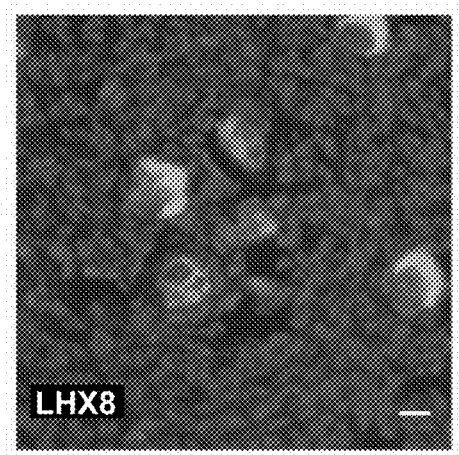
Figure 9A:
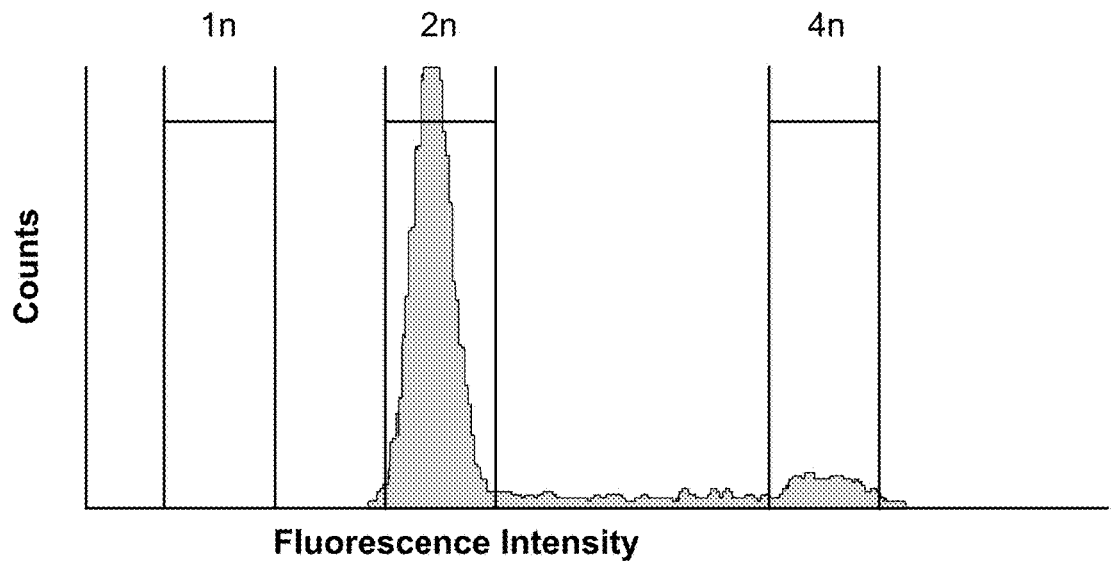
FIGS. 9a and 9b show representative FACS-based assessment of ploidy status in cultures of actively-dividing human fetal kidney fibroblasts (9a) and in mouse OSCs collected 48 hours after passage (9b). Haploid (1n) cells were only detected in the germline cultures, consistent with results from analysis of human OSCs maintained in vitro (see FIG. 7i), whereas all cultures contained diploid (2n) and tetraploid (4n) populations of cells.
Figure 9B:
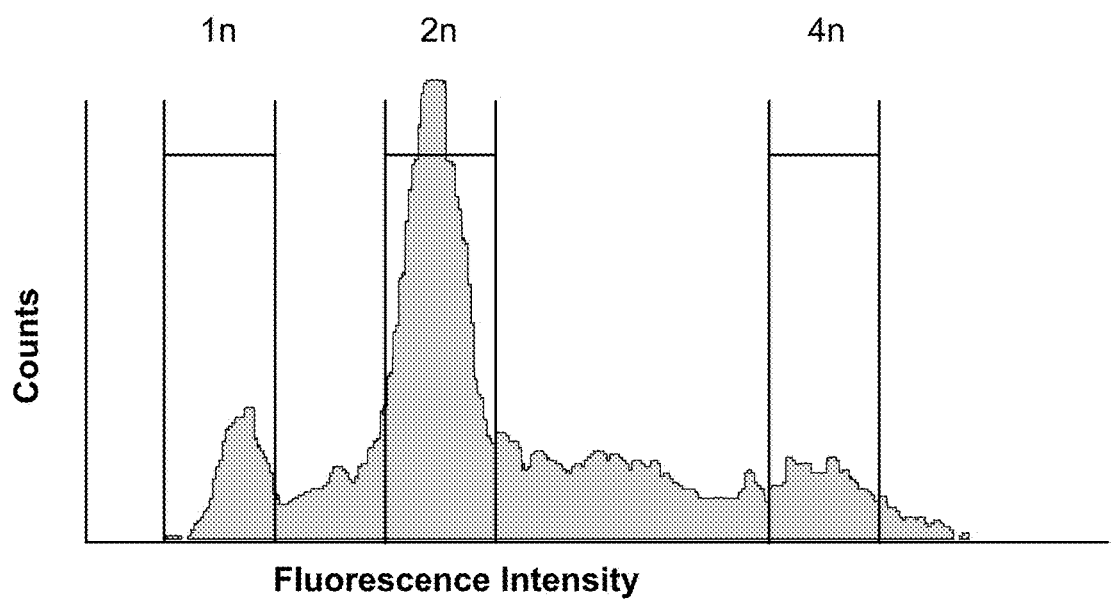

Chromosomal DNA content analysis of human OSC cultures 72 hours after passage was determined. Cultured mouse (48 hours after passage) or human (72 hours after passage) OSCs were collected by trypsinization, washed and resuspended in ice-cold PBS, and counted with a hemocytometer. After fixation in ice-cold 70% ethanol for 1 hour, cells were washed in ice-cold PBS and incubated with 0.2 mg/ml RNase-A for 1 hour at 37° C. Propidium iodide was then added (10 µg/ml final), and ploidy status was determined using a FACSARIA II® cytometer (BD Biosciences, San Jose, Calif., USA). As a control somatic cell line, these experiments were repeated using human fetal kidney fibroblasts (KEK 293, INVITROGEN®). This analysis revealed the presence of an expected diploid (2n) cell population; however, peaks corresponding to 4n and 1 n populations of cells were detected, the latter being indicative of germ cells that had reached haploid status (West et al., *Stem Cells Dev.* 2011 20:1079-1088) (FIG. 7i). In actively-dividing cultures of fetal human kidney fibroblasts analyzed as controls in parallel, only 2n and 4n populations of cells (FIG. 9a) were detected. Comparable outcomes were observed following FACS-based chromosomal analysis of mouse OSC cultures (FIG. 9b).

Example 6: Human OSCs Generate Oocytes in Human Ovarian Cortical Tissue In Vivo To confirm and extend the in-vitro observations of putative oogenesis from candidate human OSCs, in two final experiments VASA-positive cells isolated from adult human ovaries were stably transduced with a GFP expression vector (GFP-hOSCs) to facilitate cell tracking. For cell tracking experiments, human OSCs were transduced using a retrovirus to obtain cells with stable expression of GFP (GFP-hOSCs). Briefly, 1 µg of pBabe-Gfp vector DNA (Addgene plasmid repository #10668) was transfected as per the manufacturer's protocol (Lipofectarnine, INVITROGEN®) into the Platinum-A retroviral packaging cell line (Cell Biolabs). Viral supernatant was collected 48 hours after transfection. Transduction of human OSCs was performed using fresh viral supernatant facilitated by the presence of polybrene (5 µg/ml; Sigma Aldrich Corporation, St. Louis, Mo., USA). After 48 hours, the virus was removed and replaced with fresh OSC culture medium. Human OSCs with expression of GFP were purified by FACS following an initial 1 week of expansion, and the purified cells were expanded for additional 2 weeks before a second round of FACS purification to obtain GFP-hOSCs for human ovarian tissue re-aggregation or xenografting experiments.

In the first experiment, approximately $1 \times 10^5$ GFP-hOSCs were then re-aggregated with dispersed adult human ovarian cortical tissue. Human ovarian cortex was dissociated and washed as described above, and incubated with 35 µg/ml phytohemaglutannin (PHA; Sigma) plus $1 \times 10^5$ GFP-hOSCs for 10 minutes at 37° C. The cell mix was pelleted by centrifugation (9,300×g for 1 minute at 20° C.) to create the tissue aggregate, which was placed onto a Millicell 0.4 µm culture plate insert (Millipore) contained in a 6-well culture dish with 1 ml of OSC culture medium. Aggregates were incubated at 37° C. in 5% $CO_2$-95% air, and live-cell GFP imaging was performed 24, 48 and 72 hours later.

Figure 10A:
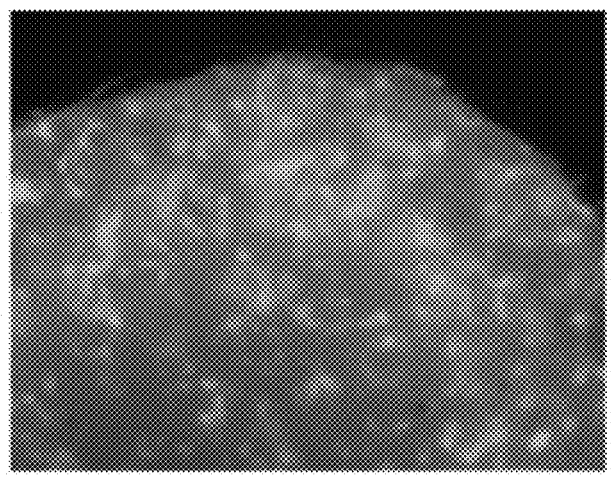
Figure 10B:
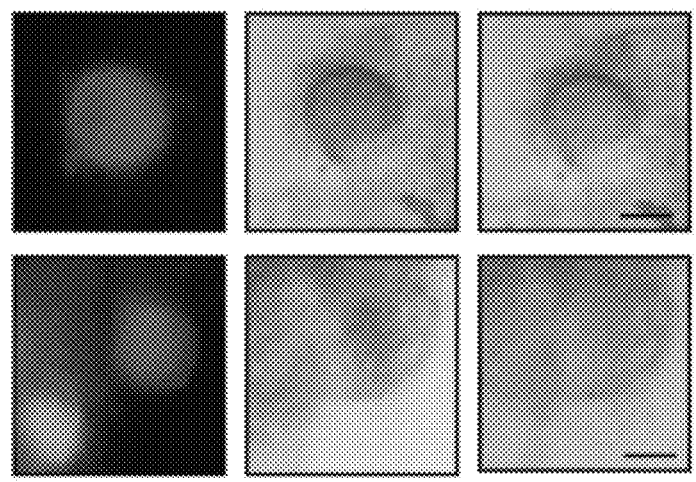
Figure 10C:
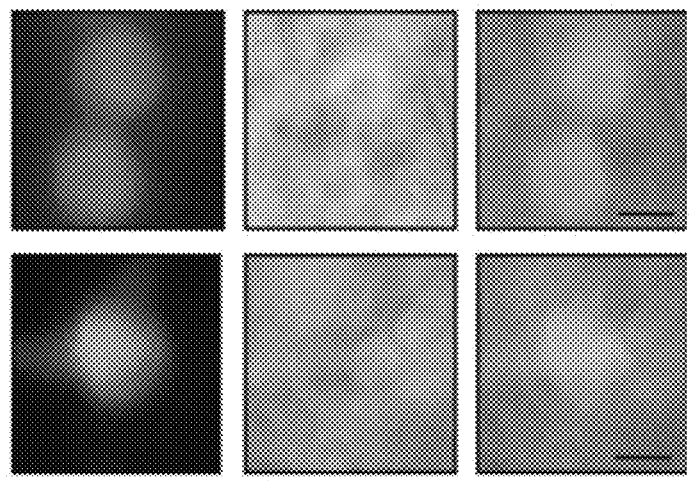

Numerous GFP-positive cells were observed, as expected, throughout the re-aggregated tissue (FIG. 10a). The aggregates were then placed in culture and assessed 24-72 hours later by direct (live cell) GFP fluorescence. Within 24 hours, several very large (≥50-µm) single cells were also observed in the aggregates, many of which were enclosed by smaller GFP-negative cells in tightly compact structures resembling follicles; these structures remained detectable through 72 hours (FIG. 10b, c). These findings indicated that GFP-expressing human OSCs spontaneously generated oocytes that became enclosed by somatic (pregranulosa/granulosa) cells present in the adult human ovarian dispersates.

Next, GFP-hOSCs were injected into adult human ovarian cortical tissue biopsies, which were then xenografted into NOD/SCID female mice (n=40 grafts total). Ovarian cortical tissue pieces (2×2×1 mm) were individually injected with approximately $1.3 \times 10^3$ GFP-hOSCs using a 10 µl NanoFil syringe with a 35-gauge beveled needle (World Precision Instruments). Recipient NOD/SCID female mice were anesthetized and a small incision was made along the dorsal flank for subcutaneous insertion of the human ovarian tissue, essentially as described (Weissman et al., *Biol. Reprod.* 1999 60:1462-1467; Matikainen et al., *Nature Genet.* 2001 28:355-360). Xenografts were removed after 7 or 14 days post transplantation, fixed in 4% PFA, paraffin-embedded and serially sectioned (6-µm) for immunohistochemical analysis using a mouse monoclonal antibody against GFP (sc9996; Santa Cruz Biotechnology) (Lee et al., *J. Clin. Oncol.* 2007 25:3198-3204). Briefly, high temperature antigen retrieval was first performed using 0.01 M sodium citrate buffer (pH 6.0). After cooling, sections were incubated for 10 minutes with 3% hydrogen peroxide in methanol to block endogenous peroxidase activity, washed and incubated in streptavidin-biotin pre-block solution as per the manufacturer's protocol (Vector Laboratories). Sections were then blocked for 1 hour at 20° C. using TNK buffer containing 1% normal goat serum and incubated overnight at 4 C with a 1:100 dilution of GFP antibody prepared in TNK buffer containing 1% normal goat serum. Sections were then washed, incubated with a 1:500 dilution of goat anti-mouse biotinylated secondary antibody for 30 minutes at 20° C., washed and reacted with Vectastain ABC reagents (Lab Vision) for 30 minutes at 20° C. prior to detection of GFP-positive cells using diaminobenzidine (DAKO). Sections were lightly counterstained with haematoxylin to visualize cell and tissue architecture. Negative controls (complete immunohistochemical staining protocol on xenografted tissues that received vehicle injections) were always run in parallel and did not show a positive signal. To confirm and extend these observations, dual immunofluorescence-based detection of GFP and either MSY2 (diplotene stage oocyte-specific marker) or LHX8 (early stage oocyte transcription factor) in xenografted human ovarian tissues was performed with DAPI counterstaining, as detailed previously in the description of immunoanalysis.

Figure 10D:
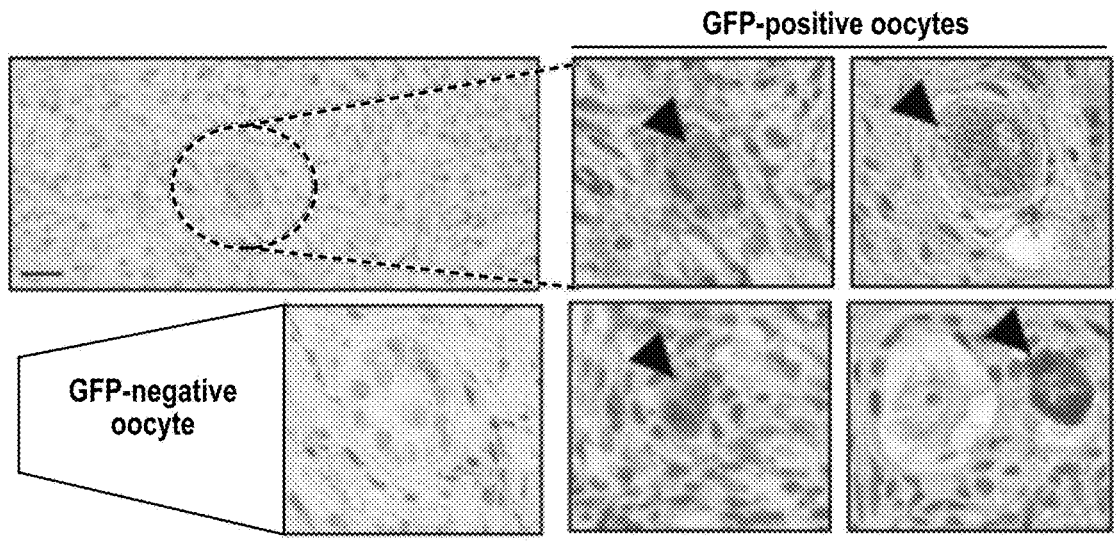
Figure 10E:
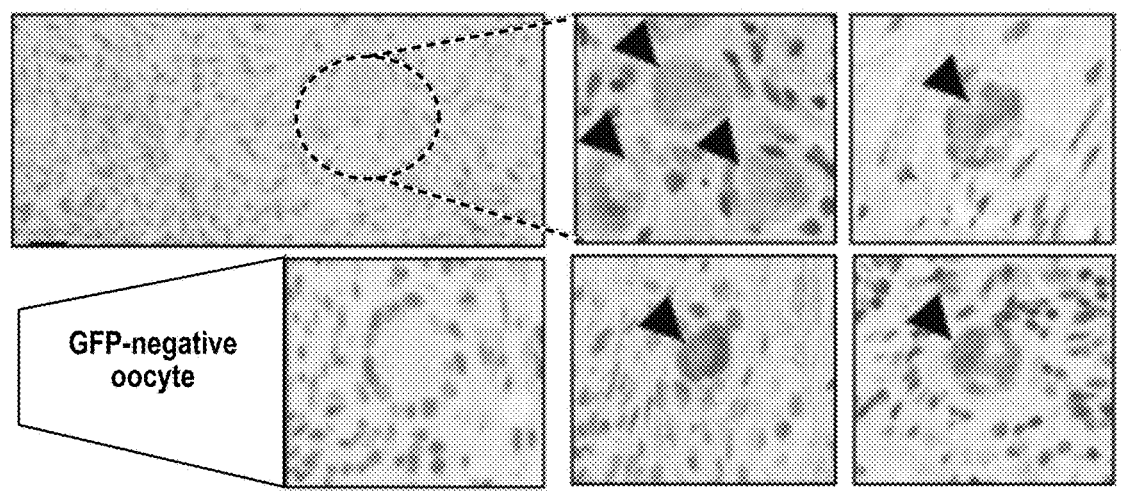
Figures 10F, 10G:
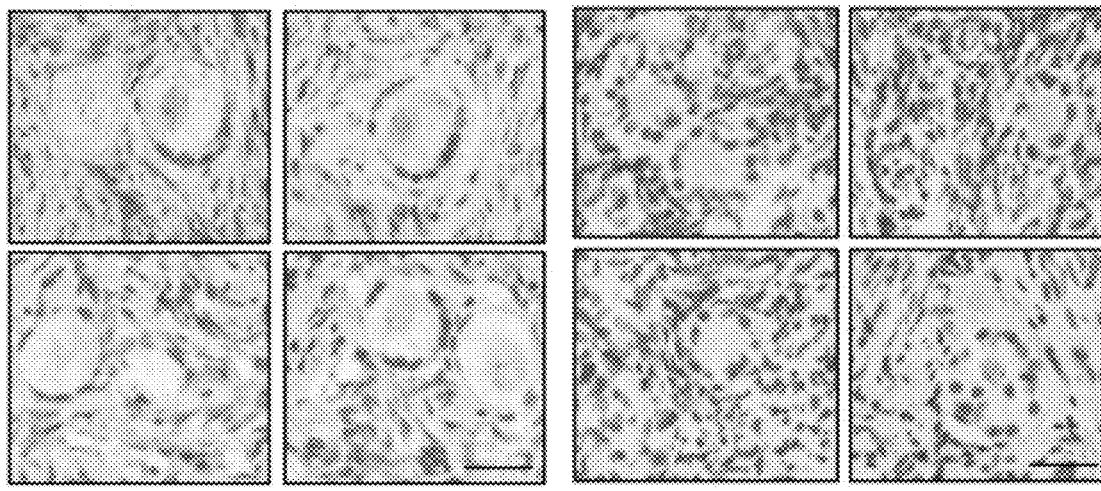
Figure 10H:
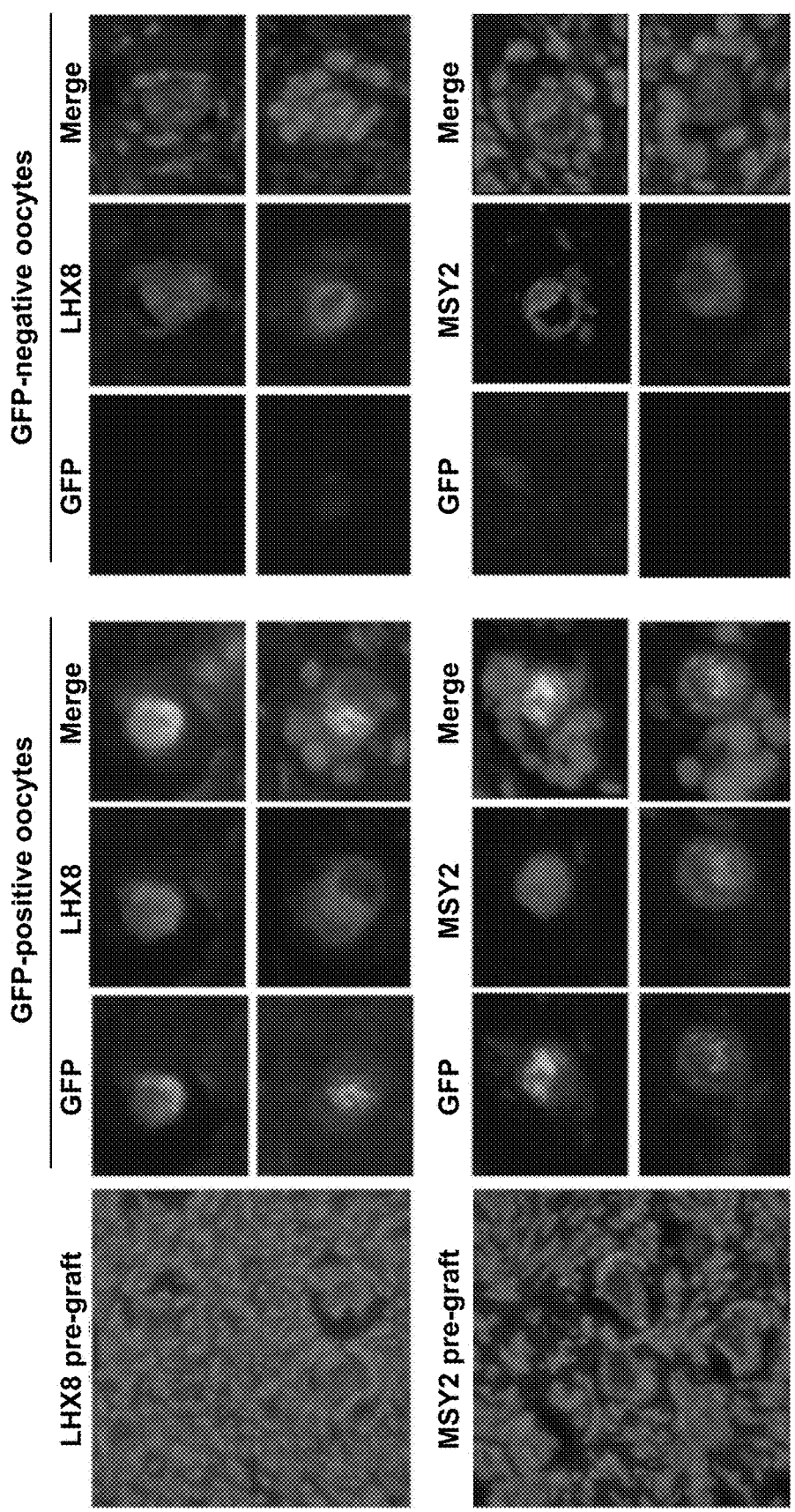
FIG. 10h shows dual immunofluorescence analysis of GFP expression (green) and either the diplotene stage oocyte-specific marker MSY2 (red) or the oocyte transcription factor LHX8 (red) in xenografts receiving GFP-hOSC injections. Note that GFP was not detected in grafts prior to GFP-hOSC injection, whereas MSY2 and LHX8 were detected in all oocytes. Sections were counterstained with DAPI (blue) for visualization of nuclei. Scale bars, 25 µm.
Figure 11:
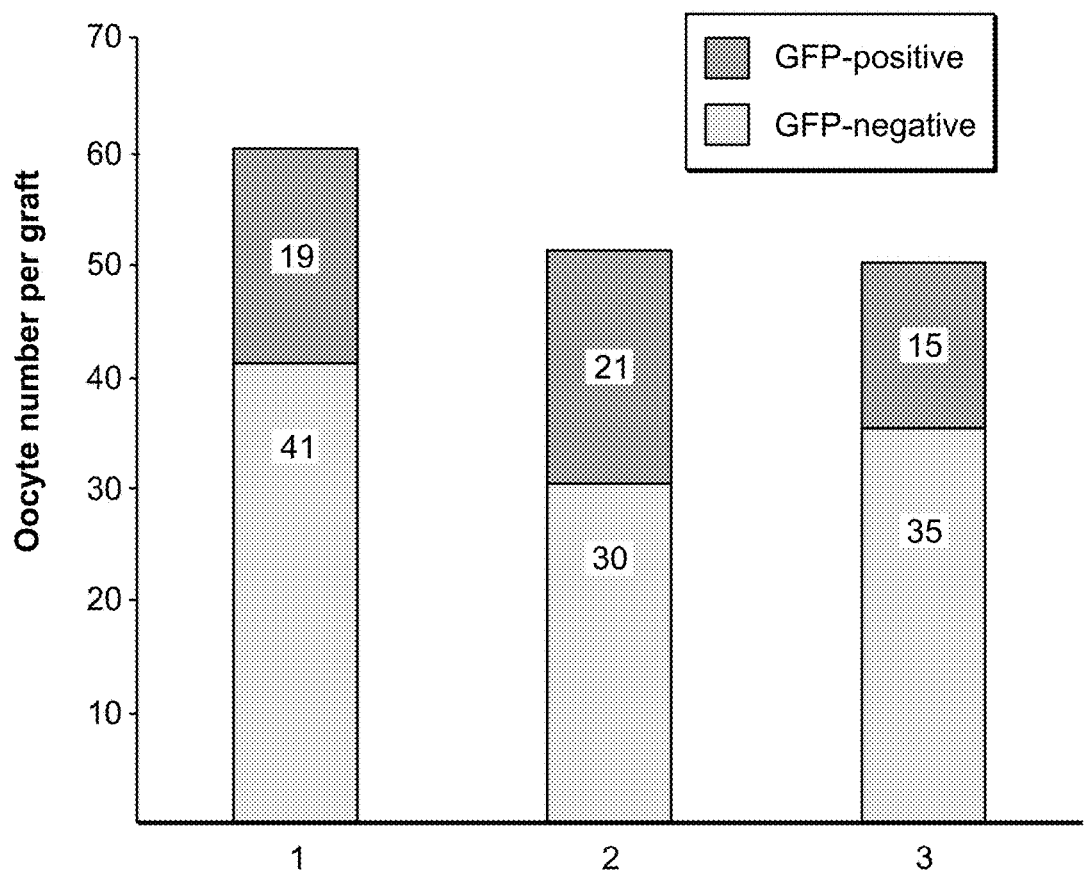
FIG. 11 depicts morphometry-based assessment of oocyte formation in human ovarian xenografts following GFP-hOSC transplantation. The total number of primordial and primary follicles in 3 randomly selected human ovarian cortical tissue samples (labeled 1, 2 and 3) are shown, 7 days after injecting GFP-hOSCs and xenografting into NOD/SCID mice, which contain GFP-negative (host-derived) or GFP-positive (OSC-derived) oocytes (see FIGS. 10d through 10g for examples).

Grafts were collected 7 or 14 days later for assessment of GFP expression. All human ovary grafts contained easily discernible primordial and primary follicles with centrally-located GFP-negative oocytes. Interdispersed among and often adjacent to these follicles, which were presumably present in the tissue prior to GFP-hOSC injection, were other immature follicles containing GFP-positive oocytes (FIG. 10*d, f*). Serial section histomorphometric analysis of 3 randomly selected human ovarian tissue biopsies injected with GFP-hOSCs revealed the presence of 15-21 GFP-positive oocytes per graft 7 days after xenografting into mice (FIG. 11). As controls, GFP-positive oocytes were never detected in human ovarian cortical tissue prior to GFP-hOSC injection (FIG. 10*e*) or in xenografts that received mock injections (vehicle without GFP-hOSCs) prior to transplantation into NOD/SCID mice (FIG. 10*g*). Dual immunofluorescence-based detection of GFP along with either the diplotene stage oocyte-specific marker MSY2 (Gu et al., *Biol. Reprod.* 1998 59:1266-1274; Yang et al., *Proc. Natl. Acad. Sci. USA* 2005 102:5755-5760) or the oocyte-specific transcription factor LHX8 (Pangas et al., *Proc. Natl. Acad. Sci. USA* 2006 103:8090-8095) identified many dual-positive cells distributed throughout xenografts injected with GFP-hOSCs (FIG. 10*h*). As expected, no GFP-positive oocytes were detected in ovarian tissue prior to GFP-hOSC injection or in xenografts that did not receive GFP-hOSC injections (not shown; see FIG. 10*e, g*); however, these oocytes were consistently positive for LHX8 and MSY2 (FIG. 10*h*; FIG. 8).

Example 7: Use of OSCs in Autologous Germline Mitochondrial Energy Transfer ("AUGMENT")

Figures 12C, 13:
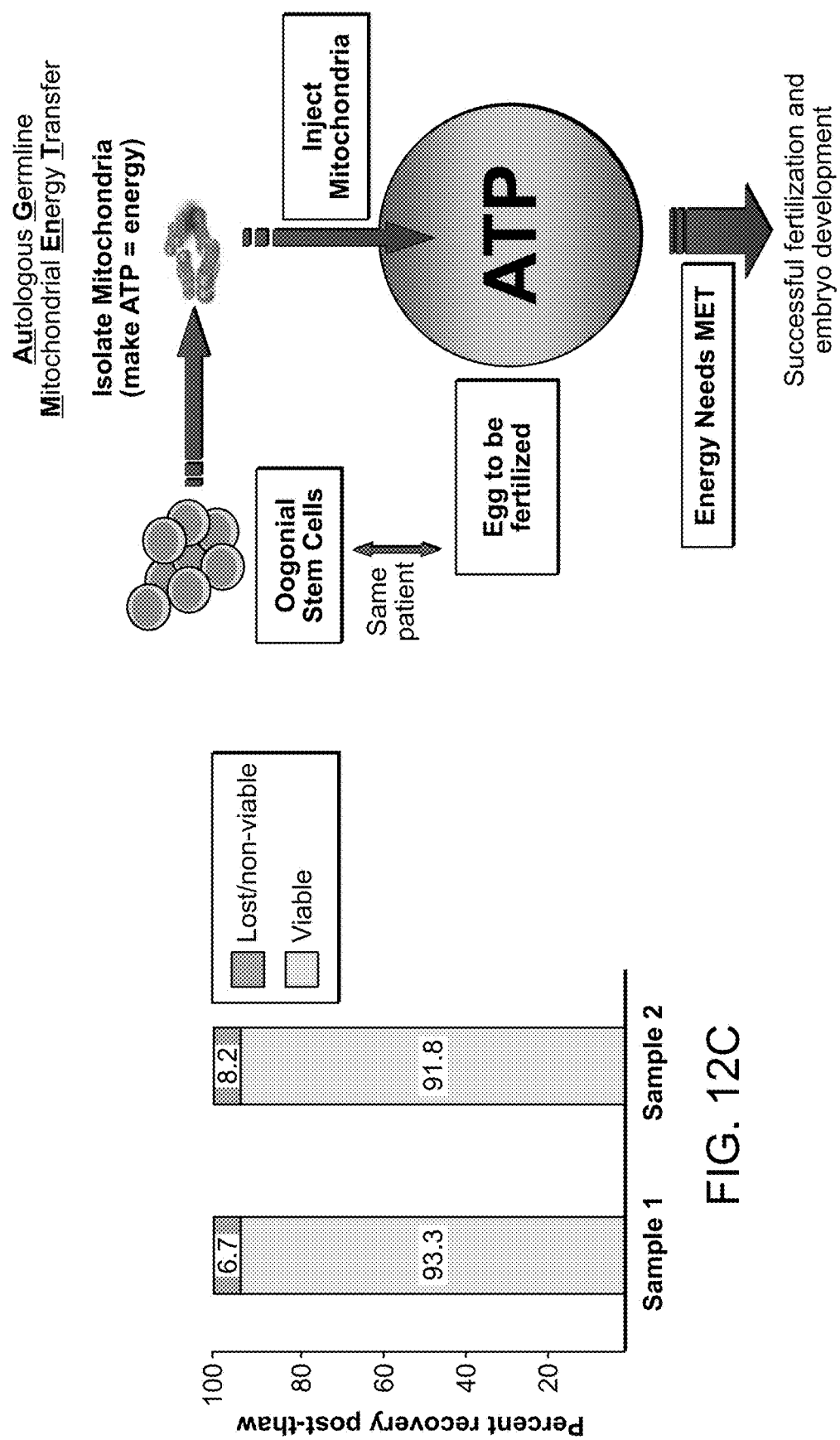
In FIG. 12c, the percent cell loss following freeze-thaw of freshly-isolated human OSCs is shown (results from two different patients).
FIG. 13 depicts an overview of an Autologous Germline Mitochondrial Energy Transfer procedure which is described in U.S. Patent Application Ser. No. 61/475,561, filed on Apr. 14, 2011, entitled "Compositions and Methods for Autologous Germline Mitochondrial Energy Transfer." Note that OSCs used as a source of mitochondria for the transfer, and the egg to be fertilized which will receive the mitochondria, are obtained from the same subject.

FIG. 13 depicts an overview of the use of OSCs as an autologous source of female germ cells for derivation of oogenic cytoplasm or mitochondrial fractions that can then be transferred into an oocyte or egg obtained from the same subject prior to or during in vitro fertilization (IVF). The resultant boost in mitochondrial DNA copy number and ATP-generating capacity in the egg after AUGMENT ensures that the egg has ample reserves of ATP for energy-driven events required for successful fertilization and embryonic development. The additional mitochondria provided to the egg by AUGMENT are derived from the natural precursor cell used by the body to produce egg cells. Furthermore, the additional mitochondria will not produce adverse effects in the egg, based on data showing that healthy embryogenesis proceeds even when the minimal threshold number of mitochondria needed for embryo development is exceeded by nearly four-fold (see Wai et al., *Biology of Reproduction* 2010 83:52-62, FIG. 6). The beneficial effects of heterologous ooplasmic transfer reported earlier by Cohen et al., *Mol Hum Reprod* 1998 4:269-80, a procedure which is restricted for human use because it results in germline genetic manipulation and mitochondrial heteroplasmy in embryos/offspring, indicate that eggs are benefited by additional mitochondria.

An exemplary clinical protocol for AUGMENT is as follows. Prior to the start of standard IVF, the subject will undergo a laparoscopy during menstrual cycle days 1-7 to collect up to three pieces (approximately 3×3×1 mm each) of ovarian epithelium (ovarian cortical biopsy) from one ovary. During this procedure, 2-3 incisions will be made within the abdomen and a device will be inserted to remove the tissue from an ovary using sterile procedures. The tissue collected will be placed in sterile solution and transported on ice to the GTP compliant laboratory where it will be cryopreserved until the time of AUGMENT/ICSI. The tissue will remain frozen until the time of enzymatic dissociation. This will serve as the source of autologous OSCs from which mitochondria will be purified.

Next, OSCs will be isolated and mitochondria will be harvested from the OSCs. After thawing the ovarian cortical biopsied tissue, the tissue will be minced and placed in solution, containing recombinant collagenase and recombinant DNase1 and homogenized to a single cell suspension. The suspension will be passed through a cell strainer to prepare a solution of single cells. The single cell suspension will be incubated with an anti-VASA antibody. Labeled cells will then be isolated by fluorescence-activated cell sorting (FACS). Standard slow cooling cryopreservation procedures for freezing aliquots of OSCs will be used.

Subjects will undergo a standard IVF protocol including baseline evaluation, GnRH antagonist down-regulation and gonadotropin stimulation. Oocyte retrieval will take place within 34-38 hours after hCG administration and oocytes will be assessed for quality and maturation state. Mature oocytes will be inseminated by ICSI.

On the day of egg retrieval, the frozen OSC vial for that subject will be thawed using standard methods. OSCs will be processed to yield a mitochondrial pellet (Frezza et al. *Nature Protocols* 2007 2:287-295 or Perez et al., *Cell Death and Differentiation* 2007 3:524-33. Epub 2006 Oct. 13) or as described below in Example 10, where a FACS-based method is employed to isolate the total mitochondrial population in a tissue and optionally, further isolate the actively respiring mitochondrial population or quantitate the ratio of active to total mitochondria in a tissue. Evaluation and activity of the mitochondrial preparation will be assessed and recorded. The mitochondrial pellet will be re-suspended in media to a standardized concentration of mitochondrial activity which improves oocyte quality. This media containing the mitochondria will be aspirated into a microinjection needle that contains the spermatozoan to be delivered. Both the mitochondria and spermatozoan will be delivered together into the oocyte by ICSI.

Following fertilization and embryo culture, a maximum of three, grade 1 or grade 2 (SART grading system (50)) embryos may be transferred under ultrasound guidance after 3 or 5 days of culturing based on the assessment of embryo development. If a pregnancy is confirmed via beta hCG testing, then the subject will have subsequent observations at approximately 6 and 20-weeks gestational age.

Example 8: CR-Induced Mitochondrial Stimulation Improves Oocyte Quality and Yield in Females with Increasing Age Restricted caloric intake without malnutrition extends lifespan and attenuates severity of aging-related health complications in many species (Masoro et al., *Mech Ageing Dev* 2005 126:913-922; Mair et al., *Annu Rev Biochem* 2008 77:727-754; Fontana et al., *Science* 2010 328:321-326). A common feature of the CR response appears to be an alteration of metabolic regulators that affect mitochondrial dynamics and accumulated oxidative stress in organs with age (Sohal et al. *Mech Ageing Dev* 1994 74:121-133, Barja et al. 2002 *Ageing Res Rev* 1:397-411, Barja et al. *Biol Rev Camb Philos Soc* 2004 79:235-251). For example, the growth hormone/insulin/insulin-like growth factor-1 axis, mammalian target of rapamycin, AMP-activated protein kinase and sirtuins have all been implicated as mediators of CR (Fontana et al., *Science* 2010 328:321-326, Sinclair et al. *Mech Ageing Dev* 2005 126:987-1002, Rodgers et al. *FEBS Lett* 2008 582:46-53, Finley et al. *Ageing Res Rev* 2009 8:173-188). Several of these pathways reportedly converge on peroxisome proliferator-activated receptor γ coactivator-1α (PGC-1α), a transcriptional regulator that is highly responsive to nutritional cues. Among its actions, PGC-1α promotes adaptation to energy deficiency by modulating expression of genes involved in mitochondrial respiration (Fontana et al., *Science* 2010 328:321-326, Sinclair et al. *Mech Ageing Dev* 2005 126:987-1002, Rodgers et al. 2008 *FEBS Lett* 582:46-53, Finley et al. *Ageing Res Rev* 2009 8:173-188, Rodgers J T, et al. *Nature* 2005 434:113-118, Lin et al. *Cell Metab* 2005 1:361-370). Surprisingly, deletion of PGC-1α in mice produces only subtle phenotypes, although several metabolic abnormalities manifest much more robustly upon a challenge such as acute fasting (Lin et al. *Cell* 2004 119:121-135, Arany Z, et al. *Cell Metab* 2005 1:259-271, Leone T C, et al. *PLoS Biol* 2005 3:672-687). However, no studies have tested the functional relationship between PGC-1α and CR in any tissue with age by subjecting Pgc-1α-null mice to a reduced calorie diet. Accordingly, a 4-year investigation was conducted to elucidate whether CR during adulthood without or with manipulation of PGC-1α influences oocyte quality in female mice on the verge of reproductive failure due to advancing maternal age.

Yield, maturational status and post-fertilization developmental competency of oocytes obtained from 12-month-old (aged) female mice returned to an ad-libitum (AL) diet for 1 month following 7.5 months of dietary CR (CR-AL-fed) initiated in a stepwise fashion at 3.5 months of age were first evaluated. This protocol was based on prior work showing that female mice maintained on CR during adulthood continue to breed and deliver offspring into advanced ages after their return to an AL diet (Selesniemi et al. 2008 *Aging Cell* 7:622-629). Mice were superovulated by injection of pregnant mare serum gonadotropin (PMSG, 10 IU; Sigma Aldrich Corporation, St. Louis, Mo., USA) followed by human chorionic gonadotropin (hCG, 10 IU; Sigma Aldrich Corporation, St. Louis, Mo., USA) 46-48 hours later. Oocytes were collected from oviducts 15-16 hours after hCG injection, denuded of cumulus cells using hyaluronidase (Irvine Scientific, Santa Ana, Calif., USA), washed with human tubal fluid (HTF; Irvine Scientific, Santa Ana, Calif., USA) supplemented with BSA (fraction V, fatty acid-free; Sigma Aldrich Corporation, St. Louis, Mo., USA), and classified as MII (first polar body in perivitelline space), maturation arrested (germinal vesicle breakdown with no polar body extrusion, or germinal vesicle intact), or degenerated.

Figure 16A:
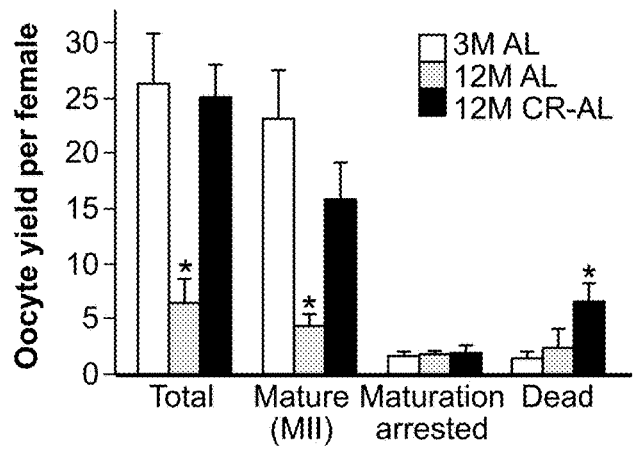
FIG. 16 depicts prevention of the aging-related decline in ovulated oocyte numbers as a result of restricted caloric intake ("CR"). (A) Yield and morphology of oocytes obtained after induced ovulation of 3-mo-old (3 M) ad-libitum (AL) diet (AL)-fed (n=6), 12-mo-old (12 M) AL-fed (n=12), and 12 M CR-AL-fed (n=6) mice (mean±SEM; *, P<0.05 vs. 3 M AL-fed females). (B) Number of in-vitro fertilized metaphase stage II (MID oocytes that developed to blastocysts per induced ovulation cycle per female (n=11-16 mice group; mean±SEM; *, P<0.05 vs. 3 M AL-fed females). (C) Number of non-atretic immature follicles per ovary in 3 M AL-fed, 12 M AL-fed and 12 M AL-CR-fed mice (mean±SEM, n=9-14 mice per group; *, P<0.05 vs. 3 M AL-fed females; **, P<0.05).

In control females allowed to AL feed during the entire study period, the total number of oocytes and number of fully mature oocytes (oocytes that reached meiotic metaphase II; designated MiI) ovulated per female decreased significantly between 3 and 12 months of age (FIG. 16A). However, the age-related decline in both total and mature oocyte yield was abrogated in 12-month-old female mice maintained on CR (FIG. 16A).

Figure 16B:
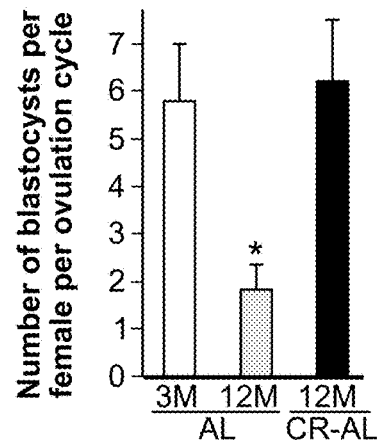
Figure 17A:
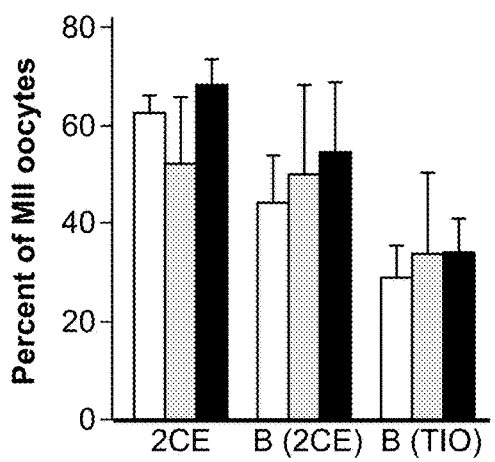
FIG. 17 depicts the lack of effect of CR on preimplantation embryonic development following IVF. (A and B) Percent of cumulus cell-denuded MIT oocytes (A) or cumulus-enclosed oocytes (B) collected from 3 M AL-fed, 12 M AL-fed and 12 M CR-AL-fed female mice that developed to 2-cell stage embryos (2CE) following in-vitro fertilization, and the percent of 2CE or total inseminated oocytes (TIO) that developed to blastocyst stage (B) embryos [B(2CE) and B(TIO), respectively]. Data are the mean±SEM of the following: (A) n=55-140 denuded MII oocytes from 3 independent experiments using a total of 6-9 mice per group; (B) n=38-144 cumulus-oocyte complexes from 3 independent experiments using a total of 5-7 mice per group.
Figure 17B:
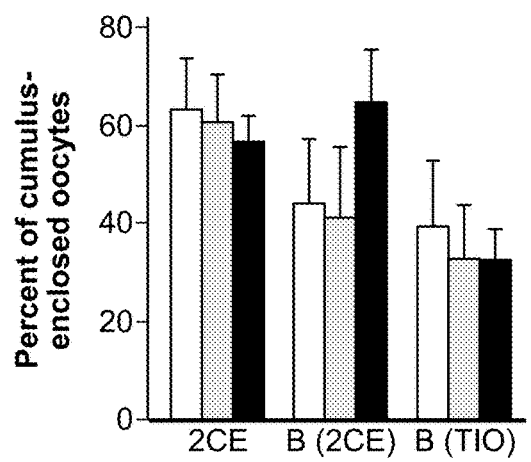
Figure 18A:
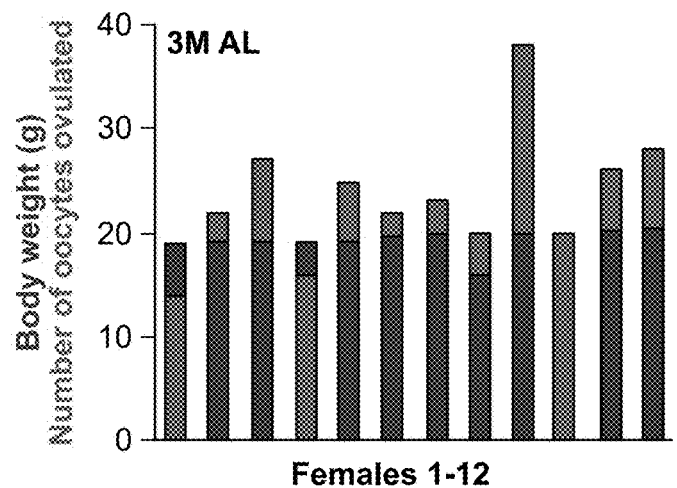
FIG. 18 depicts the relationship between oocyte yield and body weight. (A and B) Assessment of body weight versus superovulated oocyte yield in 3 M AL-fed (A), 12 M AL-fed (B) and 12 M CR-AL-fed (C) females on a mouse-by-mouse basis.
Figure 18B:
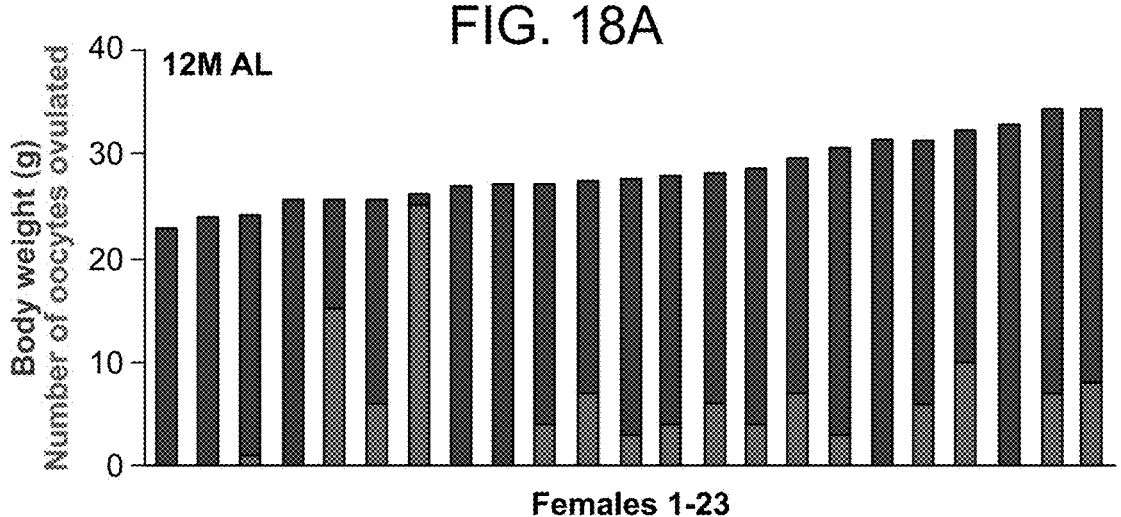
Figure 18C:
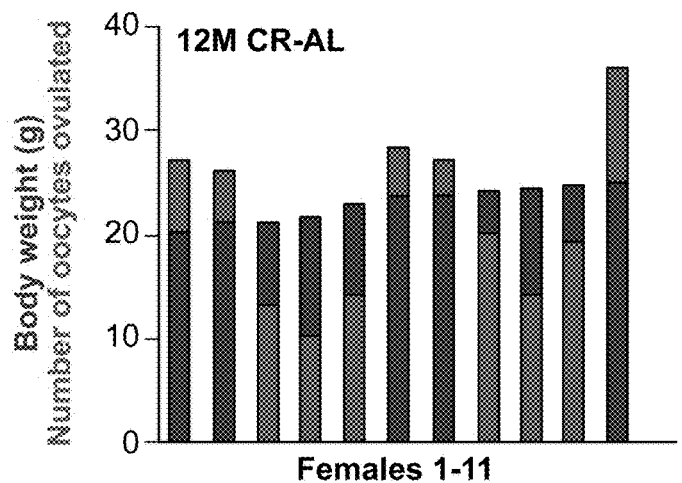

Next, in-vitro fertilization (IVF) and preimplantation embryonic development rates were assessed. Sperm were collected from the cauda epididymides of male mice into HTF supplemented with BSA and then capacitated. Denuded MII oocytes or intact cumulus-oocyte complexes were mixed with 1-2×106 sperm/ml in HTF supplemented with BSA for 6-9 hours, washed and transferred to fresh medium. The number of 2-cell embryos was used to measure IVF success rate, and blastocyst development rates from these embryos were recorded. Following analysis of 284 (3-month-old AL-fed), 93 (12-month-old AL-fed) and 198 (12-month-old CR-AL-fed) oocytes, no differences were observed with respect to in-vitro fertilization (IVF) or pre-implantation embryonic development rates (FIG. 17). However, because CR improved the yield of MII oocytes per female after an induced ovulation cycle at 12 months of age (FIG. 16A), the number of blastocysts obtained following IVF of oocytes obtained from each aged CR-AL-fed mouse was similar to that obtained using young mice and significantly higher than that using aged AL-fed mice (FIG. 16B).

Figure 16C:
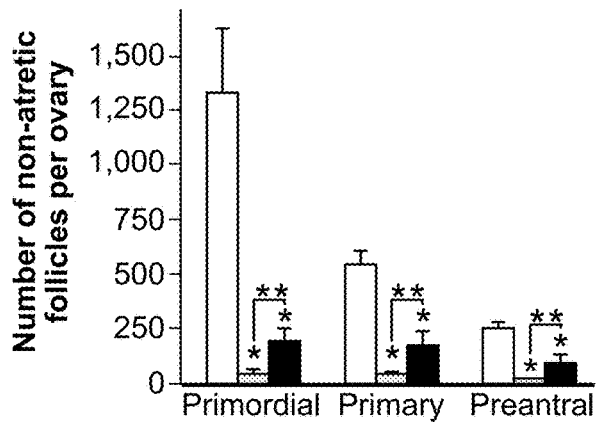

To determine if the beneficial effect of CR on maintaining oocyte yield from aging females was related to differences in body weight, superovulation rates in young AL-fed, aged AL-fed and aged CR-AL fed females on a mouse-by-mouse basis was assessed. It was observed that differences in oocyte yield per mouse, which were greatest in the aged AL-fed group, were unrelated to variations in body weight among the three groups of mice (FIG. 19). Also notable was that the reserve of oocyte-containing follicles in ovaries of both 12-month-old AL-fed and CR-AL-fed females was severely diminished compared to that of 3-month-old mice (FIG. 16C). Thus, the ability of CR to maintain a high yield of MIT oocytes from aged females does not appear linked to changes in body weight or maintenance of a follicle reserve equivalent in size to that of young females.

Next, the quality of MII oocytes collected from aged AL-fed and CR-AL-fed females was studied. Fully mature (MII) oocytes were selected for analysis because aging-related defects in oocytes are clearly evident at this maturational stage and because MII oocytes represent the fertilization-competent egg pool. To this end, chromosomal dynamics, spindle integrity and mitochondrial dynamics were assessed, which are the important events involved in ensuring developmental competency of the egg. A total of 795 mature (MII) oocytes collected from 3-month-old AL-fed (n=20 mice), 12-month-old AL-fed (n=34 mice) and 12-month-old CR-AL-fed (n=20 mice) females were fixed individually for chromosomal analysis using Tarkowski's method (Tarkowski et al. *Cytogenetics* 1966 5:394-400, Muhlhauser et al. *Biol Reprod* 2009 80:1066-1071). Preparations were stained with 4',6-diamidino-2-phenylindole dihydrochloride (DAPI; Sigma Aldrich Corporation, St. Louis, Mo., USA) and scored for aneuploidy rates under a fluorescence microscope. In MII oocytes collected from continuously AL-fed females, the incidence of hyperploidy (>20 chromosomes per cell; FIG. 10A) increased significantly from non-detectable levels at 3 months of age to nearly 5% at 12 months of age. In contrast, no hyperploidy was detected in MIL oocytes from 12-mo-old mice maintained on CR (FIG. 10B). The incidence of hypoploidy (<20 chromosomes per cell) was also significantly elevated in MIT oocytes from 12-month-old versus 3-month-old AL-fed females, and this was completely prevented by CR (FIG. 10B). A similar pattern in the incidence of premature sister chromatid separation (PSCS) was observed in mature oocytes among the 3 groups of mice, although these changes were not statistically significant (FIG. 10B).

Figure 20C:
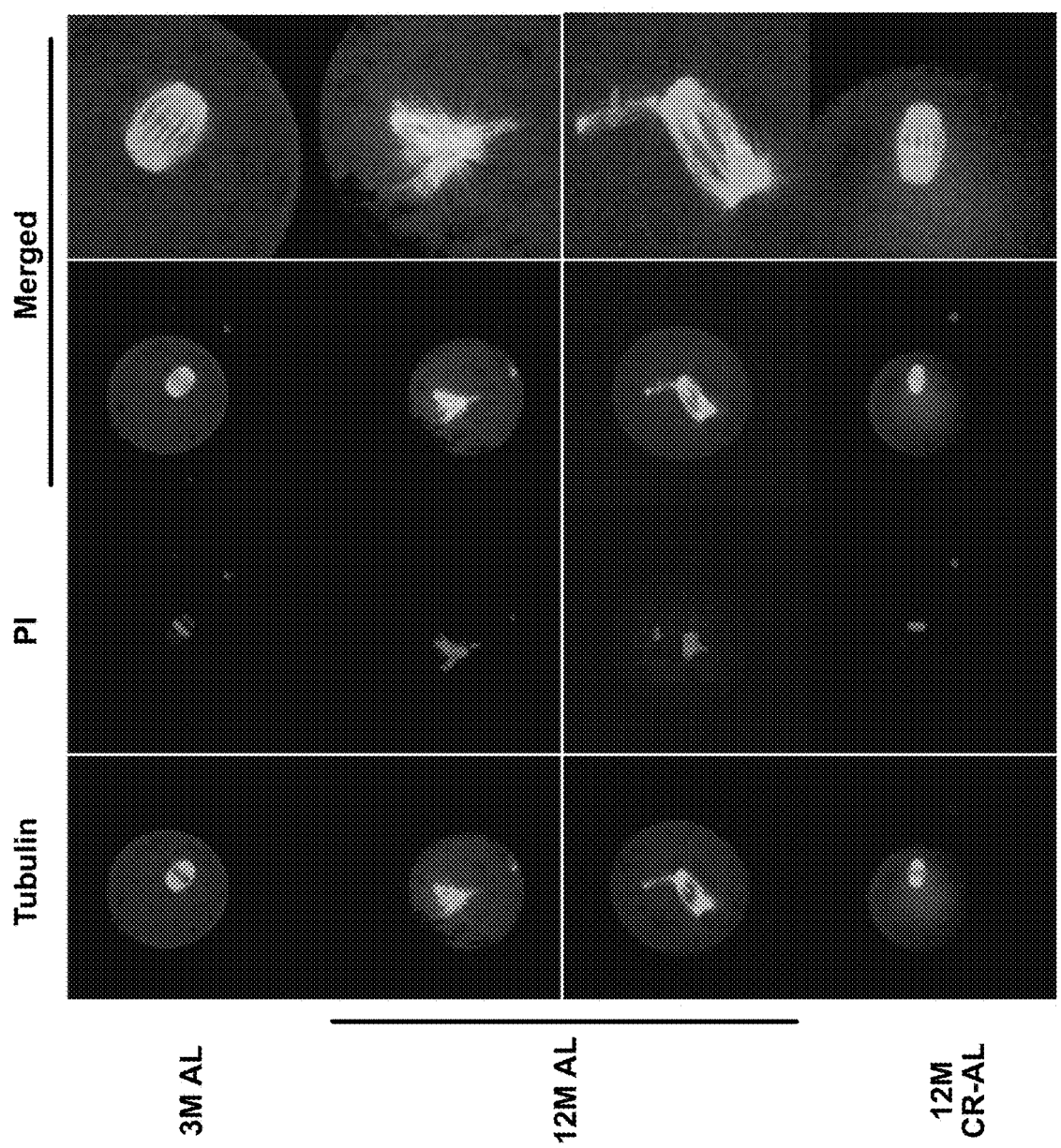
FIG. 20 depicts prevention of spindle and chromosomal alignment defects in oocytes of aged females by CR. (A and B) Incidence of spindle abnormalities (A) and chromosomal misalignment on the metaphase plate (B) in MII oocytes of 3 M AL-fed, 12 M AL-fed and 12 M CR-AL-fed mice (mean±SEM, n=3-20 oocytes analyzed per group in each experiment replicated 4-7 times using a total of 4-8 mice per group; *, P<0.05 vs. 3 M AL-fed females). (C) Representative examples of meiotic spindles in MIT oocytes from the indicated mice (n=22-72 oocytes analyzed per group), after labeling with α-tubulin antibody (green) and counterstaining of DNA with PI (red).

Confocal analysis of α-tubulin and DNA distribution were examined. Superovulated oocytes were denuded of cumulus cells, briefly incubated in Acidified Tyrode's Solution (Irvine Scientific, Santa Ana, Calif., USA) to soften the zona pellucida, and immunostained using mouse anti-α-tubulin antibody (Sigma Aldrich Corporation, St. Louis, Mo., USA) followed by goat anti-mouse IgG conjugated with Alexa Fluor-488 (Life Technologies, Carlsbad, Calif.). Oocytes were mounted using Vectashield containing propidium iodide (PI; Vector Laboratories) and analyzed by confocal microscopy. Confocal analysis of α-tubulin and DNA distribution revealed that meiotic spindles in greater than 90% of MII oocytes collected from either 3-month-old AL-fed or 12-month-old CR-AL-fed females were regular in shape and size with distinct microtubule morphology; however, less than 39% of MII oocytes retrieved from 12-month-old AL-fed mice exhibited normal meiotic spindles (FIGS. 20 A and C). Furthermore, while 64% of MIT oocytes from 12-month-old AL-fed mice exhibited incomplete or aberrant alignment of chromosomes on the metaphase plate, 25% or less of the MIT oocytes collected from either 3-month-old AL-fed or 12-month-old CR-AL-fed females exhibited chromosomal misalignment (FIGS. 20 B and C).

Whether mitochondrial aggregation, which has been linked to the decline in oocyte quality with advancing age (Tarín et al. *Biol Reprod* 2001 65:141-150), was affected by caloric intake was assessed. Oocytes were denuded of cumulus cells, incubated in MitoTracker Red CMRox (Life Technologies), and processed for microscopic analysis. Levels of ATP in individual MII oocytes were determined using a commercially available bioluminescent assay kit under the manufacturer's specifications (Sigma Aldrich Corporation, St. Louis, Mo., USA). Confocal microscopic analyses of MII oocytes stained with MitoTracker revealed that over 90% of MIT oocytes collected from 3-month-old AL-fed females exhibited even and diffuse cytoplasmic distribution of mitochondria (FIGS. 21 A and B). By comparison, nearly 50% of MII oocytes obtained from 12-month-old AL-fed females exhibited extensive mitochondrial aggregation. However, more than 90% of mature oocytes collected from 12-month-old CR-AL-fed females exhibited even and diffuse mitochondrial distribution, resembling that observed in MII oocytes retrieved from young females (FIGS. 21 A and B). Paralleling these changes in mitochondria, the aging-related decline in ATP content in oocytes of aged AL-fed females was similarly prevented by adult-onset CR (FIG. 21C).

Figure 23:
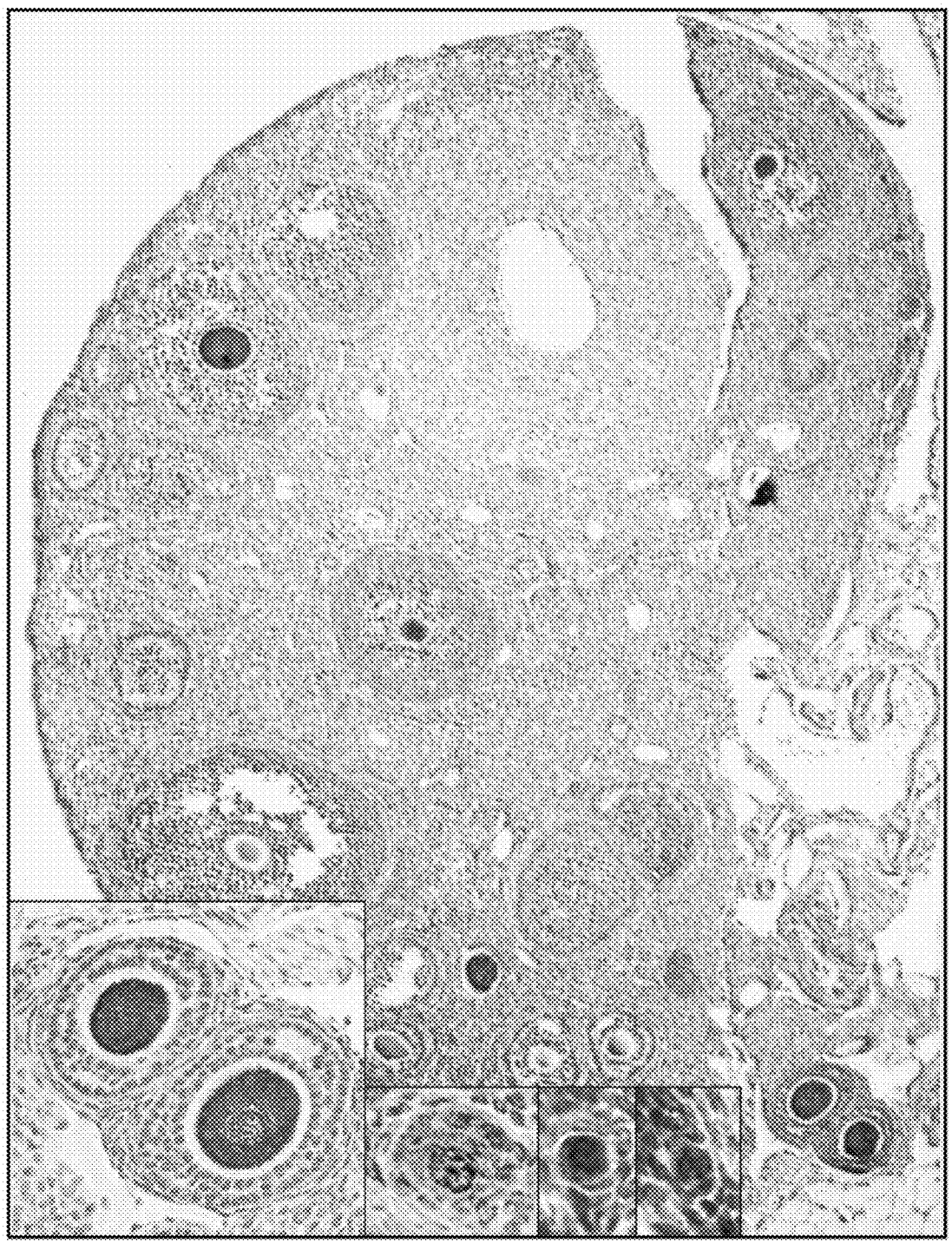
FIG. 23 depicts expression of PGC-1 is in oocytes. Immunohistochemical detection of PGC-1 (brown reaction product against blue hematoxylin counterstain) in young adult mouse ovaries. Insets show magnified images of typical positive oocytes.

Finally, gene mutant mice were used to explore if deletion of PGC-1α, which has been linked to the actions of CR in other cell types (Finley et al. 2009 *Ageing Res Rev* 8:173-188, Corton et al. *J Gerontol A Biol Sci Med Sci* 2005 60A:1494-1509, Anderson et al. *Biochim Biophys Acta* 2009 1790:1059-1066, López-Lluch et al. *Proc Natl Acad Sci* 2006 103:1768-1773) and is expressed in oocytes (FIG. 21A and FIG. 23), influences the ability of CR to maintain oocyte quality with age. Total RNA from five MII oocytes or one ovary was isolated using the RNeasy Plus Micro Kit (Qiagen, Valencia, Calif.) or Tri-Reagent (Sigma Aldrich Corporation, St. Louis, Mo., USA), respectively, and reverse transcribed (Superscript II; Life Technologies) with random primers (Promega, Madison, Wis.). The cDNA was amplified by PCR with gene-specific primers:

TABLE 5

Sequence information for primers used to detect Pgc-1α, Pgc-1β and β-actin mRNA in oocytes and ovaries (GenBank Accession numbers are provided)

| NM_008904 | Pgc-1α Forward | 5' TCCTCTGACCCCAGACTCAC 3' |
|---|---|---|
| | Pgc-1α Reverse | 5' TAGAGTCTTGGAGCTCCT 3' |
| NM_133249 | Pgc-1β Forward | 5' AACCCAACCAGTCTCACAGG 3' |
| | Pgc-1β Reverse | 5' ATGCTGTCCTTGTGGGTAGG 3' |
| NM_007393 | β-Actin Forward | 5' GATGACGATATCGCTGCGCTG 3' |
| | β-Actin Reverse | 5' GTACGACCAGAGGCATACAGG 3' |

Figure 22E:
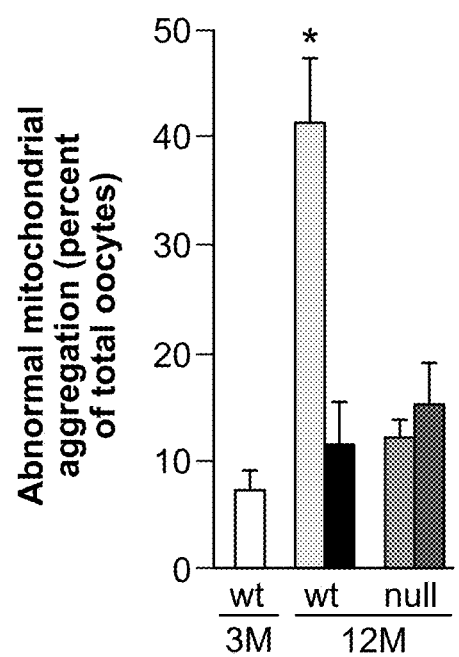
FIG. 22 depicts improvement in oocyte yield and quality in aging females resulting from the loss of peroxisome proliferator-activated receptor γ coactivator-1α (PGC-1α). (A) RT-PCR analysis of Pgc-1α and Pgc-1β mRNA levels in isolated MIT oocytes of 3 M AL-fed wild-type (wt) mice, 12 M AL-fed or CR-AL-fed wt mice, or 12 M AL-fed or CR-AL-fed Pgc-1α-null mice (Actin, control gene for sample loading; Size, molecular size marker; Ov, adult ovary RNA used as a positive control; -RT, RT-PCR analysis of ovary RNA without reverse transcriptase as a negative control). (B-E) Effects of PGC-1α deficiency in AL-fed and CR-AL-fed females on oocyte yield following superovulation (B), meiotic spindle formation (C), chromosomal alignment on the metaphase plate (D), and mitochondrial distribution (E) are shown. Legends for (D) and (E) are the same as (C). Data are the mean±SEM (n=20-117 oocytes analyzed per group for each endpoint from 3 independent experiments using a total of 3-14 mice per group; *, P<0.05 vs. all other groups).
Figure 24:
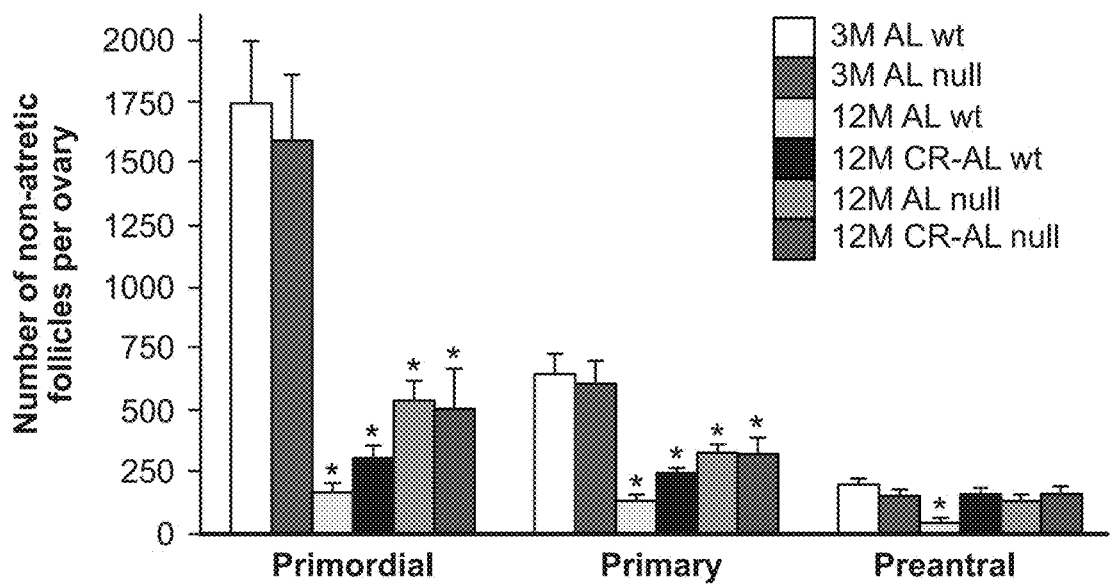
FIG. 24 depicts diminished ovarian reserve with age in mice lacking PGC-1α. Number of non-atretic quiescent (primordial) and early growing (primary, preantral) immature follicles per ovary in 3 M AL-fed, 12 M AL-fed or 12 M AL-CR-fed wild-type (wt) or PGC-1α-deficient (null) female mice. Data are the mean±SEM (n=4-12 mice per group; *, P<0.05 vs. 3 M AL-fed females of either genotype).

Consistent with past studies (Lin et al. *Cell* 2004 119:121-135), an absence of PGC-1α increased mortality in mutant offspring (90 pups of 696 total generated by breeding heterozygotes were genotyped as knockouts at day 21). Assessment of null females that survived to 12 months (36 of 47 total) showed that PGC-1α deficiency in AL-fed mice recapitulated the beneficial effects of CR on ovulated oocyte yield (FIG. 22B), meiotic spindle formation (FIG. 22C), chromosomal alignment (FIG. 22D) and mitochondrial distribution within the cytoplasm (FIG. 22E). At 12 months, AL-fed females lacking PGC-1a exhibited a slightly larger follicle reserve than their wild-type counterparts, but follicle numbers remained severely diminished compared to young adult animals of either genotype (FIG. 24). No further changes in oocyte numbers per ovary (FIG. 24), or in oocyte yield or quality (FIG. 22 B-D), were observed when mice lacking PGC-1α were subjected to CR.

Figure 25A:
FIG. 25 depicts comparable levels of PGC-1 in ovaries of young and aged female mice. (A) Western blot analysis of endogenous PGC-1 protein levels in ovaries of young (3 M) AL-fed, aged (12 M) AL-fed, and aged (12 M) CR-AL-fed females (samples prepared from 3 different mice are shown for each group). Pan-actin (ACTIN) was used as a loading control. (B) Examples of Immunohistochemical detection of PGC-1 (brown reaction product against blue hematoxylin counterstain) in ovaries of the same females that were used to obtain samples for PGC-1 Western blotting (A).
Figure 25B:
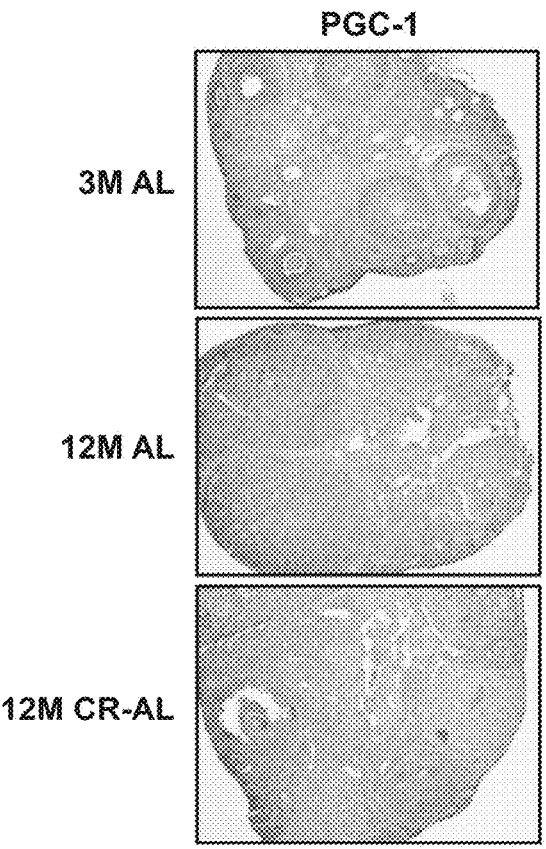

PGC-1 protein was localized in paraformaldehyde-fixed paraffin-embedded tissue sections using a rabbit anti-PGC-1 antibody (Calbiochem), as described (Matikainen et al. *Nat Genet* 2001 28:355-360). Protein samples (10 μg) were assessed by immunoblotting using antibodies against PGC-1 (Calbiochem) and pan-actin (Neomarkers, Fremont, Calif.) as a loading control. Since levels of PGC-1 protein remained essentially unchanged in ovaries of AL- or CR-AL-fed mice with age (FIG. 25), it does not appear that CR directly alters PGC-1 gene expression in this organ. However, the finding that CR and PGC-1α independently produced the same outcomes in ovulated oocytes suggests that signaling pathways activated in the two models converge at a common downstream point that is important to ensuring egg quality.

In summary, this study has uncovered striking beneficial effects of adult-onset CR on chromosomal, spindle and mitochondrial dynamics in mature oocytes of female mice at ages normally associated with poor reproductive parameters. The present study not only establishes that CR sustains female fertile potential with age through significant improvements in oocyte chromosomal dynamics, but also identifies PGC-1α as a regulator of oocyte quality. Thus, prevention of oocyte aneuploidy and spindle defects through administration of bioenergetic agents (e.g., including CR mimetics) provides a means to improve fertility and pregnancy outcomes in women of advanced reproductive age.

Figure 26:
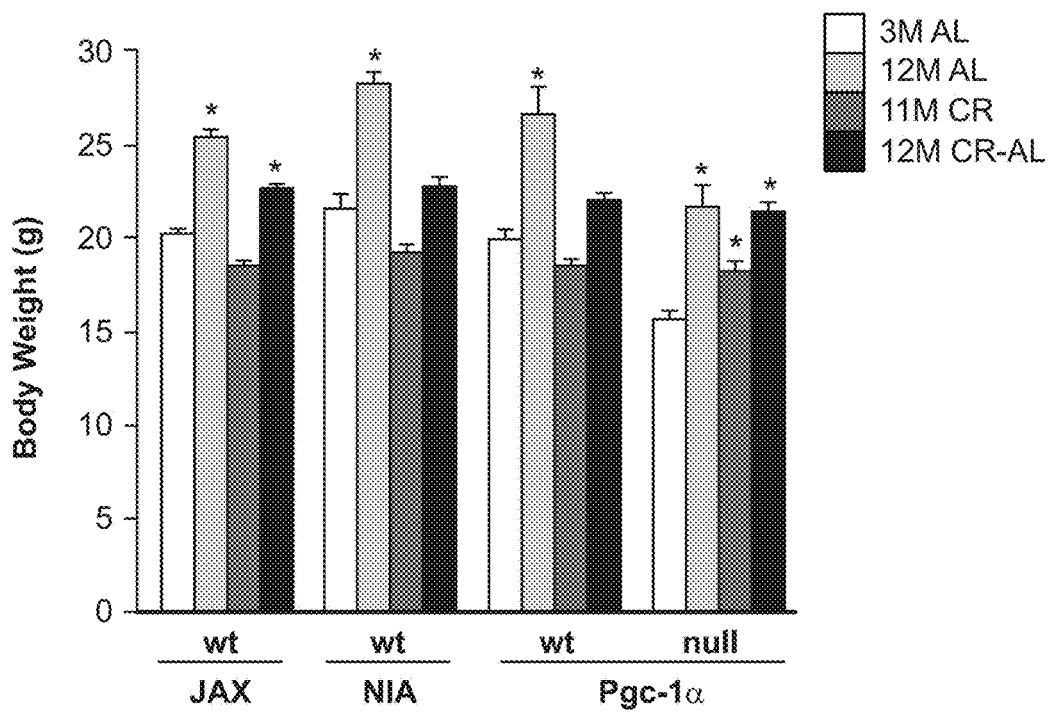
FIG. 26 depicts the effects of dietary manipulation on body weight. Body weight of female mice just prior to initiation of the CR diet (3 M), upon completion of the CR regimen (11 M), and one month following the resumption of AL feeding (12 M) are shown. Data shown are the mean±SEM from analysis of 5-23 mice per group (*, P<0.05 vs. 3 M AL-fed females in each respective group). JAX, C57BL/6 mice from Jackson Laboratories; NIA, C57BL/6 mice from the NIA; Pgc-1α, mutant mouse line obtained from B. M. Spiegelman (Lin et al. *Cell* 2004 119:121-135).
Figure 27:
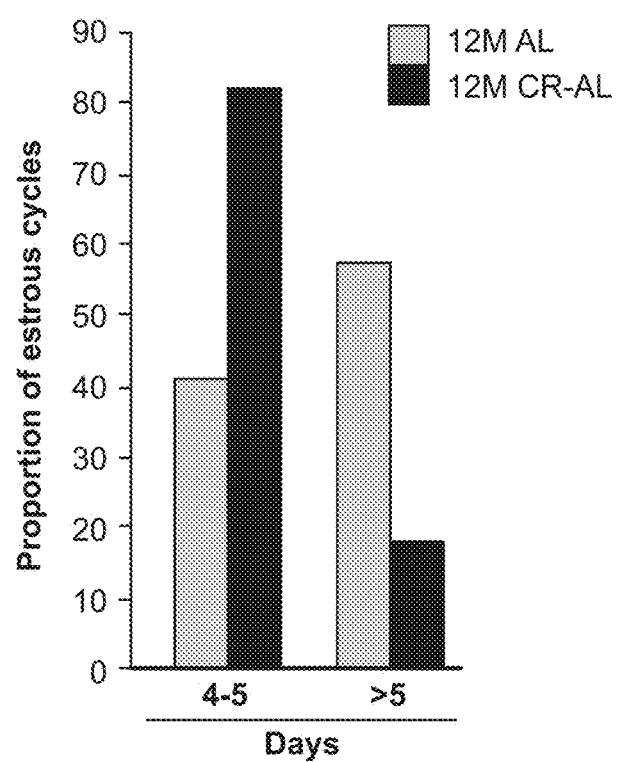
FIG. 27 depicts prevention of aging-related disruption of the female reproductive cycle by CR. Proportion of aged (12 M) AL-fed and CR-AL-fed females that exhibited a typical 4-5 day estrous cycle or atypical estrous cycles lasting longer than 5 day. Data are from analysis of 10-15 mice per group analyzed in parallel by daily vaginal smears over a 30-day period.
Figure 28:
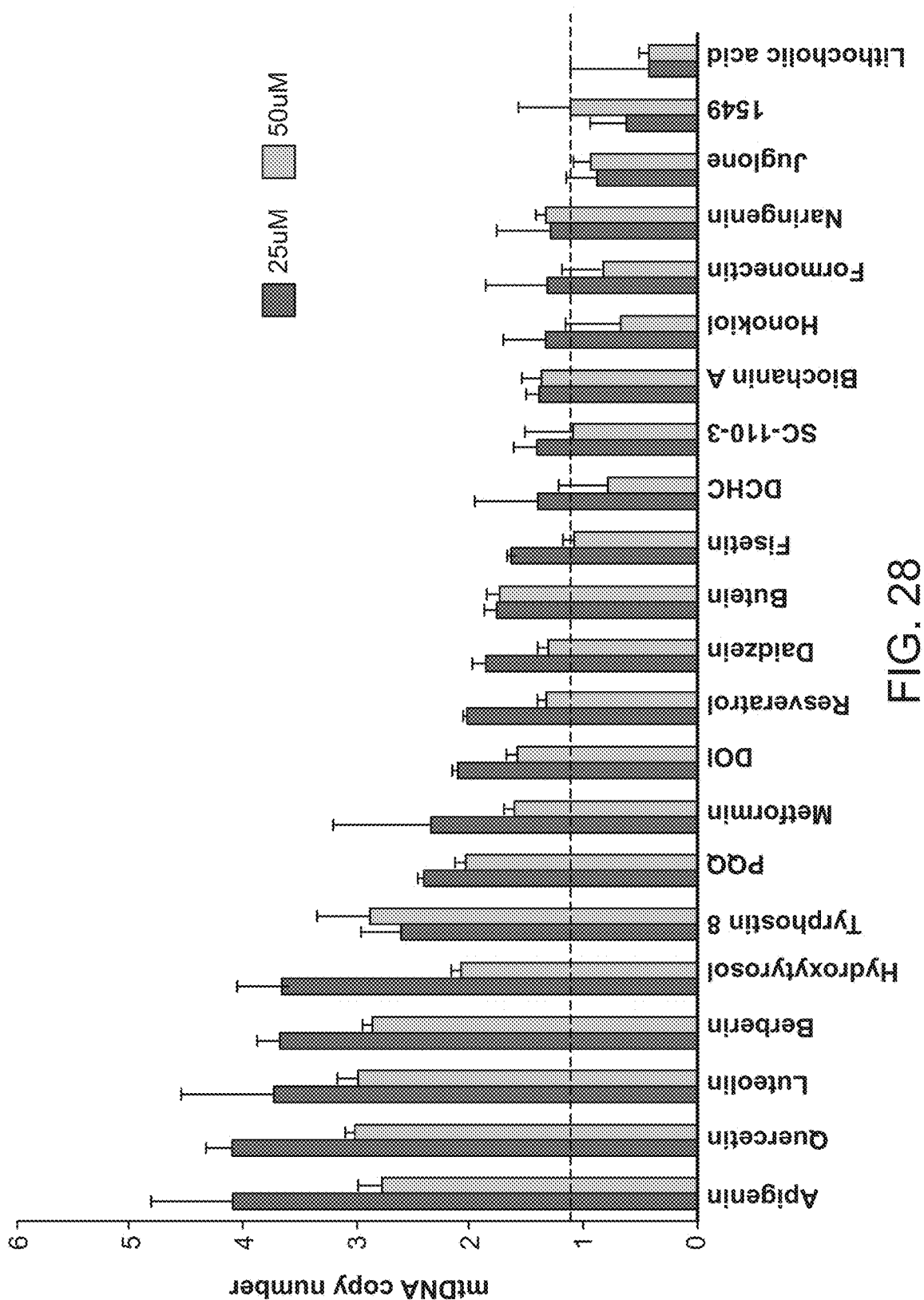
FIG. 28 depicts mitochondrial DNA copy number (relative to nuclear genome). Mouse OSCs maintained in culture (Zou et al., *Nat Cell Biol* 2009 11:631-636) were exposed to the indicated test compounds for 24 hours and then assessed for mitochondrial DNA (mtDNA) content.
Figure 29:
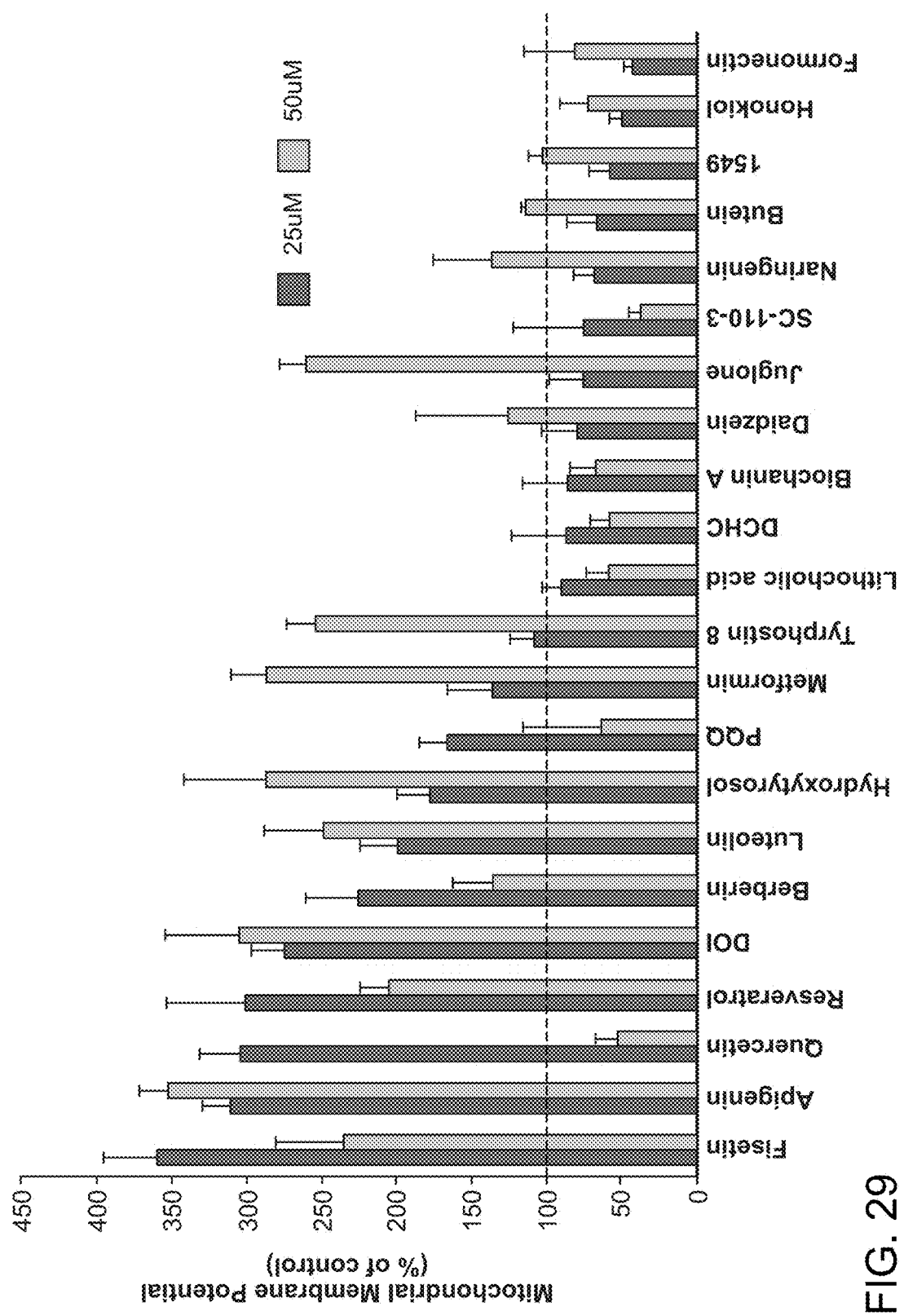
FIG. 29 depicts mitochondrial membrane potential. Mouse OSCs maintained in culture (Zou et al., *Nat Cell Biol* 2009 11:631-636) were exposed to the indicated test compounds for 24 hours and then assessed for mitochondrial membrane potential (MMP).
Figure 30:
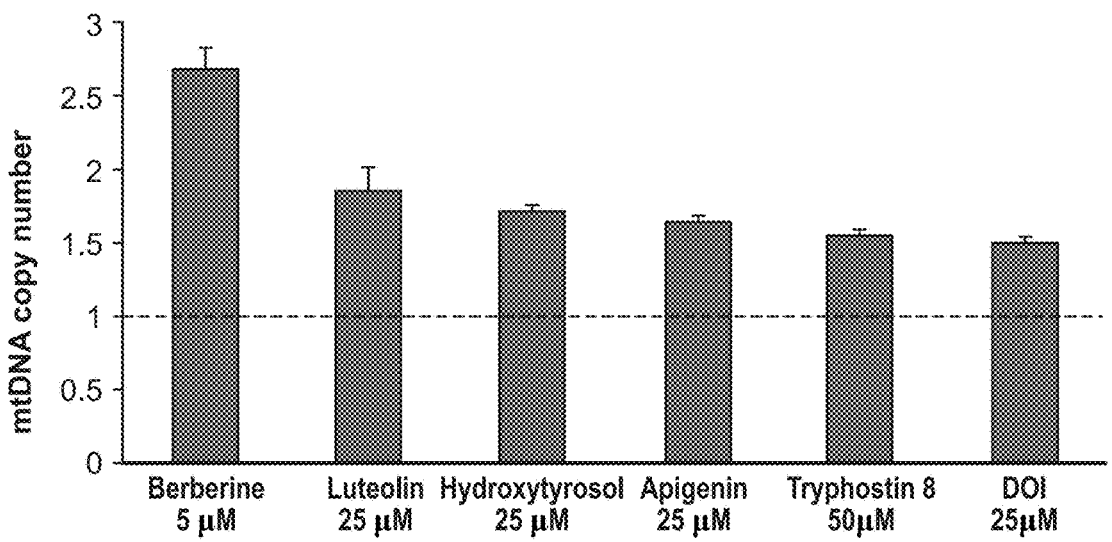
FIG. 30 depicts mitochondrial DNA copy number (relative to the nuclear genome). Mouse OSCs maintained in culture (Zou et al., *Nat Cell Biol* 2009 11:631-636) were exposed to the indicated test compounds for 24 hours and then assessed for mitochondrial DNA copy number.
Figure 31:
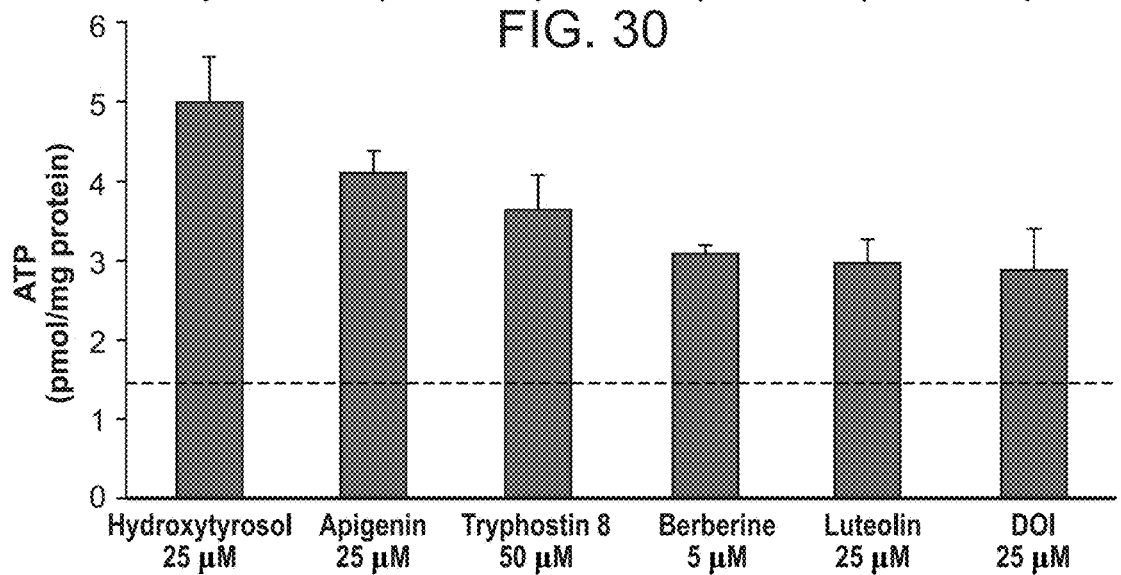
FIG. 31 depicts ATP levels as a measure of mitochondrial activity. Mouse OSCs maintained in culture (Zou et al., *Nat Cell Biol* 2009 11:631-636) were exposed to the indicated test compounds for 24 hours and then assessed for mitochondrial activity.
Figure 32:
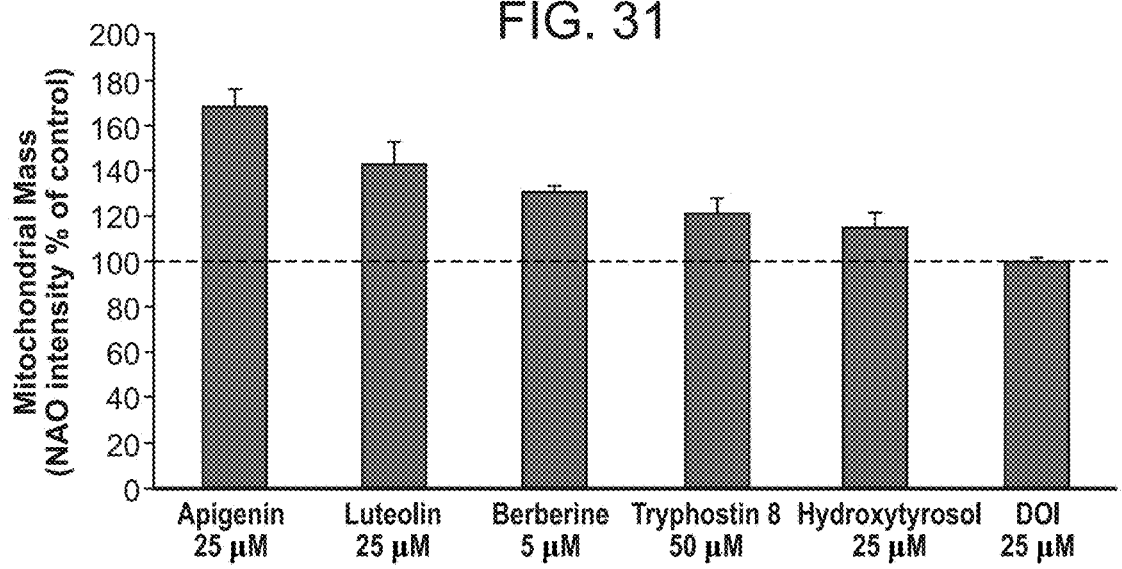
FIG. 32 depicts the percent increase in mitochondrial density as measured by the dye NAO. Mouse OSCs maintained in culture (Zou et al., *Nat Cell Biol* 2009 11:631-636)

Additional Information Regarding Experimental Procedures for CR Analysis:

An adult-onset CR protocol developed by the National Institute on Aging in their Biomarkers of Aging Study (Turturro et al. J Gerontol A Biol Sci Med Sci 1999 54A:B492-B501) was used, in which CR is initiated at 3.5 months of age in a stepwise manner over a 2-week period to achieve 40% restriction at 4 months of age. Each female was housed individually in a conventional (non-ventilated) cage and fed once daily with a rationed amount of fortified rodent diet (National Institute on Aging). The fortified rodent diet is supplemented with vitamins and minerals such that daily intake of these micronutrients is comparable to that of control animals with ad libitum (AL) access to the non-fortified (standard) rodent diet. Diet composition is otherwise identical. The CR protocol was continued until 11 months of age, at which time the mice maintained previously on CR were allowed AL access to standard rodent diet for 1 month. To confirm that the CR protocol was working as expected, the weight of each mouse was taken just prior to the start of the CR protocol (3 months of age), at the conclusion of the CR protocol (11 months of age) and one month following the return of CR mice to AL feeding (12 months of age) (FIG. 26). In addition, past studies which employed alternating days of fasting and feeding to achieve CR in female mice reported that aging-related disruption of estrous cyclicity was delayed by food restriction (Nelson et al. Biol Reprod 1985 32:515-522). These data, along with more recent observations that adult-onset CR delays the timing of reproductive failure in female mice as tested in natural mating trials (Selesniemi et al. Aging Cell 2008 7:622-629), support that the approach maintains cyclic production of reproductive hormones required for normal 45 day estrous cycles. To further confirm this under the feeding protocol employed here to achieve CR, daily vaginal cytological smears were assessed, as described (Felicio et al. Biol Reprod 1986 34:849-858), to compare estrous cyclicity in aged AL-fed and CR-AL-fed mice over a 30-day period (FIG. 27). It is well-established in mice that female reproductive aging is associated with a shift from typical 45 day estrous cycles to prolonged cycles lasting more than 5 days (Gosden et al. Biol Reprod 1983 28:255-260). For example, the proportion of young adult C57BL/6 mice exhibiting cycles lasting 45 days versus more than 5 days is approximately 80% to 20%, respectively; however, by 12 months of age nearly two-thirds of female mice exhibit prolonged estrous cycles indicative of pending ovarian failure (Felicio et al. Biol Reprod 1986 34:849-858, Gosden et al. Biol Reprod 1983 28:255-260; see also FIG. 27). All experiments were independently replicated at least 3 times. Quantitative data from experimental replicates were combined and are presented as the mean±SEM. Statistical comparisons between mean values were performed using ANOVA and Student's t-test. P values less than 0.05 were considered significant.

Example 9: Bioenergetic Factors Increase Mitochondrial Parameters in OSCs

Female infertility due to chemotherapy, aging and premature ovarian failure (POF) is due in part to a decline in mitochondrial function in oocytes and OSCs. Accordingly, OSCs from mice were used to screen for small compounds that enhance mitochondrial function ("bioenergetic status") in female germline cells. Assays for enhancing mitochondrial function included mtDNA content, ATP, NAD+/NADH, mitochondrial mass, mitochondrial membrane potential, and gene expression of known mitochondrial mass regulators and electron transport chain components.

All the compounds were dissolved in DMSO. For screening purposes the cells were treated with the vehicle (0.001% DMSO) or with 25 or 50 µM of each compound (except for berberine, which the concentrations used for the screen were 5 µM and 25 µM) for 24 hours. For validation of the top 6 hits, cells were treated with vehicle (0.001% DMSO) or either 5 or 25 µM of each compound for 24 hours. For the gene expression profile, the cells were treated with the concentration that was considered to work better in the previous validation assays.

Mitochondrial membrane potential was measured with a fluorescent probe, Tetramethylrhodamine methyl ester (TMRM) (Sigma) as described before (Rolo A. P. Biochim. Biophys. Acta 2003 1637: 127-132). Briefly the cells were loaded with 6.6 µM TMRM in HBSS buffer at 37° C. for 15 minutes in the dark. The supernatant was then aspirated, and the cells returned to the original volume with KHH. TMRM is a membrane-permeable cationic fluorophore that accumulates electrophoretically in mitochondria in proportion to their mitochondrial membrane potential (Ehrenberg B. V. et al. Biophys. J. 1988 53:785-794). Cell suspensions (200 µl containing 105 cells) were loaded into 96-well plates and fluorescence measured using excitation and emission wavelengths of 485 and 590 nm, respectively. Mitochondrial membrane potential was estimated, taking into account the complete depolarization caused by carbonyl cyanide p-(trifluoromethoxy)phenylhydrazone (FCCP).

For mtDNA analysis, total DNA was extracted with DNeasy blood and tissue kit (QIAGEN). mtDNA was amplified using primers specific for the mitochondrial cytochrome c oxidase subunit 2 (COX2) gene and normalized to genomic DNA by amplification of the ribosomal protein s18 (rps18) nuclear gene. Primers were designed using the IDT software (IDT).

ATP content was measured using a luciferase-based assay with a commercial kit according to the manufacturer's instructions (Roche Applied Science, Penzberg, Germany) and normalized to protein content in each sample.

Mitochondrial mass was evaluated using the fluorescent probe N-nonyl acridine orange (NAO), briefly the cells were incubated in culture media containing 10 nM of NAO for 30 minutes at 37° C. in the dark. The cells were then trypsinized and resuspended in culture media without NAO. The NAO fluorescence intensity was then determined by flow cytometry on the FACSCALIBUR® (BD Biosciences, San Jose, Calif., USA) using the 488 nm laser.

For gene expression analysis, RNA from skeletal muscle tissue and C2C12 cells were extracted with RNeasy mini kit (QIAGEN) according to the instructions and quantified using the NanoDrop 1000 spectrophotometer (Thermo Scientific). cDNA was synthesized with the iSCRIP cDNA synthesis kit (BioRad) using 200 ng of RNA. Quantitative RT-PCR reactions were performed using 1 µM of primers and LIGHTCYCLER® 480 SYBR® Green Master (Roche Applied Science, Penzberg, Germany) on an LIGHTCYCLER® 480 detection system (Roche Applied Science, Penzberg, Germany). Calculations were performed by a comparative method (2-ΔΔCT) using actin as an internal control. Primers were designed using the IDT software (IDT).

Several bioenergic agents known to inhibit CD38 produced activity above the baseline (DMSO alone) and were scored as a positive result, including apigenin, luteoline, tyrphostin 8, beberine and SRT-1720. Accordingly, these bioenergic agents were shown to increase mitochondrial parameters in a beneficial way.

Bioenergic agents, including apigenin, luteolin, berberine, and tyrphostin 8, were shown to raise NAD$^+$ levels and increase mitochondrial parameters in a beneficial way. In one embodiment, such agents are useful in enhancing female germ cell bioenergetics for the treatment of female infertility associated with chemotherapy, aging and premature ovarian failure.

Example 10: FACS-Based Isolation of Mitochondria

As described in this Example, FACS-based methods can be employed to isolate the total mitochondrial population in a tissue. In addition, FACS-based methods for mitochondrial isolation can employ dual-labeling using two different fluorescent dyes (mitochondrial membrane potential (MMP)-dependent and MMP-independent) to isolate only the functional (e.g., actively respiring) mitochondrial population or quantitate the ratio of functional to total mitochondria in a tissue, cell, lysed cell or fraction derived thereof.

The non-oxidation dependent MitoTracker Green FM (INVITROGEN® M7514) mitochondrial tracking probe, which indicates mitochondrial mass, was prepared and utilized as described below. MitoTracker stock solution (1-5 mg/ml dissolved in anhydrous dimethylsulfoxide (DMSO)) was diluted in serum free growth medium to reach a working concentration of between 25-500 nM. Freshly isolated or thawed OSCs were pelleted by centrifugation at 300×g for 5 minutes. The supernatant was aspirated and the cell pellet was resuspended in 200 µl of the diluted MitoTracker stock solution.

Cells were incubated at 37° C. for 45 minutes, washed in pre-warmed (37° C.) serum free growth medium and pelleted by centrifugation at 300×g for 5 minutes (alternatively, cells can be lysed prior to incubation with a probe of interest). Supernatant was aspirated and cells were resuspended in 100 µl mitochondrial lysis buffer and transferred to a FACS sort tube for lysis by mechanical permeabilization using rapid osmotic shock. Following lysis, cells were equilibrated cells on ice for 15-30 minutes, incubated in 200 µl (minimum volume) ice cold PBS and vortexed. As shown in FIG. 36, three distinct populations were observed: residual M7514 positive cells (Cells MT+), high fluorescent mitochondria (functional, Mito MT high), and low expressing mitochondria (non-functional, Mito MT Low). The ratio of functional to non-functional mitochondria post lysis was approximately 1:1 (1552 mitochondria 743 were gated as functional and 716 were gated as non-functional; accumulation the gates are drawn around populations in FIG. 36). Therefore, functional mitochondria can be sorted and collected, with residual unlysed cells and non-functional mitochondria excluded based on size and fluorescence intensity. Dual-labeling using multiple probes or a JC-1 probe (red spectrum; INVITROGEN® T3168) can help to further distinguish functional from non-functional mitochondria. Probes for use in dual labeling include, but are not limited, to reduced oxidative state mitotracker probes (e.g., MitoTracker Red CM-H2XRos (INVITROGEN® M7513), MitoTracker Orange CM-H2TMRos (INVITROGEN® M7511) and accumulation dependent probes: JC-1 (red spectrum; INVITROGEN® T3168), MitoTracker Deep Red FM (INVITROGEN® M22426) and JC-1 (green spectrum; INVITROGEN® T3168).

Example 11: Mitochondrial Isolation Using Differential Centrifugation

As described in this Example, differential centrifugation procedures can be employed to isolate and/or fractionate mitochondria present in a tissue. The key steps when isolating mitochondria from any tissue or cell are: (i) rupturing of cells by mechanical and/or chemical means, (ii) differential centrifugation at low speed to remove debris and extremely large cellular organelles (SPIN 1), and (iii) centrifugation at a higher speed to isolate and collect mitochondria (SPIN 2).

The tissue is weighed and washed twice with 1.5 ml of a commercially available Wash Buffer (MitoSciences). The tissue is minced and placed in a pre-chilled Dounce homogenizer. Up to 2.0 ml of a commercially available Isolation Buffer (MitoSciences) is added. The cells are ruptured using the Dounce homogenizer (20-40 strokes), and the homogenate is transferred to Eppendorf tubes. Each tube is filled to 2.0 ml with Isolation Buffer. The homogenate is centrifuged at 1,000 g for 10 minutes at 4° C. The supernatant is reserved and transferred into new tubes, each of which is filled to 2.0 ml with Isolation Buffer. The tubes are centrifuged at 12,000 g for 15 minutes at 4° C. The pellet is reserved. If desired, the supernatant is analysed for quality. The pellet is washed twice by resuspending in 1.0 ml of Isolation Buffer supplemented with 10 µl of a commercially available protease inhibitor cocktail (MitoSciences). The tubes are centrifuged at 12,000 g for 15 minutes at 4° C. After washing, the pellets are combined and resuspended in 500 µl of Isolation Buffer supplemented with protease inhibitor cocktail. If desired, aliquots are stored at −80° C. until use.

In one approach, mitochondria integrity is tested by Western blot screening for cytochrome c, porin, or cyclophilin D in the isolated mitochondria versus in the supernatant fraction using commercially available antibodies, such as MitoSciences' antibodies MSA06, MSA03, and MSA04. In another approach, mitochondrial samples are probed by Western blot to detect components of the mitochondrial complex, for example, using the commercially available OXPHOS Complexes Detection cocktail (MitoSciences).

Example 12: Mitochondrial Isolation Using Sucrose Gradient Separation

The protocal employs the following reagents, which are commercially available: n-dodecyl-β-D-maltopyranoside (Lauryl maltoside; MitoSciences MS910), Phosphate buffered saline (PBS), Sucrose solutions 15, 20, 25, 27.5, 30 and 35%, double distilled water, a protease inhibitor cocktail (MitoSciences), and 13×51 mm polyallomer centrifuge tubes (Beckman 326819).

The sucrose gradient separation procedure is a protein subfractionation method optimized for mitochondria. This method resolves a sample into at least 10 fractions. It is possible to separate solubilized whole cells into fractions of much lower complexity but when analyzing already isolated mitochondria the fractions are even more simplified. The sucrose gradient separation technique is designed for an initial sample volume of up to 0.5 ml at 5 mg/ml protein.

Therefore 2.5 mg or less of total protein should be used. For larger amounts, multiple gradients can be prepared or larger scale gradients are made.

The sample is solubilized in a non-ionic detergent. It has been determined that at this protein concentration mitochondria are completely solubilized by 20 mM n-dodecyl-β-D-maltopyranoside (1% w/v lauryl maltoside). The key to this solubilisation process is that the membranes are disrupted while the previously Membrane embedded multisubunit OXPHOS complexes remain intact, a step necessary for the density based sucrose separation procedure described herein. One important exception is the pyruvate dehydrogenase enzyme (PDH). In order to isolate PDH at a protein concentration of 5 mg/ml mitochondria, the required detergent concentration is only 10 mM (0.5%) lauryl maltoside. The PDH enzyme should also be centrifuged at lower speeds, a centrifugal force of 16 000 g is maximum for the PDH complex.

To a mitochondrial membrane suspension at 5 mg/ml protein in PBS, lauryl maltoside is added to a final concentration of 1%. This is mixed well and incubated on ice for 30 minutes. The mixture is then centrifuged at 72,000 g for 30 minutes. A Beckman Optima benchtop ultracentrifuge is recommended for small sample volumes. However, at a minimum a benchtop microfuge, on maximum speed (e.g., about 16 000 g) should suffice. After centrifugation, the supernatant is collected and the pellet discarded. A protease inhibitor cocktail is added to the sample, which is maintained on ice until centrifugation is performed. In samples very rich in mitochondria the cytochromes in complexes III and IV may give the supernatant a brown color, which is useful when checking the effectiveness of the following separation.

A discontinuous sucrose density gradient is prepared by layering successive decreasing sucrose densities solutions upon one another. The preparation and centrifugation of a discontinuous gradient containing sucrose solutions from 15-35% is described in detail below. This gradient gives good separation of the mitochondrial OXPHOS complexes (masses ranging from 200 kDa to 1000 kDa). However this setup can be modified for the separation of a particular complex or for the separation of larger amounts of material.

The gradient is prepared by layering progressively less dense sucrose solutions upon one another; therefore the first solution applied is the 35% sucrose solution. A steady application of the solutions yields the most reproducible gradient. To aid in this application, a Beckman polyallomer tube is held upright in a tube stand. Next a 200 µl pipette tip is placed on the end of a 1000 µl pipette tip. Both snugly fitting tips are held steady by a clamp stand and the end of the yellow tip is allowed to make contact with the inside wall of the tube. Now sucrose solutions are placed inside the blue tip and fed into the tube slowly and steadily, starting with the 35% solution (0.25 ml).

Once the 35% solution has drained into the tube, the 30% solution (0.5 ml) is be loaded into the tube on top of the 35% solution. This procedure is continued with the 27.5% (0.75 ml), 25% (1.0 ml), 20% (1.0 ml) and 15% (1.0 ml), respectively. Enough space is left at the top of the tube to add the 0.5 ml sample of solubilized mitochondria.

Once the sucrose gradient is poured discrete layers of sucrose are visible. Having applied the sample to the top of the gradient the tube is loaded into the rotor very carefully, and centrifugation begins. All centrifugation procedures require a balanced rotor therefore another tube containing precisely the same mass is generated. In practice this means 2 gradients must be prepared although the second gradient need not contain an experimental sample but could contain 0.5 ml water in place of the 0.5 ml protein sample.

The polyallomer tubes should be centrifuged in a swinging bucket SW 50.1 type rotor (Beckman) at 37,500 rpm (RCF av 132,000×g) for 16 hours 30 minutes at 4° C. with an acceleration profile of 7 and deceleration profile of 7. Immediately after the run the tube should be removed from the rotor, taking great care not to disturb the layers of sucrose. When separating a sample rich in mitochondria, discrete colored protein layers may be observed. Most often these are Complex III (500 kDa—brown color) approximately 10 mm from the bottom of the tube and Complex IV (200 kDa—green color) 25 mm from the bottom of the tube. In some circumstances additional bands can be observed. These are the other OXPHOS complexes.

For fraction collection, the tube is held steady and upright using a clamp stand. A tiny hole is introduced into the very bottom of the tube using a fine needle. The hole is just big enough to allow the sucrose solution to drip out at approximately 1 drop per second. Fractions of equal volume are collected in eppendorf tubes below the pierced hole. A total of 10×0.5 ml fractions are appropriate however collecting more fractions which are thus smaller in volume is also possible (e.g. 20×0.25 ml fractions). The fractions are stored at −80° C. until analysis. collected fractions are analysed to determine mitochondrial integrity using any of the methods described herein (e.g., in Example 10, 11) or known in the art.

Example 13: Agents that Increase NAD$^+$ Levels Increase Oocyte Production

As shown in FIG. 37, NAD$^+$ is synthesized via three main pathways: (i) the NAD Salvage pathway (via NAMPT and NMNAT1-3 from nicotinamide, NAM to NMN to NAD$^+$; (ii) from tryptophan, via the de novo pathway, via quinolinic acid (FIG. 38); and (iii) from nicotinamide riboside, a molecule found in milk and other food products (FIG. 38). Until recently, NAD$^+$ was regarded simply as a coenzyme, carrying electrons from one reaction to another. It has now been discovered that NAD$^+$ is a primary signal for low caloric intake, coordinating the activities of major metabolic pathways, in large part, by stimulating the activity of sirtuins. Two critical downstream mediators are SIRT1 (a nuclear sirtuin) and SIRT3 (a mitochondrial sirtuin), which act synergistically to increase respiration and fatty acid oxidation in heart and skeletal muscle in response to fasting and exercise. In oogonical stem cells, SIRT1 controls the expression of a critical transcription factor that regulates the differentiation of oogonial stem cells into oocytes.

During aging, however, NAD$^+$ levels in the nucleus and mitochondria decline, reducing the activity of these two sirtuins and severely compromising mitochondrial function. NAD$^+$ levels can be increased by incubating cells with a NAD precursor such as NMN (e.g. FIG. 39), by injecting or otherwise delivering an NAD precursor to cells in vivo (FIG. 42), by increasing the expression of genes that synthesize NAD$^+$ e.g. NAMPT, NMNAT1-3; or by inhibiting NAD degradation, via PARPs or CD38 inhibition. (see FIG. 37 CD38 inhibitors include, but are not limited to those listed herein above in Tables 2A and 2B and are described by Dong M. et al. *Org. Biomol. Chem.* 2011 (9): 3246-3257 and Kellenberger E. et al. *Bioorg Med Chem Lett.* 2011 21(13): 3939-42, the contents of which are incorporated herein by reference. Increasing NAD+ in cells can be achieved by other methods, such as applying substrates for the TCA cycle (e.g. Pyruvate, fatty acids) The following experiments were carried out to determine whether genes and small molecules that raise NAD+ levels and/or activate the sirtuins delay or reverse the effects of aging and cell stress/damage on female fertility in vivo and in vitro.

Oogonial stem cells were isolated from dissociated ovaries using a FACS based sorting protocol to purify OSCs free of contaminating oocytes (for details, see Example 1), Cells were maintained in culture medium consisted of minimum essential medium α (MEMα), 10% FBS, 1 mM sodium pyruvate, 1 mM no amino acids, 2 mM L-1-glutamine, 0.1 mM β-mercaptoethanol (Sigma), 10 ng/ml-1 LIF (Millipore), 1× N-2 MAX Media Supplement (R&D) 10 ng/ml EGF (Epidermal growth factor, Recombinant human; Gibco Division of Thermofisher Scientific, Waltham, Mass., USA), 40 ng/nil human GDNF (glial cell line-derived neurotrophic factor; R&D systems), 1 ng/ml human bFGF (basic fibroblast growth factor; Gibco Division of Thermofisher Scientific, Waltham, Mass., USA)

For all experiments 25,000 cells were plated in each well of a 24 well plate. Cells were allowed to attach for twenty-four hours and then were treated with NMN (β-Nicotinamide mononucleotide; Sigma). Unless otherwise stated, NMN was added twice to the cells, first at twelve hours and then again at six hours prior to analysis (12+6 h). Mitochondrial DNA Copy number was analysed as follows. Total cellular DNA was isolated from cells at the indicated time points using DNeasy Blood & Tissue Kit (Qiagen) according to the manufacturer's instructions. Mitochondrial DNA copy number was quantified using LIGHTCYCLER 480 SYBR® Green I Master (Roche Applied Science, Penzberg, Germany) using the following primers on a LIGHTCYCLER480 PCR machine (Roche Applied Science (Penzberg, Germany).

MT-ND2:

```
F: AAGGGATCCCACTGCACATA
R: AGTCCTCCTCATGCCCCTAT
```

RPS18 Nuclear

```
F: CCAGAGGTTGCATTTTCCCAAG
R: TAAGGCCGATAAGGCAAACGAA
```

Following treatment with NMN, NAD+/NADH levels were measured according to the manufacturer's instructions using the NAD/NADH Quantitation Kit (Biovision) Raising NAD+ levels in cells and in vivo dramatically increased mitochondrial function and mitochondrial content, which is generally recognized as a major determinant of female fertility, metabolic health, brain function, cardiovascular health and glucose metabolism/type f1 diabetes. OSCs and oocytes treated with an NAD precursor (e.g. nicotinamide riboside ie. "NMN", see FIG. 38) had increased NAD+, NAD+:NADH, and mitochondrial DNA content (FIG. 40).

To determine whether increasing NAD+ levels had an effect on oocyte production, spontaneous oocyte formation was assayed. Each well of a 24-well plate was seeded with 25,000 OSCs. The number of oocytes formed and released into the medium per well was assessed the second day after seeding as well as the designated time points after NMN treatment. NMN treatment increased the rate of egg formation (EFA), (FIGS. 37, 38, and 41). Based on these results, compounds and genes that increase NAD+ in vivo or in vitro are expected to reduce or reverse infertility associated with mitochondrial damage, energetic defects, and aging of the ovary in female subjects. NMN treatment is also expected to enhance the function of OCSsOSCs, oocytes, granulose cells, and blood vessels in the ovary.

NMN and other compounds that increase NAD+ levels are useful for increasing fertility or otherwise reducing or reversing infertility in a female subject. In one embodiment, such compounds are delivered to a subject orally, by intraperitoneal injection (IP), or subcutaneously to increase the probability that the subject will conceive and deliver healthy offspring. Systemic administration of the NAD+ precursor NMN raised NAD+ levels in vivo in young and old mice. Cardiac [NAD+] declines with age. This decline in NAD+ was reversed by NMN treatment (n=3; 200 mg·kg·d. I.P. for 1 week)(FIG. 42). NMN treatment also had a restorative effect on mitochondrial function (FIG. 43). In another embodiment, NMN and other compounds that increase NAD+ levels are delivered to an OSC, oocyte, blasotcyst, sperm, or isolated mitochondria in vitro. For example, such compounds are delivered to a germ cell prior to, during or following IVF. In another embodiment, a compound of the invention is used to enhance the yield or preservation of mitochondria from an OSC, oocyte, blasotcyst, sperm, or isolated mitochondria in vitro.

Example 14: Oral Intake of Apigenenin, Luteolin, and SRT1720 Improve Quality of Oocytes in Aged Females Female mice (8 months old, strain C57BL/6) were maintained on a 12:12 light dark cycle and provided ad-libitum access to water and food. Conditions within rooms were maintained at 21°±1° C. with 50%±20% relative humidity. Mice were placed on the experimental diets at 8.5 months of age and were maintained for 3 months on the diets. All diets were custom made, ordered from Research Diets: OpenStandard Diet (20 kcal % Protein, 15 kcal % Fat and 65 kcal % Carbohydrate) and the experimental groups consisted of regular OpenStandard Diet, OpenStandard Diet+Apigenin at 0.5 g/kg of body weight, OpenStandard Diet+Luteolin at 0.5 g/kg, and OpenStandard Diet+SRT-1720 at 2 g/kg. Food intake was measured weekly and average weight gain was assessed every two weeks. Each experimental group consisted of 12 randomly allocated mice. When mice were euthanized an additional group of 3-month old C57BL/6 females (3 M) were used as positive controls. In all groups, oocyte numbers were assessed following hormonal stimulation for superovulation.

It was determined that 11.5 month control mice in this study ovulate very few if any oocytes, and apigenenin, luteolin, and SRT-1720 all increase oocyte yield (FIG. 44). The 12 M control group fed OpenStandard Diet failed to ovulate a sufficient number of oocytes for subsequent analyses (approximately 1.3 oocytes/mouse, n=12 mice). Because of the extremely low yield of oocytes from the aged control females, historical data for oocyte yield from 12-month-old C57BL/6 females (referred to as "Hist 12 M"; from Selesniemi et al., Proc Natl Acad Sci USA. 2011 July 26; 108(30): 12319-12324) can be used as an additional reference point for an aged control group.

Figure 45A:
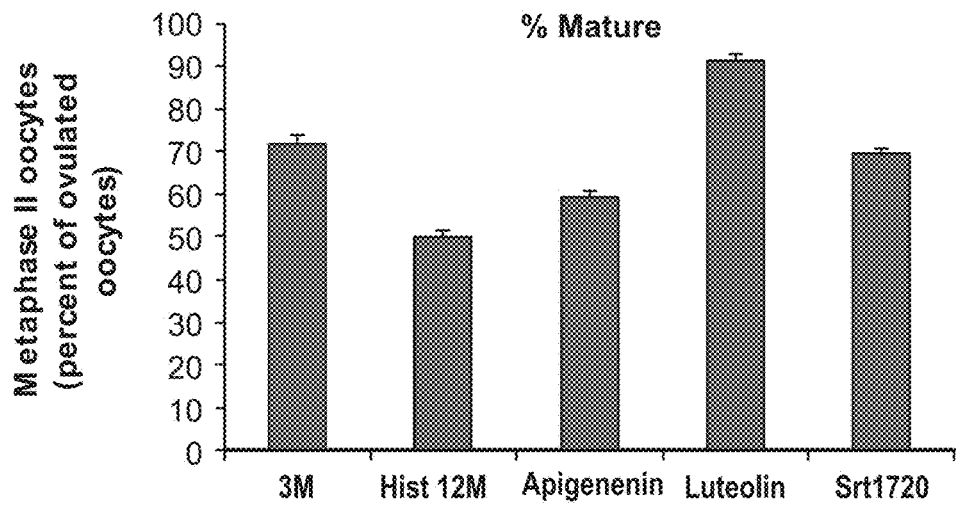
Figure 45B:
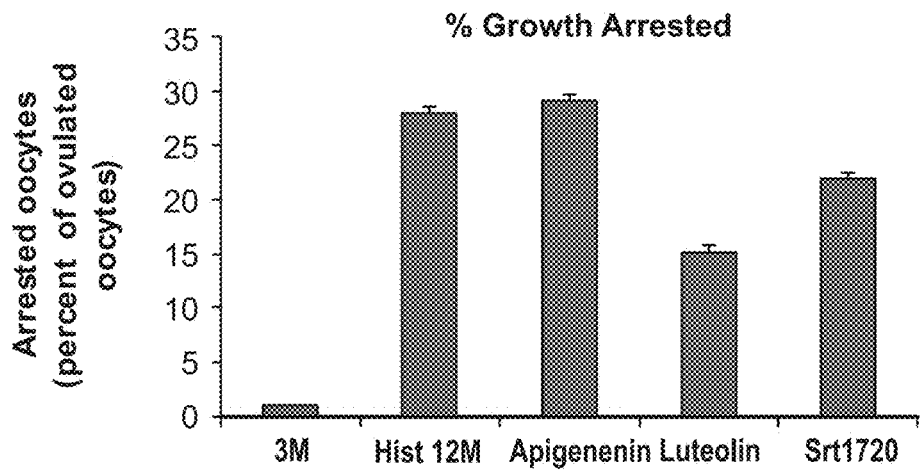
Figure 45C:
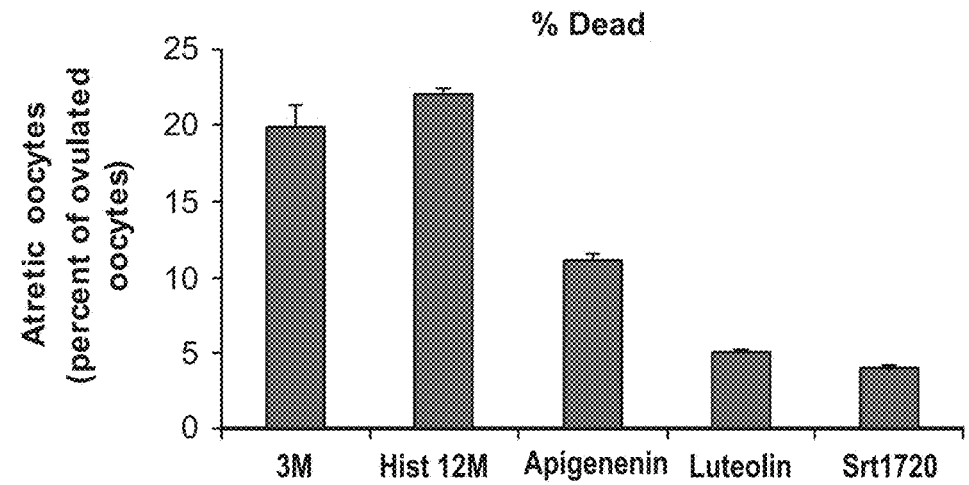

It was also determined that apigenenin, luteolin, and SRT-1720 do not affect the percentage of mature, metaphase II oocytes retrieved following superovulation as compared to age appropriate controls (Hist 12 M). In FIG. 45A, the percentage of oocytes assessed at metaphase II is shown. In FIG. 45B, the percentage of oocytes arrested at the germinal vesicle (immature) stage is shown. In FIG. 45C, the percentage of atretic (dead) oocytes is shown.

Figure 46A:
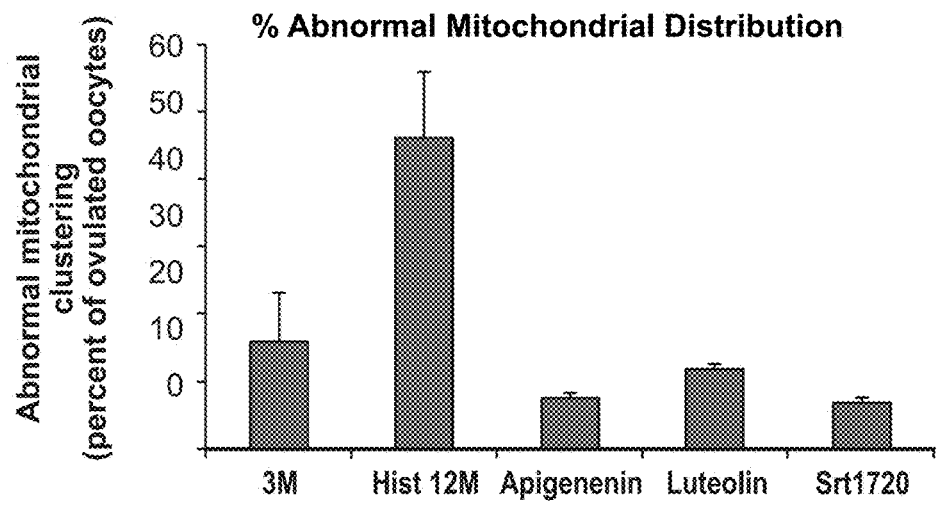
Figure 46B:
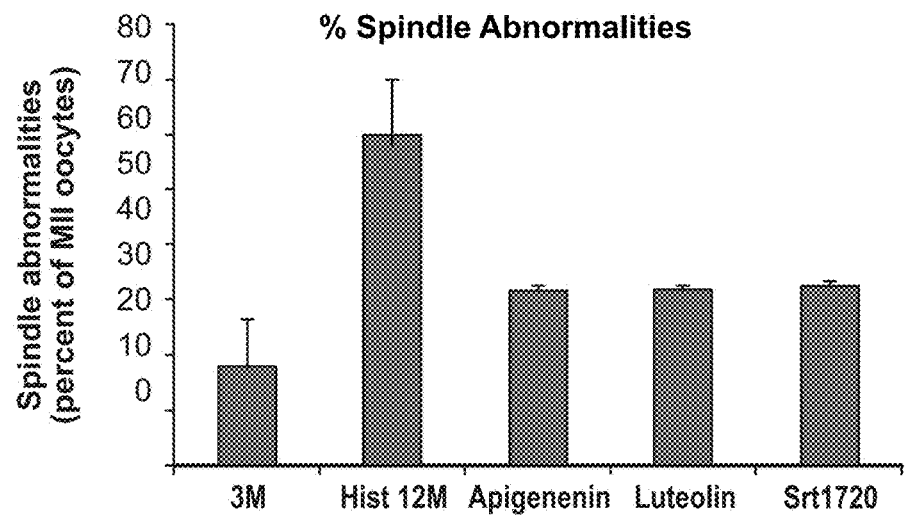
Figure 46C:
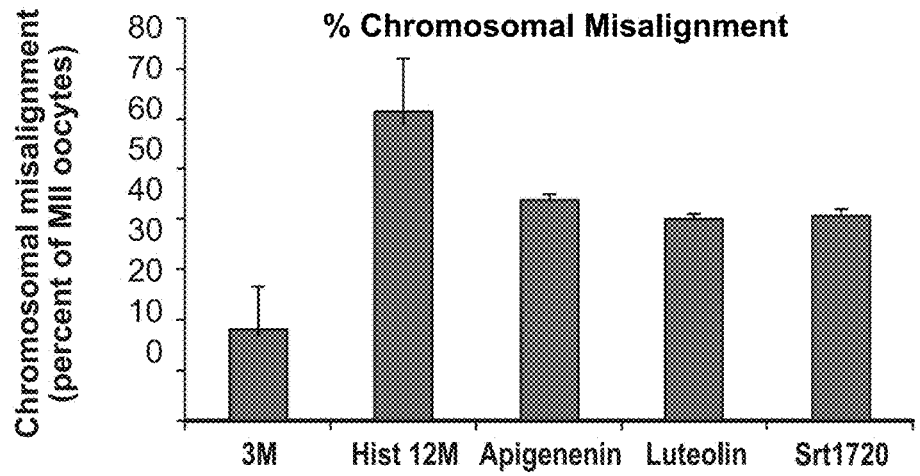

It was also determined that apigenenin, luteolin, and SRT-1720 improve the quality of oocytes in aged mice as compared to age appropriate controls (Hist 12 M). In FIG. 46A, it is shown that the percentage of oocytes exhibiting abnormal mitochondrial clustering is reduced in mice fed apigenin, luteolin, or SRT-1720 (methods are described in Selesniemi et al., *Proc Natl Acad Sci USA*. 2011 Jul. 26; 108(30): 12319-12324). In FIGS. 46B and 46C respectively, it is shown that mice fed apigenenin, luteolin, or SRT-1720 have a reduced percentage of spindle abnormalities as well as reduced chromosomal misalignment in MII oocytes. Methods for determining spindle abnormalities and chromosomal misalignment are described above in Example 8. Abnormal mitochondrial distribution was determined to be present in 16.13% of oocytes from 3 M mice, 46% of oocytes from Hist 12 M mice, 7.7% of oocytes following supplementation with apigenenin, 12% of oocytes following supplementation with luteolin and 6.9% of oocytes following supplementation with SRT-1720. Spindle abnormalities were determined to be present in 18.3% of oocytes in 3 M mice, 60% of oocytes in Hist 12 M mice, 32% of oocytes following supplementation with apigenenin, 32% of oocytes following supplementation with luteolin and 32.8% of oocytes following supplementation with SRT-1720. Chromosomal misalignment was determined to be present 18.3% of oocytes in 3 M mice, 62% of oocytes in Hist 12 M mice, 44% of oocytes from mice supplemented with apigenenin, 40% of oocytes following supplementation with luteolin and 40.9% of oocytes following supplementation with SRT-1720.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

This application contains subject matter that may be related to U.S. provisional patent application Ser. Nos. 61/475,561, filed Apr. 14, 2011, Ser. No. 61/600,505, filed Feb. 17, 2012, and Ser. No. 61/502,588, filed Jun. 29, 2011, and PCT Application No. PCT/US2012/033643, filed Apr. 13, 2012, the entire disclosures of each of which are incorporated herein by reference. All patents and publications mentioned in this specification are herein incorporated by reference to the same extent as if each independent patent and publication was specifically and individually indicated to be incorporated by reference.

What is claimed is:

1. A method of culturing a mammalian oocyte, a mammalian oogonial stem cell (OSC), the progeny of a mammalian OSC or a mammalian preimplantation zygote, wherein the OSC is obtained from ovarian tissue, is an isolated non-embryonic stem cell, and is mitotically competent and expresses Vasa, Oct-4, Dazl and Stella and, optionally, a stage-specific embryonic antigen, said method comprising:
   culturing said oocyte, OSC, progeny of an OSC or preimplantation zygote in a medium comprising a CD38 inhibitor and a nicotinamide adenine dinucleotide (NAD) precursor,
   wherein the CD38 inhibitor is a compound selected from the group consisting of apigenin, luteolin, tyrphostin-8, berberine and SRT-1720,
   wherein the NAD precursor is a compound selected from the group consisting of nicotinamide, mononucleotide, nicotinamide riboside or nicotinic acid, and
   wherein the CD38 inhibitor and the NAD precursor are present in the medium in an amount effective to enhance the bioenergetic status of said oocyte, OSC, progeny of an OSC or preimplantation zygote cultured in said medium.

2. The method of claim 1, wherein the medium is selected from the group consisting of cell culture medium, oocyte retrieval solution, oocyte washing solution, oocyte in vitro maturation medium, ovarian follicle in vitro maturation medium, oocyte in vitro fertilization medium, vitrification solution and cryopreservation solution.

3. The method of claim 1, wherein the NAD precursor is nicotinamide riboside.

4. The method of claim 1, wherein the NAD precursor is nicotinic acid.

5. The method of claim 1, wherein a mammalian OSC is cultured.

6. The method of claim 1, wherein the mammalian oocyte, or OSC, progeny of an OSC or preimplantation zygote is from a human female.

7. The method of claim 6, wherein the human female is selected from the group consisting of females of advanced maternal age, females suffering from oocyte-related infertility and females with low ovarian reserve.

8. The method of claim 1, wherein the CD38 inhibitor and the NAD precursor are present in the medium in an amount effective to increase the number of functional mitochondria in the mammalian oocyte, OSC, progeny of an OSC or preimplantation zygote cultured in said medium.

9. The method of claim 1, wherein the CD38 inhibitor and the NAD precursor are present in the medium in an amount effective to increase the mitochondrial energy of the mammalian oocyte, OSC, progeny of an OSC or preimplantation zygote cultured in said medium.

10. The method of claim 1, wherein the CD38 inhibitor and the NAD precursor are present in the medium in an amount effective to increase the cellular energy of the mammalian oocyte, OSC, progeny of an OSC or preimplantation zygote cultured in said medium.

11. The method of claim 1, wherein the CD38 inhibitor is present at a concentration $\geq 25$ µM.

12. The method of claim 1, wherein the NAD precursor is present at a concentration $\geq 100$ µM.

13. The method of claim 1, wherein the medium further comprises ovarian tissue, ovarian follicles, bone marrow, umbilical cord blood or peripheral blood.

14. The method of claim 1, wherein the mammalian OSC expresses a stage-specific embryonic antigen.

* * * * *

SEQUENCE LISTING

```
<160> NUMBER OF SEQ ID NOS: 73

<210> SEQ ID NO 1
<211> LENGTH: 4
<212> TYPE: PRT
<213> ORGANISM: Unknown
<220> FEATURE:
<223> OTHER INFORMATION: Description of Unknown: DEAD box motif peptide
      sequence

<400> SEQUENCE: 1

Asp Glu Ala Asp
1

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cggaaagcaa cccaaagcaa tac                                                 23

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cctcggaacc ataggaaaca ttc                                                 23
```

-continued

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cccaatgaag gaccctgaaa c                                           21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aatggctcac tgtcccgttc a                                           21

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gttatcacca ttgttagtgt catc                                        24

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aatgagtgtt acacctgcgt g                                           21

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgccaatatg atcaggcact cg                                          22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
actgcgtata gcacctgtca cc                                          22

<210> SEQ ID NO 10

-continued

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggaaaccagc agcaagtgat                                                 20

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tggagtcctc atcctctgg                                                  19

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtgtgtcgaa gggctatgga t                                               21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
acaggcagct gatatccagt g                                               21

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cctccccact ttcccataat                                                 20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aatgggtggg gaagaaaaac                                                 20

<210> SEQ ID NO 16
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agcagagagc ttggtcggg                                                19

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tccggtgagc tgtcgctgtc                                               20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctcacgcttc cacaacaaga                                               20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tctcggggct gtcataaatc                                               20

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cccttcagtc acagtttccg t                                             21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gtctctactc tagtgccttc g                                             21

<210> SEQ ID NO 22
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 22
cgtcagtccc aaccattctt                                                 20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ttgttggtga gcatccatgt                                                 20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgcctccttc cctcatcttg                                                 20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cacttccccc gctcacacag                                                 20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gtccgactcc tgcagagaac                                                 20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tgatggtgaa gcgctgatag                                                 20

<210> SEQ ID NO 28
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 28
aaggtcttga gcaggaacga                                                    20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gggtggaaag tagtgcggta                                                    20

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ccgagctgtg caattcccag a                                                  21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aaccctctga gccaagggtg a                                                  21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gatgacgata tcgctgcgct g                                                  21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gtacgaccag aggcatacag g                                                  21

<210> SEQ ID NO 34
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 34
aaacatgacc ggctacaaga ccct                                          24

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ggcacacctt gcattggtat ggtt                                          24

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
agcagtcctc agggaaatcg aaga                                          24

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tatggctgaa gtggcttggt gtct                                          24

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
atgtcgtctg gtccctgttc                                               20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gggatgacga tgagcagaat                                               20

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 40
agacggtgtg caccaacatc taca                                            24

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tgtcgagtca gcttgagcag gaat                                            24

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ttgttgctgt tggacaagtg ggtg                                            24

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gcaacaagaa ctgggcactt tcca                                            24

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tcgaactggt gtgtccaaag gcta                                            24

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
taggattcat cgtggttgtg ggct                                            24

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46 acccta cccca gtaccctgct                                              20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gcaagaaaag caaccaggag                                                20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tatggtgtcc tccggaaaaa                                                20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
aactccaact ccttccagca                                                20

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ataaacgccg agagattgcc caga                                           24

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
aagtctggtc agaagtcagc agca                                           24

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 52
caagcacaat ttgctcagga                                              20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ggcacgtagg cagaataagc                                              20

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tcacctctac aacactgttc ggct                                         24

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
aaggttgaag gaggctggtc acat                                         24

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
cgccatgttc tctgtctcaa                                              20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cgtttgttca catcccagtg                                              20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
```
tcttcttcgc ccttgtgact                                              20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ctcagggtga gcttttctgg                                              20

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
agcaggaccc agatgaactc aaca                                         24

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
aagcccactg ctctacttca tggt                                         24

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
catgtacgtt gctatccagg c                                            21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ctccttaatg tcacgcacga t                                            21

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
tcctctgacc ccagactcac                                              20

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
tagagtcttg gagctcct                                                18

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
aacccaacca gtctcacagg                                              20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
atgctgtcct tgtgggtagg                                              20

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gatgacgata tcgctgcgct g                                            21

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gtacgaccag aggcatacag g                                            21

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
aagggatccc actgcacata                                              20

```
<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
agtcctcctc atgccctat                                                    20

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ccagaggttg cattttccca ag                                                22

<210> SEQ ID NO 73
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
taaggccgat aaggcaaacg aa                                                22
```